US010343903B2

(12) United States Patent
Zink et al.

(10) Patent No.: US 10,343,903 B2
(45) Date of Patent: Jul. 9, 2019

(54) CATIONIC POLYMER COATED MESOPOROUS SILICA NANOPARTICLES AND USES THEREOF

(71) Applicant: The Regents of the University of California, Oakland, CA (US)

(72) Inventors: Jeffrey I. Zink, Sherman Oaks, CA (US); Andre E. Nel, Sherman Oaks, CA (US); Tian Xia, Los Angeles, CA (US); Zhaoxia Ji, Wellesley, MA (US); Huan Meng, Los Angeles, CA (US); Zongxi Li, Boston, MA (US); Monty Liong, Foster City, CA (US); Min Xue, Chino Hills, CA (US); Derrick Y. Tarn, Santa Ana, CA (US); Sanaz Gardner, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/698,486

(22) Filed: Sep. 7, 2017

(65) Prior Publication Data
US 2018/0155189 A1 Jun. 7, 2018

Related U.S. Application Data

(63) Continuation of application No. 13/428,830, filed on Mar. 23, 2012, now abandoned, which is a continuation-in-part of application No. PCT/US2011/043874, filed on Jul. 13, 2011.

(60) Provisional application No. 61/479,751, filed on Apr. 27, 2011, provisional application No. 61/469,190, filed on Mar. 30, 2011, provisional application No. 61/466,581, filed on Mar. 23, 2011, provisional application No. 61/363,945, filed on Jul. 13, 2010.

(51) Int. Cl.
| | |
|---|---|
| *A61K 9/14* | (2006.01) |
| *B82Y 5/00* | (2011.01) |
| *A61K 9/00* | (2006.01) |
| *A61K 9/51* | (2006.01) |
| *A61K 31/704* | (2006.01) |
| *A61K 31/713* | (2006.01) |

(52) U.S. Cl.
CPC ............ *B82Y 5/00* (2013.01); *A61K 9/0019* (2013.01); *A61K 9/5115* (2013.01); *A61K 9/5146* (2013.01); *A61K 9/5192* (2013.01); *A61K 31/704* (2013.01); *A61K 31/713* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,622,684 A | 4/1997 | Pinnavaia et al. | |
| 6,615,855 B2 | 9/2003 | Lopez et al. | |
| 6,755,621 B2 | 6/2004 | Lopez et al. | |
| 6,767,531 B2 | 7/2004 | Fritzberg et al. | |
| 6,902,806 B2 | 6/2005 | Fujiwara et al. | |
| 6,913,825 B2 | 7/2005 | Ostafin et al. | |
| 6,929,636 B1 | 8/2005 | von Alten | |
| 7,163,658 B2 | 1/2007 | Bension | |
| 7,258,874 B2 | 8/2007 | Barbe et al. | |
| 7,354,602 B2 | 4/2008 | Barbe et al. | |
| 7,354,603 B2 | 4/2008 | Barbe et al. | |
| 7,357,948 B2 | 4/2008 | Barbe et al. | |
| 7,563,451 B2 * | 7/2009 | Lin ..................... | A61K 9/0019 424/400 |
| 9,993,437 B2 | 6/2018 | Liong et al. | |
| 2003/0152759 A1 | 8/2003 | Chao et al. | |
| 2004/0076681 A1 | 4/2004 | Dennis et al. | |
| 2005/0130167 A1 | 6/2005 | Bao et al. | |
| 2006/0154069 A1 | 7/2006 | Lin et al. | |
| 2006/0216239 A1 | 9/2006 | Zhang et al. | |
| 2007/0151038 A1 | 7/2007 | Lai et al. | |
| 2008/0031960 A1 | 2/2008 | Wilson et al. | |
| 2008/0107598 A1 | 5/2008 | Yang et al. | |
| 2008/0175992 A1 | 7/2008 | Plieth et al. | |
| 2008/0206146 A1 | 8/2008 | Akhtari et al. | |
| 2009/0196826 A1 | 8/2009 | Gao et al. | |

(Continued)

FOREIGN PATENT DOCUMENTS

| | | |
|---|---|---|
| KR | 10-0924786 B1 | 11/2009 |
| WO | WO-0076556 A2 * 12/2000 | ......... A61K 51/0478 |

(Continued)

OTHER PUBLICATIONS

Liong, M.; Lu, J.; Kovochich, M.; Xia, T.; Ruehm, S.; Nel, A. E.; Tamanoi, F.; Zink, J. Multifunctional Inorganic Nanoparticles for Imaging, Targeting, and Drug Delivery. ACS Nano, vol. 2, No. 5 p. 889-896. (Year: 2008).*

(Continued)

*Primary Examiner* — Jessica Worsham
(74) *Attorney, Agent, or Firm* — Tom Hunter; Weaver Austin Villeneuve & Sampson LLP

(57) ABSTRACT

A submicron structure having a silica body defining a plurality of pores is described. The submicron body may be spherical or non-spherical, and may include a cationic polymer or co-polymer on the surface of said silica body. The submicron structure may further include an oligonucleotide and be used to deliver the oligonucleotide to a cell. The submicron structure may further include a therapeutic agent and be used to deliver the therapeutic agent to a cell. An oligonucleotide and therapeutic agent may be used together. For example, when the oligonucleotide is an siRNA, the composition may be used to decrease cellular resistance to the therapeutic agent by decreasing translation of a resistance gene.

23 Claims, 76 Drawing Sheets
(49 of 76 Drawing Sheet(s) Filed in Color)
Specification includes a Sequence Listing.

(56) References Cited

U.S. PATENT DOCUMENTS

| | | | |
|---|---|---|---|
| 2010/0016610 A1 | 1/2010 | Keinan | |
| 2010/0143263 A1 | 6/2010 | Cheon et al. | |
| 2010/0255103 A1 | 10/2010 | Liong et al. | |
| 2010/0284924 A1 | 11/2010 | Zink et al. | |
| 2010/0310465 A1 | 12/2010 | Zink et al. | |
| 2011/0104073 A1 | 5/2011 | Zeng et al. | |
| 2011/0268791 A1 | 11/2011 | Liu et al. | |
| 2012/0021034 A1 | 1/2012 | Zink et al. | |
| 2012/0207795 A1 | 8/2012 | Zink et al. | |
| 2013/0046274 A1 | 2/2013 | Zink et al. | |
| 2016/0008283 A1 | 1/2016 | Nel et al. | |
| 2017/0095418 A1 | 4/2017 | Zink et al. | |

FOREIGN PATENT DOCUMENTS

| | | |
|---|---|---|
| WO | WO 2006/015757 A1 | 2/2006 |
| WO | WO 2006/032136 A1 | 3/2006 |
| WO | WO 2007/010574 A1 | 1/2007 |
| WO | WO 2007/015105 A2 | 2/2007 |
| WO | WO 2007/131286 A1 | 11/2007 |
| WO | WO 2009/064964 A2 | 5/2009 |
| WO | WO 2009/078924 A2 | 6/2009 |
| WO | WO 2009/094568 A1 | 7/2009 |
| WO | WO 2009/094580 A2 | 7/2009 |
| WO | WO 2009/097439 A1 | 8/2009 |
| WO | WO 2010/071831 A2 | 6/2010 |
| WO | WO 2010/078569 A2 | 7/2010 |
| WO | WO 2012/009448 A2 | 1/2012 |
| WO | WO 2013/012891 A1 | 1/2013 |
| WO | WO 2014/138278 A1 | 9/2014 |

OTHER PUBLICATIONS

McBain, S.C.; Yiu, H.H.P.; El Haj, E.; Dobson, J. Polyethyleneimine functionalized iron oxide nanoparticles as agents for DNA delivery and transfection. Journal of Materials Chemistry, 17, 2561-2565. (Year: 2007).*

Tang, G. P.; Zeng, J.M. Gao, S.J.; Ma, Y.X.; Shi, L.;Li, Y.; Too, H.P.; Wang, S. Polyethylene glycol modified polyethylenimine for improved CNS gene transfer: effects of PEGylation extent. Biomaterials, 24, 2351-2362. (Year: 2003).*

Thierry, B.; Zimmer, L.; McNiven, S.; Finnie, K.; Barbe, C.; Griesser, H.J. Electrostatic Self-Assembly of PEG Copolymers onto Porous Silica Nanoparticles. Langmuir, 24, 8143-8150. (Year: 2008).*

U.S. Office Action (Restriction Requirement), dated Dec. 5, 2011 issued in U.S. Appl. No. 12/746,375.

U.S. Office Action, dated Mar. 14, 2012, issued in U.S. Appl. No. 12/746,375.

U.S. Final Office Action, dated Nov. 26, 2012, issued in U.S. Appl. No. 12/746,375.

U.S. Office Action, dated May 8, 2014, issued in U.S. Appl. No. 12/746,375.

U.S. Final Office Action, dated Mar. 2, 2015, issued in U.S. Appl. No. 12/746,375.

U.S. Office Action, dated Jan. 6, 2016, issued in U.S. Appl. No. 12/746,375.

U.S. Final Office Action, dated Aug. 29, 2016, issued in U.S. Appl. No. 12/746,375.

U.S. Office Action, dated Mar. 31, 2017, issued in U.S. Appl No. 12/746,375.

U.S. Notice of Allowance, dated Jan. 17, 2018, issued in U.S. Appl. No. 12/746,375.

U.S. Notice of Allowance (Corrected), dated Feb. 8, 2018, issued in U.S. Appl. No. 12/746,375.

U.S. Office Action, dated Jul. 10, 2012, issued in U.S. Appl. No. 12/812,359.

U.S. Office Action, dated Feb. 14, 2013, issued in U.S. Appl. No. 12/812,359.

U.S. Final Office Action, dated Jul. 26, 2013, issued in U.S. Appl. No. 12/812,359.

U.S. Final Office Action (Letter Restarting Period for Response), dated Jul. 29, 2013, issued in U.S. Appl. No. 12/812,359.

U.S. Office Action (Before the Patent Trial and Appeal Board, Examiner's Answer to Appeal Brief), dated Aug. 28, 2014, issued in U.S. Appl. No. 12/812,359.

U.S. Office Action (Before the Patent Trial and Appeal Board, Decision on Appeal), dated Aug. 31, 2016, issued in U.S. Appl. No. 12/812,359.

U.S. Office Action, dated Oct. 25, 2017, issued in U.S. Appl. No. 15/288,322.

U.S. Final Office Action, dated Jul. 27, 2018, issued in U.S. Appl. No. 15/288,322.

U.S. Office Action (Restriction Requirement), dated May 21, 2012, issued in U.S. Appl. No. 12/841,331.

U.S. Office Action, dated Aug. 13, 2012, issued in U.S. Appl. No. 12/841,331.

U.S. Office Action, dated Apr. 30, 2013, issued in U.S. Appl. No. 12/841,331.

U.S. Final Office Action, dated Dec. 26, 2013, issued in U.S. Appl. No. 12/841,331.

U.S. Office Action, dated Dec. 10, 2014, issued in U.S. Appl. No. 12/841,331.

U.S. Final Office Action, dated May 13, 2015, issued in U.S. Appl. No. 12/841,331.

U.S. Office Action, dated Jan. 20, 2016, issued in U.S. Appl. No. 12/841,331.

U.S. Final Office Action, dated Aug. 18, 2016, issued in U.S. Appl. No. 12/841,331.

U.S. Office Action, dated Nov. 22, 2017, issued in U.S. Appl. No. 12/841,331.

U.S. Office Action (Restriction Requirement), dated Nov. 26, 2012, issued in U.S. Appl. No. 13/140,714.

U.S. Office Action, dated May 10, 2013, issued in U.S. Appl. No. 13/140,714.

U.S. Final Office Action, dated Feb. 28, 2014, issued in U.S. Appl. No. 13/140,714.

U.S. Office Action, dated Mar. 13, 2015, issued in U.S. Appl. No. 13/140,714.

U.S. Final Office Action, dated Nov. 20, 2015, issued in U.S. Appl. No. 13/140,714.

U.S. Office Action, dated Dec. 2, 2016, issued in U.S. Appl. No. 13/140,714.

U.S. Office Action (Restriction Requirement), dated Jul. 7, 2015, issued in U.S. Appl. No. 13/550,374.

U.S. Office Action, dated Dec. 16, 2015, issued in U.S. Appl. No. 13/550,374.

U.S. Final Office Action, dated Oct. 7, 2016, issued in U.S. Appl. No. 13/550,374.

U.S. Office Action, dated Jan. 12, 2018, issued in U.S. Appl. No. 13/550,374.

U.S. Notice of Allowance, dated Oct. 9, 2018, issued in U.S. Appl. No. 13/550,374.

U.S. Office Action (Restriction Requirement), dated Mar. 29, 2013, issued in U.S. Appl. No. 13/428,830.

U.S. Office Action, dated Oct. 3, 2013, issued in U.S. Appl. No. 13/428,830.

U.S. Final Office Action, dated Aug. 1, 2014, issued in U.S. Appl. No. 13/428,830.

U.S. Office Action, dated Dec. 5, 2014, issued in U.S. Appl. No. 13/428,830.

U.S. Final Office Action, dated Jul. 23, 2015, issued in U.S. Appl. No. 13/428,830.

U.S. Office Action, dated May 16, 2016, issued in U.S. Appl. No. 13/428,830.

U.S. Final Office Action, dated Mar. 7, 2017, issued in U.S. Appl. No. 13/428,830.

PCT International Search Report and Written Opinion dated May 14, 2009 issued in PCT/US08/13476.

PCT International Preliminary Report on Patentability and Written Opinion dated Jun. 8, 2010 issued in PCT/US08/13476.

PCT International Search Report and Written Opinion dated May 19, 2009 issued in PCT/US09/031872.

(56) References Cited

OTHER PUBLICATIONS

PCT International Preliminary Report on Patentability dated Aug. 5, 2010 issued in PCT/US09/031872.
PCT International Search Report and Written Opinion dated Mar. 27, 2009 issued in PCT/US2009/032451.
PCT International Preliminary Report on Patentability and Written Opinion dated Aug. 12, 2010 issued in PCT/US2009/032451.
PCT International Search Report and Written Opinion dated May 28, 2009 issued in PCT/US2009/031891.
PCT International Preliminary Report on Patentability and Written Opinion dated Aug. 5, 2010 issued in PCT/US2009/031891.
PCT International Search Report dated Sep. 3, 2010 issued in PCT/US2009/068816.
PCT International Preliminary Report on Patentability and Written Opinion dated Jun. 30, 2011 issued in PCT/US2009/068816.
PCT International Search Report dated Apr. 6, 2012 issued in PCT/US2011/043874.
PCT International Preliminary Report on Patentability dated Jan. 24, 2013 issued in PCT/US2011/043874.
PCT International Search Report and Written Opinion dated Jun. 24, 2014 issued in PCT/US2014/020857.
PCT International Report on Patentability and Written Opinion dated Sep. 17, 2015 issued in PCT/US2014/020857.
European Extended Search Report dated Jul. 27, 2016 issued in Application No. EP 14 760 467.2.
Tamanoi (2006) Nanodelivery: Towards controlled release of anticancer drugs. Oral Presentation on Dec. 6, 2006 (see NanoBio-Tokyo 2006 Program), 7 pages. Abstract provided in *Proceedings of UT Symposium on NanoBio Integration Program* and Abstract provided.
Stöber et al., (1968) "Controlled growth of monodisperse silica spheres in the micron size range," *J Colloid and Interface Sci.*, 26:62-69.
Angelos et al., (2007) "Photo-Driven Expulsion of Molecules from Mesostructured Silica Nanoparticles," *J Phys Chem C*, 111:6589-6592.
Nguyen et al., (2007) "Versatile Supramolecular Nanovalves Reconfigured for Light Activation," *Adv. Funct. Mater.*, 17:2101-2110.
Leung et al., (2006) "Supramolecular Nanovalves Controlled by Proton Abstraction and Competitive Binding," *Chem. Mater.*, 18:5919-5928.
Nguyen et al., (2005) "A reversible molecular valve," *Proc. Natl. Acad. Sci. U.S.A.*, 102:10029-10034.
Nguyen et al., (2007) "Design and optimization of molecular nanovalves based on redox-switchable bistable rotaxanes," *Journal of the American Chemical Society*, 129(3):626-634.
Abigerges et al., (1995) *Clin. Oncol.*, 13:210-221.
Al Shamsi et al., (2010) Chem. Res. Toxicol., 23(11):1796-1805.
Alvaro et al., (2005) *Chem. Mater.*, 17:4958-4964.
Angelos et al., (2007) "Mesostructured silica supports for functional materials and molecular machines," *Adv. Funct. Mater.*, 17:2261-2271.
Angelos et al., (2008) "PH-Responsive supramolecular nanovalves based on cucurbit[6]uril pseudorotaxanes," *Agnew. Chem. Int. Ed.*, 47:2222-2226.
Angelos et al., (2009) "pH Clock-Operated Mechanized Nanoparticles," *J. Am. Chem. Soc.*, 131:12912-12914.
Aprahamian et al., (2007) "A Clicked Bistable [2]Rotaxane," *Org. Lett.*, 9(7):1287-1290.
Arnida et al., (2009) "Cellular Uptake and Toxicity of Gold Nanoparticles in Prostate Cancer Cells: A Comparative Study of Rods and Spheres," *J. Appl. Toxicol.*, 30:212-217.
Arnold et al., (2004) "Activation of Integrin Function by Nanopatterned Adhesive Interfaces," *ChemPhysChem*, 5:383-388.
Arola et al., (2000) "Acute Doxorubicin Cardiotoxicity Involves Cardiomyocyte Apoptosis," *Cancer Res.*, 60:1789-1792.

Arruebo et al., (2006) "Development of Magnetic Nanostructured Silica-Based Materials as Potential Vectors for Drug-Delivery Applications," *Chem. Mater.*, 18:1911-1919 (Published online Mar. 14, 2006).
Arruebo et al., (2006) *Nanotechnology*, 17:4057-4064 (Published Jul. 18, 2006).
Aznar et al., (2009) "pH—and Photo-Switched Release of Guest Molecules from Mesoporous Silica Supports," *J. Am. Chem. Soc.*, 131(19):6833-6843.
Bagwe et al., (2006) "Surface Modification of Silica Nanoparticles to Reduce Aggregation and Nonspecific Binding," *Langmuir*, 22:4357-4362 (Apr. 25, 2006).
Barbe et al., (2004) "Silica particles: A novel drug-delivery system," *Adv. Mater.*, 16:1959-1966.
Beck et al., (1992) "A new family of mesoporous molecular sieves prepared with liquid crystal templates," *J. Am. Chem. Soc.*, 114:10834-10843.
Belloc et al., (1994) "A Flow Cytometric Method Using Hoechst 33342 and Propidium Iodide for Simultaneous Cell Cycle Analysis and Apoptosis Determination in Unfixed Cells," *Cytometry*, 17:59-65.
Bernardos et al., (2009) "Enzyme-Responsive Controlled Release Using Mesoporous Silica Supports Capped with Lactose," *Angew. Chem. Int. Ed.*, 48:5884-5887.
Berry et al. (2003) "Functionalization of magnetic nanoparticles for applications in biomedicine," *J. Phys. D: Appl. Phys.*, R198-206, 10pp.
Berry et al., (2005) "Self-Assembly of nanoparticles on live bacterium: An avenue to Fabricate Electronic Devices," *Angew. Chem., Int. Ed.*, 44:6668-6673.
Besson et al., (2005) *J. Mater. Chem.*, 15:803-809.
Bettio et al., (2006) *J. Nucl. Med.*, 47:1153-1160.
Bharali et al., (2005) *Proc. Natl. Acad. Sci. U.S.A.*, 102:11539-11544.
Blow et al., (2007) *Nature*, 450:1117-1120.
Bonoiu et al., (2009) *Proc. Natl. Acad. Sci. U.S.A.*, 106(14):5546-5550.
Borm et al., (2006) *Toxicol. Sci.*, 90:23-32.
Botella et al., (2007) "Single gold nanoparticles encapsulated in monodispersed regular spheres of mesostructured silica produced by pseudomorphic transformation," *Chem. Mater*, 19:1979-1983.
Boussif et al., (1995) *Proc. Natl. Acad. Sci. U.S.A.*, 92:7297-7301.
Braunschweig et al., (2007) *Chem. Asian J.*, 2:634-637.
Brigger et al., (2002) "Nanoparticles in cancer therapy and diagnosis," *Advanced Drug Delivery Reviews*, 54:631-651.
Brust et al., (1994) "Synthesis of Thiol-Derivatised Gold Nanoparticles in a Two-Phase Liquid-Liquid System," *Chem. Commun.* 801-802.
Butler et al., (2006) "Purified Integrin Adhesion Complexes Exhibit Actin-Polymerization Activity," *Curr. Biol.*, 16:242-251.
Cai et al., (2001) "Dilute Solution Routes to Various Controllable Morphologies of MCM-41 Silica with a Basic Medium," *Chem. Mater.*, 13(2):258-263.
California Nano Systems Institute 2005 Annual Research Report: "Powered Artificial Nano-Machines: Molecular Valves and Impellers," URL:http://www.cnsi.ucla.edu/spheres/ResReport-2005.pdf [retrieved on Jul. 8, 2010], p. 51.
Canonico et al., (1969) *J. Cell Biol.*, 43:367-371.
Cauda et al., (2010) *Micropor. Mesopor. Mat.*, 132:60-71.
Cavalcanti-Adam et al., (2007) "Cell Spreading and Focal Adhesion Dynamics Are Regulated by Spacing of Integrin Ligands," *Biophys. J.*, 92:2964-2974.
Celano et al., (2004) "Cytotoxic effects of Gemcitabine-loaded liposomes in human anaplastic thyroid carcinoma cells," BMC Cancer, 4(63):5 pages.
Champion et al., (2006) "Role of Target Geometry in Phagocytosis," *Proc. Natl. Acad. Sci. U.S.A.*, 103:4930-4934.
Champion et al., (2007) "Making Polymeric Micro—and Nanoparticles of Complex Shapes," *Proc. Natl. Acad. Sci. U.S.A.*, 104:11901-11904.
Champion et al., (2007) "Particle shape: A New Design Parameter for Micro—and Nanoscale Drug Delivery Carriers," *J. Control. Release*, 121:3-9.
Chen et al., (1988) *J. Biol. Chem.*, 263(18):8754-8758.

(56) References Cited

OTHER PUBLICATIONS

Chen et al., (1996) "Requirement of CDC42 for Salmonella-Induced Cytoskeletal and Nuclear Responses," *Science*, 274:2115-2118.
Chen et al., (2007) "Immuno Gold Nanocages with Tailored Optical Properties for Targeted CH Photothermal Destruction of Cancer Cells," *Nano Lett.*, 7(5):1318-1322 (Published online Apr. 15, 2007).
Chen et al., (2008) "Functional $Fe_3O_4/TiO_2$ core/shell magnetic nanoparticles as photokilling agents for pathogenic bacteria," *Small*, 4(4):485-491.
Chen et al., (2009) *Small*, 5(23):2673-2677.
Chithrani et al., (2006) "Determining the Size and Shape Dependence of Gold Nanoparticle Uptake into Mammalian Cells," *Nano Lett.*, 6:662-668.
Chithrani et al., (2007) "Elucidating the Mechanism of Cellular Uptake and Removal of Protein-Coated Gold Nanoparticles of Different Sizes and Shapes," *Nano Lett.*, 7:1542-1550.
Cho et al., (2008) *Clin. Cancer Res.*, 14(5):1310-1316.
Chung et al., (2007) *Biomaterials*, 28:2959-2966 (Published online Mar. 19, 2007).
Clottens et al., (1997) *Occup. Environ. Med.*, 54:376-387.
Conner et al., (2003) "Regulated Portals of Entry into the Cell," *Nature*, 422:37-44.
Corot et al., (2006) "Recent Advances in Iron Oxide Nanocrystal Technology for Medical Imaging," *Adv. Drug Delivery Rev.*, 58:1471-1504.
Coti et al., (2009) "Mechanised Nanoparticles for Drug Delivery," *Nanoscale*, 1(1):16-39.
Cunha et al., (2002) *Mutagenesis*, 17(2): 141-147.
Darbre et al., (2006) *Chem. Res.*, 39:925-934.
Darzynkiewicz et al., (1997) "Cytometry in Cell Necrobiology: Analysis of Apoptosis and Accidental Cell Death (Necrosis)," *Cytometry*, 27:1-20.
Dausend et al., (2008) "Uptake Mechanism of Oppositely Charged Fluorescent Nanoparticles in HeLa Cells," *Macromol. Biosci.*, 8:1135-1143.
Davis et al., (2008) "Nanoparticle therapeutics: an emerging treatment modality for cancer," *Nature Reviews Discovery*, 7:771-782.
Davis et al., (2009) *Mol. Pharm.*, 6:659-668.
De Smedt et al., (2000) *Pharmaceutical Research*, 17(2):113-126.
de Wolf et al., (2007) *Int. J. Pharm.*, 331:167-175.
Decuzzi et al., (2008) "The Receptor-Mediated Endocytosis of Nonspherical Particles," *Biophys. J.*, 94(10):3790-3797.
Decuzzi et al., (2010) "Size and Shape Effects in the Biodistribution of Intravascularly Injected Particles," *J. Control. Release*, 141:320-327.
Denny et al., (2004) "Tumor-activated Prodrugs-A New Approach to Cancer Therapy," *Cancer Invest.*, 22(4):604-619.
Derfus et al., (2007) *Adv. Mater.*, 19:3932-3936.
Dhanikula et al., (2006) "Synthesis and Evaluation of Novel Dendrimers with a Hydrophilic Interior as Nanocarriers for Drug Delivery," *Bioconjugate Chem.*, 17:29-41.
Dharmawardhane et al., (2000) "Regulation of Macropinocytosis by p21-activated Kinase-1," *Mol. Biol. Cell*, 11:3341-3352.
Dietrich et al., (2001) "Effects of Particle Size and Molecular Weight of Polyethylenimine on Properties of Nanoparticulate Silicon Dispersions," *J. Am. Ceram. Soc.*, 84(4):806-812.
Dichtel et al., (2006) *J. Am. Chem. Soc.*, 128(32): 10388-10390.
Discher et al., (2005) "Tissue Cells Feel and Respond to the Stiffness of Their Substrate," *Science*, 310:1139-1143.
Doshi et al., (2010) "Macrophages Recognize Size and Shape of Their Targets," *PLoS ONE*, 5(4):e10051, 6pp.
Duan et al., (2007) *J. Am. Chem. Soc.*, 129:3333-3338.
Duncan et al., (2005) *Endocr-Relat. Cancer.*, 12:S189-S199.
Duncan et al., (2006) *J. Drug Target.*, 14:337-341.
Elbakry et al., (2009) *Nano Lett.*, 9(5):2059-2064.
Fan et al., (2004) "Self-Assembly of Ordered, Robust, Three-Dimensional Gold Nanocrystal/Silica Arrays," *Science*, 304:567-571.
Fan et al., (2006) "Ordered Nanocrystal/Silica Particles Self-Assembled from Nanocrystal Micelles and Silicate," *Chem. Commun.*, 2323-2325 (Published online Mar. 29, 2006).
Fang et al., (2004) "Factors and Mechanism of "EPR" Effect and the Enhanced Antitumor Effects of Macromolecular Drugs Including SMANCS," *In Polymer Drugs in the Clinical Stage, Springer US*, 519:29-49.
Fang et al., (2011) *Adv. Drug Delivery Rev.*, 63:136-151.
Faris et al., (1991) *Clin. Phys. Physiol. Meas.*, 12(4):353-358.
Febvay et al., (2010) *Nano Lett.*, 10:2211-2219.
Fenske et al., (2001) *Curr. Opin. Mol. Ther.*, 3(2):153-158.
Ferrari et al., (2005) "Cancer Nanotechnology: Opportunities and Challenges" *Nat. Rev. Cancer*, 5:161-171.
Ferris et al., (2009) "Light-Operated Mechanized Nanoparticles," *J. Am. Chem. Soc.*, 131:1686-1688.
Finnie et al., (2009) *J. Sol-Gel. Sci. Techn.*, 49:12-18.
Fiorentini et al., (2001) "Activation of Rho GTPases by Cytotoxic Necrotizing Factor 1 Induces Macropinocytosis and Scavenging Activity in Epithelial Cells," *Mol. Biol. Cell*, 12:2061-2073.
Florea et al., (2002) *AAPS PharmSci.*, 4(3)article 12:E12, 11 pages.
Fortin et al., (2007) "Size-Sorted Anionic Iron Oxide Nanomagnets as Colloidal Mediators for Magnetic Hyperthermia," *J. Am. Chem. Soc.*, 129(9):2628-2635.
Frangioni et al., (2003) "In vivo near-infrared fluorescence imaging," *Curr. Opin. Chem*, 7:626-634.
Frisch et al., (1996) "Nanocomposites Prepared by Threading Polymer Chains through Zeolites, Mesoporous Silica, or Silica Nanotubes," *Chem. Mater.*, 8(8):1735-1738.
Fritze et al., (2006) "Remote loading of doxorubicin into liposomes driven by transmembrane phosphate gradient," *Biochimica Et Biophysica Acta (BBA)—Biomembranes*, Elsevier, Amsterdam, NL, 1758(10):1633-1640.
Fuchs et al., (2006) *Cancer Treat. Rev.*, 32:491-503.
Fuller et al., (2008) "Intracellular delivery of core-shell fluorescent silica nanoparticles," *Biomaterials*, 29:1526-1532.
Fusaro et al., (2008) "NMR Study of the Reversible Trapping of $SF_6$ by Cucurbit[6]uril in Aqueous Solution," *J. Phys. Chem. B*, 112(47):15014-15020.
Gamen et al., (2000) "Doxorubicin Treatment Activates a Z-VAD-Sensitive Caspase, Which Causes $\Delta\bullet_m$ Loss, Caspase-9 Activity, and Apoptosis in Jurkat Cells," *Exp. Cell Res.*, 258:223-235.
Gao et al., (2004) "In Vivo Cancer Targeting and Imaging with Semiconductor Quantum Dots," *Nat. Biotechnol.*, 22(8):969-976.
Garg et al., (2002) "Editorial: Hepatic Steatosis, Insulin Resistance, and Adipose Tissue Disorders," *J. Clin. Endocrinol. Metab.*, 87:3019-3022.
Geiger et al., (2009) "Environmental Sensing Through Focal Adhesions," *Nat. Rev. Mol. Cell Biol.*, 10:21-33.
Gemeinhart et al., (2005) *Biotechnol. Prog.*, 21:532-537.
Georganopoulou et al., (2005) "Nanoparticle-Based Detection in Cerebral Spinal Fluid of a Soluble CA Pathogenic Biomarker for Alzheimer's Disease," *Proc. Natl. Acad. Sci. USA* 102(7):2273-2276.
Gerion et al., (2001) "Synthesis and Properties of Biocompatible Water-Soluble Silica-Coated CdSe/ZnS Semiconductor Quantum Dots," *J. Phys. Chem. B*, 105(37): 8861-8871.
Giri et al., (2005) "Stimuli-Responsive Controlled-Release Delivery System Based on Mesoporous Silica Nanorods Capped with Magnetic Nanoparticles," *Angew. Chem. Int. Ed.*, 44:5038-5044.
Glass et al., (2003) "Micro-Nanostructured Interfaces Fabricated by the Use of Inorganic Block Copolymer Micellar Monolayers as Negative Resist for Electron-Beam Lithography," *Adv. Funct. Mater.*, 13:569-575.
Glass et al., (2004) "Block Copolymer Micelle Nanolithography on Non-Conductive Substrates," *New J. of Phys.*, 6:101, 18 pages.
Gobin et al., (2007) "Near-Infrared Resonant Nanoshells for Combined Optical Imaging and Photothermal Cancer Therapy," *Nano Lett.*, 7(7):1929-1934 (Published online Jun. 6, 2007).
Godbey et al., (1999) *Proc. Natl. Acad. Sci. U.S.A.*, 96:5177-5181.
Gopin et al., (2006) *Bioconjug. Chem*, 17:1432-1440.
Gorelikov et al., (2008) "Single-step coating of mesoporous silica on cetyltrimethyl ammonium bromide-capped nanoparticles," *Nano Letters*, 8(1):369-373.

(56) References Cited

OTHER PUBLICATIONS

Gottesman et al., (2002) "Mechanisms of Cancer Drug Resistance," *Annu. Rev. Med.*, 53:615-627.
Gratton et al., (2008) "The Effect of Particle Design on Cellular Internalization Pathways," *Proc. Natl. Acad. Sci. U.S.A.*, 105(33):11613-11618.
Grün et al., (1997) "The Synthesis of Micrometer—and Submicrometer-Size Spheres of Ordered Mesoporous Oxide MCM-41," *Adv. Mater.*, 9(3):254-257.
Guiotto et al., (2004) "Synthesis, Characterization, and Preliminary in Vivo Tests of New Poly(ethylene glycol) Conjugates of the Antitumor Agent 10-Amino-7-ethylcamptothecin" J. Med. Chem., 47(5):1280-1289 [ABSTRACT— 2pages].
Guo et al., (2008) "Biocompatible, luminescent silver@phenol formaldehyde resin core/shell nanospheres: Large-scale synthesis and application for in vivo bioimaging," *Advance Functional Materials*, 18:872-879.
Gupta et al. (2005) "Synthesis and surface engineering of iron oxide nanoparticles for biomedical applications," *Biomaterials*, 26:3995-4021.
Han et al., (1999) *J. Am. Chem. Soc.*, 121(142):9897-9898.
Han et al., (2008) "Reverse microemulsion-mediated synthesis of silica-coated gold and silver nanoparticles," *Langmuir*, 24:5842-5848.
Harada, (2001) "Cyclodextrin-Based Molecular Machines," *Accounts of Chemical Research*, 34:456-464.
Harvey et al., (1998) *Amer. Zool.*, 38:426-441.
Hasegawa et al., (1996) "Involvement of CPP32/Yama(-like) Proteases in Fas-mediated Apoptosis," *Cancer Res*, 56:1713-1718.
Hayakawa et al., (2008) "Actin Stress Fibers Transmit and Focus Force to Activate Mechanosensitive Channels," *J. Cell Sci*, 121:496-503.
Hayek et al., (2005) *N. Engl. J. Med.*, 352:2456-2457.
He et al., (2011) *Small*, 7:271-280.
Hernandez et al., (2001) *J. Am. Chem. Soc.*, 123:1248-1249.
Hernandez et al., (2004) *Am. Chem. Soc.*, 126:3370-3371.
Hertzberg et al., (1989) *J. Med. Chem.* 32(3):715-729.
Hetrick et al., (2008) "Bactericidal efficacy of nitric oxide-releasing silica nanoparticles," *ACS Nano*, 2(2):235-246.
Heuser et al., (1989) *J. Cell Biol.*, 108:389-400.
Hillaireau et al., (2009) "Nanocarriers' Entry into the Cell: Relevance to Drug Delivery," *Cell. Mol. Life Sci.*, 66:2873-2896.
Hiramatsu et al., (2004) "A Simple Large-Scale Synthesis of Nearly Monodisperse Gold and Silver Nanoparticles with Adjustable Sizes and with Exchangeable Surfactants," *Chem. Mater.*, 16(13):2509-2511.
Hirano et al., (1979) *Makromol. Chem.*, 180:1125-1131.
Ho et al., (2004) "Nanoseparated polymeric networks with multiple antimicrobial properties," *Adv. Mater*, 16(12):957-961.
Höbel et al., (2008) *Eur. J. Pharm. Biopharm.*, 70:29-41.
Hoet et al., (1999) *Toxicol. Sci.*, 52:209-216.
Hoet et al., (2001) *Toxicol. Appl. Pharmacol.*, 175:184-190.
Hu et al., (2008) "Core/Single-Crystal-Shell Nanospheres for Controlled Drug Release via a Magnetically Triggered Rupturing Mechanism," *Adv. Mater.*, 20:2690-2695.
Hu et al., (2010) "Nanoparticle-assisted combination therapies for effective cancer treatment," *Therapeutic Delivery*, 1(2):323-334.
Huang et al., (1998) *Langmuir*, 14:7331-7333.
Huang et al., (2006) "Cancer Cell Imaging and Photothermal Therapy in the Near-Infrared Region by CG Using Gold Nanorods," *J. Am. Chem. Soc.*, 128(6):2115-2120 (Published online Jan. 21, 2006).
Huang et al., (2010) "The Effect of the Shape of Mesoporous Silica Nanoparticles on Cellular Uptake and Cell Function," *Biomaterials*, 31:438-448.
Hughes (2005) "Nanostructure-mediated drug delivery," *Nanomedicine: Nanotechnology, Biology, and Medicine*, 1:22-30.
Huh et al., (2003) *Chem. Mater.*, 15:4247-4256.
Iyer et al., (2006) *Drug Discovery Today*, 11(17/18):812-818.
Jabr-Milane et al., (2008) *Cancer Treat. Rev.*, 34:592-602.

Jana et al., (2004) "Size—and Shape-Controlled Magnetic (Cr, Mn, Fe, Co, Ni) Oxide Nanocrystals via a Simple and General Approach," *Chem. Mater.*, 16(20):3931-3935.
Jana et al., (2007) "Synthesis of Water-Soluble and Functionalized Nanoparticles by Silica Coating," *Chem Mater*, 19:5074-5082.
Jang et al., (2009) "Critical Enhancements of MRI Contrast and Hyperthermic Effects by Dopant-Controlled Magnetic Nanoparticles," *J. Angew. Chem., Int. Ed.*, 48:1234-1238.
Jiang et al., (2006) "Aerosol-Assisted Self-Assembly of Single-Crystal Core/Nanoporous Shell Particles as Model Controlled Release Capsules," *J. Am. Chem. Soc.*, 128:4512-4513 (Published online Mar. 16, 2006).
Jin et al., (2007) "Toxicity of Luminescent Silica Nanoparticles to Living Cells," *Chem. Res. Toxicol.* 20(8):1126-1133 (Published online Jul. 13, 2007).
Judge et al., (2006) *Mol. Ther.*, 13:494-505.
Jun et al., (2005) "Nanoscale Size Effect of Magnetic Nanocrystals and Their Utilization for Cancer Diagnosis via Magnetic Resonance Imaging," *J. Am. Chem. Soc.*, 127:5732-5733.
Jun et al., (2008) "Chemical Design of Nanoparticle Probes for High-Performance Magnetic Resonance Imaging," *J. Angew. Chem., Int. Ed.*, 47:5122-5135.
Kalin et al., (2010) "Macropinocytotic Uptake and Infection of Human Epithelial Cells with Species B2 Adenovirus Type 35," *J. Virol.*, 84:5336-5350.
Kam et al., (2005) "Carbon Nanotubes as Multifunctional Biological Transporters and Near-Infrared Agents for Selective Cancer Cell Destruction," *Proc. Natl. Acad. Sci. USA*, 102(33):11600-11605.
Kandutsch et al., (2008) *Eur. J. Surg. Oncol.*, 34:1231-1236.
Karmali et al., (2009) "Targeting of albumin-embedded paclitaxel nanoparticles to tumors," *Nanomedicine*, 5:73-82.
Kataoka et al., (2001) *Adv. Drug Delivery Rev.*, 47:113-131.
Kaul et al., (2004) "Biodistribution and Targeting Potential of Poly(ethylene glycol)-modified Gelatin Nanoparticles in Subcutaneous Murine Tumor Model," *J. Drug Target.*, 12:585-591.
Kawano et al., (2006) *J. Controlled Release*, 111:382-389.
Keane et al., (1998) *J. Urol.*, 160:252-256.
Kim (2002) "Mechanically interlocked molecules incorporating cucurbituril and their supramolecular assemblies," *Chem. Soc. Rev.*, 32:96-107.
Kim et al., (2006) "Magnetic Fluorescent Delivery Vehicle Using Uniform Mesoporous Silica Spheres Embedded with Monodisperse Magnetic and Semiconductor Nanocrystals," *J. Am. Chem. Soc.*, 128:688-689 (Published online Dec. 31, 2005).
Kim et al., (2006) *J. Vet. Sci.*, 7(4):321-326.
Kim et al., (2008) *Angew. Chem., Int. Ed.*, 47:8438-8441.
Kircheis et al., (1999) *J. Gene. Med.*, 1:111-120.
Kircheis et al., (2002) *Cancer Gene. Ther.*, 9:673-680.
Kneuer et al., (2000) *Bioconjugate Chem.*, 11:926-932.
Kobler et al., (2008) "Colloidal suspensions of functionalized mesoporous silica nanoparticles," *ACS Nano*, 2(4):791-799.
Kocer et al., (2005) *Science*, 309:755-758.
Kohler et al., (2006) "Methotrexate-Immobilized Poly(ethylene glycol) Magnetic Nanoparticles for MR Imaging and Drug Delivery," *Small*, 2(6):785-792.
Kónya et al., (2003) "Synthetic Insertion of Gold Nanoparticles into Mesoporous Silica," *Chem Mater*, 15(6): 1242-1248.
Kremer et al., (1996) "Computer Visualization of Three-dimensional Image Data Using IMO," *J. Struct. Biol*, 116:71-76.
Kresge et al., (1992) "Ordered mesoporous molecular sieves synthesized by a liquid-crystal template mechanism," *Nature*, 359:710-712.
Kumar et al., (2008) "Silver-nanoparticle-embedded antimicrobial paints based on vegetable oil," *Nat. Mater.*, 7:236-241.
Kunath et al., (2002) *Pharm. Res.*, 19:810-817.
Kursa et al., (2003) *Bioconjugate Chem.*, 14:222-231.
Lai et al., (2003) "A Mesoporous Silica Nanosphere-Based Carrier System with Chemically Removable CdS Nanoparticle Caps for Stimuli-Responsive Controlled Release of Neurotransmitters and Drug Molecules," *JACS*, 125:4451-4459.
Lang et al., (2004) "A Fast and Efficient ion-Exchange Procedure to Remove Surfactant Molecules from MCM-41 Materials," *Chem. Mater.*, 16:1961-1966.

(56) References Cited

OTHER PUBLICATIONS

Laurent et al., (2008) "Magnetic Iron Oxide Nanoparticles: Synthesis, Stabilization, Vectorization, Physicochemical Characterizations, and Biological Applications" *Chem. Rev.*, 108(6):2064-2110.
Lee et al., (1994) "Delivery of Liposomes into Cultured KB Cells via Folate Receptor-Mediated Endocytosis," *J. Biol. Chem.*, 269(5):3198-3204.
Lee et al., (2005) *Nat. Biotechnol.*, 23(12): 1517-1526.
Lee et al., (2006) "Dual-Mode Nanoparticle Probes for High-Performance Magnetic Resonance and Fluorescence Imaging of Neuroblastoma," *Angew. Chem., Int. Ed.*, 118:8340-8342 (Published online Nov. 14, 2006).
Lee et al., (2007) "Artificially Engineered Magnetic Nanoparticles for Ultra-Sensitive Molecular Imaging," *Nat. Med.*, 13(1):95-99 (Published online Dec. 24, 2006).
Lee et al., (2009) "Shaping Nano-/Micro-particles for Enhanced Vascular Interaction in Laminar Flows," *Nanotechnology*, 20:495101, 12 pp.
Lee et al., (2009) *Adv. Funct. Mater.*, 19:215-222.
Lee et al., (2010) *Angew. Chem. Int. Ed.*, 49:8214-8219.
Lee et al., (2010) *Mol. Pharm.*, 7:1195-1208.
Li et al., (1999) "Preparation of $Ag/SiO_2$ nanosize composites by a reverse micelle and sol-gel technique," *Langmuir*, 15:4328-4334.
Li et al., (2003) "Facilitation of $Ca^{2+}$—-Dependent Exocytosis by Rac1-GTPase in Bovine Chromaffin," *Cells. J. Physiol.*, 550:431-445.
Li et al., (2008) "The Translocation of Fullerenic Nanoparticles into Lysosome via the Pathway of Clathrin-Mediated Endocytosis," *Nanotechnology*, 19:145102, 13 pp.
Li et al., (2008) *Molecular Pharmaceutics*, 5(4):496-504.
Lichstein et al., (1994) *J. Bacteriol.*, 47:231-238.
Lim et al., (1997) *J. Am. Chem. Soc.*, 119:4090-4091.
Lin et al., (2005) "Well-Ordered Mesoporous Silica Nanoparticles as Cell Markers," *Chem. Mater.*, 17:4570-4573.
Lin et al., (2006) "Multifunctional Composite Nanoparticles: Magnetic, Luminescent, and Mesoporous," *Chem. Mater.*, 18(22):5170-5172 (Published online Oct. 10, 2006).
Lin et al., (2009) *Chem. Mater.*, 21:3979-3986.
Liong et al., (2008) "Multifunctional inorganic nanoparticles for imaging, targeting and drug delivery," *ACS Nano*, 2(5):889-896 [and supporting information attached].
Liong et al., (2009) "Antimicrobial Activity of Silver Nanocrystals Encapsulated in Mesoporous," *Advanced Materials*, 21:1684-1689.
Liong et al., (2009) "Mesostructured Multifunctional Nanoparticles for Imaging and Drug Delivery," *J. Mater. Chem.*, 19(35):6251-6257.
Litvak et al., (1999) "Inhibition of gastric cancer by camptothecin involves apoptosis and multiple cellular pathways," *Surgery*, 125(2):223-230.
Liu et al., (2002) "Self-Directed Assembly of Photoactive Hybrid Silicates Derived from an Azobenzene-Bridged Silsesquioxane," *J. Am. Chem. Soc.*, 124:14540-14541.
Liu et al., (2003) *Angew. Chem. Int. Ed., Engl.*, 42:1731-1734.
Liu et al., (2003) *Chem. Comm.*, 10:1144-1145.
Liu et al., (2004) *J. Nano Lett.*, 4:551-554.
Liu et al., (2008) "Tunable Redox-Responsive Hybrid Nanogated Ensembles," *Am. Chem. Soc.*, 130:14418-14419.
Liu et al., (2009) "Porous Nanoparticle Supported Lipid Bilayers (Protocells) as Delivery Vehicles," *Journal of the American Chemical Society*, 131(4):1354-1355.
Liu et al., (2009) "Preparation of spherical large particle MCM-41 with a broad particle size distribution by modified pseudomorphic transformation," *Microporous and mesoporous materials*, 121:73-78.
Liu et al., (2011) *Biomaterials*, 32:1657-1668.
Lobo et al., (2007) "Paclitaxel Albumin-Bound Particles (Abraxane(TM)) in Combination with Bevacizumab with or without Gemcitabine: Early Experience at the University of Miami/Braman Family Breast Cancer Institute," *Biomed. Pharmacother.*, 61:531-533.
Loher et al., (2008) "Micro-organism-triggered release of silver nanoparticles from biodegradable oxide carriers allows preparation of self-sterilizing polymer surfaces," *Small*, 4(6):824-832.
Lok et al., (2006) "Proteomic analysis of the mode of antibacterial action of silver nanoparticles," *Journal of Proteome Research*, 5:916-924.
Lu et al., (1997) *Nature*, 389:364-368.
Lu et al., (2002) "Modifying the Surface Properties of Superparamagnetic Iron Oxide Nanoparticles through a Sol-Gel Approach," *Nano Letter*, 2(3):183-186.
Lu et al., (2007) "Mesoporous Silica Nanoparticles as a Delivery System for Hydrophobic Anticancer Drugs," *Small*, 3(8):1341-1346 (Published online Jun. 13, 2007).
Lu et al., (2007) "Mesoporous Silica Nanoparticles for Cancer Therapy: Energy-Dependent Cellular Uptake and Delivery of Paclitaxel to Cancer Cells," *Nanobiotechnology*, 3:89-95.
Lu et al., (2008) "Light-Activated Nanoimpeller-Controlled Drug Release In Cancer Cells," *Small*, 4(4):421-426.
Lu et al., (2010) *Small*, 6:1794-1805.
Ludwig et al., (2006) *Cancer Res.*, 66:4808-4815.
Luo et al., (2000) *Nat. Biotechnol.*, 18:893-895.
Maeda et al., (2009) *Eur. J. Pharm. Biopharm.*, 71:409-419.
Maeda et al., (2010) *Bioconjugate Chem.*, 21:797-802.
Mal et al., (2003) "Photo-Switched Storage and Release of Guest Molecules in the Pore Void of Coumarin-Modified MCM-41," *Chem. Mater.*, 15(17):3385-3394.
Mal et al., (2003) *Nature*, 421:350-353.
Mao et al., (2005) *Pharm. Res.*, 22:2058-2068.
Masson et al., (2009) "Kinetic vs Thermodynamic Self-Sorting of Cucurbit[6]uril, Cucurbit[7]uril, and a Spermine Derivative," *Org. Lett.*, 11(17):3798-3801.
Masuda et al., (1992) *J. Clin. Oncol.*, 10:1225-12229.
Medarova et al., (2007) "In Vivo Imaging of siRNA Delivery and Silencing in Tumors," *Nat. Med.*, 13(3):372-377 (Published online Feb. 25, 2007).
Meng et al., (2009) "A Predictive Toxicological Paradigm for the Safety Assessment of Nanomaterials," *ACS Nano*, 3:1620-1627.
Meng et al., (2010) "Autonomous in Vitro Anticancer Drug Release from Mesoporous Silica Nanoparticles by pH—Sensitive Nanovalves," *J. Am. Chem. Soc.*, 132:12690-12697.
Meng et al., (2010) "Engineered Design of Mesoporous Silica Nanoparticles to Deliver Doxorubicin and P-Glycoprotein siRNA to Overcome Drug Resistance in a Cancer Cell Line," *ACS Nano*, 4(8):4539-4550.
Meng et al., (2010) "Potent Angiogenesis Inhibition by the Particulate Form of Fullerene Derivatives," *American Chemical Society*, 4(5):2773-2783.
Meng et al., (2011) "Aspect Ratio Determines the Quantity of Mesoporous Silica Nanoparticle Uptake by a Small GTPase-Dependent Macropinocytosis Mechanism," *ACS Nano*, 5(6):4434-4447.
Meng et al., (2011) "Use of Size and a Copolymer Design Feature To Improve the Biodistribution and the Enhanced Permeability and Retention Effect of Doxorubicin Loaded Mesoporous Silica Nanoparticles in a Murine Xenograft Tumor Model," *ACS Nano*, 5(5):4131-4144.
Mercer et al., (2009) Virus Entry by Macropinocytosis, *Nat. Cell Biol.*, 11:510-520.
Mignot et al., (2001) "Distribution of s-layers on the surface of *Bacillus cereus* strains: phylogenetic origin and ecological pressure," *Environ. Microbiol.*, 3(8):493-501.
Miljanić et al., (2006) *Org. Lett.*, 8(21):4835-4838.
Miller et al., (2004)*Invest. New Drugs*, 22:69-73.
Minko et al., (2000) *Pharm. Res.*, 17:505-517.
Minoofar et al., (2002) "Placement and characterization of pairs of luminescent molecules in spatially separated regions of nanostructured thin films," *J. Am Chem. Soc.*, 124:14388-14396.
Minoofar et al., (2005) "Multiply doped nanostructured silicate sol-gel thin films: Spatial segregation of dopants, energy transfer, and distance measurements," *J. Am. Chem. Soc.*, 127:2656-2665.
Mitragotri et al., (2009) "J. Physical Approaches to Biomaterial Design," *Nat. Mater.*, 8:15-23.
Moazed et al., (2009) *Nature*, 457:413-420.

(56) References Cited

OTHER PUBLICATIONS

Mock et al., (1990) "A Cucurbituril-based Molecular Switch," *Journal of the Chemical Society, Chemical Communications*, 21:1509-1511.
Mock, (1995) "Cucurbituril," *Top. Curr. Chem.*, 175:1-24.
Moller et al., (2007) "Colloidal Suspensions of Nanometer-Sized Mesoporous Silica," *Adv. Funct. Mater.*, 17:605-612.
Muggia et al., (1996) "Camptothecin and Its Analogs," and attachments, *Ann. N.Y. Acad. Sci.*, 803:213-223, 124 pages.
Mulvaney, (1996) "Surface Plasmon Spectroscopy of Nanosized Metal Particles," *Langmuir*, 12:788-800.
Munoz et al., (2003) *Chem. Mater.*, 15(2):500-503.
Muro et al., (2008) "Control of Endothelial Targeting and Intracellular Delivery of Therapeutic Enzymes by Modulating the Size and Shape of ICAM-1-targeted Carriers," *Mol. Ther.*, 16:1450-1458.
Na et al., (2007) "Development of a $T_1$ Contrast Agent for Magnetic Resonance Imaging Using MnO Nanoparticles," *Angew. Chem., Int. Ed.*, 46:5397-5401 (Published online Mar. 13, 2007).
Nakamura et al., (2007) "Direct synthesis of monodispersed thiol-functionalized nanoporous silica spheres and their application to a colloidal crystal embedded with gold nanoparticles," *J Mater Chem*, 17:3726-3732.
Nakase et al., (2004) "Cellular Uptake of Arginine-Rich Peptides: Roles for Macropinocytosis and Actin Rearrangement," *Mol. Ther.*, 10:1011-1022.
Nel et al., (2009) "Understanding Biophysicochemical Interactions at the Nano—Bio Interface," *Nat. Mater.*, 8:543-557.
Neu et al., (2005) *J. Gene. Med.*, 7:992-1009.
Nguyen et al., (2006) "Construction of a pH-Driven Supramolecular Nanovalve," *Organic Letters*, 8(15):3363-3366.
Nie et al., (2007) *Annu. Rev. Biomed. Eng.*, 9:12.1-12.32.
Noguchi et al., (1998) *Cancer Sci.*, 89:307-314.
Nomura et al., (2007) *Am. J. Roentgenol.*, 189:1484-1488.
Ohsuna et al., (2005) "Characterization of Chiral Mesoporous Materials by Transmission Electron Microscopy," *Small*, 1:233-237.
Onishi et al., (2005) *Curr. Drug Discovery Technol.*, 2(3):169-183.
Osada et al., (1999) "Effect of Mechanical Strain on Gastric Cellular Migration and Proliferation During Mucosal Healing: Role of Rho Dependent and Rac Dependent Cytoskeletal Reorganisation," *Gut*, 45:508-515.
Paciotti et al., (2006) "Colloidal Gold Nanoparticles: A Novel Nanoparticle Platform for Developing Multifunctional Tumor-Targeted Drug Delivery Vectors," *Drug Dev Res*, 67:47-54.
Padilla De Jesús et al., (2002) *Bioconjug Chem.*, 13:453-461.
Pal et al., (2007) "Does the Antibacterial Activity of Silver Nanoparticles Depend on the Shape of the Nanoparticle? A Study of the Gram-Negative Bacterium *Escherichia coli*," *Applied and Environmental Microbiology*, 73(6): 1712-1720.
Pantos et al., (2005) *Langmuir*, 21:7483-7490.
Paranjpe et al., (2004) "Tumor-targeted bioconjugate based deliver of camptothecin: design, synthesis and in vitro evaluation," *Journal of Controlled Release*, 100:275-292.
Park et al., (2004) "Ultra-Large-Scale Syntheses of Monodisperse Nanocrystals," *Nat. Mater.*, 3:891-895.
Park et al., (2007) "Controlled Release of Guest Molecules from Mesoporous Silica Particles Based on a pH-Responsive Polypseudorotaxane Motif," *Angew. Chem. Int. Ed.*, 46:1455-1457.
Park et al., (2008) *Int. J. Pharm.*, 359:280-284.
Park et al., (2009) "Photoresponsive Cyclodextrin-Covered Nanocontainers and Their Sol-Gel Transtion Induced by Molecular Recognition," *Angew. Chem. Int. Ed.*, 48:1275-1278.
Pasqua et al., (2007) "Preparation of bifunctional hybrid mesoporous silica potentially useful for drug targeting," *Microporous and Mesoporous Materials*, 103:166-173 (Published online Feb. 3, 2007).
Patel et al., (2008) Enyzme-Responsive Snap-Top Covered Silica Nanocontainers, *J. AM. CHEM. SOC.*, published on web, 130:2382-2383.
Patil et al., (2009) *Biomaterials*, 31:358-365.
Pearse et al., (1987) *Annu. Rev. Biophys. Biophys. Chem.*, 16:49-68.

Peng et al., (2009) *Bioconjugate Chem.*, 20:340-346.
Perrault et al., (2009) *Nano Lett.*, 9:1909-1915.
Petersen et al., (2002) *Bioconjugate Chem.*, 13:845-854.
Phillips et al., (2008) "Rapid and Efficient Identification of Bacteria Using Gold-Nanoparticle-Poly(para-phenyleneethynylene) Constructs," *Angew. Chem., Int. Ed.*, 47:2590-2594.
Portney et al., (2006) *Anal. Bioanal. Chem.*, 386:620-630.
Radu et al., (2004) "A Polyamidoamine Dendrimer-Capped Mesoporous Silica Nanosphere-Based Gene Transfection Reagent," *J. Am. Chem. Soc.*, 126(41):13216-13217.
Radu et al., (2004) "A Polyamidoamine Dendrimer-Capped Mesoporous Silica Nanosphere-Based Gene Transfection Reagent," *J. Am. Chem. Soc.*, 126:13216-13217 [and supporting information attached].
Radu et al., (2005) "Fine-tuning the degree of organic functionalization of mesoporous silica nanosphere materials via an interfacially designed co-condensation method," *Chem. Commun.*, 1264-1266.
Ridley et al., (1992) "The Small GTP-binding Protein Rae Regulates Growth Factor-Induced Membrane Ruffling," *Cell*, 70:401-410.
Roiter et al., (2008) "Interaction of Nanoparticles with Liquid Membrane," *Nano Lett.*, 8:941-944.
Roma et al. (2000) *Hepatology*, 32(6): 1342-1356.
Rosenholm et al., (2009) *ACS Nano*, 3:197-206.
Rostovtsev et al., (2002) *Angew. Chem., Int. Ed.*, 41:2596-2599.
Ruenraroengsak et al., (2010) *J. Controlled Release*, 141:265-276.
Saad et al., (2008) *Nanomedicine*, 3:761-776.
Saha et al., (2005) "A Photoactive Molecular Triad as a Nanoscale Power Supply for a Supramolecular Machine," *Chem. Euro. J.*, 11:6846-6858.
Saha et al., (2007) "Nanovalves," *Adv. Funct. Mater.*, 17:685-693.
Sahay et al., (2010) "Endocytosis of Nanomedicines," *J. Control. Release*, 145:182-195.
Samson et al., (1979) *J. Pharmacal. Exp. Ther.*, 208(3):411-417.
Sandgren et al., (2010) "A Differential Role for Macropinocytosis in Mediating Entry of the Two Forms of Vaccinia Virus into Dendritic Cells," *PLoS Pathog.*, 6(4):e1000866, 16 pages.
Santra et al., (2004) *Chem. Commun.*, 2810-2811.
Santra et al., (2005) "Folate Conjugated Fluorescent Silica Nanoparticles for Labeling Neoplastic Cells," *Journal of Nanoscience and Nanotechnology*, 5(6):899-904.
Schiestel et al., (2004) "Controlled Surface Functionalization of Silica Nanospheres by Covalent Conjugation Reactions and Preparation of High Density Streptavidin Nanoparticles," *Journal of Nanoscience and Nanotechnology*,4(5):504-511.
Schlossbauer et al., (2009) "Biotin-Avidin as a Protease-Responsive Cap System for Controlled Guest Release from Colloidal Mesoporous Silica," *Angew. Chem. Int. Ed.*, 48:3092-3095.
Schrijvers et al., (2004) "Flow Cytometric Evaluation of a Model for Phagocytosis of Cells Undergoing Apoptosis," *J. Immunol. Methods*, 287:101-108.
Scott et al., (1993) *Pharm. Res.*, 10(3):335-342.
Sheldon et al., (2009) "Active Involvement of Robo 1 and Robo4 in Filopodia Formation and Endothelial Cell Motility Mediated via WASP and Other Actin Nucleation-Promoting Factors," *FASEB J.*, 23:513-522.
Shidhaye et al., (2008) "Nanogel Engineered Polymeric Micelles for Drug Delivery," *Current Drug Therapy*, 3(3):209-217.
Shim et al., (2009) *J. Control. Release.*, 133:206-213.
Shrivastava et al., (2007) "Characterization of enhanced antibacterial effects of novel silver nanoparticles," *Nanotehnology*, 18:225103(9pp).
Sierocki et al., (2006) *J. Phys. Chem. B*, 110:24390-24398.
Slowing et al., (2006) "Effect of Surface Functionalization of MCM-41-Type Mesoporous Silica Nanoparticles on the Endocytosis by Human Cancer Cells," *J. Am. Chem. Soc.*, 128:14792-14793 (Published online Nov. 2, 2006).
Slowing et al., (2006) "Effect of Surface Functionalization of MCM-41-Type Mesoporous Silica Nanoparticles on the Endocytosis by Human Cancer Cells—Supporting Information," *J. Am. Chem. Soc.*, 11 pages.
Slowing et al., (2007) "Mesoporous Silica Nanoparticles for Intracellular Delivery of Membrane-CF Impermeable Proteins," *J. Am. Chem. Soc.*, 129:8845-8849 (Published online Jun. 23, 2007).

(56) References Cited

OTHER PUBLICATIONS

Slowing et al., (2007) "Mesoporous Silica Nanoparticles for Drug Delivery and Biosensing Applications" *Adv. Funct. Mater.*, 17:1225-1236.
Slowing et al., (2008) "Mesoporous silica nanoparticles as controlled release drug delivery and gene transfection carriers," *Adv. Drug Deliv. Rev.*, 60:1278-1288.
Slowing et al., (2009) "Mesoporous Silica Nanoparticles for Reducing Hemolytic Activity Towards Mammalian Red Blood Cells," *Small*, 5:57-62.
Sonawane et al., (2002) *J. Biol. Chem.*, 277:5506-5513.
Sondi et al., (2004) "Silver nanoparticles as antimicrobial agent: a case study on E. coli as a model for Gram-negative bacteria," *Journal of Colloid and Interface Science*, 275:177-182.
Soppimath et al., (2007) "Multifunctional Core/Shell Nanoparticles Self-Assembled from pH-Induced Thermosensitive Polymers for Targeted Intracellular Anticancer Drug Delivery," *Adv. Funct. Mater.*, 17:355-362 (Published online Jan. 9, 2007).
Souris et al., (2010) *Biomaterials*, 31:5564-5574.
Stein et al., (2000) "Hybrid Inorganic-Organic Mesoporous Silicates-Nanoscopic Reactors Coming of Age," *Adv. Mater.*, 12(19):1403-1419.
Sudimack et al., (2000) "Targeted Drug Delivery Via the Folate Receptor," *Adv. Drug Delivery Rev.*, 41:147-162.
Sugahara et al., (2010) *Science*, 328:1031-1035.
Sun et al., (2004) "Monodisperse $MFe_2O_4$ (M=Fe, Co, Mn) Nanoparticles," *J. Am. Chem. Soc.*, 126(1):273-279.
Suzuki et al., (1981) *J. Natl. Cancer Inst.*, 67:663-669.
Szakacs et al., (2006) *Nat. Rev. Drug Discov.*, 5:219-234.
Tarimala et al., (2006) "New Approach to antibacterial treatment of cotton fabric with silver nanoparticle-doped silica using sol-gel process," *J. Appl. Poly. Sci.*, 101:2938-2943.
Taylor et al., (2008) "Mesoporous Silica Nanospheres as Highly Efficient MRI Contrast Agents," *J. Am. Chem. Soc.*, 130:2154-2155.
Thery et al., (2006) "Anisotropy of Cell Adhesive Microenvironment Governs Cell Internal Organization and Orientation of Polarity," *Proc. Natl. Acad. Sci. U.S.A.*, 103:19771-19776.
Thiel et al., (2007) "Antibacterial Properties of Silver-Doped Titania," *Small*, 3(5):799-803.
Thomas et al., (Jul. 2010) "Noninvasive remote-controlled release of drug molecules in vitro using magnetic actuation of mechanized nanoparticles," *Journal of American Chemical Society*, 132:10623-10625.
Tietze et al., (2006) *Angew. Chem. Int. Ed.*, 45:6574-6577.
Torchilin et al., (2011) *Adv. Drug Deliver. Rev.*, 63:131-135.
Torney et al., (2007) *Nat. Nanotechnol.*, 2:295-300.
Tornøe et al., (2002) *J. Org. Chem.*, 67:3057-3064.
Trewyn et al., (2004) "Morphological Control of Room-Temperature Ionic Liquid Templated Mesoporous Silica Nanoparticles for Controlled Release of Antibacterial Agents," *Nano Letter*, 4(11):2139-2143.
Trewyn et al., (2007) "Synthesis and Functionalization of a Mesoporous Silica Nanoparticle Based on the Sol-Gel Process and Applications in Controlled Release," *Accounts of Chemical Research*, 40(9):846-853.
Trewyn et al., (2008) "Biocompatible mesoporous silica nanoparticles with different morphologies for animal cell membrane penetration," *Chem. Engineering Journal*, 137:23-29 [published on Oct. 5, 2007].
Tsai et al., (2008) "High-Contrast Paramagnetic Fluorescent Mesoporous Silica Nanrods as a Multifunctional Cell-Imaging Probe," *Small*, 4(2):186-191 (Published online Jan. 18, 2008).
Ueda et al., (2008) Activation of the Small GTPase Rac1 by a Specific Guanine-Nucleotide-Exchange Factor Suffices to Induce Glucose Uptake into Skeletal-Muscle Cells, *Biol. Cell.*, 100:645-657.
Ung et al., (1998) "Controlled Method for Silica Coating of Silver Colloids. Influence of Coating on the Rate of Chemical Reactions," *Langmuir*, 14:3740-3748.
Urban-Klein et al., (2005) *Gene Ther.*, 12:461-466.
Vallet-Regi et al., (2001) *Chem. Mater.*, 13:308-311.
Vallet-Regi et al., (2007) "Mesoporous Materials for Drug Delivery," *Angew. Chem., Int. Ed.*, 46:7548-7558.
van Vlerken et al., (2007) *Cancer Res.*, 67:4843-4850.
Veiseh et al., (2009) *Biomaterials*, 30:649-657.
Verbaan et al., (2004) *J. Gene Med.*, 6:64-75.
Vivero-Escoto et al., (2009) *J. Am. Chem. Soc.*, 131:3462-3463.
Wagner et al., (Oct. 2006) *Nat. Biotechnol.*, 24(10):1211-1217.
Wang et al., (2002) "Gene Expression Profiling in Multidrug Resistant KB Cells Using Cdna Microarrays," *Chinese J. Cancer Res.*, 14(1):5-10.
Wang et al., (2007) "Fluorescent Nanoparticles for Multiplexed Bacteria Monitoring," *Bioconjugate Chem.*, 18:297-301 (Published online Mar. 7, 2007).
Wang (2009) "Ordered mesoporous materials for drug delivery," *Microporous and Mesoporous Materials, Department of Chemical Engineering*, 117:pp. 1-9 (Published online, Jul. 9, 2008).
Wani et al., (1971) *J. Am. Chem. Soc.*, 93:2325-2327.
Weh et al., (2002) *J. Microporous Mesoporous Mater.*, 54:15-26.
Weissleder, (2000) "In vivo magnetic resonance imaging of transgene expression," *Nat. Med.*, 6(3):351-354.
Wessing et al., (1993) *J. Comp. Physiol.*, 163:452-462.
West et al., (1989) "Distinct Endocytotic Pathways in Epidermal Growth Factor-Stimulated Human Carcinoma A431 Cells," *J. Cell Biol.*, 109:2731-2739.
Woodroofe et al., (2003) *J. Am. Chem. Soc.*, 125:11458-11459.
Word Counts of Abstract (AN12/841331), one page.
Wu et al., (2002) "Immunofluorescent Labeling of Cancer Marker Her2 and Other Cellular Targets with Semiconductor Quantum Dots," *Nat. Biotechnol.*, 21:41-46.
Wu et al., (2007) *J Pharm. Pharmaceut. Sci.*, 10:350-357.
Wu et al., (2008) "Multifunctional Mesoporous Silica Nanoparticles for Intracellular Labeling and Animal Magnetic Resonance Imaging Studies," *Chem Bio Chem.*, 9:53-57 (Published online Nov. 12, 2007).
Xia et al., (2006) "Comparison of the Abilities of Ambient and Manufactured Nanoparticles to Induce Cellular Toxicity According to an Oxidative Stress Paradigm," *Nano Lett.*, 6(8): 1794-1807.
Xia et al., (2008) "Comparison of the Mechanism of Toxicity of Zinc Oxide and Cerium Oxide Nanoparticles Based on Dissolution and Oxidative Stress Properties," *ACS Nano*, 2(10):2121-2134.
Xia et al., (2008) "Cationic Polystyrene Nanosphere Toxicity Depends on Cell-Specific Endocytic and Mitochondrial Injury Pathways," *ACS Nano*, 2(1):85-96.
Xia et al., (2009) "Polyethyleneimine Coating Enhances the Cellular Uptake of Mesoporous Silica Nanoparticles and Allows Safe Delivery of SiRNA and DNA Constructs," *ACS Nano*, 3(10):3273-3286.
Xing et al., (2005) *J. Nanosci. Nanotechnol.*, 5:1688-1693.
Xu et al., (2003) "Room-Temperature Preparation and Characterization of Poly(ethylene glycol)—Coated Silica Nanoparticles for Biomedical Applications," *J. Biomed. Mater. Res., Part A* 66A:870-879.
Yager et al., (2006) "Novel photo-switching using azobenzene functional materials," *Journal of Photochemistry and Photobiology, A: Chemistry*, 182:250-261.
Yagmurca et al., (2004) *Clinica. Chimica. Acta.*, 348:27-34.
Yang et al., (2006) "On the Origin of Helical Mesostructures," *J. Am. Chem. Soc.*, 128:10460-10466.
Yang et al., (2007) "Siliceous Nanopods from a Compromised Dual-Templating Approach," *Angew. Chem. Int. Ed. Engl.*, 46:8579-8582.
Yezhelyev et al., (2008) *J. Am. Chem. Soc.*, 130(28):9006-9012.
Yi et al., (2006) "Nanoparticle Architectures Templated by $SiO_2/Fe_2O_3$ Nanocomposites," *Chem. Mater.*, 18(3):614-619.
Yin et al. (2015) "How does fluorescent labeling affect the binding kinetics of proteins with intact cells?," *Biosens Bioelectron.*, 66: 412-416 [HHS Public Access—Author manuscript—11 pages].
Ying et al., (1999) "Synthesis and Applications of Supramolecular-Templated Mesoporous Materials," *Angew. Chem., Int. Ed*, 38:56-77.
Yiu et al. (2007) "A triple-layer design for polyethyleneimine-coated, nanostructured magnetic particles and their use in DNA binding and transfection," *Nanotechnology*, 18:1-6.

(56) References Cited

OTHER PUBLICATIONS

Yu et al., (2004) "Synthesis of Monodisperse Iron Oxide Nanocrystals by Thermal Decomposition of Iron Carboxylate Salts," *Chem. Commun.*, 2306-2307.

Zhang et al., (2007) "Synthesis of Poly(ethylene glycol) (PEG)-Grafted Colloidal Silica Particles with Improved Stability in Aqueous Solvents," *J. Colloid Interface Sci.*, 310:446-455 (Feb. 14, 2007).

Zhang et al., (2008) "Fabrication of a Magnetic Helical Mesostructured Silica Rod," *Nanotechnology*, 19:435608, 8 pages.

Zhang et al., (2010) *Biomaterials*, 31:952-963.

Zhang et al., (2011) *ACS Nano*, 5(4):2756-2769.

Zhao et al., (2004) "In situ formation of silver nanoparticles inside pore channels of ordered mesoporous silica," *Mater. Lett.*, 58:2152-2156.

Zhao et al., (2009) "Mesoporous Silica Nanoparticle-Based Double Drug Delivery System for Glucose-Responsive Controlled Release of Insulin and Cyclic AMP," *J. Am. Chem. Soc.*, 131:8398-8400.

Zhou et al., (Sep. 2006) "Zirconium Phosphonate-Modified Porous Silicon for Highly Specific Capture of Phosphopeptides and MALDI-TOF MS Analysis," *Journal of Proteome Research*, 5:2431-2437.

Zhu et al., (2004) *Biotechnol. Appl. Biochem.*, 39:179-187.

Zhu et al., (2007) "Installing Dynamic Molecular Photomechanics in Mesopores: A Multifunctional Controlled-Release Nanosystem," *Angew. Chem. Int. Ed.*, 46:2241-2244 (Published online Feb. 13, 2007).

\* cited by examiner

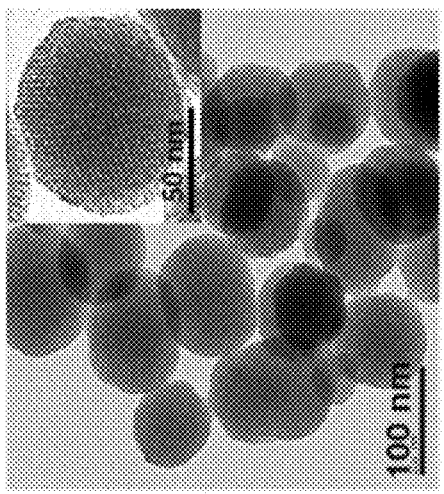
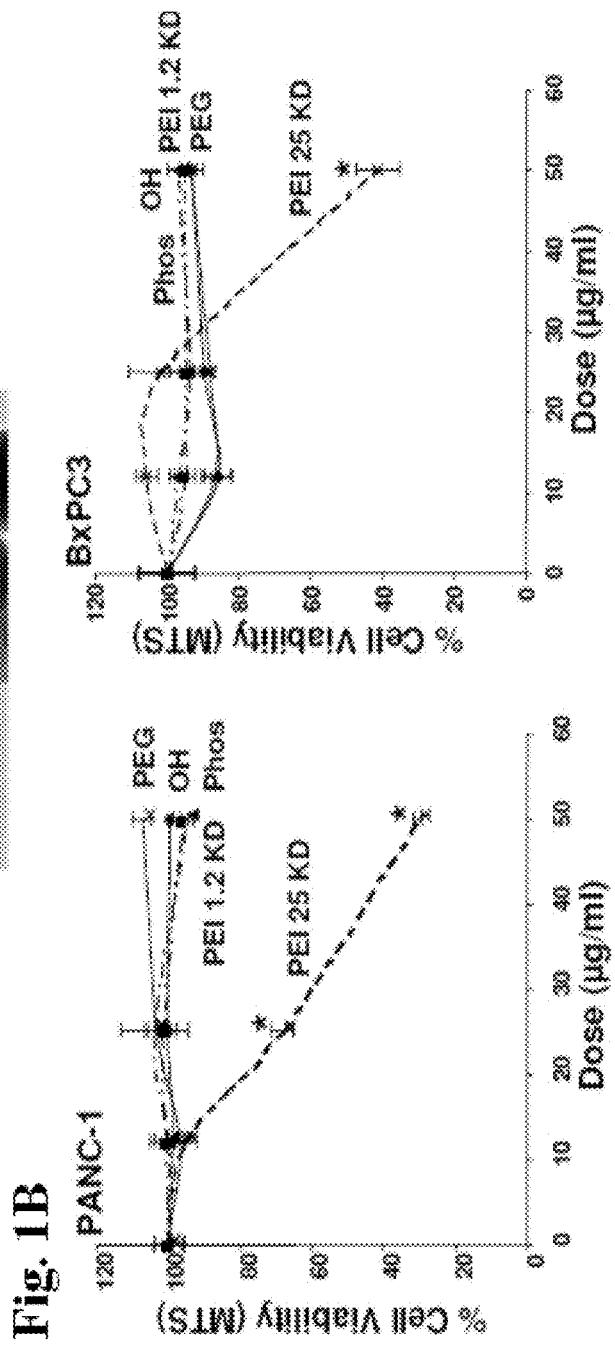
Fig. 1A
Fig. 1B

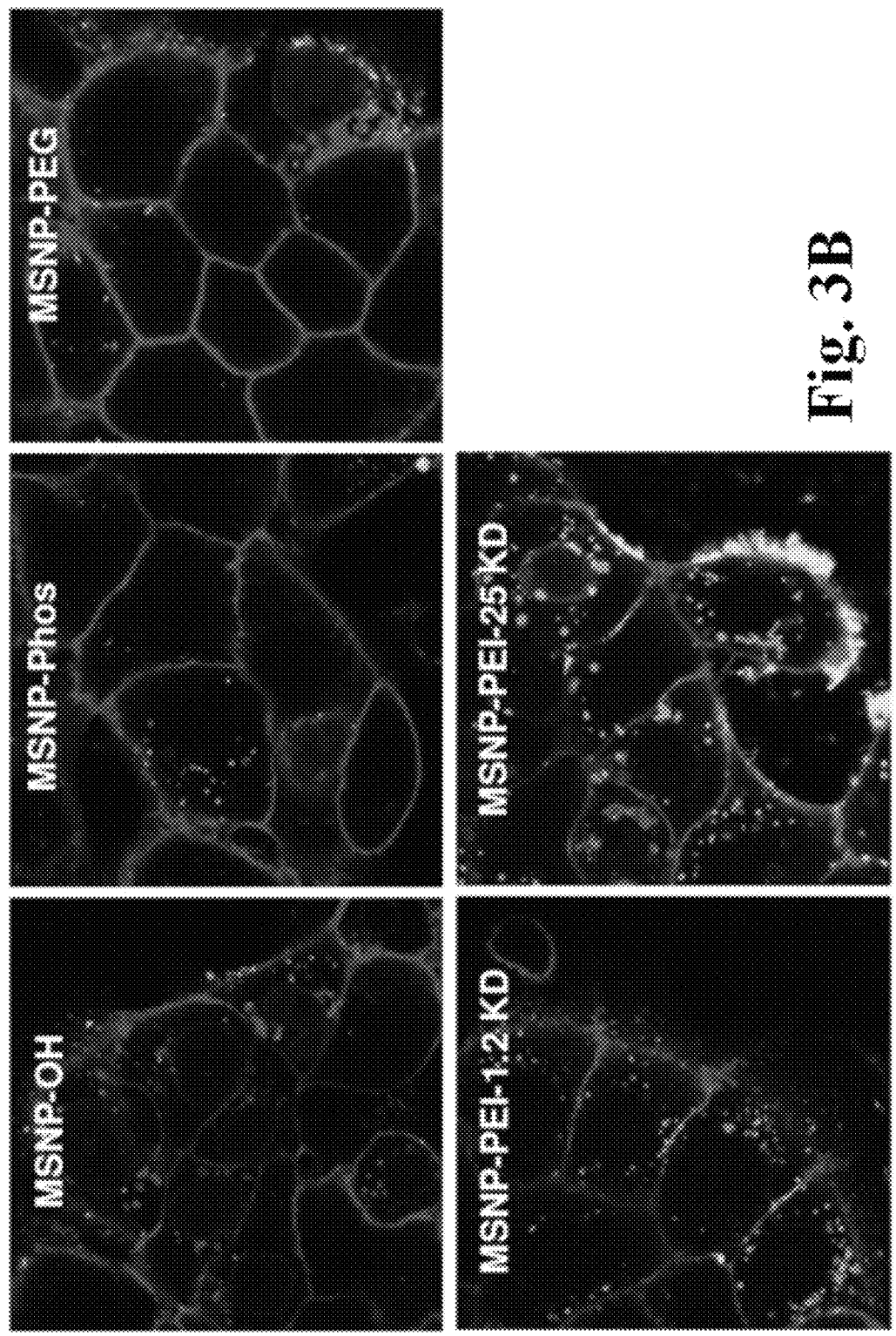

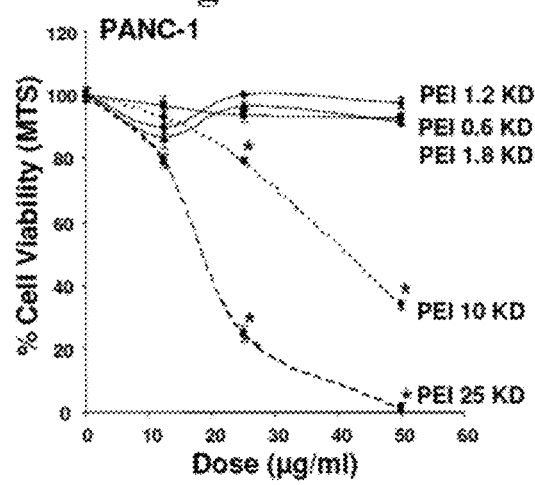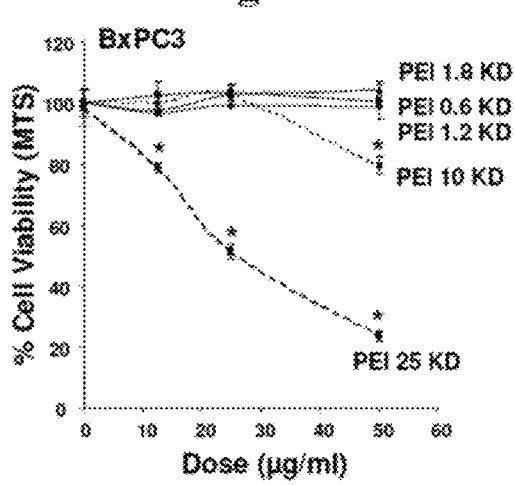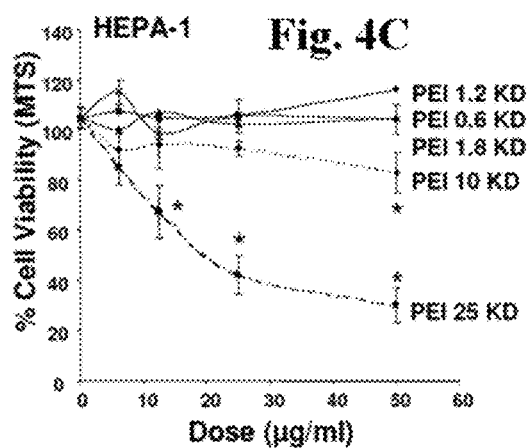

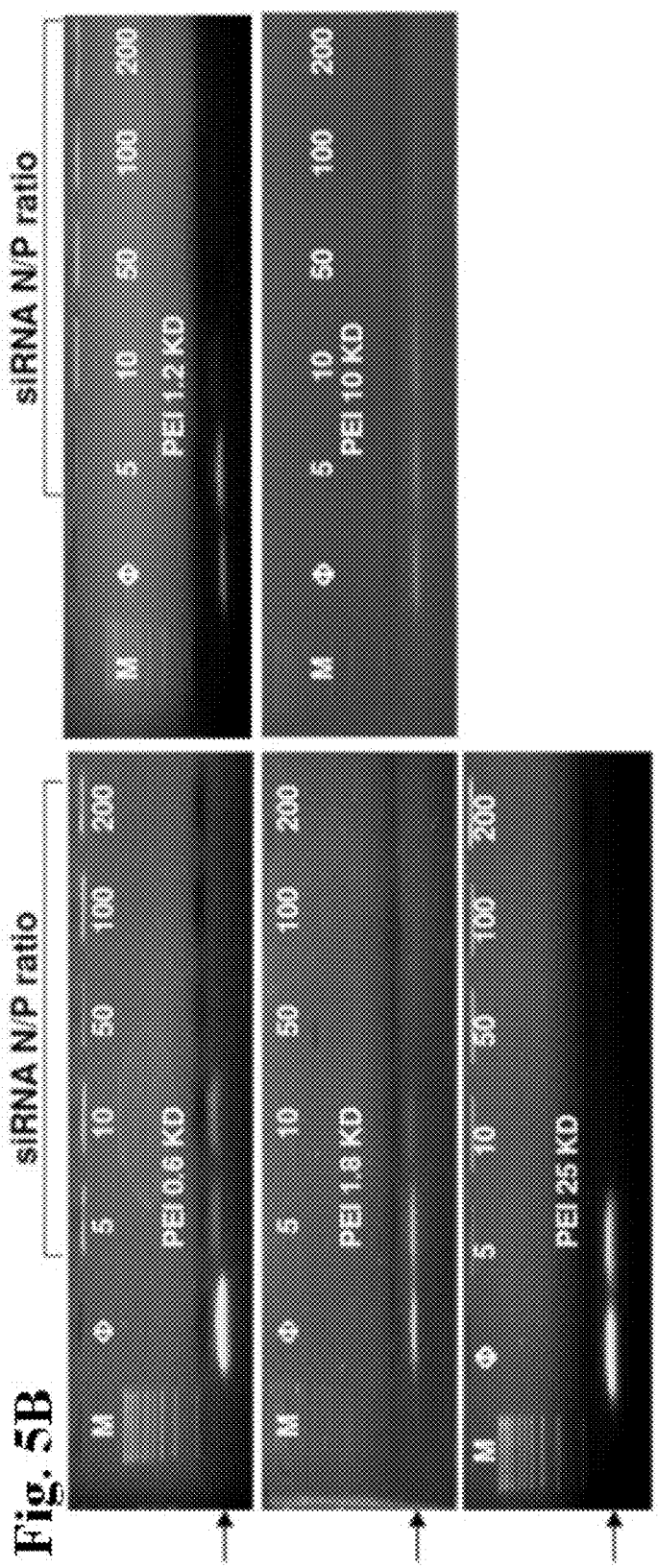
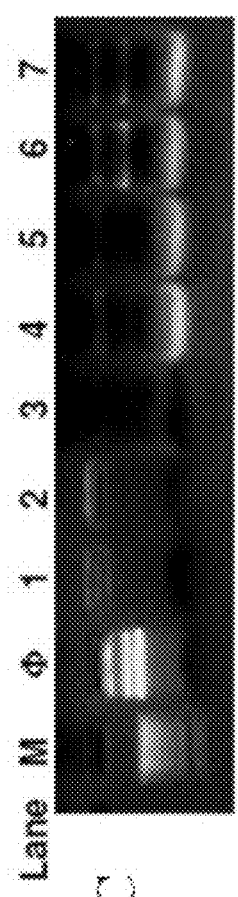
Fig. 5B
Fig. 5C

| MSNP Exterior | Size in H$_2$O (nm) | Size in BSA (nm) | Size in CDMEM (nm) | Zeta Potential in H$_2$O / CDMEM (mV) |
|---|---|---|---|---|
| PEI 1.8 kD-MSNP | 1201 | 360 | 294 | +29.5/-4.6 |
| PEI 10 kD-MSNP | 758 | 241 | 261 | +34.1/-3.8 |
| PEI 25 kD-MSNP | 1152 | 247 | 252 | +31.7/-3.7 |

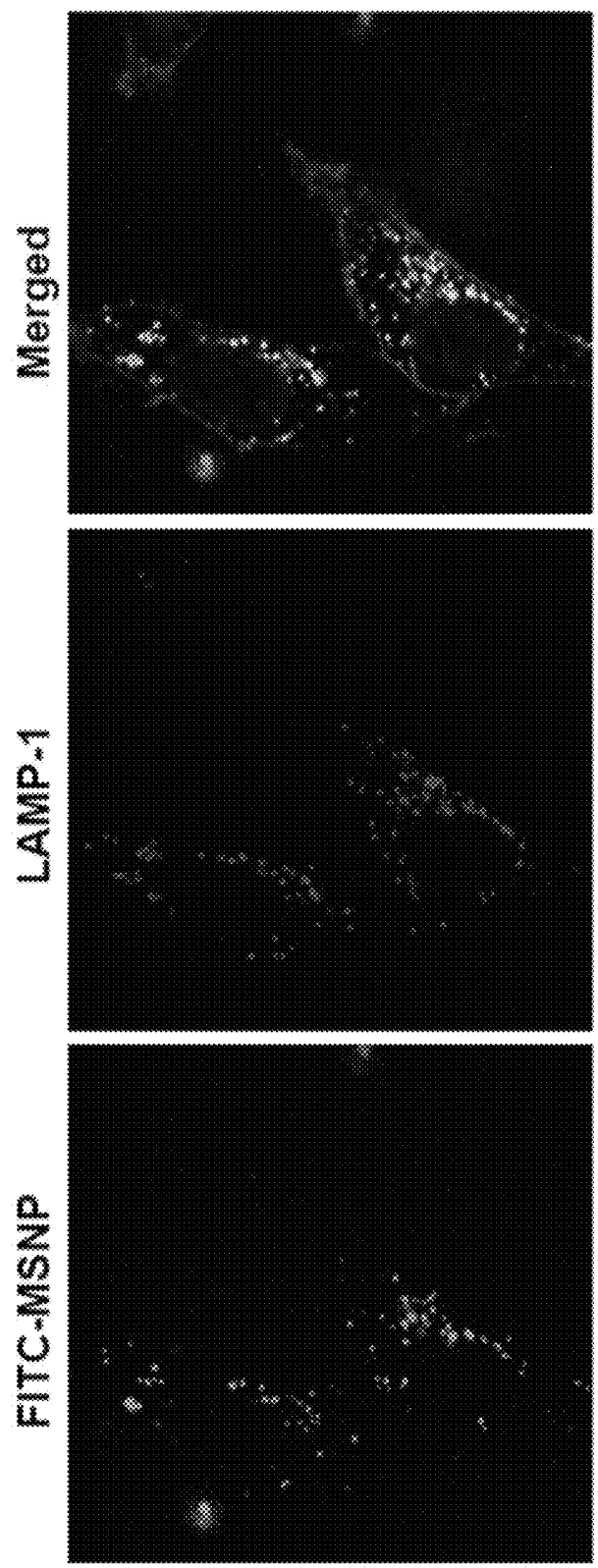

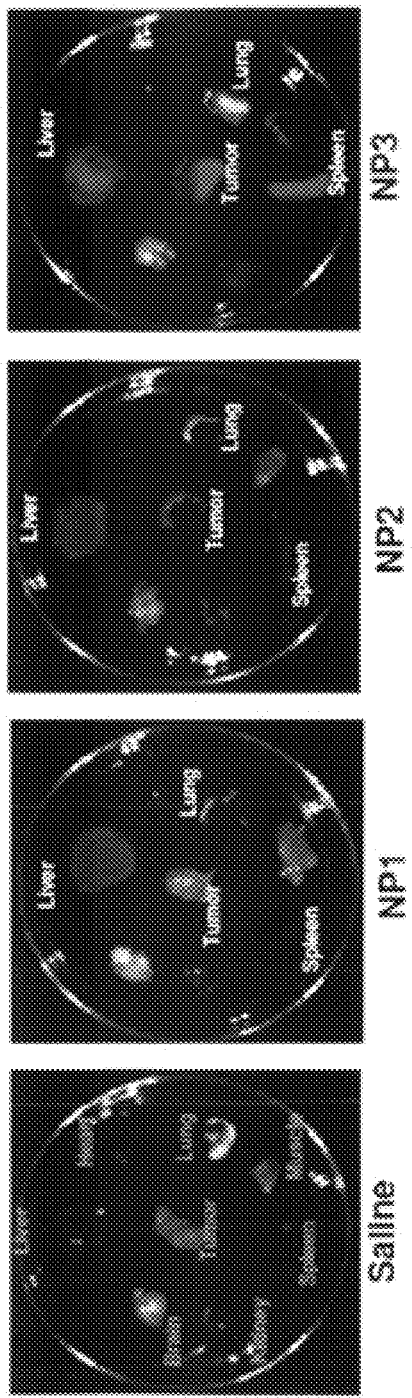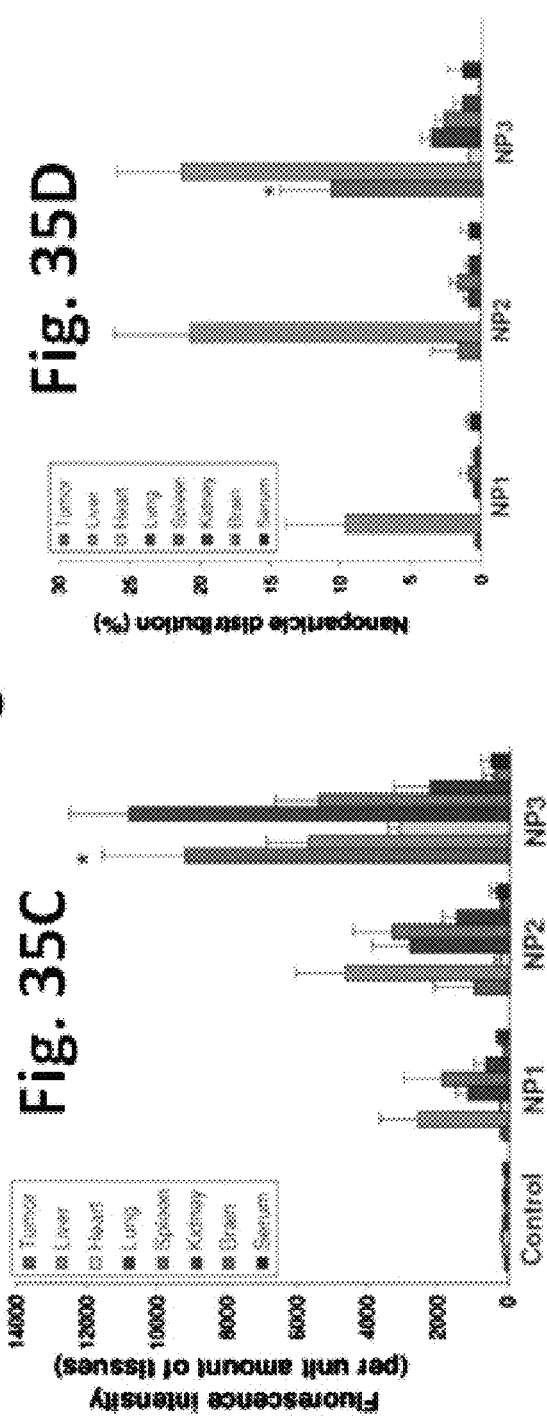
Fig. 35B, Fig. 35C, Fig. 35D

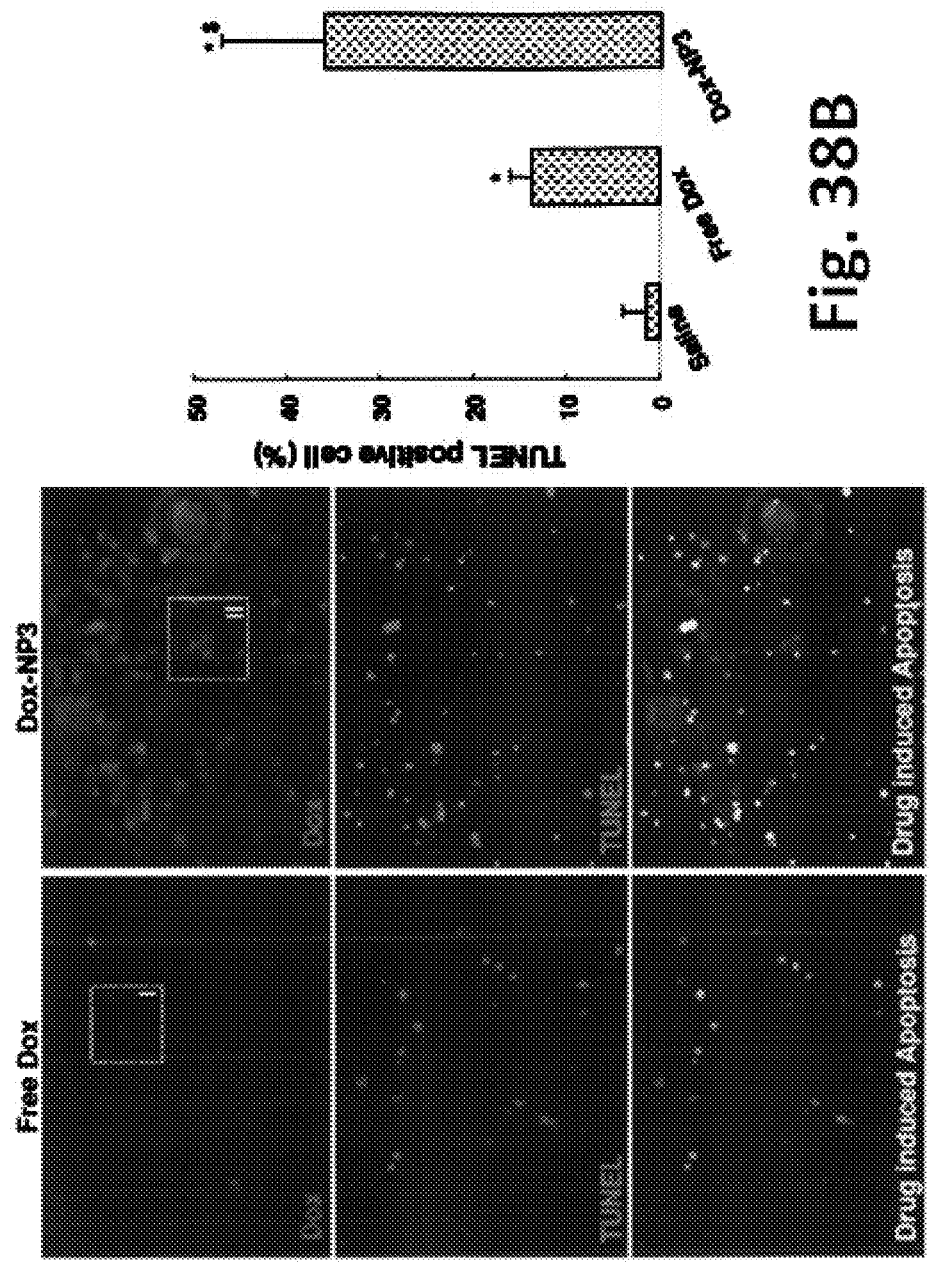

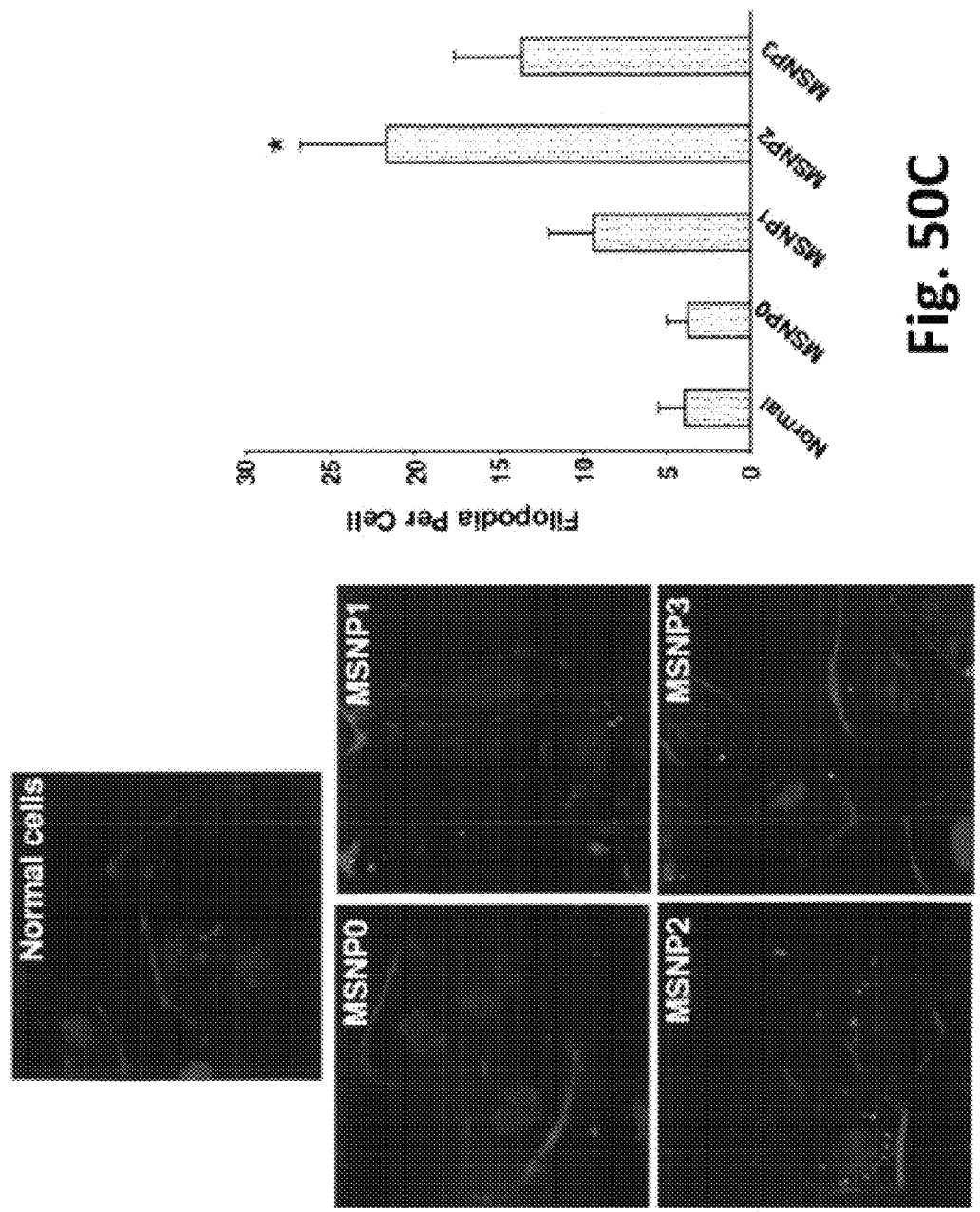

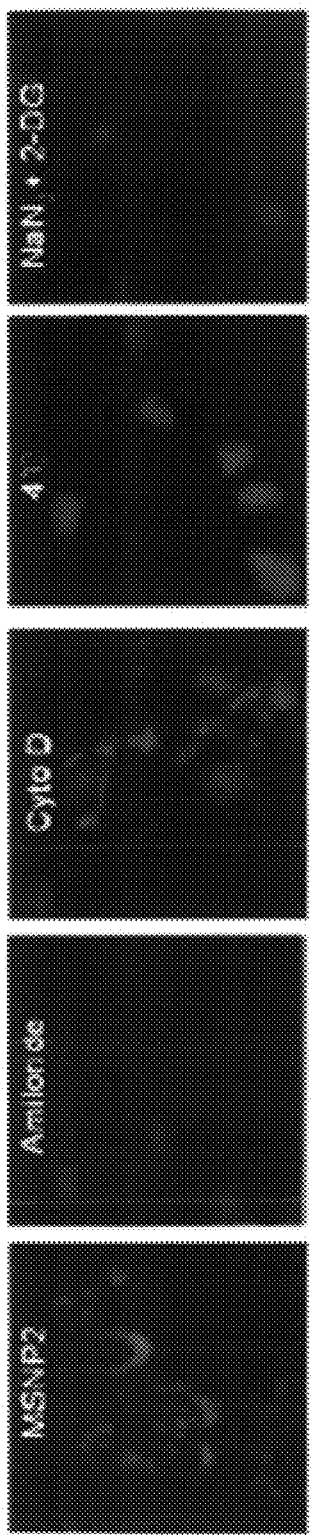
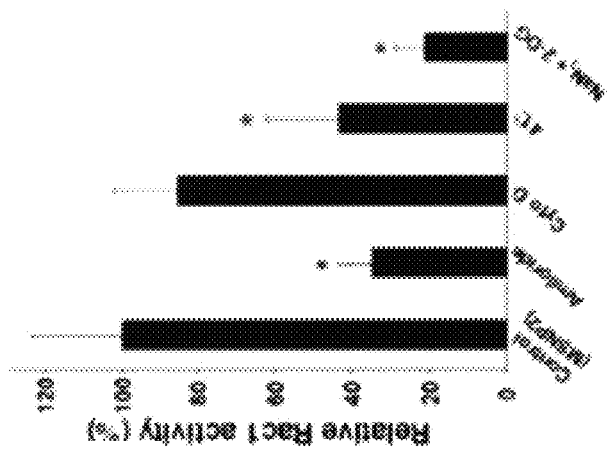
Fig. 58A
Fig. 58B

CATIONIC POLYMER COATED MESOPOROUS SILICA NANOPARTICLES AND USES THEREOF

CROSS-REFERENCE OF RELATED APPLICATION

This application is a Continuation of U.S. Ser. No. 13/428,830, filed on Mar. 23, 2012, which is a Continuation-in-Part of International Application Number PCT/US11/43874, filed Jul. 13, 2011, which claims priority to U.S. Provisional Application No. 61/363,945 filed Jul. 13, 2010. U.S. Ser. No. 13/428,830 claims priority to U.S. Provisional Application No. 61/466,581 filed Mar. 23, 2011, U.S. Provisional Application No. 61/469,190 filed Mar. 30, 2011, and U.S. Provisional Application No. 61/479,751 filed Apr. 27, 2011. The entire contents of each are hereby incorporated by reference.

STATEMENT OF GOVERNMENTAL SUPPORT

This invention was made with government support under Grant Number HDTRA1-08-1-0041, awarded by the U.S. Department of Defense, Defense Threat Reduction Agency and Grant Numbers CA133697, ES016746, ES018766, ES019528, awarded by the National Institutes of Health and Grant Number 0830117, awarded by National Science Foundation. The government has certain rights in the invention.

BACKGROUND

Field of Invention

The current invention relates to submicron structures having a silica body defining a plurality of pores and an outer surface between pore openings of said plurality of pores and a cationic polymer on the surface of said silica body. Such submicron structures may be combined with oligonucleotides and therapeutic compounds for drug delivery, transfection, and cancer therapy.

Discussion of Related Art

Based on properties such as large surface area and ordered porous channels that can be used to encapsulate molecules, mesoporous silica nanoparticles (MSNP) have emerged as an efficient drug delivery platform (Kim et al., *Angew. Chem., Int. Ed.*, vol. 47, pp. 8438-8441, 2008; Liong et al., *ACS Nano*, vol. 2, pp. 889-896, 2008; Lu et al., *Small*, vol. 3, pp. 1341-1346, 2007; Slowing et al., *Adv. Drug Delivery Rev.*, vol. 60, pp. 1278-1288, 2008; Vallet-Regi et al., *Angew. Chem., Int. Ed.*, vol. 46, pp. 7548-7558, 2007). In addition to the well-developed surface chemistry, silica materials are known to be safe, biodegradable and potentially biocompatible (Borm et al., *Toxicol. Sci.*, vol. 90, pp. 23-32, 2006; Finnie et al., *J Sol-Gel. Sci. Techn.*, vol. 49, pp. 12-18, 2009). This drug transport system is suitable for the delivery of anticancer drugs, including camptothecin, paclitaxel, and doxorubicin (Kim et al., *Angew. Chem., Int. Ed.*, vol. 47, pp. 8438-8441, 2008; Liong et al., *ACS Nano*, vol. 2, pp. 889-896, 2008; Vivero-Escoto et al., *J Am. Chem. Soc.*, vol. 131, pp. 3462-3463, 2009). The chemical stability of the particles contributes to their therapeutic utility by allowing the attachment of functional groups for imaging and targeting applications along with the placement of a series of nanovalves for on-demand drug release (Liong et al., *ACS Nano*, vol. 2, pp. 889-896, 2008; Nguyen et al., *Org. Lett.*, vol. 8, pp. 3363-3366, 2006; Rosenholm et al., *ACS Nano*, vol. 3, pp. 197-206, 2009).

RNA interference describes natural processes that lead to gene silencing by siRNA (Moazed et al., *Nature*, vol. 457, pp. 413-420, 2009). siRNA has been widely used as an experimental tool that is now also becoming the focus of the pharmaceutical industry (Blow et al., *Nature*, vol. 450, pp. 1117-1120, 2007). Currently there are a number of clinical trials underway that include the use of siRNAs to treat various disease processes (Davis et al., *Mal. Pharm.*, vol. 6, pp. 659-668, 2009; Judge et al., *Mal. Ther.*, vol. 13, pp. 494-505, 2006). As for most molecular therapies, in vivo delivery is a major hurdle in successful implementation and has sparked a number of strategies to increase siRNA circulatory half-life, facilitate transduction across biological membranes, and achieve cell-specific delivery (Davis et al., *Mol. Pharm.*, vol. 6, pp. 659-668, 2009; Judge et al., *Mol. Ther.*, vol. 13, pp. 494-505, 2006).

There are a number of circumstances where drug and siRNA delivery could achieve a synergistic therapeutic outcome. One example is the restoration of drug sensitivity in cancer cells by knockdown of genes that are involved in the resistance to one or more chemotherapeutic agents. An example is the inducible P-glycoprotein (Pgp) gene that encodes for a gene product known as the multiple drug resistance protein 1 (MDR-1) (Gottesman et al., *Annu. Rev. Med.*, vol. 53, pp. 614-627, 2002). Pgp is constitutively expressed in normal cells such as capillary endothelial cells in the blood brain barrier but also is selectively overexpressed in carcinomas of the stomach, breast, pancreas and cervix in response to a number of chemotherapeutics agents (Szakacs et al., *Nat. Rev. Drug Discov.*, vol. 5, pp. 219-234, 2006). If overexpressed, Pgp could lead to drug resistance because MDR-1 contributes to the formation of a drug efflux pump that prevents the intracellular buildup of chemotherapeutic agents (Jabr-Milane et al., *Cancer Treat. Rev.*, vol. 34, pp. 592-602, 2008).

Mesoporous silica nanoparticle (MSNP) is a multifunctional delivery platform that has been shown at cellular and in vivo levels to be capable of delivering chemotherapeutic agents and DNA/siRNA to a variety of cancer cell types (Lu et al., *Small*, vol. 3, pp. 1341-1346, 2007; He et al., *Small*, vol. 7, pp. 271-280, 2011; Lee et al., *Adv. Funct. Mater.*, vol. 19, pp. 215-222, 2009; Liong et al., *ACS Nano*, vol. 2, pp. 889-896, 2008; Meng et al., *ACS Nano*, vol. 4, pp. 4539-4550, 2010; Meng et al., *J Am. Chem. Soc.*, vol. 132, pp. 12690-12697, 2010; Xia et al., *ACS Nano*, vol. 3, pp. 3273-3286, 2009; Radu et al., *J Am. Chem. Soc.*, vol. 126, pp. 13216-13217, 2004; Slowing et al., *J Am. Chem. Soc.*, vol. 129, pp. 8845-8849, 2007). This delivery platform allows effective and protective packaging of hydrophobic and charged anticancer drugs for controlled and on demand delivery, with the additional capability to also image the delivery site (Liong et al., *ACS Nano*, vol. 2, pp. 889-896, 2008). The key challenge now is to optimize the design features for efficient and safe in vivo drug delivery (He et al., *Small*, vol. 7, pp. 271-280, 2011; Lee et al., *Angew. Chem. Int. Ed.*, vol. 49, pp. 8214-8219, 2010; Liu et al., *Biomaterials*, vol. 32, pp. 1657-1668, 2011; Al Shamsi et al., *Chem. Res. Toxicol.*, vol. 23, pp. 1796-1805, 2010), which be assessed through the use of human xenograft tumors in nude mice (Lu et al., *Small*, vol. 6, pp. 1794-1805, 2010).

While the availability of nanocarrier drug delivery systems is an exciting development that holds the promise of a fundamental change in cancer chemotherapy, it remains at a relatively early stage of the implementation of this technology that often contains overblown claims of drug delivery nanoparticles acting as magic bullets. Such claims include the putative ability of active tumor targeting with the ability of selectively sparing all normal tissues. However, the reality is that most nanocarriers are particulates that are recognized by and are effectively removed by the mononuclear phagocytic cells in the reticuloendothelial system (RES) of the liver and spleen (Davis et al., *Nat. Rev. Drug Discov.*, vol. 7, pp. 771-782, 2008). This sequestration is often enhanced by the surface coating of nanoparticles with a corona of proteins that lead to opsonization and enhance phagocytosis by the RES (Nel et al., *Nat. Mater.*, vol. 8, pp. 543-557, 2009). Moreover, there is also a possibility that the encapsulated drugs could be lost from the carrier or degraded, as well as the fact that the colloidal instability of the carrier could lead to agglomeration in the circulation and may therefore be excluded from the intended "target site". It is also possible that the nanocarrier may reach the target site but that the drug is not released from the particle or that the carrier is not taken up effectively in the tumor cells. Both effects will conspire to insufficient intracellular drug delivery. Finally, there is also the concern that the heterogeneity among different tumor types could lead to considerable variation in the magnitude of the enhanced permeability and retention (EPR) effect due to differences in vascularity or lymphatic drainage (Ruenraroengsak et al., *J Controlled Release*, vol. 141, pp. 265-276, 2010). Given these constraints, it is not a surprise that drug delivery to the tumor site seldom achieves more than 10% of the total administered dose. In fact, few publications show the actual calculation of the EPR effect of the nanocarriers being described (de Wolf et al., *Int. J Pharm.*, vol. 331, pp. 167-175, 2007).

There are a number of nanomaterial design options for improving the pharmacokinetics, biodistribution and delivery of anticancer drugs to the tumor site (Nie et al., *Annu. Rev. Biomed. Eng.*, vol. 9, pp. 12.1-12.32, 2007; Perrault et al., *Nano Lett.*, vol. 9, pp. 1909-1945, 2009; Ferrari et al., *Nat. Rev. Cancer*, vol. 5, pp. 161-171, 2005). The EPR effect is due to a combination of the abnormally large fenestrations of tumor vasculature and the inefficient lymphatic drainage, which generates the retention effect (Maeda et al., *Eur. J. Pharm. Biopharm.*, vol. 71, pp. 409-419, 2009; Torchilin et al., *Adv. Drug Deliver. Rev.*, vol. 63, pp. 131-135, 2011; Iyer et al., *Drug Discov. Today*, vol. 11, pp. 812-818, 2006). A frequent strategy that is being used is to decorate the particle surface with polyethylene glycol (PEG) to provide steric hindrance to improve particle dispersion (Xia et al., *ACS Nano*, vol. 3, pp. 3273-3286, 2009). Because this feature also leads to interference in particle opsonization, there is a concomitant increase in circulatory half-life as well as an improvement in the EPR effect (He et al., *Small*, vol. 7, pp. 271-280, 2011; Maeda et al., *Eur. J Pharm. Biopharm.*, vol. 71, pp. 409-419, 2009; Maeda et al., Factors and Mechanism of "EPR" Effect and the Enhanced Antitumor Effects of Macromolecular Drugs Including SMANCS. In Polymer Drugs in the Clinical Stage, Springer US, vol. 519, pp. 29-49, 2004). The potential downside of surface coating is that PEG may also interfere in particle uptake by the tumor cells and that the longer circulation time may increase drug leakage from the carrier (Xia et al., *ACS Nano*, vol. 3, pp. 3273-3286, 2009).

SUMMARY

Embodiments of the invention include a submicron structure having a silica body defining a plurality of pores and an outer surface between pore openings of said plurality of pores, and a cationic polymer on the surface of said silica body. Said submicron structure has a maximum dimension less than one micron.

In some embodiments, the submicron structure also includes a cationic therapeutic compound. The cationic therapeutic compound may be, for example, in the interior or in the pores of the submicron structure. In some embodiments, the submicron structure also includes an oligonucleotide electrostatically bound to the cationic polymer. Some embodiments include both a cationic therapeutic compound and an oligonucleotide. In some embodiments, the oligonucleotide is an siRNA that reduces translation of a protein that causes resistance in a cell. In some embodiments, the siRNA reduces translation of a protein that causes resistance to the therapeutic compound in the cell. In some embodiments, the siRNA reduces translation of p-glycoprotein. In some embodiments, the therapeutic compound is doxirubicin.

In some embodiments, the cationic polymer is electrostatically bound to the silica body. In some embodiments, the cationic polymer is selected from the group consisting of polyethyleneimine, polyamidoamine, polylysine, poly(allylamine), and poly(diallyldimethylammonium chloride). In some embodiments, the cationic polymer is polyethyleneimine.

Some embodiments include an oligonucleotide electrostatically bound to the cationic polymer. The oligonucleotide may be DNA or RNA. When the oligonucleotide is RNA, is may be a small inhibiting RNA (siRNA).

Some embodiments include a therapeutic compound within the silica body or pores of the silica body. The therapeutic compound may be hydrophobic, neutral (i.e. uncharged), cationic or anionic at physiologic pH.

In some embodiments, the silica body is mesoporous. In some embodiments, the pores are substantially cylindrical and have an ensemble average diameter between about 1 nm and about 10 nm.

In some embodiments, the silica body is substantially spherical and has a diameter between about 50 nm and about 1000 nm. In some embodiments, the substantially spherical silica body has a diameter between about 100 nm and about 500 nm.

In some embodiments, the silica body has a plurality of anionic molecules attached to an outer surface of the silica body. In some embodiments, the plurality of anionic molecules have a phosphonate moiety. In some embodiments, the plurality of anionic molecules are derived from reaction between the silica body surface and trihydroxysilylpropyl methylphosphonate.

In some embodiments, the submicron structure further includes a light-emitting compound, peptide, protein, oligonucleotide, sugar, oligosaccharide, or polysaccharide covalently bonded to the surface of the silica body. Some embodiments have a light emitting compound covalently bonded to the surface of the silica body.

In some embodiments, the submicron structure further includes a core structure within the silica body. In some embodiments, the core structure is a superparamagnetic nanocrystal, silver nanocrystal or gold nanocrystal. In some embodiments, the core structure is a superparamagnetic iron oxide nanocrystal.

Embodiments of the invention include pharmaceutical compositions having a submicron structure according to the invention and a pharmaceutically acceptable carrier or excipient. Embodiments of the invention include use of the submicron structures according to the invention for the manufacture of a medicament or pharmaceutical composition for the treatment of a disease or disorder.

Embodiments of the invention include therapeutic methods have the step of administering an effective amount of a submicron structure according to the invention to a subject in need of treatment. Embodiments include use of the submicron structures according to the invention for the treatment of a disease or disorder by administering the submicron structure to a subject in need of treatment.

Embodiments of the invention include methods of treating drug resistant cancer where the submicron structure includes an siRNA that reduces translation of a protein causing resistance in the drug resistant cancer. Embodiments of the invention includes the use of a submicron structure according to the invention having an siRNA that reduces translation of a protein causing drug resistance to treat drug resistant cancer.

Embodiments of the invention include methods of transfecting a cell by administering a submicron structure according to the invention having an oligonucleotide. Embodiments of the invention include the use of a submicron structure according to the invention including an oligonucleotide to transfect a cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of the description, drawings, and examples.

FIGS. 1A and 1B show transmission electron microscopy (TEM) of the MSNP and cell viability detection by the MTS assay. FIG. 1A shows TEM image shows the particle size and the ordered pore structure. FIG. 1B shows cell viability after addition of appropriately dispersed MSNP exhibiting a range of surface modifications to pancreatic cancer cell lines at doses ranging from 12.5-50 μg/ml for 16 hrs, cells were incubated with the MTS reagent for 30 min and the absorbance was measured at 490 nm. All the MTS values were normalized according to the value of the control (no particle exposure)—this was regarded as 100% cell viability. The $IC_{50}$ values of MSNP-PEI-25 KD in PANC-1 and BxPC3 cells were 37 μg/ml and 46 μg/ml, respectively. The results were reproduced 3 times.

FIG. 2A shows a representative histogram showing the shift in fluorescence intensity in PANC-1 cells treated with 25 μg/ml FITC-MSNP that contain different surface modifications (left panel). The fold-increase in MFI after 3 hr was calculated and used to generate the graph. RITC-labeled MSNP-Phos served as a control particle to show that coating with PEI leads to enhanced uptake in the same particle type in the same cell (right panel). FIG. 2B shows confocal microscopy used to study the cellular uptake of FITCMSNP in PANC-1 cells. Cells were exposed to 25 μg/ml FITC-labeled particles for 3 hr. After cell membrane staining with 5 μg/ml red fluorescent wheat germ agglutinin (WGA), cells were visualized using a Confocal 1P/FCS Inverted microscope. Data are representative of 3 separate experiments. *$p<0.01$ compared with control.

FIGS. 3A and 3B show cellular uptake of FITC-labeled MSNP in BxPC3 cells. BxPC3 cells were exposed to FITC-labeled MSNP and flow cytometry and confocal microscopy were conducted as in FIG. 2. FIG. 3A shows a representative histogram showing the shift in fluorescence intensity (left panel). The fold-increase in MFI after 3 hr was calculated and used to generate the graph. RITC-labeled MSNP-Phos served as a control particle to show that coating with PEI leads to enhanced uptake in the same particle type in the same cell (right panel). FIG. 3B shows confocal microscopy used to study the cellular uptake of FITC-MSNP. Cells were exposed to 25 μg/ml FITC-labeled particles for 3 hr. After cell membrane staining with 5 μg/ml red fluorescent wheat germ agglutinin (WGA), cells were visualized using a Confocal 1P/FCS Inverted microscope. Data are representative of 3 separate experiments. *$p<0.01$ compared with control.

FIGS. 4A-4C show cell viability detection by the MTS assay. After incubation with particles coated with polymers of MW 0.6-25 KD at doses of 6-100 μg/ml for 16 hrs, PANC-1 (FIG. 4A), BxPC3 (FIG. 4B), and HEPA-1 (FIG. 4C) cells were incubated with the MTS reagent for 30 min and the absorbance was measured at 490 nm. All the MTS values were normalized as described in FIG. 1. The experiment was reproduced 3 times.

FIGS. 5A-5C show gel retardation and DNase I protection assays. Agarose gel electrophoresis of PEI-MSNP/plasmid DNA (pEGFP) (FIG. 5A) and PEI-MSNP/siRNA (FIG. 5B) complexes at various nanoparticle to nucleic acid (N/P) ratios. Anionic phosphonate-coated MSNP was used as a control. M=MW marker. FIG. 5C shows DNase I protection assay. M: DNA marker. φ: naked plasmid DNA (pEGFP), as negative control. Lane 1, pDNA/PEI-1.2 KD complex. Lane 2, pDNA/PEI 25 KD complex. Lane 3, naked pDNA treated with DNase I, positive control. Lane 4, pDNA/PEI 1.2 KD complex treated with DNase I before pDNA was released by 1% SDS. Lane 5, pDNA/PEI 25 KD complex treated with DNase I before pDNA was released by 1% SDS. Lane 6, pDNA/PEI 1.2 KD complex treated with 1% SDS. Lane 7, pDNA/PEI 25 KD complex treated with 1% SDS.

FIG. 6A shows GFP knockdown assessed by flow cytometry in which GFP MFI was normalized to the value of control untransduced cells (100%). FIG. 6B shows confocal pictures showing GFP knockdown in GFP-HEPA cells. TEX 615-labeled siRNA was used to show the cellular localization of the nucleic acid bound particles (red dots). "X" represents scrambled siRNA. The experiment was reproduced 3 times.

FIG. 7A shows a representative histogram showing the shift in green fluorescence intensity in HEPA-I cells after transfection with Lipofectamine 2000 or MSNP-PEI-10 KD. FIG. 7B shows confocal pictures showing GFP expression in transfected HEP A-I cells. This demonstrates differences in the transfection efficiency as judged by fluorescent intensity and proportion of cells in the population showing GFP expression. The experiment was reproduced 3 times.

FIG. 10A shows cell viability following treatment with MSNP displaying different surface modifications, wise determined by the MTS assay as described in FIG. 1. Cells were exposed to MSNP at doses of 12.5-50 µg/ml for 16 hrs. All the MTS values were normalized as outlined in FIG. 1. The $IC_{50}$ values for image NP-PEI-25 KD in RAW 264.7 and BEAS-2B cells are 40.6 µg/ml and 9.7 µg/ml, respectively. FIG. 10B shows cell death and mitochondrial depolarization after treatment with MSNP-phosphonate and MSNP-PEI backspace-25 kD was determined using PI and JC-1, respectively.

FIG. 11A shows cell viability comparing non-modified with succinic anhydride treated particles in RAW 264.7 cells using MTS assay. FIG. 11B shows the conversion confirmed using fluorescamine, which yields green fluorescence when complexed to the primary $NH_2$ groups. The decline in fluorescence intensity was followed in a fluorometer.

FIG. 13A shows a representative histogram showing the shift in fluorescence intensity in RAW 264.7 cells treated with 25 µg/ml FITC-MSNP exhibiting different surface modifications for 3 hrs (left panel). The fold-increase in MFI was calculated and used to generate the graph. RITC-labeled MSNP was used as a control as discussed in FIG. 2 (right panel). FIG. 13B shows confocal microscopy to study the cellular uptake of FITC-MSNP in RAW 264.7 cells. Cells were exposed to 25 µg/ml FITC-labeled particles for 3 hr. After the cell membrane was stained with 5 µg/ml red fluorescent wheat germ agglutinin (WGA), cells were visualized in a confocal 1P/FCS inverted microscope. Data are representative of 3 separate experiments. *p<0.01 compared with control.

FIG. 15A shows HEPA-1 cells with stable GFP expression was used for siRNA knockdown as described in FIG. 6. The procedure, including use of particles coated with different polymer lengths and the control agent, Lipofectamine 2000, was carried out as described in FIG. 6. However, instead of using confocal microscopy, cells were lysed and the lysates used to conduct anti-GFP immunoblotting. The blotting membrane was also overlaid with an antibody recognizing β-actin to correct for protein loading. FIG. 15B shows MFI of siRNA was calculated to show relative quantity of siRNA uptake into cells transfected by PEI-MSNP in HEPA-1 cells (arbitrary units).

FIG. 17A shows animal weight was monitored after particle injections. FIG. 17B shows histology of liver, kidney, spleen was performed by UCLA Division of Laboratory Animal Medicine (DLAM) diagnostic laboratory services. The sections were stained with hematoxylin-eosin and examined by light microscopy.

FIG. 18A shows TEM images of phosphonate-MSNP before and after coating with the 10 kD PEI polymer. The arrows indicate that the polymer decorates the MSNP surface but leaves the porous interior accessible to drug loading. FIG. 18B shows particle size and zeta potential in pure water, after stabilization with 1 mg/mL BSA in water, or in DMEM cell culture medium were measured. All of the size and zeta potential data are significantly unchanged when the MSNP were loaded with Dox and siRNA (Table 3).

FIG. 19A shows agarose gel electrophoresis of PEI-coated MSNP to which Pgp siRNA was complexed at various nanoparticle to nucleic acid (N/P) ratios. M is molecular weight marker. The φ lane contains Pgp siRNA only. Dox loading did not change the N/P ratio or the electrophoretic mobility. The results indicate that all siRNA was bound when the N/P ratio >16 (PEI 1.8 kD), >16 (PEI 10 kD), and >8 (PEI 25 kD). FIG. 19B shows confocal microscopy to demonstrate Texas red-labeled siRNA uptake in association with FITC-labeled PEI coated MSNP. The cell membrane and nucleus were stained by WGA 633 and Hoechst 33342, respectively. The panels on the right show merging of the images to show Pgp siRNA co-localization with FITC-MSNP. FIG. 19C shows quantitative comparison of labeled Pgp siRNA uptake by measuring fluorescent intensity of Texas red in various PEI groups, using Imaging J software. *p<0.05. FIG. 19D shows detection of Pgp knockdown by siRNA-PEI-MSNP using western blotting. Lipofectamine 2000 was used as positive control. The relevant Pgp expression was calculated by the signal intensity of the protein bands. "X" stands for cells treated by scrambled siRNA-PEI-MSNP.

FIGS. 20A-20F show that phosphonate-MSNP effectively binds Dox via a proton-sensitive mechanism. FIG. 20A shows modeling studies using positively and negatively charged MSNP under abiotic conditions. Loading yield of Dox in MSNP with various surface modifications. A photograph of the Dox-loaded MSNP (20 mg/ml) containing various surface modifications were taken. Consistent with loading yield, the phosphonate-MSNP was more intensively stained (red) than other particle types. FIG. 20B shows loading yield measurements for PEI-coated phosphonate MSNP. The yields were similar to that of non-coated particles in (FIG. 20A). FIG. 20C shows time-dependent release profile of Dox from drug loaded phosphonate MSNP in phenol red free DMEM acidified to pH 5.0. The effect of PBS or treatment with PBS containing 10% ethanol is shown for comparison. *P<0.05. $I_t$ is the fluorescent intensity of released Dox at certain time point; $I_0$ as the total Dox fluorescence signal intensity that can be recovered by repeated acid washing (considered as 100% release). The release percentage equals $(I_t/I_0) \times 100\%$. FIG. 20D shows Dox release from phosphonate-MSNP coated with the 10 kD PEI polymer under similar acidification conditions; this demonstrates that the polymer does not interfere in drug release. FIG. 20E shows confocal microscopy showing FITC-labeled MSNP uptake into the LAMP-1$^+$ compartment in KB-V1 cells. The yellow spots in the merged image show the co-localization. Calculation of co-localization ratio by Imaging J software indicates >55% co-localization of the green-labeled particles with the red-labeled lysosomes. FIG. 20F shows confocal microscopy showing Dox release from the MSNP to the nucleus in KB-V1 cells 72 hrs after the introduction the particles. The bottom panel shows that the lysosomal pH neutralizer, $NH_4Cl$, interferes in drug release.

FIG. 21A shows quantitative comparison of Dox levels using a fluorescent readout of cellular drug levels 72 hrs after introduction of treatment, using 2 µg/ml free Dox or the equivalent amount of drug loaded into MSNP before or after PEI coating or PEI coating followed by the attachment of Pgp siRNA. FIG. 21B shows confocal images showing drug uptake in KB-V1 cells that treated by 5 µg/ml free Dox or the equivalent amount of drug loaded into various MSNPs for 72 hrs. Please note that while free Dox could not be maintained intracellularly, Dox delivered by MSNP (Dox-MSNP) were retained in the particles that localized in the peri-nuclear region. PEI-Dox-MSNP significantly enhanced particle uptake compared to the unmodified MSNP. However, while much of the drug remained confined to the particles, nuclear staining could be observed when Pgp siRNA was added to this platform. Thus, Pgp knockdown is likely effective at maintaining the Dox that is released from the particles long enough to allow the drug to find its way to the nucleus. The cell membrane was stained by Alexa 633-conjugated WGA (cyan color). Dox staining is in red. FIG. 21C shows quantitative analysis of the nuclear fluorescence signal in KB-V1 nuclei was performed by the use of Image J software.

FIG. 22A shows MTS cell viability assay showing that MSNP delivery of Dox concomitant with Pgp siRNA is capable of improving the induction of cytotoxicity by free Dox or Dox delivered by PEI-coated MSNP not attached to siRNA. The broken line is the cell killing curve of free Dox in parental cell line (KB-31, Dox sensitive). FIG. 22B shows annexin V-SYTOX staining showing enhanced apoptosis and cell death by siRNA-PEI-Dox compared to the other Dox modalities mentioned in FIG. 22A. The flow cytometry data was further confirmed by TUNEL staining assay (FIG. 29).

FIG. 23A shows cytotoxicity profiles of Dox in KB-31 (parental line) and KB-V1 cells (resistant cell line). FIG. 23B shows immunoblotting showing Pgp expression in KB-31 and KB-V1 cell.

FIG. 26A shows MTS assay assessment of the viability of the cells incubated with the polymer-coated MSNP. FIG. 26B shows MTS assay assessment of cell viability in response to 100 µg/ml MSNP coated with the 10 kD polymer. The cell viability began to decrease at 36 hrs time-point (*p<0.05).

FIG. 27A shows loading yield of Hoechst 33342 in MSNP with different surface modifications. Positively charged Hoechst 33342 dye (pKa=11.9), has a strong interaction with the particles with a negatively charged porous surface, showing higher loading yield. FIG. 27B shows Hoechst 33342-loaded MSNP was incubated in H$^+$ (pH=5.0) and 10% (v/v) ethanol containing DMEM for 3 hrs. The supernatant was collected for released dye measurement. H$^+$ induced Hoechst 33342 release is significantly higher than ethanol induced release (*p<0.05).

FIG. 32A shows loading yield of CPT in modified MSNP. As shown in FIG. 32A, MSNP with different surface modifications were compared for their loading capacity to CPT. The loading yield of MSNP varied from 3.8% (w/w) to 6.2% (w/w) when different surface modifications were used. The amounts of CPT stored within the surface functionalized particles were similar, although storing lesser amounts than the silanol surface. FIG. 32B shows the release profile of CPT loaded into phosphonate-MSNP in response to acidification or induction of ethanol into the wash medium. PBS treatment was set as control. The ethanol-induced CPT release is significantly higher than acid-induced release. The loading and release mechanisms for hydrophilic cargo (e.g. Dox) and hydrophobic cargo (e.g. CPT) are different since there is a phase transfer process for hydrophobic cargo during drug loading. Loading capacity is independent of the functional groups that are used, and the cargo can be quickly released by an organic solvent in which the cargo is dissolvable.

FIG. 34A shows particle size and zeta potential in pure water and saline were assessed with a ZetaSizer Nano (Malvern), with the particle concentrations at 100 µg/mL. Note that the size and zeta potential were not significantly changed before and after doxorubicin loading (not shown). FIG. 34B shows TEM images to demonstrate particle size and dispersal in saline. Photographs are of the particles suspended in saline at 20 mg/mL against an appropriate background were taken and supplemented with the illustrations to show that NP3 coated with PEI-PEG had optical transparency because of electrostatic monodispersion while the other particle types agglomerated for reasons discussed in the manuscript.

FIGS. 35A-35D show the biodistribution of NIR dye-labeled MSNP to the KB-31-luc tumor xenograft model in nude mice. Particle labeling was performed with Dylight 680 dye as described in Materials and Methods. FIG. 35A shows an IVIS optical imaging system (Xenogen) was used to study the biodistribution of NIR dye labeled-MSNP in the tumor-bearing mice. To visualize the luciferase expression in the KB-31 cells, anesthetized mice received intraperitoneal injection of 75 mg/kg D-Luciferin, followed 8 min later by obtaining the bioluminescence images using 10 s exposure time. Reference fluorescence images were captured before intravenous injection of 50 mg/kg NIR-labeled particles into the tumor-bearing mice. Pronate and supine images were obtained at the indicated time intervals following the particle injection. FIG. 35B shows results 72 h after injection, the animals were sacrificed and tumor tissues as well as major organs (heart, lung, spleen, liver, kidney, brain and muscle) were collected for ex vivo imaging. FIG. 35C shows the fluorescence intensities of individual organs from mice treated with each particle type. Around 100-200 mg tissue for each organ was accurately weighted, homogenized and the fluorescence intensity obtained at excitation and emission wavelength of 680/715 nm in a microplate reader (SpectraMax M5e, Molecular Device, USA). The data represent the mean fluorescence intensity of 1 mg of tissue from the tumor or each organ.*, $p<0.05$, compared with NP1 and NP2. FIG. 35D shows the biodistribution of each particle type was expressed as % of total load of each nanoparticle distributing to the individual organs. This % is determined according to the formula: [(tissue fluorescent intensity per mg mass tissue× tissue weight in mg)/(total injected particle fluorescent intensity)]×100%. NP3 yielded a passive tumor accumulation of ~12% of the injected dose, which is significantly higher compared to the treatments using NP1 and NP2. *, $p<0.05$, compared to NP1 and NP2.

FIG. 37A shows a comparison of the tumor inhibition effect of doxorubicin-loaded NP3 (Dox-NP3) versus free drug (free Dox), empty particles and saline in the KB-31 xenograft model. The tumor-bearing mice were intravenously injected with 120 mg/kg doxorubicin-loaded NP3 weekly for 3 weeks. This particle dose is equivalent to 4 mg/kg doxorubicin being delivered to each animal. The animals receiving the free drug were injected with the same amount of doxorubicin weekly for 3 weeks. To compare the effect of NP3 alone, empty particles were intravenously injected at 120 mg/kg, weekly for 3 weeks. The saline group received intravenous saline administration at the same time points. Tumor size was accurately measured twice a week by the same observer. Tumor weight was calculated according to the formula: Tumor weight (mg)=(length in mm)× (width in mm)$^2$/2. *, $p<0.05$, compared to saline; $, $p<0.05$, compared to free doxorubicin. FIG. 37B shows results at the end of this experiment, tumor tissue was collected from each sacrificed animal and a photograph of the tumor tissue was obtained.

FIGS. 38A-38C show a TUNEL staining assay showing enhanced apoptosis and cell death by doxorubicin-loaded NP3 (Dox-NP3) compared to the free drug. FIG. 38A shows doxorubicin-induced apoptosis in the tumor tissue, where tumor sections were used for TUNEL staining and visualized under a fluorescence microscope. Briefly, a TUNEL detection kit (Invitrogen) was used according to the manufacturer's instructions. Slides of the tumors were washed, fixed, and permeabilized before TUNEL staining. The number of TUNEL positive cells (in green) was scored under the fluorescence microscope (200×). Utilizing its red fluorescence properties, the doxorubicin signal could be captured in the same tumor section. After merging of the images, the composite yellow spots suggest the presence of delivered drug inside the apoptotic cells. Higher magnification images, including Hoechst nuclear staining of regions "I" and "II" were obtained to further distinguish between free drug and NP3 encapsulated doxorubicin (see panel C). FIG. 38B shows quantitative analysis of TUNEL positive cells for each treatment. At least three fields were counted by the same investigator to calculate the percentage of TUNEL positive cells. *, $p<0.05$, compared to free doxorubicin. FIG. 38C shows Higher magnification images of regions "I" and "II" representing free or Dox-NP3 treated animals. Hoechst dye staining was used to demonstrate the localization of the red fluorescent specks in relation to the nucleus (as indicated by number). In contrast, the free drug yielded more diffuse and dull fluorescence, suggesting that the specks may indeed represent particles, some being displayed in a perinuclear distribution. This is indicative of particle uptake in the tumor cells.

FIG. 39A shows animal weights recorded twice a week and expressed for the three-week experimental duration. FIG. 39B shows histological analysis of liver and kidney sections were performed by UCLA DLAM diagnostic laboratory services. The sections were stained with hematoxylin/eosin (H&E) and examined by light microscopy. Representative images are shown. The hepatic histology reveals steatosis of the liver in the free doxorubicin treated group. In contract, the liver histology was normal for animal treated with the same amount of drug encapsulated in NP3. The liver histology of animals receiving empty NP3 or saline was also documented as normal (see FIG. 43). The kidney histology demonstrates the generation of glomerular swelling and nephrotoxicity by free doxorubicin while animals treated with the encapsulated drug had no histological abnormalities. The histology was also reported as normal in animals receiving empty NP3 or saline (see FIG. 43).

FIG. 41A shows ICP-MS analysis showing the Si concentrations in the collected organs of NP3 vs saline treated animals. FIG. 41B shows NP3 biodistribution was expressed as a % of the total particle amount for each of the indicated organs. This % was determined according to the formula: [(Si concentration per unit amount of tissue×tissue total weight)/(total injected Si mass)]×100%.

FIG. 48A shows scanning electron microscope and transmission electron microscope images of MSNP exhibiting different AR values. The arrows point out the periodical "fringes" along the short axes of the rod-shaped particles; these represent ordered helical hexagonal pore arrangements. FIG. 48B shows XRD profiling of MSNP. The peaks confirm the two-dimensional hexagonal symmetry (p6m) in the particles. The d-spacing of the rods was calculated to be 4 nm, using the first diffraction peak and the cell parameter, $\alpha$=4.6 nm.

FIG. 49A shows Hela cells treated with 20 µg/mL FITC-labeled particles for 6 h. The fold-increase in mean fluorescence intensity (MFI) compared to spherical FITC-labeled MSNP (MSNP0) was used for comparison. RITC-labeled nanosphere uptake was used as another internal control for comparing each FITC-labeled particles type to an alternatively labeled sphere. The RITC-labeled particles were introduced 1 h prior to the PBS washing and introduction of the FITC-labeled particles and PBS washing. Prior experimentation have shown that pre-incubation with RITC-labeled spheres do not interfere in subsequent uptake of FITC-labeled particles. *, p<0.05, compared with spherical FITC-labeled particle (MSNP0); #, p<0.05, compared with FITC-labeled MSNP1; $, p<0.05, compared with FITC-labeled MSNP3. FIG. 49B shows Hela cells seeded into 8-well chamber slides before addition of the FITC-labeled particles at 20 µg/mL for 6 h. After fixation and permeabilization, cells were stained with 5 µg/mL wheat germ agglutinin 633 and Hoechst 33342 dye, following by visualization under a confocal 1P/FCS inverted microscope. FIG. 49C shows the fold-increase in MFI of FITC-labeled rods compared to sphere at 0 to 6 h. Hela cells were exposed to different FITC-labeled MSNP at 20 µg/mL, and flow cytometry were conducted at the indicated time points.*, p<0.05 compared with spherical FITC-labeled particle (MSNP0); #, p<0.05 compared with FITC-labeled MSNP1; $, p<0.05 compared with FITC-labeled MSNP3.

FIGS. 50A-50E show TEM ultrastructural analysis and confocal microscopy elucidating the role of MSNP uptake by macropinocytosis in Hela cells. FIG. 50A shows electron microscopy to determine the ultrastructural changes in Hela cells following exposure to 20 µg/mL MSNP for 3 h. Please notice the increased pinocytotic activity in cells treated with MSNP2 compared to larger or shorter rod-shaped particles. Not only was exposure to MSNP2 accompanied by more prominent membrane ruffles and filopodia formation but these particles were also taken up more abundant than MSNP1 and MSNP3. "N" denotes nuclear. Additional TEM images are displayed in FIG. 55, while a 3D reconstruction using electron tomography is shown in FIG. 56. FIG. 50B shows confocal microscopy showing the rearrangement of actin fibers as determined by phalloidin staining. Cells were treated with 20 µg/mL spheres or rods for 6 h, fixed, permeabilized, and then stained with Alexa 594-labeled phalloidin. Confocal microscopy was performed as in FIG. 49. FIG. 50C shows quantitative image analysis to determine the number of filopodia per cell. At least 20 cells for each exposure in FIG. 50B were used to count the number of actin spikes that comprise the filopodium core. * denotes a significant increase (p<0.05) in cells treated with MSNP2 compared with other particle types. FIG. 50D shows confocal microscopy showing inhibition of filopodia formation and FITC-labeled MSNP2 uptake in the presence of amiloride (which is capable of inhibiting $Na^+/H^+$ exchange) or cytochalasin D (Cyto D) (which is capable of binding to actin filaments and inhibiting actin polymerization). The effect of cooling of the sample to 4° C. was determined as well as ATP depletion ($NaN_3$ plus 2-DG) on filopodia formation and particle uptake. FIG. 50E shows quantitative expression of the effect of above inhibitors on particle uptake and filopodia formation. * and # denote a significant decrease of the number of MSNP2 or the number of filopodia, respectively, under the various inhibitory conditions compared with treatments using MSNP2 alone.

FIG. 51A shows cells that were serum-starved for 4 h before introduction of the particles, which were dispersed in complete RPMI. In order to correct for effect of serum growth factors on Rac1 activity, a serum-starved control was included that was treated with complete RPMI for 30 min. Particles were introduced at 20 µg/mL for 30 min. After fixation and permeabilization, cells were stained with primary antibodies recognizing GTP-Rac1 or total Rac1, which were subsequently visualized with Alexa 594 or FITC-labeled secondary antibodies, respectively. Nuclei were stained with Hoechst dye. FIG. 51B shows the fluorescence intensity of GTP-Rac1 in FIG. 51A was quantitatively analyzed using Image J software. The fluorescence intensity of serum-starved control cells exposed to complete medium for 30 min (FIG. 51A, first row) was used as the reference value for calculating the particle-induced increase in Rac1 activation. At least 20 cells from the selection shown in FIG. 51A were used to perform the analysis. * denotes a significant decrease (p<0.05) for each particle type with the control. #, p<0.05, compared with MSNP1; $, p<0.05, compared with MSNP3.

FIG. 52A shows comparison of the CPT effects in Hela cells. After incubation with the particles for 36 h at doses of 6.25-200 µg/mL (which agrees with CPT concentrations of 0.1-8.0 µg/mL), the cells were incubated with the MTS reagent for 2 h and the absorbance measured at 490 nm. FIG. 52B shows the same experiment performed using Taxol. The cells were treated for 36 h at particle concentration at 6.25-200 µg/mL, which equals Taxol concentrations of 0.1-2.0 µg/mL for 36 h. The MTS assay was performed as in panel FIG. 52A.

FIG. 54A shows A549 cells treated with 20 µg/mL FITC-labeled particles for 6 h. The fold increase in mean fluorescence intensity (MFI) compared to spherical FITC-labeled MSNP (MSNP0) was used for making comparisons. RITC-labeled nanosphere uptake was used as an internal control for comparing to each FITC-labeled particle type. The RITC-labeled particles were introduced 1 h prior to the PBS washing and introduction of the FITC-labeled particles followed by another PBS washing. *, p<0.05, compared with spherical FITC-labeled particle (MSNP0); #, p<0.05, compared with FITC-labeled MSNP1; $, p<0.05, compared with FITC-labeled MSNP3. FIG. 54B shows A549 cells seeded into 8-well chamber slides before addition of the FITC-labeled particles at 20 µg/mL for 6 h. After fixation and permeabilization, cells were stained with 5 µg/mL wheat germ agglutinin 633 and Hoechst dye, following by visualization under a confocal 1P/FCS inverted microscope.

FIGS. 58A and 58B show confocal microscopy to show the effects of the chemical inhibitors and low temperature on Rac1 activation in Hela cells. FIG. 58A shows cells pre-cultured for 3 h in serum free RPMI 1640 medium containing amiloride (75 μM), Cyto D (2.5 μg/mL), or 0.1% $NaN_3$/50 mM 2-DG for 3 h. Alternatively, cells were placed at 4° C. for 3 h. Subsequently, the media was exchanged using fresh complete RPMI 1640 that contained 20 μg/mL FITC-labeled MSNP2 as well as one of the chemical inhibitors (amiloride, Cyto D or $NaN_3$/50 mM) for a further 6 h. The 4° C. culture was maintained at this temperature. After fixation and permeabilization, cells were stained with a primary antibody recognizing GTP-Rac1 and an Alexa 594-labeled secondary antibody. Nuclei were stained with Hoechst dye. FIG. 58B shows the fluorescence intensity of GTP-Rac1 was analyzed by Image J software. The fluorescence intensity of GTP-Rac1 in cells incubated with MSNP2 was regarded as 100% for comparison with the fluorescence intensity of cells treated with MSNP2 in the presence of inhibitors. *, $p<0.05$, demotes a significant decrease compared with the treatment using MSNP2 alone.

DETAILED DESCRIPTION

Figure 2A:
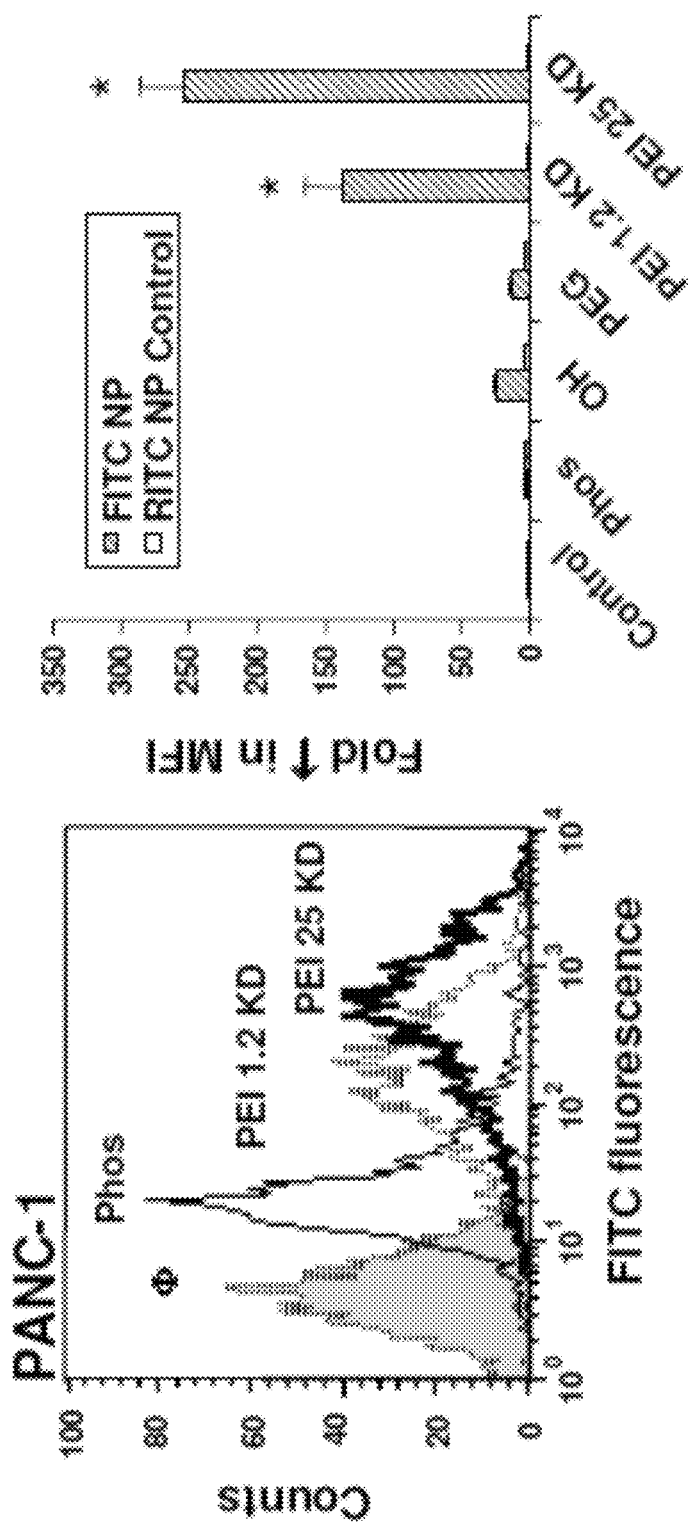
FIGS. 2A and 2B show cellular uptake of FITC-labeled MSNP in PANC-1 cells. MSNP were labeled with FITC as described in Example 1.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Embodiments of the invention include submicron structures of a silica body defining a plurality of pores and an outer surface between pore openings of said plurality of pores and a cationic polymer on the surface of said silica body. The submicron structure has a maximum dimension less than one micron (μm).

Compared with an existing anticancer drug delivery system (e.g. DOXIL®, doxorubicin HCl liposome injection, Centocor Ortho Biotech Products), MSNP is a multifunctional delivery platform that has been shown at cellular and in vivo levels to be capable of delivering multiple pharmaceutical components (e.g. chemotherapeutic agents and DNA/siRNA) to a variety of cancer cell types and the tumor site in nude mice. This delivery platform allows effective and protective packaging of hydrophobic and charged anticancer drugs for controlled and on demand delivery, with the additional capability to also image the delivery site. Advantages of using MSNP to deliver anticancer drugs can include: (1) MSNP have minimal cytotoxicity, they are used extensively as food additives; MSNP is biologically inert when injected intravenously at high dose in rodents and are also biologically degradable and excretable. (2) Low cost and ease of large-scale production; (3) Easy to modify physicochemical characteristics (e.g. particle size, surface charge, hydrophilicity) and simple purification procedures (centrifugation); (4) Establish the possibility to co-deliver of two or more drugs or therapeutic modalities for combination therapy; (5) Versatile functionalization methods (organosilanes) allows ligand (e.g. folate, transferrin) conjugation for targeted delivery of drugs in a cell- or tissue-specific manner; (6) visualization of sites of drug delivery by combining therapeutic agents with imaging modalities such as iron oxide nanoparticles for MM or probes for fluorescent imaging; (7) extension of the economic life of proprietary drugs.

Preliminary studies using MSNP with a ~100 nm primary particle size has shown that these particles could be taken up and accumulate in a human breast cancer (MCF-7) xenograft in nude mouse. However, the EPR effect was not calculated in that study and it has subsequently been recognized that the original synthesis method yielded particles that tend to agglomerate considerably in biological media. This could make them relatively ineffective from the perspective that particle sizes <200 nm are better suited for achieving improved EPR effects. Thus, size reduction may be helpful to increase their passive targeting but has to take into consideration that to overcome this agglomeration by salt and protein in biological fluids may require an additional design feature.

In some embodiments, size reduction and surface functionalization of mesoporous silica nanoparticles (MSNP) with cationic polymers, including cationic co-polymers reduces particle opsonization while enhancing the passive delivery of monodisperse, 50 nm doxorubicin-laden MSNP to a human squamous carcinoma xenograft in nude mice following intravenous injection. Using near infrared (NIR) fluorescence imaging and elemental Si analysis, accumulation of ~12% of the injected particle load at the tumor site, where there is effective cellular uptake and the delivery of doxorubicin to HeLa cells. This was accompanied by the induction of apoptosis and an enhanced rate of tumor shrinking compared to free doxorubicin. The improved drug delivery was accompanied by a significant reduction in systemic side effects such as animal weight loss as well reduced liver and renal injury. These results demonstrate that it is possible to achieve effective passive tumor targeting by MSNP size reduction as well as introducing steric hindrance and electrostatic repulsion through coating.

Some embodiments of the current invention can be implemented in practice to deliver anticancer drugs (e.g. doxorubicin, camptothecin, paclitaxel) in carcinoma disease that can benefit from a nanotherapeutic MSNP platform, and eventually in human beings. However, some embodiments of the current invention can also be practiced for diseases other than cancer where increased vascular fenestration could lead to passive delivery and accumulation of a wide range of drugs. An example, without limitation, is inflammatory disease processes.

Silica Body.

The submicron structure includes a silica body that defines a plurality of pores therein. For example, the silica body can be a mesoporous silica nanoparticle. The fact that we refer to the body as a silica body does not preclude materials other than silica from also being incorporated within the silica body. In some embodiments, the silica body may be substantially spherical with a plurality of pore openings through the surface providing access to the pores. However, the silica body can have shapes other than substantially spherical shapes in other embodiments of the current invention. Generally, the silica body defines an outer surface between the pore openings, as well as side walls within the pores. The pores can extend through the silica body to another pore opening, or can extend only partially through the silica body such that it has a bottom surface of the pore defined by the silica body.

In some embodiments, the silica body is non-spherical. As used herein, a non-spherical silica body has an average aspect ratio (AR) greater than 1.3, and where said submicron structure has a maximum dimension less than one micron. In some embodiments the silica body may have an average aspect ratio greater than 1.4, greater than 1.5, greater than 1.7, greater than 1.8, greater than 1.9, greater than 2.0, greater than 2.1, greater than 2.2, or greater than 2.5. In some embodiments, the silica body may have an aspect ratio less than about 5, less than about 4.7, less than about 4.5, less than about 4.3, less than about 4.0, less than about 3.7, less than about 3.5, less than about 3.3, less than about 3.0, or less than about 2.7. As used herein, the average AR values were determined by a Transmission Electron Microscope (TEM), measuring the length and diameter of at least 30 randomly selected particles and averaging the individual AR values to produce the average AR.

In some embodiments, the silica body is mesoporous. In other embodiments, the silica body is microporous. As used herein, "mesoporous" means having pores with a diameter between 2 nm and 50 nm, while "microporous" means having pores with a diameter smaller than 2 nm. In general, the pores may be of any size, but in some embodiments are large enough to contain one or more therapeutic compounds therein. In such embodiments, the pores allow small molecules, for example, therapeutic compound such as anticancer compounds to adhere or bind to the inside surface of the pores, and to be released from the silica body when used for therapeutic purposes. In some embodiments, the pores are substantially cylindrical.

Some embodiments of the invention include nanoparticles having pore diameters between about 1 nm and about 10 nm in diameter. Other embodiments include nanoparticles having pore diameters between about 1 nm and about 5 nm. Other embodiments include particles having pore diameters less than 2.5 nm. In other embodiments, the pore diameters are between 1.5 and 2.5 nm. Silica nanoparticles having other pore sizes may be prepared, for example, by using different surfactants or swelling agents during the preparation of the silica nanoparticles.

The submicron structures according to some embodiments of the current invention may be referred to as nanoparticles. The term nanoparticles as used herein is intended the include particles as large as 1000 nm. In general, particles larger than 300 nm become ineffective in entering living cells. In some embodiments, colloidal suspensions may be formed using a plurality of submicron structures according to some embodiments of the invention. In that case, larger particles can tend to settle rather than remaining suspended in Brownian motion. As used herein, size of the submicron structure refers to the size of the primary particles, as measured by transmission electron microscopy (TEM) or similar visualization technique. Particle size does not refer to agglomerates in solution or suspension. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm. In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm.

In some embodiments, the surface of the submicron structure or nanoparticle is unmodified. As used herein, an "unmodified" nanoparticle has had no other functional groups added to the surface after formation of the nanoparticle. Unmodified nanoparticles have an anionic charge due to free silyl hydroxide moieties present on the surface.

Cationic Polymer

As used herein, the term "polymer" is a macromolecule composed of repeating structural units, usually in a linear or branched sequence.

The cationic polymer may be any polymer bearing an overall positive charge, such as, for example, poly(ethyleneimine) (PEI), polyamidoamine, polylysine, poly(allylamine) or poly(diallyldimethylammonium chloride). Other cationic polymers will be apparent to those of skill in the art, and may be found, for example, in "Polymer Handbook, 4th Edition, Edited by: Brandrup et al.; John Wiley & Sons, 1999; and De Smedt et al., Pharmaceutical Research, vol. 17, no. 2, pp. 113-126). Other examples include, chitosan, poly(N-isopropyl acrylamide-co-Acrylamide), Poly(N-isopropyl acrylamide-co-acrylic acid), poly(L-lysine), diethylaminoethyl-dextran, poly-(N-ethyl-vinylpyridinium bromide), poly(-dimethylamino)ethyl methacrylate), poly(ethylene glycol)-co-poly(trimethylaminoethylmethacrylate chloride). Cationic polymer modified nanoparticles have a positive charge. In some embodiments, the cationic polymer is poly(ethyleneirnine) (PEI).

In some embodiments, the cationic polymer is a co-polymer. A co-polymer contains more than one repeating unit. Any co-polymer may be used, so long as the co-polymer bears an overall positive charge. The co-polymer may be a random co-polymer, alternating co-polymer, periodic co-polymer, statistical co-polymer, graft co-polymer, or block co-polymer. In some embodiments, the co-polymer may be a block co-polymer of poly(ethyleneimine) (PEI) and poly(ethylene glycol) (PEG).

The cationic polymer may be bound covalently or electrostatically to the surface of the silica body. In some embodiments, the cationic polymer is electrostatically bound to the surface of the silica body. For example, the cationic polymer may bind electrostatically to an unmodified silica body, which has an overall negative charge, or to a surface-modified silica body bearing a plurality of negatively charged surface modifying groups such that the silica body has an overall negative charge. Surface modification of the silica body is described in detail below.

In some embodiments, the cationic polymer has a weight average molecular weight less than about 30,000, less than about 25,000, less than about 20,000, less than about 15,000, or less than about 10,000. In some embodiments, the cationic polymer has a weight average molecular weight greater than about 600, greater than about 1000, greater than about 1500, or greater than about 1800, greater than about 2000, greater than about 3000, or greater than about 4000, or greater than about 5000. The range of molecular weight may be between any recited endpoints.

When a block co-polymer is used, each portion may have a weight average molecular weight within the above ranges. For example, if PEG is used, the PEG may have a weight average molecular weight, greater than about 2000, greater than about 3000, greater than about 4000, or greater than about 5000. Alternatively, the PEG may have a weight average molecular weight less than about 20,000, less than about 16,000, less than about 12,000, or less than about 10,000.

Core Structure

In some embodiments, the silica body may have a core structure. As used herein, a core structure is a metal crystal or nanocrystal in the interior of the silica body. In some embodiments, the silica body does not include a metal nanoparticle or metal nanocrystal as a core structure. In some embodiments, the core structure is superparamagnetic metal, silver, or gold. Other embodiments include submicron structures having more than one core structure in the nanoparticle, such as, for example, a silver and gold nanocrystal in the core structure, or a silver nanocrystal and superparamagnetic iron nanocrystal. In some embodiments, the core structure is a superparamagnetic nanocrystal, such as, for example, an iron oxide nanocrystal. A superparamagnetic nanocrystal core makes the particles visible using magnetic resonance imaging (MM). The nanoparticle may be used as MM contrast agents in addition to any transfection or anti-cancer activity. The superparamagnetic nanocrystal in the core of the nanoparticle also allows the particles to be manipulated or collected by a magnetic field, for example. In other embodiments, the core structure is a gold nanocrystal.

Surface Modification

Other embodiments include submicron structures as described above, which further include a surface modification. As used herein, "surface modification" means attaching or appending molecules or other materials to the surface of the silica body, in addition to the cationic polymer. Surface modification also modifies the surface of the pores of the silica body. The surface modification may be covalent, electrostatic or a combination of both. For example, the surface may include a covalent surface modification and an electrostatic surface modification on the same nanoparticle. In some embodiments, the surface modification may be further derivatized, for instance, by further covalent or electrostatic bonds. Surface modifications, as described herein, may be used on any silica body having an unreacted silica surface, including nanodevices having stoppers, impellers or valves, as described below.

In some embodiments, the surface modification comprises a plurality of anionic or electrostatic molecules attached to an outer surface of said silica body, wherein the anionic or electrostatic molecules provide hydrophilicity or aqueous dispersability to the nanoparticle and are suitable to provide repulsion between other similar submicron structures. Anionic surface modified nanoparticles are described, for example, in International Application No. PCT/US2008/013476, filed Dec. 8, 2008, published as WO 2009/078924, the contents of which are incorporated herein by reference in its entirety.

In some embodiments, the plurality of anionic molecules include at least one phosphonate moiety. In some embodiments, the plurality of anionic molecules are trihydroxysilylpropyl methylphosphonate. Trihydroxysilylpropyl methyl phosphonate surface modifications are prepared, for example, by treating the silica body with trihydroxysilyl propyl methylphosphonate.

In some embodiments, the surface modification is covalently bonded to the surface of the silica body. In other words, the surface modification has a functional group covalently bonded to the surface. As used herein, the "functional group" defines a chemical moiety linked to the surface of the nanoparticle, either directly, or via a linker. In some embodiments, the functional group is a phosphonate, amine, sulfhydryl, disulfide, carboxylic acid, epoxide, halide (i.e. fluorine, chorine, bromine, or iodine), azide, alkyne, or hydrophobic moiety. In some embodiments, the functional group is a phosphonate or an amide. In some embodiments, the functional group may be further bonded, covalently or electrostatically to a further compound.

In general, any reaction capable of reacting with the silyl hydroxide surface of the silica body may be used to covalently modify the surface. For example, the surface of the silica body may be treated with a trialkoxysilyl compound or trihydroxylsilyl compound. The compound reacts with the silyl hydroxide surface of the silica body, forming covalent silicon-oxygen bonds. Trialkoxysilyl and trihydroxylsilyl compounds bearing various functional groups may be used to modify the surface of the nanoparticle.

In some embodiments, the covalent surface modification comprises a phosphonate, amine, sulfhydryl, disulfide, carboxylic acid, epoxide or hydrophobic organic moiety. As discussed above, various functional groups may be present on the surface modification, depending on the reagents used to modify the surface. In some embodiments, the functional group (i.e. phosphonate, amine, sulfhydryl, disulfide, carboxylic acid, epoxide, halide, azide, alkyne, or hydrophobic organic moiety) may be separated from the silica surface by a linker. In some embodiments, the functional group is covalently bonded to the silica surface via a $C_1$ to $C_{12}$ alkyl linker. In other words, a $C_1$ to $C_{12}$ alkyl group is present between the atom covalently bonded to the surface and the functional group (i.e. phosphonate, amine, sulfhydryl, disulfide, carboxylic acid, epoxide or hydrophobic organic moiety). In other embodiments, the functional group is covalently bonded to the silica surface via a $C_1$ to $C_6$ alkyl linker. Nanoparticles bearing a surface modification are called surface-modified nanoparticles.

As used herein a $C_1$ to $C_{12}$ alkyl chain includes linear, branched and cyclic structures having 1 to 12 carbon atoms, and hybrids thereof, such as cycloalkylalkyl. Examples of alkyl chains include methylene ($CH_2$), ethylene ($CH_2CH_2$), propylene ($CH_2CH_2CH_2$), and so forth.

As used herein, surface modification having a phosphonate (also known as phosphonate-modified nanoparticles) have at least one phosphonic acid (—P(O)(OH)2) group or phosphinic acid (—P(O)(OH)R, where R is an $C_1$ to $C_{12}$ alkyl group). The phosphonic or phosphinic acid may be charged or uncharged, depending on the pH. At physiological pH, phosphonic acids and phosphinic acids are negatively charged, or anionic. Phosphonate modifications may be prepared, for example, by treating the silica body surface with a phosphonate bearing trialkylsiloxane compound or phosphonate-bearing trihydroxylsilyl compound, such as (trihydroxylsilyl)propyl methylphosphonate.

In some embodiments, the surface modification has a phosphonate (i.e. phosphonic acid or phosphinic acid) group. Functionalization of the particle surface with a phosphonate group provides electrostatic binding of positively charged (i.e. cationic) hydrophilic therapeutic compounds (e.g. doxorubicin) to the porous interior, from where the drug could be released by acidification of the medium under abiotic and biotic conditions. In addition, phosphonate modification also improves exterior coating with the cationic polymer, PEI, which endows the MSNP with the ability to contemporaneously bind and deliver siRNA.

As used herein, surface modifications having an amine (also known as amine modified nanoparticles) will have at least one primary (—$NH_2$), secondary (—NHR), tertiary (—$NR_2$) or quaternary amine. An amine-modified surface may be charged or uncharged, depending on the amine and pH. Amine modifications may be prepared, for example, by treating the silica body surface with an amine bearing trialkoxysilane compound, such as aminopropyltriethoxysilane, 3-(2-aminoethylamino)propyl-trimethoxysilane, or 3-trimethoxysilylpropyl ethylenediamine. An amine modified silica body may have an overall negative charge at certain pH, and when combined with anionic surface modifications, as discussed above.

As used herein, surface modifications having a sulfhydryl (or thiol) group will have at least one —SH moiety. Such a modification may be prepared, for example, by treating the surface of the nanoparticle with a sulfhydryl bearing trialkoxysilane compound, such as 3-mercaptopropyltriethoxysilane.

As used herein, surface modifications having a disulfide group will have at least one —S—S— moiety. Such a modification may be prepared, for example, by treating the surface of the nanoparticle with a disulfide bearing trialkoxysilane compound, or by treating a sulfhydryl modified surface with 2,2'-dithiodipyridine or other disulfide.

Surface modifications having a carboxylic acid group will have at least one —$CO_2H$, or salt thereof. Such a modification may be prepared, for example, by treating the surface with a carboxylic acid bearing trialkoxysilane compound, or by treating the surface with a trialkoxysilane compound bearing a functional group that may be converted chemically into a carboxylic acid. For example, the surface may be treated with 3-cyanopropyltriethoxysilane, followed by hydrolysis with sulfuric acid.

Surface modifications having an epoxide will have at least one epoxide present on the surface of the nanoparticle. Such a modification may be prepared, for example, by treating the surface with an epoxide bearing trialkoxysilane compound, such as glysidoxypropyltriethoxysilane.

Surface modifications having a hydrophobic moiety will have at least one moiety intended to reduce the solubility in water, or increase the solubility in organic solvents. Examples of hydrophobic moieties include long chain alkyl groups, fatty acid esters, and aromatic rings.

Different surface modifications may be combined. For example, an anionic surface modification (such as, for example, a phosphonate modification) may be combined with an amine modification, thiol modification, or hydrophobic modification if desired. In some embodiments, the modified silica body has an overall negative charge before being combined with a cationic polymer. If the silica body has an overall negative charge, a cationic polymer may bind electrostatically to the surface of the silica body.

Surface Derivatization

Any of the covalent surface modifications described above may be further derivatized, for example, by further covalent or electrostatic bonds. In some embodiments, the surface modification is further covalently bonded to another compound, such as a light-emitting molecule, targeting compound, polymer, peptide, protein, nucleic acid, sugar, oligosaccharide, or polysaccharide. Light emitting molecules include compounds which emit light by either fluorescence or phosphorescence. Light emitting molecules include dyes, such as fluorescent dyes. Examples of light emitting molecules include fluorescent dyes such as fluorescein, and rhodamine B. Light emitting molecules may be covalently bonded to the surface modified silica body by any useable method. For example, amine-modified nanoparticles having a free NH2 group may be reacted with fluorescent dyes bearing amine-reactive groups such as isocyanates, isothiocyanates, and activated esters, such as N-hydroxysuccinimide (NETS) esters. Examples of fluorescent dyes bearing amine reactive groups include, for example, fluoresceine isothiocyanate, N-hydroxysuccinimide-fluorescein, rhodamine B isothiocyanate, or tetramethylrhodamine B isothiocyanate. Other dyes will be apparent to those of skill in the art. Nanoparticles bearing light-emitting molecules may be used, for example, for fluorescence imaging, for instance when the nanoparticles interact with the surface of a microbe.

In some embodiments, the surface modification is further bonded to a polymer, such as, for example, polyethylene glycol (PEG). Polymers covalently bonded to the surface modification should be covalently bonded at only one location to prevent crosslinking. For example, the surface may be modified with poly(ethylene glycol) methyl ether, which has only one reactive end. The reactive end may be activated, for example with an N-hydroxysuccinimide ester. Activated PEG may react, for example, with free amines, including PEI. For example, modification of a PEI-coated MSNP with polyethylene glycol (PEG) would produce an MSNP with a block-copolymer of PEI and PEG (PEI-PEG).

In some embodiments, the surface modification is further bonded to a peptide or protein. Peptides include polypeptides having at least 2 amino acids. Various amino acid residues on peptides or proteins may form a covalent bond with surface-modified nanoparticles. For example, carboxylic acid residues (from aspartic acid and glutamic acid) may react with amine-modified nanoparticles bearing a free NH2 group. Likewise, amine residues on proteins (i.e. from lysine) may react with carboxylic acid bearing surface modifications or with epoxide bearing surface modifications. Sulfhydryl surface modifications may react with disulfide bonds (e.g. from cystine residues) in the protein via thiol exchange. Disulfide surface modifications, such as 2-thiopyridine disulfides may react with free thiols (e.g. from cysteine residues) in the protein to form a covalent bond with the protein. Other suitable methods for conjugating the proteins to the surface-modified nanoparticles will be evident to those of skill in the art.

In some embodiments, the polymer, protein, peptide, oligonucleotide, sugar, oligosaccharide, or polysaccharide is covalently attached to the surface modifying group via a linker. Various bifunctional crosslinkers are known to those in the art for covalently bonding to proteins, any of which may be used to covalently link a surface modified nanoparticle to a protein. For example, heterobifunctional crosslinkers such as succinimidyl-4[N-maleimidomethyl]cyclohexane-1-carboxylate (SMCC) and melaimido butyryloxysuccinimide ester (GMBS) may be used to react with amine-modified nanoparticles (via the succinimide esters), and then form a covalent bond with a free thiol in the protein (via the maleimide). Other crosslinkers, such as succinimidyl 3-(2-pyridyldithio)-propionate (SPDP) may react with amine-modified nanoparticles (via the succinimide ester), and form a covalent bond with a free thiol in the protein via thiol exchange. Other difunctional crosslinkers include suberic acid bis(N-hydrosuccinimide ester), or disuccinimidyl carbonate which can react with amine-modified, hydroxyl-modified, or unmodified nanoparticles, and free amines or hydroxyl groups on the polymer (such as poly(ethyleneglycol) methyl ether) or protein (e.g. from lysine residues). Other bifunctional and heterobifunctional crosslinkers useable with various surface modifications will be evident to those of skill in the art.

In some embodiments, the surface modifying material is a polymer, protein, peptide, nucleic acid, sugar, oligosaccharide, polysaccharide, or combination thereof.

Surface-modified nanoparticles bearing a protein are also called protein-modified nanoparticles. The protein may be bonded covalently (directly to the surface modification or via a linker) or may be electrostatically bonded to the modified or unmodified nanoparticles as discussed above. The protein may be a targeting protein or an antibody. A "targeting protein" as used herein, means a protein which binds to a particular surface feature of a cell. Antibodies and peptides are also used to bind to particular surface features of cells, and may be used to modify the nanoparticles of the invention. Protein-modified nanoparticles may be used to selectively target specific cells, by interacting specifically or selectively to a cell of interest.

In some embodiments, the surface modification is electrostatically bonded to the surface. As used herein "electrostatically bonded" means bonded based on the attraction of opposite charges. An unmodified nanoparticle has a negative charge, due to the presence of free silyl hydroxide residues on the surface of the nanoparticle. The particle may also bear a surface modification having a negative charge (such as a phosphonate modification), such that the overall charge of the surface is negative. The surface may be modified with material bearing a positive charge, which will bind to the surface electrostatically.

In other embodiments, in addition to the cationic polymer, a protein may bind to the surface electrostatically. A protein having a net positive charge will bind electrostatically to unmodified nanoparticles or surface modified nanoparticles bearing a negative charge. For example, proteins such as Bovine Serum Albumin (BSA) and protein solutions such as Fetal Bovine Serum (FBS) bind electrostatically to unmodified or negatively charged nanoparticles.

A protein having a net negative charge will bind electrostatically to modified nanoparticles having a positive charge, such as amine-modified nanoparticles, or nanoparticles modified by cationic polymers. For example, negatively charged proteins bind electrostatically to nanoparticles bearing a cationic polymer, as described herein.

Oligonucleotides

In some embodiments, the submicron structure further includes an oligonucleotide. The oligonucleotide binds electrostatically to the cationic polymer and outside surface of the silica body.

As used herein, an oligonucleotide is a nucleic acid polymer, and may be a ribonucleic acid polymer (RNA) or deoxyribonucleic acid polymer (DNA). DNA may be double stranded, and may be, for example a plasmid. RNA may be single stranded or double stranded and may be, for example a siRNA. Other oligonucleotides include, for example, microRNA (miRNA) and small hairpin RNA (shRNA).

Without wishing to be bound by theory, the cationic polymer envelopes and protects the oligonucleotide from degradation. Oligonucleotide-containing structures according to the invention may, for example, deliver oligonucleotides to the interior of a cell when the submicron structure enters the cell. Genes or therapeutic oligonucleotides (such as siRNA) may thus be successfully delivered into a cell. In other words, oligonucleotide-containing submicron structures may be used for transfection.

Therapeutic Compounds

In some embodiments, the submicron structure further includes a therapeutic compound within the silica body or pores of the silica body. As used herein, a therapeutic compound is a small molecule used to treat a disease or disorder. In principle any type of therapeutic compound may be incorporated into the pores of the silica body. In some embodiments, the therapeutic compound is an anticancer compound (i.e. used to treat cancer). In some embodiments, the therapeutic compound is hydrophobic. Examples of hydrophobic therapeutic compounds include, for example paclitaxel and camptothecin and related compounds. In some embodiments, the therapeutic compound is cationic. Cationic compounds electro statically bind to the surface of the silica body. Even in the presence of a cationic polymer on the surface of the silica body, cationic compounds may bind to the interior of the silica body or within the pores of the silica body. Examples of cationic therapeutic compounds include, for example, daunomycin, doxorubicin or related compounds. In some embodiments, the therapeutic compound is anionic. Anionic compounds may bind in pores or surface of the silica body, for example, by binding electrostatically to amine-modified surfaces or to cationic-polymer bound silica bodies.

Oligonucleotide-Therapeutic Compound Combinations

In some embodiments, the submicron structure includes both an oligonucleotide and therapeutic compound. The benefits of both the oligonucleotide and therapeutic compound may be realized. In some embodiment, the oligonucleotide may be a DNA plasmid. In some embodiments, the oligonucleotide may be an RNA polymer. In some embodiments, the oligonucleotide may be a small interfering RNA (siRNA). In some embodiments, the oligonucleotide may be a siRNA that decreases translation of a gene that produces drug resistance. In some embodiments, the siRNA decreases translation of a gene that produces drug resistance in a cancer cell, and the therapeutic compound is an anticancer compound. By co-delivering siRNA and therapeutic compounds, the siRNA may decrease the resistance of the cell to the therapeutic compound. In the context of cancer, for example, the siRNA may reduce translation of the p-glycoprotein (pgp), implicated in multiple drug resistance (MDR). Other resistance genes that may be suppressed by siRNA include, for example, MRP 1 (ABC transporters), breast cancer resistance protein (BCRP, ABC transporters), glucosylceramide synthase (GCS) and c-Myc (oncogene regulating MDR1 expression. Other resistance genes will be apparent to one of ordinary skill in the art.

The therapeutic compound, may be, for example doxirubicin. As a result, a cancer cell that is normally resistant to doxirubicin may become susceptible to doxirubicin activity. In this way, multiple drug resistant cancers may be treated.

Additional Structural Features

In some embodiments, the submicron structure described above further includes a stopper assembly attached to the silica body. The stopper assembly has a blocking unit arranged proximate at least one pore and has a structure suitable to substantially prevent material from entering or being released when the blocking unit is arranged in a blocking configuration. The stopper assembly is responsive to the presence of a predetermined stimulus such that the blocking unit is released in the presence of the predetermined stimulus to allow material to enter or be released. The predetermined stimulus is a predetermined catalytic activity that is suitable to cleave, hydrolyze, oxidize, or reduce a portion of the stopper assembly. Examples of stopper assemblies are described, for example, in International Application No. PCT/US2009/031891, filed Jan. 23, 2009, now published as WO 2009/094580 and incorporated herein by reference in its entirety.

In some embodiments the stopper assembly can include a thread onto which the blocking unit can be threaded. The thread has a longitudinal length that is long relative to a transverse length and is suitable to be attached at one longitudinal end to the silica body. The stopper assembly can also have a stopper attached to a second longitudinal end of the thread in some embodiments. The stopper can be selected among a wide range of possible stoppers based on the type of environment.

For example, according to some embodiments, a synthetic strategy can involve the use of a snap-top "precursor". The assembly of the snap-top precursors can be performed step-wise from the silica nanoparticle surfaces outward. For instance, the silica nanoparticles are treated with aminopropyltriethoxysilane (APTES) to achieve an amine-modified nanoparticle surface. An azide terminated tri(ethylene)glycol thread is attached to the amine-modified nanoparticles. The precursor is completed through the addition of α-cyclodextrin as the blocking unit at 5° C., which complexes with the threads at the low temperature. The precursor can enable the preparation of many different systems based on a common general structure in which different stoppers can be attached depending on the specific desired application. For example, stoppers may be selected that respond to enzymes (for example, ester linked or peptide linked), pH (for example, vinyl ether linked), and redox (for example disulfide linked) stimulation. However, the broad concepts of the current invention are not limited to only these specific examples. There are a wide range of possible stoppers that may be selected according to the particular application.

Other embodiments include submicron structures further including an impeller attached to the silica body. Silica bodies modified by impellers are described, for example in International Application No. PCT/US2009/031871, filed Jan. 23, 2009, published as WO 2009/094568, the contents of which are incorporated herein in their entirety. The term "impeller" as used herein is intended to have a broad meaning to include structures which can be caused to move and which can in turn cause molecules located proximate the impeller to move in response to the motion of the impeller.

In operation, the impellers are driven by an energy transfer process. The energy transfer process can be, but is not limited to, absorption and/or emission of electromagnetic energy. For example, illuminating with light at an appropriate wavelength can cause the plurality of impellers to wag back and forth between two molecular shapes. The motion of the plurality of impellers causes motion of molecules (for example, peptides, proteins, ions, drugs or antibiotics) of interest into and/or out of the silica body. On the other hand, in the absence of excitation energy, the plurality of impellers can remain substantially static, at least for time periods long enough for the desired application, to act as impediments to block molecules from exiting and/or entering the storage chamber.

The impellers can be, but are not limited to, azobenzenes according to some embodiments of the current invention. For example, the azobenzenes can include the following: 1) One phenyl ring derivatized with a functional group that enables attachment directly to the silica surface or to a modified silica surface as described later. The list of suitable functional groups contains but is not limited to: alcohols, (—ROH), anilinium amines (—NH$_2$) primary amines (—RNH$_2$), secondary amines (—R$_1$R$_2$NH), azides (N$_3$), alkynes (RC≡CH), isocyanates (—RNCO), isothiocyanates (—RNCS), acid halides (RCOX), alkyl halides (RX) and succinimidyl esters. 2) other functional groups on the other phenyl ring (which is the moving end of the machine). The list of these functional groups includes but is not limited to: —H (here the phenyl ring is underivatized), esters (—OR), primary and secondary amines, alkyl group, polycyclic aromatics, and various generations of dendrimers. The bulkiness of these functional groups can be designed for specific systems. For example, large dendritic functionalities might be required when very large pore openings or very small guest molecules are employed.

When illuminated or irradiated with light of a particular wavelength, the azobenzene undergoes photoisomerization, causing the second phenyl group to move.

In other embodiments, impellers are based on redox of copper complexes. The copper complexes can include bifunctional bidentate stators that contain diphosphine and/or diimine bidentate metal chelators on one end of the stator, while at the other end functionalities such as alkoxysilanes (for immobilization on silica and silicon substrates) and thiols (for immobilization on gold substrates) are present. The copper complexes can contain a rotator that is a rigid bidentate diimine metal chelator, which rotates and changes the shape of the overall molecule upon redox or photons. These copper complexes exist in two oxidation states, each of which corresponds to a specific shape. Copper (I) is tetrahedral while copper (II) is square planar. The different oxidation states, and hence different shapes that are caused by a 90° rotation of the rotator, can be generated in three ways: Reduction and oxidation (1) using electrodes and an electric current (2) by use of chemical reducing and oxidizing agents, and (3) by the photo-excitation of light of the appropriate wavelength.

Some embodiments include submicron structure further including a valve assembly attached to the silica body. Porous nanoparticles having valves are described, for example, in International Application No. PCT/US2009/032451, filed Jan. 29, 2009, published as WO 2009/097439, the contents of which are incorporated herein in their entirety. In some embodiments, the valve assembly is operable in an aqueous environment. The valve assembly has a valve arranged proximate the at least one pore and has a structure suitable to substantially prevent material from entering or being released while the valve is arranged in a blocking configuration. The valve assembly is responsive to a change in pH such that the valve moves in the presence of the change in pH to allow the material to enter or be released from the silica body.

According to some embodiments of the current invention, the pH-responsive valve assembly relies on the ion-dipole interaction between cucurbit[6]uril (CB[6]) and bisammonium stalks, and that can operate in water. CB[6], a pumpkin-shaped polymacrocycle with $D_{6h}$ symmetry consisting of six glycouril units strapped together by pairs of bridging methylene groups between nitrogen atoms has received considerable attention because of its highly distinctive range of physical and chemical properties. Of particular interest in the field of supramolecular chemistry is the ability of CB[6] to form inclusion complexes with a variety of polymethylene derivatives, especially diaminoalkanes: the stabilities of these 1:1 complexes are highly pH-dependent. The pH-dependent complexation-decomplexation behavior of CB[6] with diaminoalkanes has enabled the preparation of dynamic supramolecular entities which can be controlled by pH. In some embodiments, [2]pseudorotaxanes having bisammonium stalks and CB[6] rings, may be constructed on the surface of the mesoporous silica nanoparticles, and the pH-dependent binding of CB[6] with the bisammonium stalks is exploited to control the entry or release of molecules from the silica nanoparticles. At neutral and acidic pH values, the CB[6] rings encircle the bisammonium stalks tightly, blocking the nanopores efficiently when employing suitable lengths of tethers. Deprotonation of the stalks upon addition of base results in spontaneous dethreading of the CB[6] rings and unblocking of the pores.

Pharmaceutical Compositions

Embodiments include pharmaceutical compositions comprising any of the submicron structures according to the invention.

In certain embodiments, the composition may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

In certain embodiments, the compositions may be in a form suitable for administration by sterile injection. To prepare such a composition, the nanoparticles are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed.

Formulations suitable for parenteral administration usually comprise a sterile aqueous preparation, which may be, for example, isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intratumoral, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Methods

Embodiments include methods for using the submicron structures according to any embodiment of the invention for treatment of a disease or disorder by administering to a subject in need of treatment an effective amount of a submicron structure of the invention.

The submicron structures may be administered, for example, as a pharmaceutical composition. Administration may be achieved by any suitable means. In certain embodiments, the compositions may be administered systemically, for example, formulated in a pharmaceutically-acceptable buffer such as physiological saline. Routes of administration include, for example, subcutaneous, intravenous, intraperitoneal, intramuscular, or intradermal injections that provide continuous, sustained levels in the patient. Administration to human patients or other animals is generally carried out using a physiologically effective amount of a compound of the invention in a physiologically-acceptable carrier. Suitable carriers and their formulation are described, for example, in Remington's Pharmaceutical Sciences by E. W. Martin.

The composition may be administered parenterally by injection, infusion or implantation in dosage forms, formulations, or via suitable delivery devices or implants containing conventional, non-toxic pharmaceutically acceptable carriers and/or adjuvants. In some embodiments, the compositions are added to a retained physiological fluid, such as cerebrospinal fluid, blood, or synovial fluid. The compositions of the invention can be amenable to intravenous (i.v.) injection and direct injection (i.e. intratumoral injection), application or infusion at a site of disease or injury.

By "disease" is meant any condition or disorder that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "subject" is meant an animal. In some embodiments, a subject may be a mammal, including, but not limited to, a human or non-human mammal, such as a bovine, equine, canine, ovine, or feline.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

Embodiments of the invention include methods of treating drug resistant cancer by administering to a patient in need a submicronstructure according to the invention having an siRNA that reduces the translation of a gene responsible for the drug resistance, and an anticancer compound. The anticancer compound is a compound to which the cancer is resistant but becomes susceptible to treatment upon co-administration with an siRNA that reduces the translation of a resistance gene.

In addition to being used for the delivery of chemical therapeutic agents, MSNP have the potential as hybrid organic-inorganic materials that can act as carriers for nucleic acids and therefore potentially useful for the delivery of small interfering RNAs (siRNAs) and other forms of gene therapy (Park et al., Int. J. Pharm., vol. 359, pp. 280-284, 2008; Radu et al., J. Am. Chem. Soc., vol. 126, pp. 13216-13217, 2004; Tomey et al., Nat. Nanotechnol., vol. 2, pp. 295-300, 2007). As opposed to other gene delivery systems based on inorganic materials, the porous structure of MSNP allows both the binding of nucleotides on the surface as well as the encapsulation of small molecules within the particles. It is even possible to combine these modules to achieve dual delivery of drugs and nucleic acids (Tomey et al., Nat. Nanotechnol., vol. 2, pp. 295-300, 2007). To maximize the delivery of negatively charged nucleic acids to cells, the silica surface may be converted into positive charge in order to bind DNA and siRNA. Some of the methods for introducing cationic charge on inorganic materials, which include silica, iron oxide, and gold, typically involve surface grafting with amine groups and coating with cationic polymers (e.g. polyethyleneimine, polyamidoamine, polylysine) through either covalent or electrostatic association (Radu et al., J Am. Chem. Soc., vol. 126, pp. 13216-13217, 2004; Bharali et al., Proc. Natl. Acad. Sci. U.S. A., vol., 102, pp. 11539-11544, 2005; Bonoiu et al., Proc. Natl. Acad. Sci. U.S. A., vol. 106, pp. 5546-5550, 2009; Elbakry et al., Nano Lett., vol. 9, pp. 2059-2064, 2009; Fuller et al., Biomaterials, vol. 29, pp. 1526-1532, 2008; Kneuer et al., Bioconjugate Chem., vol. 11, pp. 926-932, 2000; McBain et al., J Mater. Chem., vol. 17, pp. 2561-2565, 2007; Zhu et al., Biotechnol. Appl. Biochem., vol. 39, pp. 179-187, 2004. The gene delivery capabilities of these surface modified materials have been demonstrated and may prove useful as alternatives to traditional viral vectors.

The effects of polyethyleneimine (PEI) coating on the MSNP in terms of cellular uptake, cytotoxicity, and efficiency of nucleic acid delivery were studied. PE is are synthetic cationic polymers that compact DNA and siRNA into complexes that are effectively taken up in cells to make nucleic acid delivery and gene therapy possible (Boussif et al., Proc. Natl. Acad. Sci. U.S. A., vol. 92, pp. 7297-7301, 1995; Godbey et al., Proc. Natl. Acad. Sci. U.S. A., vol. 96, pp. 5177-5181, 1999; Urban-Klein et al., Gene Ther., vol. 12, pp. 461-466, 2005). Although the polymer itself is used as a delivery vehicle, PEI can also be attached to nanoparticle surfaces through covalent and electrostatic interactions to achieve the same goal (Park et al., Int. J Pharm., vol. 359, pp. 280-284, 2008; Elbakry et al., Nano Lett., vol. 9, pp. 2059-2064, 2009; Fuller et al., Biomaterials, vol. 29, pp. 1526-1532, 2008; McBain et al., J Mater. Chem., vol. 17, pp. 2561-2565, 2007; Liong et al., Adv. Mater., vol. 21, pp. 1684-1689, 2009). Complexing the polymer with the nanoparticles has the potential advantage of facilitating DNA and siRNA delivery by a multifunctional platform that also allows imaging, targeting and concurrent drug delivery. PEI was chosen as the polymer coating to enhance the particle uptake into cells and facilitate endosomal escape for the nucleotide delivery (Duan et al., J Am. Chem. Soc., vol. 129, pp. 3333-3338, 2006). It is documented that while low MW PEI is not cytotoxic, these polymers are ineffective at transfecting nucleotides in contrast to the high MW PEI. In this regard, it has been demonstrated that the size (MW), compactness and chemical modification of PEI affect the efficacy and toxicity of this polymer (Florea et al., AAPS PharmSci., vol. 4, p. El 2, 2002; Neu et al., J Gene. Med., vol. 7, pp. 992-1009, 2005). Therefore, several PEI polymer sizes ranging from MW of 0.6 to 25 KD were investigated in order to balance the efficiency of nucleic acid delivery and cellular toxicity, which proceed by the proton sponge effect that involves proton sequestration on the polymer surface, heightened activity of the proton pump, osmotic swelling lysosomal injury, intracellular Ca2+ flux and mitochondrial damage (Xia et al., Nano Lett. Vol. 6, pp. 1794-1807, 2006; Xia et al., ACS Nano, vol. 2, pp. 85-96, 2008). The large number of amine groups of PEI also allows the polymer-coated particles to move across cell membranes through rapid endocytosis. Cellular uptake of PEI-coated MSNP may be enhanced by at least two orders of magnitude compared to that of the MSNP which are unmodified (silanol surface) or coated with phosphonate or poly(ethylene glycol) groups. Furthermore, with coating of PEI MW 10 KD, it is possible to achieve both increased cellular uptake and high transfection efficacy while minimizing the toxicity normally observed with higher molecular weight PEI.

In some embodiments, surface functionalization with polyethyleneimine (PEI) polymers may enhance oligonucleotide (i.e. DNA, RNA, shRNA or siRNA) binding. The tight complexing between PEI and nucleic acids on the particle surface protects these cargo molecules from enzymatic degradation. The positive charge of PEI-coated nanoparticles may also lead to strong electrostatic interaction with the negatively charged cell surface membrane, which may facilitate particle cellular uptake and lysosomal release via a proton sponge mechanism. In addition, the molecular weight of PEI polymer may be carefully selected in order to reduce possible cytotoxicity.

Surface coating with PEI yields cationic MSNP with therapeutically useful nucleic acid delivery properties that include high binding avidity of DNA and siRNA as well as a high rate of cellular uptake. siRNA complexed to the MSNP-PEI surface is quite effective to achieve green fluorescent protein (GFP) knockdown in transduced HEPA-I cells, while plasmid DNA delivery is comparable to a commercially available transfection agent. The facilitated cellular uptake of cationic particles may enhance the ability of MSNP to deliver hydrophobic chemotherapeutic agents, such as paclitaxel, to pancreatic cancer cells. A potential downside of cationic functionalization to achieve drug or nucleic delivery is induction of cytotoxicity, best demonstrated by the use of MSNP-PEI-25 KD. However, this toxicity could be reduced or eliminated by attaching shorter length polymers that retain nucleic acid and drug delivery capabilities. Thus, the therapeutic use of the MSNP platform can be extended to deliver of DNA and siRNA constructs.

Packaging siRNA on the surface of cationic MSNP may provide several benefits. First, the MSNP surface can be functionalized to enhance siRNA binding through the attachment of PEI polymers, for example, which in their own right have been used as effective siRNA compacting and transducing agents. The tight complexing between PEI and nucleic acids on the particle surface protects these molecules from enzymatic degradation as demonstrated for DNA. Furthermore, the positive charge of PEI-coated nanoparticles leads to strong electrostatic interaction with the negatively charged cell surface membrane, leading to facilitated particle wrapping and cellular uptake. This is in agreement with the recent demonstration that PEI-coated nanoparticles is taken up into cells at high efficiency (Rosenholm et al., ACS Nano, vol. 3, pp. 197-206, 2009; Duan et al., J. Am. Chem. Soc., vol. 129, pp. 3333-3338, 2006). However, the latter study did not look at nucleic acid delivery but did show that the attachment of the ligand such as folic acid further enhance uptake in cancer cells (Liong et al., ACS Nano, vol. 2, pp. 889-896, 2008; Rosenholm et al., ACS Nano, vol. 3, pp. 197-206, 2009). While PEI can be used in various ways to make siRNA delivery complexes, coating it onto the surface of MSNP utilizes this therapeutic platform as a carrier with large surface area, which is inexpensive and simple to synthesize, and which can be decorated with functional groups and fluorescent tags and can be used for magnetic resonance imaging through the inclusion of superparamagnetic iron oxide nanocrystals (Liong et al., ACS Nano, vol. 2, pp. 889-896, 2008). Not only may PEI coating enhance siRNA delivery, but the particles also are capable of anticancer compound such as paclitaxel delivery, which constitutes a significant advance for the use of MSNP as a therapeutic platform. One can envisage using siRNA and drug delivery simultaneously, e.g., delivery of siRNA that knocks down the expression of the P-glycoprotein (Pgp) drug exporter at the same time as delivering a chemotherapeutic agent that is exported by Pgp (Ludwig et al., Cancer Res., vol. 66, pp. 4808-4815, 2006). This may be an effective strategy for the treatment of cancers that have developed a drug resistance due to the activity of this exporter.

Several advantages of MSNP-PEI for the delivery of siRNA also hold true for plasmid DNA transduction. In fact, a number of modifications of the PEI polymer, including various polymer sizes, degrees of branching, thiol crosslinking and covalent attachment have been used as gene transfer agents since the 90's and are enjoying increasing popularity because of the high transfection efficiency of plasmid DNA and siRNA into cells and live animals (Boussif et al., Proc. Natl. Acad. Sci. U.S. A., vol. 92, pp. 7297-7301, 1995; Godbey et al., Proc. Natl. Acad. Sci. U.S. A., vol. 96, pp. 5177-5181, 1999; Urban-Klein et al., Gene Ther., vol. 12, pp. 461-466, 2005; Kircheis et al., J. Gene. Med., vol. 1, pp. 111-120, 1999). An advantage of using PEI for gene transfer lies in the simplicity with which the polymer can be mixed with DNA/siRNA without involving covalent attachment. Moreover, PEI protects the nucleic acids from degradation by nucleases. In all of these therapeutic applications, however, one has to keep in mind that high MW polymer could cause toxicity (Florea et al., AAPS Pharm. Sci., vol. 4, p. El 2, 2002). As demonstrated by the present invention, it is now possible to deal with a toxicity problem while maintaining effective nucleic acid delivery by using intermediate length polymers. These intermediate length polymers may provide effective cellular uptake and siRNA/plasmid DNA delivery. Moreover, this approach may produce transfection of >70% cells in the population, which may increase effectiveness from the perspective of gene therapy.

Figure 8A:
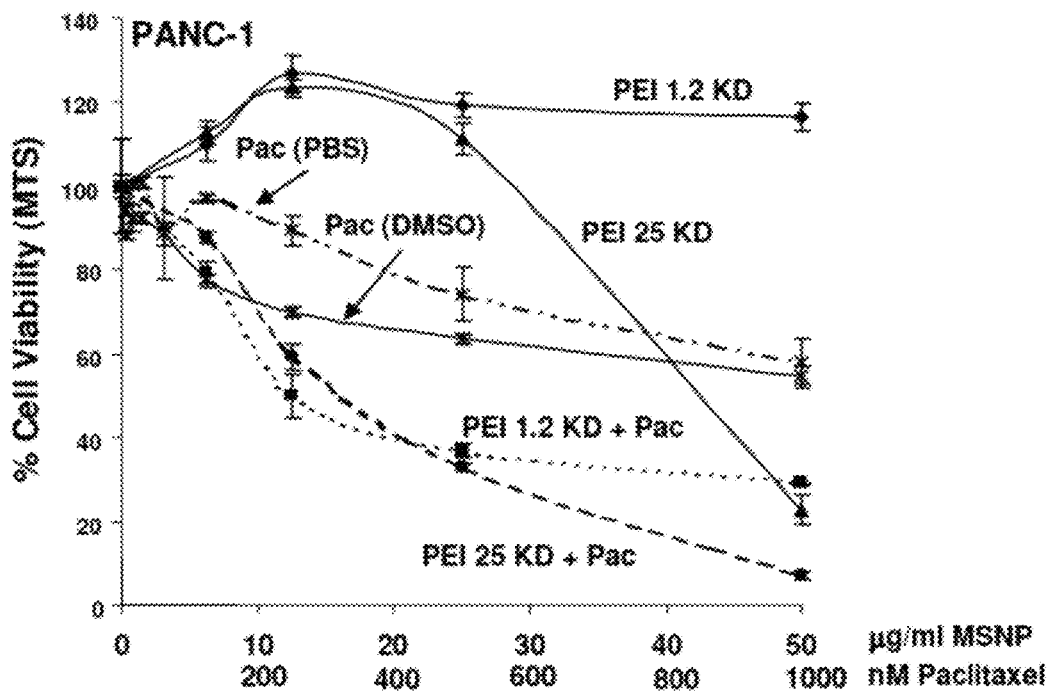
FIGS. 8A and 8B show drug delivery to PANC-I and BxPC3 cells using PEI-MSNP. A MTS assay was conducted for the paclitaxel-loaded MSNP delivered to these cells at doses of 3-50 µg/ml over a 48 hrs period in PANC-1 (FIG. 8A) and BxPC3 (FIG. 8B) cells. The controls were cells treated with particles only and cells treated with paclitaxel suspended in culture medium with and without the addition of DMSO carrier. The experiment was reproduced 2 times.
Figure 8B:
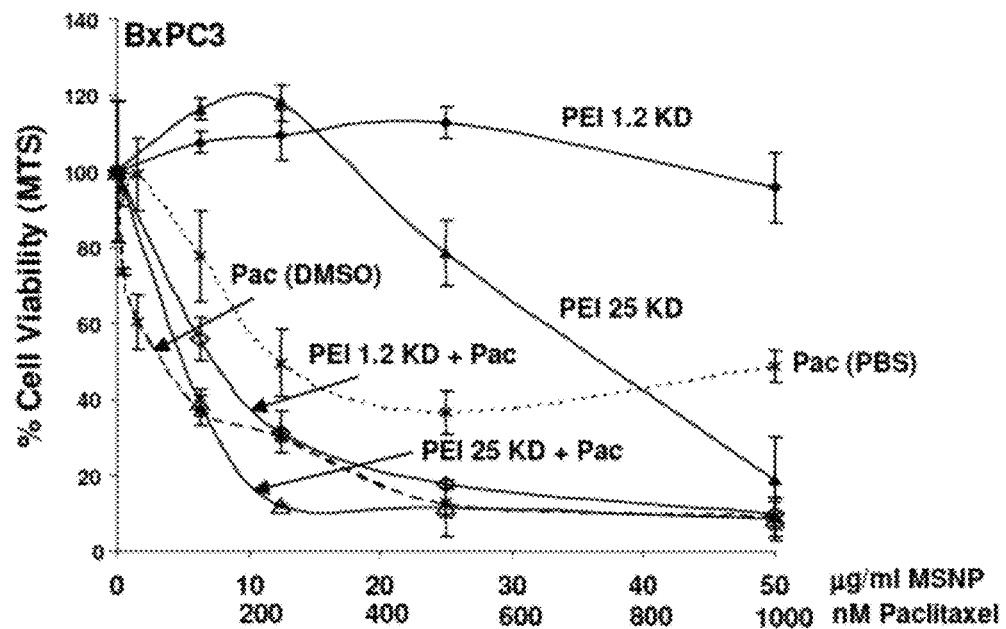

Other than mediating its effect through high cellular uptake, the efficient gene transduction ability of PEI proceed via the proton sponge effect, implying that the primary amines buffer the protons being pumped into the lysosomal compartment by the v-ATPase (proton pump) (Boussif et al., Proc. Natl. Acad. Sci. U.S. A., vol. 92, pp. 7297-7301, 1995; Xia et al., ACS Nano, vol. 2, pp. 85-96, 2008; Yezhelyev et al., J. Am. Chem. Soc., vol. 130, pp. 9006-9012, 2008). This results in heightened pump activity, leading to the accumulation of a $Cl^-$ and a water molecule for each proton that is retained; ultimately this leads to osmotic rupture of the endosome (Sonawane et al., J. Biol. Chem., vol. 277, pp. 5506-5513, 2002). While effective for delivering the nucleic acid cargo to the cytosol, the effect of PEI or cationic particles on the proton pump is a major contributory factor in cationic cytotoxicity (Xia et al., ACS Nano, vol. 2, pp. 85-96, 2008). Cationic nanoparticle toxicity can lead to clinically significant adverse health effects (Clottens et al., Occup. Environ. Med., vol. 54, pp. 376-387, 1997; Hoet et al., Toxicol. Appl. Pharmacol., vol. 175, pp. 184-190, 2001; Hoet et al., Toxicol. Sci., vol. 52, pp. 209-216, 1999). Methods to reduce cationic toxicity while maintaining effective cargo delivery are therefore desired (Nel et al., Nat. Mater., vol. 8, pp. 543-557, 2009). Experimental examples of how PEI toxicity has been reduced include neutralizing the cationic charge by anhydride, differential ketalization, altering PEI crosslinking through adjustment of disulfide content and using shorter polymers (Xia et al., ACS Nano, vol. 2, pp. 85-96, 2008; Shim et al., J Control. Release., vol. 133, pp. 206-213, 2009; Veiseh et al., Biomaterials, vol. 30, pp. 649-657, 2009; Hobel et al., Eur. J Pharm. Biopharm., vol. 70, pp. 29-41, 2008 Peng et al., Bioconjugate Chem., vol. 20, pp. 340-346, 2009). The latter principal can also be applied to PEI-coated MSNP, cytotoxicity may be reduced or eliminated while maintaining efficient nucleic acid delivery. Thus, by attaching a 10 KD polymer, it was possible at particle doses<50 µg/ml to obtain highly efficient transduction without any cell death. Preliminary data also indicate that the PEI-coated MSNP can be intravenously injected into mice without causing acute toxicity. It appears, therefore, that cationic toxicity can be controlled to achieve a therapeutically useful outcome. While the gene transduction efficiency is significantly reduced with lower MW (0.6-1.8 KD) polymers, the facilitated MSNP uptake is good enough for delivering paclitaxel (FIG. 8).

To use the MSNP delivery system, the first step is to conduct toxicity test in mice. Results show that i,v. injection of MSNP in mice has no obvious toxic effects to the major organs or systems of the animals. It is interesting that MSNP-PEI 25 KD showed toxicity to cultured cells while no toxicity in vivo. This may be because of the dilution of the MSNP in the blood system, the huge number of cells in the body, and strong defense/clearance capability in living organisms. Until now, there are only limited in vivo data regarding the toxicity, biodistribution, and biopersistence of mesoporous silica nanoparticles (Kim et al., Angew. Chem., Int. Ed., vol. 47, pp. 8438-8441, 2008; Barb et al., Adv. Mater., vol. 16, pp. 1959-1966, 2004; Taylor et al., J. Am. Chem. Soc., vol. 130, pp. 2154-2155, 2008; Wu et al., ChemBioChem, vol. 9, pp. 53-57, 2008). Several groups used MM agent to coat mesoporous silica nanoparticles for in vivo imaging, they found that MSNP were in the blood vessel 30 min after administration, then MSNP tended to accumulate more in the RES systems such as liver and spleen tissue than in kidney, lung, and heart; in fact MSNP appeared to have cleared kidney after 2 h (Kim et al., Angew. Chem., Int. Ed., vol. 47, pp. 8438-8441, 2008; Wu et al., ChemBioChem, vol. 9, pp. 53-57, 2008). Long-term MRI tracking study revealed that the MRI signal gradually disappeared after 90 days, which means that MSNP were resistant to decomposition and not easily excreted from the body, suggesting a potential candidate for long-term liver/spleen MRI monitoring and targeted drug delivery (Wu et al., ChemBioChem, vol. 9, pp. 53-57, 2008). Another interesting finding is MSNP accumulate preferentially at tumor sites through their enhanced permeability and retention (EPR) effect in tumor targeting (Kim et al., Angew. Chem., Int. Ed., vol. 47, pp. 8438-8441, 2008). To achieve the full potential of MSNP, more in vivo tests may be done regarding to their toxicity, biodistribution, pharmacokinetics, and targeting.

Due to its unique structure and ease with which the surface can be functionalized, mesoporous silica nanoparticles (MSNP) constitute a multi-functional platform that can be used for drug (Lu et al., *Small*, vol. 4, pp. 421-426, 2008; Coti et al., *Nanoscale*, vol. 1, pp. 16-39, 2009; Slowing et al., Adv. Drug Deliv. Rev., vol. 60, pp. 1278-1288, 2008; Liong et al., *ACS Nano*, vol. 2, pp. 889-896, 2008) and nucleic acid delivery (Xia et al., *ACS Nano*, vol. 3, pp. 3273-3286, 2009). For therapeutic purposes, nanoparticles that contain a phosphonate surface coating may be beneficial because of the ease of particle dispersal, good bio-safety index as well as the ability to adsorb cationic polyethylenimine (PEI) polymers for complexing and delivery of DNA and siRNA (Xia et al., *ACS Nano*, vol. 3, pp. 3273-3286, 2009). Since the polymer attachment leaves the porous interior free for drug binding and delivery, it establishes the potential to achieve simultaneous drug and nucleic acid delivery (Astrid et al., J. Am. Ceram. Soc., vol. 84, pp. 806-812, 2001). It was envisaged that there some disease conditions such as multidrug resistant cancer might benefit from the delivery of both agents. Dual delivery might, therefore achieve simultaneous drug and siRNA delivery, leading to a synergistic therapeutic outcome.

Significant uncertainties remained, however. For example, it was uncertain whether the cationic polymer would interfere with a therapeutic compound binding to the porous interior of the silica body. For example, binding a cationic polymer to the surface might block access to the interior of the silica body. Particularly for cationic therapeutic compounds, a cationic polymer might displace any cationic therapeutic compound bound to the silica body, could even be loaded into the silica body with the cationic polymer pre-bound. Assuming a therapeutic compound could bind to the interior of the silica body in the presence of the cationic polymer, it was unclear whether the cationic polymer would prevent drug release inside a cell.

Through experimentation, the inventors successfully met these challenges and prepared a dual delivery system. As demonstrated in the present invention, for example, a cationic polymer, such as PEI, will not interfere in drug binding to the porous interior. Furthermore, as demonstrated herein, cationic therapeutic compounds, such as doxirubicin can be loaded into the silica body, but only after a cationic polymer, such as PEI is coated on the surface of the silica body. Furthermore, loading therapeutic compounds, such as doxirubicin or paclitaxel did not disturb siRNA binding, as demonstrated herein. Finally, as demonstrated herein, the dual delivery system could be preferentially taken up by drug resistant cancer cells and was capable of acting synergistically to overcome drug resistance. In other words, the cationic polymer did not prevent release of the therapeutic compound in the cell.

In order to test the utility of MSNP as a dual delivery platform, drug-resistant squamous carcinoma cell line, KB-V1, was investigated to see if Pgp knockdown restores doxorubicin (Dox) sensitivity. KB-V1 cells exhibit MDR as a result of Pgp overexpression (Ludwig et al., Cancer Res., vol. 66, pp. 4808-4815, 2006). In order to effectively engineer particles to deliver Dox as well as Pgp siRNA, particle functionalization by the attachment of negative (phosphonate) as well as positive (PEI) surface groups are functionally effective. Moreover, because PEI delivery of siRNA constructs to the cytosol may require intermediary lysosomal processing, it was uncertain whether this endocytic route was appropriate for doxorubicin (Dox) delivery. As shown in the current invention, Dox can be stably attached to the porous interior by a proton-sensitive electrostatic binding interaction that allows effective drug release from the acidifying LAMP-I-positive compartment. Pgp siRNA co-delivery increases intracellular Dox concentrations with improved cytotoxic killing. The improvement of Dox resistance provides proof-of-principal testing that MSNP can be engineered to provide contemporaneous drug and siRNA delivery by effective use of charge and the state of protonation or deprotonation at the particle surface.

As shown herein, MSNP can be functionalized to deliver a chemotherapeutic
agent as well as Pgp siRNA to a drug-resistant cancer cell line. The functionalization of the particle surface with a phosphonate group allows electrostatic binding of Dox to the porous interior, from where the drug could be released by acidification of the medium under abiotic and biotic conditions. In addition, phosphonate modification also allows exterior coating with the cationic polymer, PEI, which endows the MSNP with the ability to contemporaneously bind and deliver Pgp siRNA. The dual delivery of Dox and siRNA in KB-V1 cells was capable of increasing the intracellular as well as intranuclear drug concentration to levels exceeding that of free Dox or the drug being delivered by MSNP without siRNA co-delivery. This reflects the ability of the siRNA to effectively knock down Pgp expression and therefore interfering in drug efflux as one of the resistance mechanisms in KB-V1 cells. Unlike hydrophobic cargo (FIG. 32), Dox can be released from the lysosome by a proton-sensitive mechanism. While clearly effective at improving cytotoxic killing through its dual delivery capabilities, siRNA-PEI-MSNP could not restore Dox sensitivity in KB-V1 to the level seen in drug-sensitive KB-31 cells. This may be due to the extremely high levels of Pgp expression, as confirmed in FIG. 23.

Two of the major problems in cancer chemotherapy are toxic side effects as well as development of MDR in cancer cells. Nanoparticle drug delivery is capable of overcoming both problems through tumor cell targeting as well as the capability to overcome drug resistance (Jabr-Milane et al., Cancer Treat. Rev., vol. 34, pp. 592-602, 2008; Ferrari et al., Nat. Rev. Cancer, vol. 5, pp. 161-171, 2005). MDR can basically be divided into two distinct categories, namely pump and non-pump resistance (Jabr-Milane et al., Cancer Treat. Rev., vol. 34, pp. 592-602, 2008; Saad et al., Nanomedicine, vol. 3, pp. 761-776, 2008). Pump resistance refers to the inducible formation of membrane-bound channels or pores that actively expel a series of structural and functionally distinct chemotherapeutic agents from the cell. Drug efflux significantly decreases the intracellular concentration that limits their cytotoxic potential. The key proteins involved in pump resistance are Pgp and MRP-1, while the major mechanism in non-pump resistance is activation of cellular anti-apoptotic defense pathways, including drug-induced expression of Bcl-2 protein (Saad et al., Nanomedicine, vol. 3, pp. 761-776, 2008). Moreover, the pump and non-pump resistance mechanisms could be mutually interactive (Jabr-Milane et al., Cancer Treat. Rev., vol. 34, pp. 592-602, 2008). Given this background, a number of nanomaterial design strategies can be used to overcome drug resistance:

The first is co-delivery of the chemotherapeutic drug with a pharmaceutical agent that interferes in pump activity or in non-pump pathways. One example is the use of verapamil as a Pgp inhibitor that have been combined with Dox, aimed at reducing cardiotoxicity of Dox as well as overcoming Pgp-mediated MDR (Wu et al., J Pharm. Pharmaceut. Sci., vol. 10, pp. 350-357, 2007). In Dox-resistant K562 leukemia cells, a liposomal Dox-verapamil complex doubled the cytotoxicity index (ICso=1 1.4 µM) of free Dox (1Cso=23.4 µM) (Wu et al., J Pharm. Pharmaceut. Sci., vol. 10, pp. 350-357, 2007). Another example is using a polymeric nanoparticle formulation of poly(ethyleneoxide)-poly(epsilson-caprolactone) to co-administer ceramide that is capable of lowering the apoptotic threshold to paclitaxel, thereby enhancing paclitaxel-induced cytotoxicity in a MDR human ovarian cancer cell line (van Vlerken et al., Cancer Res., vol. 67, pp. 4843-4850, 2007).

A second strategy is to use nanoparticles to deliver the chemotherapeutic together with siRNA that interfere in key protein expression in pump-dependent or independent drug resistance pathways, as demonstrated herein. There are reports demonstrating that compared to the free drug, dual delivery with a nucleic acid is capable of enhancing the efficacy in a synergistic fashion (Chen et al., *Small*, vol. 5, pp. 2673-2677, 2009; Patil et al., Biomaterials, vol. 31, pp. 358-365, 2009). Chen et al showed that MSNP served as a drug delivery vehicle to deliver Dox and Bcl-2 siRNA that can effectively silence the Bcl-2 mRNA and significantly suppress the non-pump resistance, and therefore result in enhanced cell killing capability of Dox in multidrug resistant A2780/AD human ovarian cancer cells (Chen et al., Small, vol. 5, pp. 2673-2677, 2009). Another example is paclitaxel that was delivered by poly(d,1-lactide-co-glycolide) nanoparticles along with Pgp siRNA to the MDR murine mammary cancer cell line, JC. The dual delivery system showed significantly higher cytotoxicity in vitro and significantly greater inhibition of tumor growth in vivo than nanoparticles loaded with paclitaxel alone (Patil et al., Biomaterials, vol. 31, pp. 358-365, 2009).

The third strategy is to deliver the drug together with a combination of siRNA's that interfere in both pump (e.g. Pgp) and non-pump (e.g. Bcl-2) mechanisms. Such an approach may be necessitated by the co-existence of pump and non-pump resistance mechanisms (Jahr-Milane et al., Cancer Treat. Rev., vol. 34, pp. 592-602, 2008; Saad et al., Nanomedicine, vol. 3, pp. 761-776, 2008). In this regard, it has been demonstrated that the increase in intracellular drug concentration as a result of the suppression of drug efflux pumps leads to almost proportional activation of anti-apoptotic cellular defense (Gottesman et al., Annu. Rev. Med., vol. 53, pp. 614-627, 2002; Jabr-Milane et al., Cancer Treat. Rev., vol. 34, pp. 592-602, 2008). As one example, a cationic liposome carrier system was developed to deliver Dox contemporaneously with two species of siRNA targeting of MRP-1 as well as Bcl-2 (Saad et al., Nanomedicine, vol. 3, pp. 761-776, 2008). This triple component (Dox, MRP-1 siRNA, and Bcl-2 siRNA) delivery system demonstrated enhanced Dox cytotoxicity in human MDR H69AR lung cancer cells which showed>100 fold enhancement in cytotoxicity (Saad et al., Nanomedicine, vol. 3, pp. 761-776, 2008). Similar attempts in experiments in KB-V1 cells where Bcl-2 was combined with Pgp siRNA and Dox did not improve the cytotoxicity or $IC_{50}$ significantly (not shown).

Figure 20A:
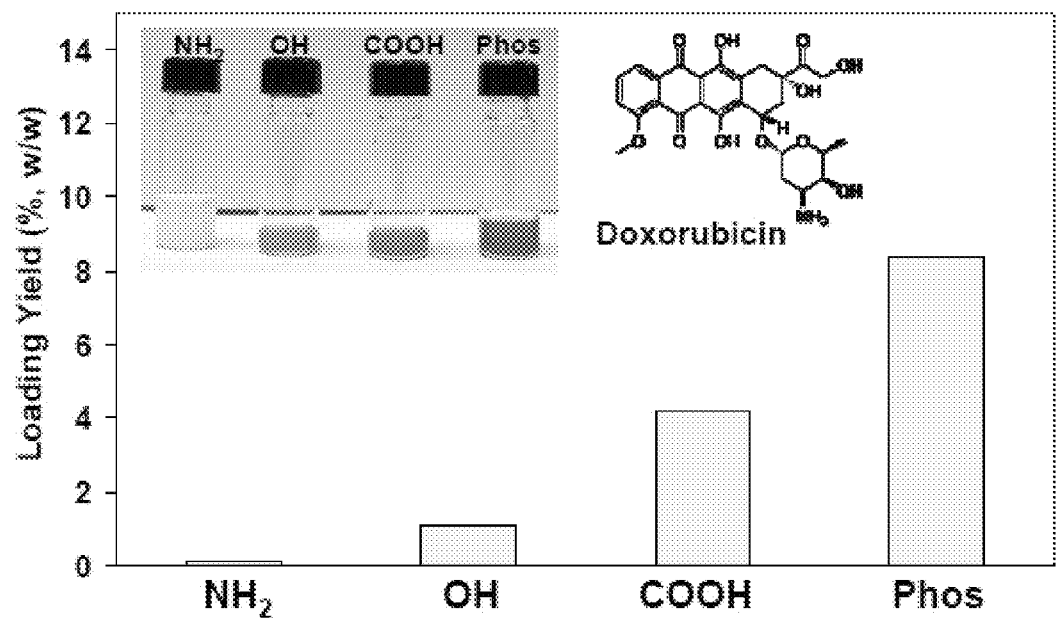
Figure 20B:
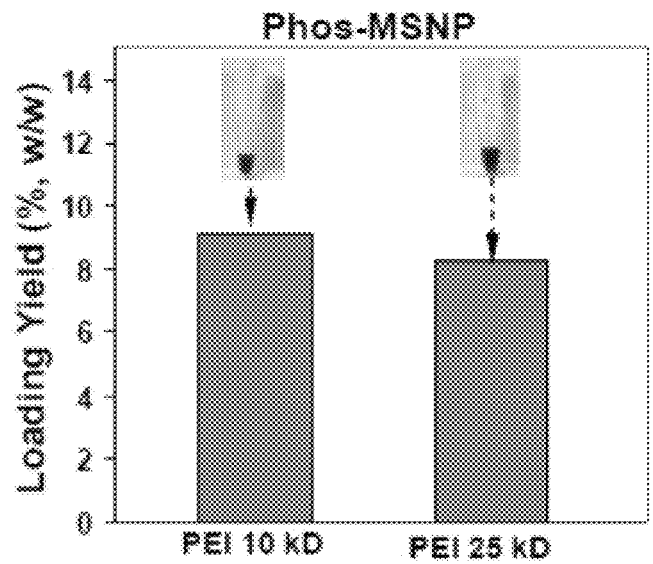
Figure 20C:
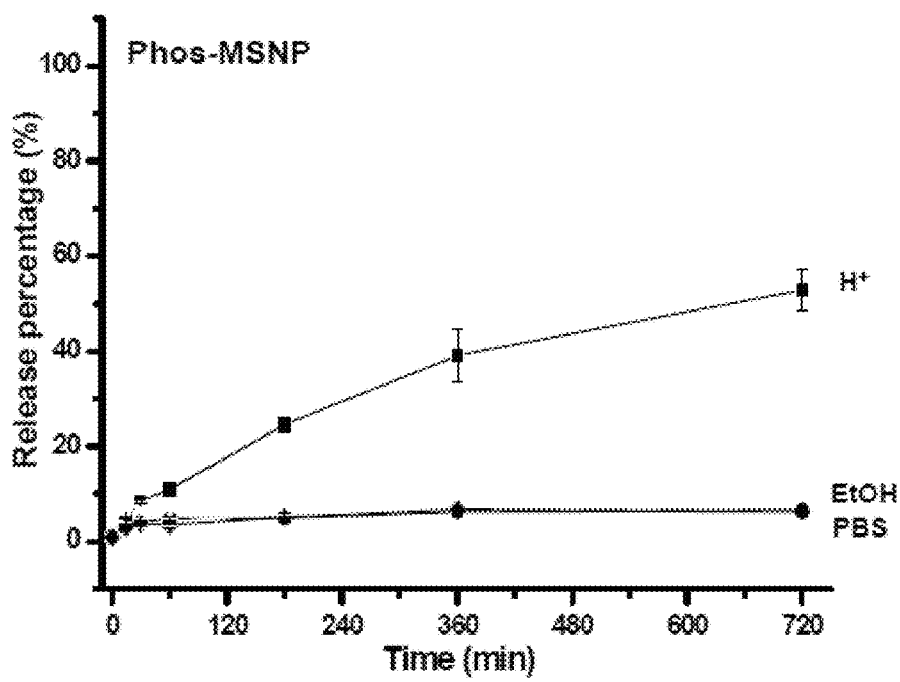

In some embodiments, this invention demonstrates how MSNP can be engineered to effectively deliver a drug together with siRNA. Because Dox (pKa=8.2) is positively charged at physiological pH, a number of surface charge modifications were used to demonstrate the utility of using electrostatic charge to bind and deliver Dox from the MSNP surface (FIG. 20A, 21B). These studies demonstrated that Dox as well as the cationic dye, Hoechst 33342 (pKa=11.9) (FIG. 27), are capable of binding to negatively charged surfaces from where both agents could be released by dropping the environmental pH (FIG. 20C-F). Thus, when the MSNP are suspended in buffered cell culture medium (pH=7.4), the attached phosphonate (pKa=2) and carboxylate (pKa=5) groups are de-protonated and assume a negative charge, whereas unmodified OH-MSNP (pKa=7) is near its isoelectric point and therefore not quite as effective for electrostatic binding (FIG. 20A). By contrast, the amine groups (pKa ~9) are protonated at physiological pH and exhibit a positive charge that prevents electrostatic binding of the same agents (Bagwe et al., Langmuir vol. 22, pp. 4357-4362, 2006; Santra et al., Chem. Commun., pp. 2810-2811, 2004). From a therapeutic perspective, phosphonate-MSNP exhibit good particle dispersibility and biocompatibility. The ability to release Dox from the interior surface by proton interference allowed Dox delivery inside the cell in an acidifying compartment (FIG. 20F, upper panel). The role of the lysosomal proton pump is supported by the finding that $NH_4Cl$ interferes in Dox release to the nucleus (FIG. 20F, lower panel). Phosphonate attachment also facilitates the binding of cationic PEI to the particle exterior (FIG. 18, right panel). This binding interaction is sufficiently strong to allow the polymer and attached siRNA to stay on the particle surface until entry into the lysosomal compartment. PEI may play a role in firm cellular attachment and selection of the initial endosomal compartment. Importantly, the polymer is attached to the particle surface to leave the pores accessible to Dox binding (FIG. 20B).

Figure 26A:
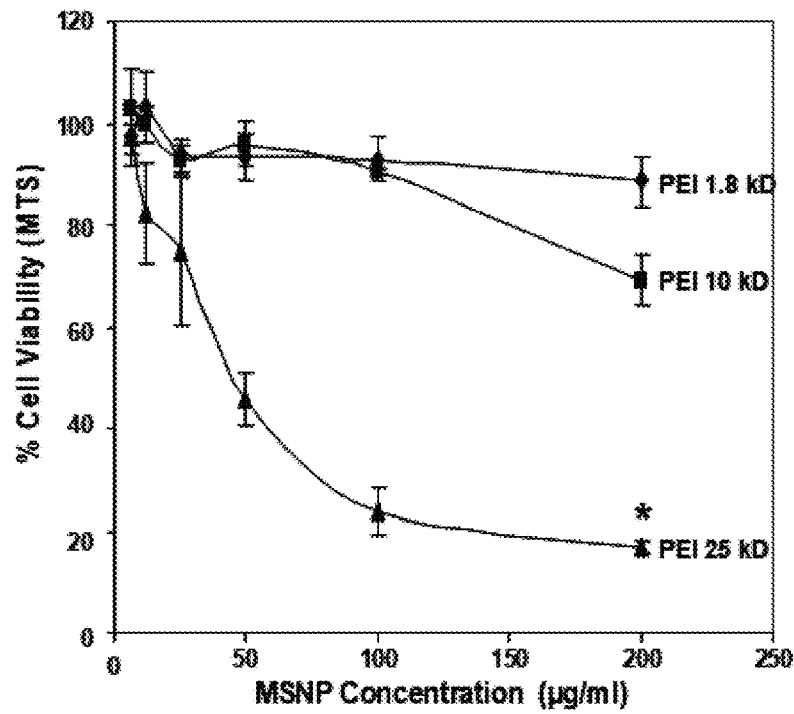
FIGS. 26A and 26B show assessment of PEI-MSNP safety in KB-V1 cells.
Figure 26B:
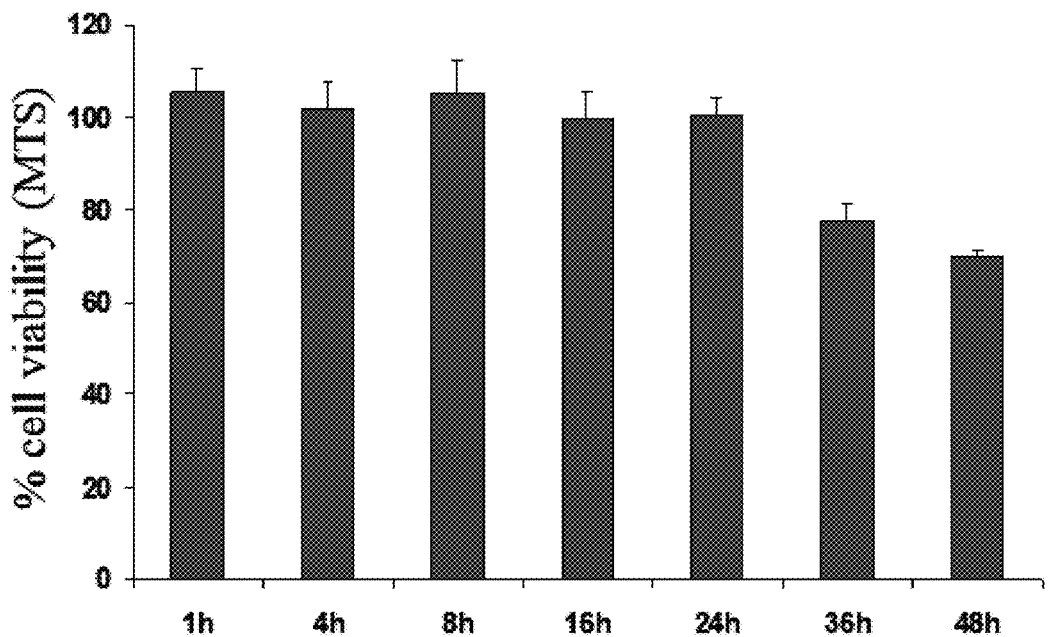

It is important to briefly mention the importance of selecting the correct PEI polymer size to prevent particle toxicity (Xia et al., *ACS Nano*, vol. 3, pp. 3273-3286, 2009; Meng et al., *ACS Nano*, vol. 3, pp. 1620-1627, 2009; Lin et al., Chem. Mater., vol. 21, pp. 3979-3986, 2009). It is well known that PEI exerts cytotoxic effects when used by itself or attached to the nanoparticle surface as a polyplexing agent (Xia et al., *ACS Nano*, vol. 3, pp. 3273-3286, 2009). In this regard, 25 kD PEI polymer as well as high doses of the 10 kD polymer can render the MSNP toxic as a result of the proton sponge effect in the lysosome (Xia et al., *ACS Nano*, vol. 3, pp. 3273-3286, 2009). For these reasons, the particle dose and exposure time may be limited to within safe limits to conduct Dox and siRNA delivery with PEI 10 kD polymer (FIG. 26). Curiously and somewhat paradoxically, siRNA delivery to the cytosol is also dependent on the proton sponge effect of the PEI-coated particle and in this case, the lysosome appears to be a key organelle in the dual drug delivery paradigm.

Figure 32A:
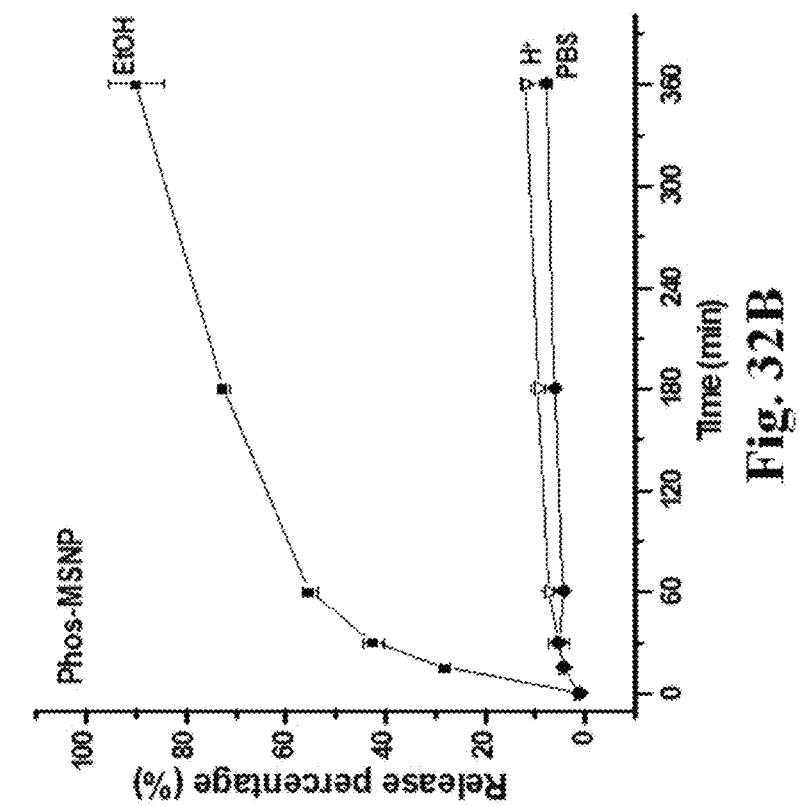
FIGS. 32A and 32B show loading and release profile of CPT loaded MSNP with various surface modifications.
Figure 32B:
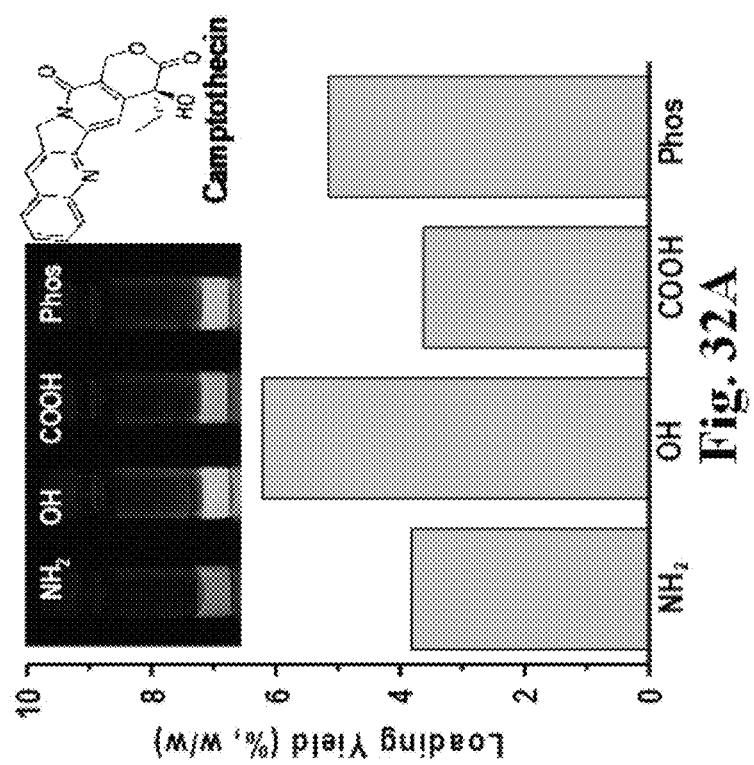

Above design features extend the utility of MSNP as a drug delivery platform for chemotherapeutic agents. In addition to being able to deliver hydrophobic drugs such as campthothecin and paclitaxel, it is also possible to deliver water soluble drugs by a packaging and release mechanism that is quite different from the phase transition principle involved in hydrophobic drug delivery (see FIG. 32). While it is not possible to release hydrophobic drugs through an acidification mechanism, camptothecin can be extracted from phosphonate-MSNP pores by ethanol treatment (FIG. 32). The release characteristics of Dox are exactly opposite, namely a release response to protons but not ethanol (FIGS. 20C and D). Taken together, these results demonstrate the dynamic features of MSNP for obtaining optimal drug packaging and delivery.

Because Pgp overexpression is one of the major mechanisms of multiple drug resistance (MDR) in cancer cells, knockdown of Pgp gene expression by nanoparticle siRNA delivery could help to restore the intracellular drug levels to the concentrations required for induction of apoptosis and cytotoxicity. Thus, dual drug and siRNA delivery by nanoparticles can be used to overcome drug resistance in MDR cancer cells. The feasibility of the MSNP platform to improve the cytotoxicity of Dox by co-delivery of Pgp siRNA is demonstrated as proof-of-principle. Downregulation of Pgp expression allowed the intranuclear Dox levels to increase above the threshold required for inducing apoptosis and cell death. However, since the KB-V1 cell line expresses very high Pgp level that may go beyond the clinically relevant expression level, it may not be possible to restore drug sensitivity to the level seen in KB-31. It is reasonable to expect that the MSNP delivery platform will be more effective in a lesser Pgp expressing cell type. In addition, the MDR phenotype is quite complex and often involve a combination of drug resistance mechanisms such as increased efflux, blocked apoptosis, decreased drug influx, increased drug metabolism, and increased DNA repair (Gottesman et al., Annu. Rev. Med., vol. 53, pp. 614-627, 2002; Jabr-Milane et al., Cancer Treat. Rev., vol. 34, pp. 592-602, 2008). Preliminary research has revealed that 36 genes were either up- or down-regulated in KB-V1 cells compared to KB-31 cells. These genes can be categorized into several groups, including oxidative stress regulation (HBB, IDH), drug metabolism (HMGCS1, ACAT1), signal transduction (CGA, SGK), tumor suppression (PTEN), etc (Wang et al., Chin. J. Cancer Res., vol., 14, pp. 5-10, 2002). It is possible that these gene products could contribute to MDR besides Pgp overexpression. What additional mechanisms are involved is still uncertain but apparently does not involve Bcl-2 as inclusion of Bcl-2 with Pgp siRNA did not significantly improved cell killing. Understanding of abovementioned MDR mechanisms may provide new opportunity to develop more therapeutic components or combinations to achieve better therapeutic effects.

In conclusion, MSNP can be functionalized to act as a dual delivery vehicle for Dox as well as Pgp siRNA in a drug-resistant cancer cell line. To improve the drug sensitivity of KB-V1 cells, phosphonate attachment was used to deliver the therapeutic compound as well as the siRNA via a lysosomal processing pathway. This dual delivery system increased the intracellular Dox levels to the extent that it improves cytotoxic killing in this KB-V1 MDR cell line. This strategy could be an effective new approach for the treatment of cancers that develop multiple drug resistance.

Tuning Aspect Ratio of Mesoporous Silica Nanoparticles

Embodiments of the invention include submicron structure having a silica body defining a plurality of pores and an outer surface between pore openings of said plurality of pores, where the submicron structure has an average aspect ratio (AR) greater than 1.3, and where said submicron structure has a maximum dimension less than one micron.

In some embodiments the silica body may have an average aspect ratio greater than 1.4, greater than 1.5, greater than 1.7, greater than 1.8, greater than 1.9, greater than 2.0, greater than 2.1, greater than 2.2, or greater than 2.5. In some embodiments, the silica body may have an aspect ratio less than about 5, less than about 4.7, less about 4.5, less than about 4.3, less than about 4.0, less than about 3.7, less than about 3.5, less than about 3.3, less than about 3.0, less than about 2.7, or less than about 2.5.

As used herein, the average AR values were determined by a Transmission Electron Microscope (TEM), measuring the length and diameter of at least 30 randomly selected particles and averaging the individual AR values to produce the average AR.

In some embodiments, the submicron structure having an average AR greater than 1.3 may further include a core structure. Any core structure described herein may be used in these submicron structures, and may be prepared in the same way as spherical particles as modified to produce structures having AR greater than 1.3.

In some embodiments, the submicron structure having an average AR greater than 1.3 may further include a surface modification. Any surface modification described herein may be used in these submicron structures, and may be prepared in the same way as spherical particles described previously.

In some embodiments, the submicron structure having an average AR greater than 1.3 may further include a surface derivitization. Any surface derivitization described herein may be used in these submicron structures, and may be prepared in the same way as spherical particles.

In some embodiments, the submicron structure having an average AR greater than 1.3 may further include an oligonucleotide. Any oligonucleotide described herein may be used in these submicron structures, and may be prepared in the same way as spherical particles.

In some embodiments, the submicron structure having an average AR greater than 1.3 may further include a therapeutic compound. Any therapeutic compound described herein may be used, and may be prepared in the same way as spherical particles.

In some embodiments, the submicron structure having an average AR greater than 1.3 may further include an oligonucleotide-therapeutic compound combination. Any oligonucleotide-therapeutic compound composition described herein may be used, and may be prepared in the same way as spherical particles.

In some embodiments, the submicron structure having an average AR greater than 1.3 may further include an additional structural feature. Any additional structure feature described herein may be used, and may be prepared in the same way as spherical particles.

Submicron structure having an average AR greater than 1.3 may be used in any pharmaceutical compositions described herein, and may be prepared in the same way as pharmaceutical compositions of spherical particles.

Submicron structure having an average AR greater than 1.3 may be used in any method described herein, and may be used in the same way as spherical particles.

Although the aspect ratio (AR) of engineered nanomaterials (ENMs) is one of the key physicochemical parameters that could determine biological outcome, not much is understood about how this material property generates biological effects. By using a mesoporous silica nanoparticle (MSNP) library that has been constructed by a new anisometric synthesis method to cover a range of different lengths, it was discovered that the AR of rod-shaped particles determines the rate and abundance of MSNP uptake by an act of cellular uptake process in Hela and A549 cancer cell lines. For example, MSNPs with an AR of 2.1-2.5 were taken up in larger quantities compared to shorter or longer length rods by a process that is sensitive to amiloride, cytochalasin D, azide and 4 degrees C. inhibition, though all non-spherical MSNPs showed improved uptake. In some embodiments, rods with intermediary AR also induced the maximal number of filopodia, actin polymerization and activation of a small GTP-binding protein, Rac1, which controls the actin assembly and filopodia formation. When assessing the role of AR in the delivery of paclitaxel or camptothecin, rods with AR 2.1-2.5 may be the most efficient for drug delivery and generation of cytotoxic killing in Hela cells. These data suggest an active sensing mechanism by which Hela and A549 cells are capable of detecting AR differences in MSNP to the extent that accelerated macropinocytosis can be used for more efficient drug delivery.

Some embodiments of the current invention may include non-spherical MSNP nanocarriers that are capable of maximizing delivering efficiency and bioavailability to a variety of cancer cells. Moreover, there is active recognition of particles with a long AR, which may form the basis for developing nanoparticle shapes that can be used for studying biological response pathways that can be used for understanding basic cellular mechanisms of improved drug delivery by nanocarriers.

Compared with spherical MSNP nanocarrier, key advantages of rod-shaped MSNP can include:

(1) Unlike existing technology for enhancing cellular uptake by cationic surface functionalization of MSNP, AR tuning of MSNP is capable of promoting cellular uptake and thereby improving the bio-availability of MSNP nanocarrier by activating a specific cellular acute uptake process (macropinocytosis). This method of enhancing MSNP uptake is not associated with the potential cytotoxicity of cationic carriers.

(2) The AR effect allows us to add a shape design feature to the list of tunable MSNP properties that can be exploited to improve drug delivery. This additional feature may be combined with other approaches, described herein, to deliver therapeutic compounds.

In general, compared with other nanocarriers capable of drug delivery, advantages of MSNP based nanocarriers can include:

(1) MSNP has little or no intrinsic toxic potential, are extensively used as food additives; MSNP is biologically inert when injected intravenously at high dose in rodents and are also biologically degradable and excretable.

(2) MSNP constitute an efficient multi-functional platform including cargo delivery (e.g. anticancer drugs, siRNA/DNA), targeting, controlled release, and for the purposes of bio-imaging because of its unique silica-based composition and ease of surface modification.

(3) Ease of chemical synthesis and versatile functionalization methods allowing us to design various and customized MSNP including changing AR. Physicochemical characteristics (e.g. particle size, surface charge, hydrophilicity, pore size) are tunable.

(4) Improved ability to deliver poorly water-soluble drugs by making use of phase transition trapping in the pores;

(5) Allows co-delivery of two or more drugs or therapeutic modalities (e.g., drugs and siRNA) for combination therapy;

(6) Versatile functionalization methods (organo-silanes) allowing ligand (e.g. folate, transferrin) conjugation for targeted delivery of drugs in a cell- or tissue-specific manner;

(7) Visualization of sites of drug delivery (theranostics) by combining therapeutic agents with imaging modalities such as iron oxide nanoparticles for MM or probes for fluorescent imaging;

(8) Potential to extend of the patent life of proprietary drugs that are being delivered more efficiently as a new drug formulation.

(9) Low cost and ease of large-scale production; It is simple for particle purification through centrifugation procedures.

Briefly, MSNP with different AR may be chemically synthesized by a sol-gel approach using a surfactant/co-structure direct agent (CSDA) mixture as template.

In some non-limiting embodiments described further in the examples below, different shaped MSNP and AR were synthesized by varying the PFONCT AB molar ratio as follows: 0 (AR=1), 0.015 (AR=1.5-1.7); 0.03 (AR=2.1-2.5), 0.06 (AR=4-4.5). The PFOA/CTAB mixture was stirred at 600 rpm for 1 h at room temperature before the addition of 2.1 mL 2 M NaOH. Subsequently, the solution temperature was raised to 80° C. before the addition of 4.1 mL of silica precursor. This mixture was stirred for an additional 2 h and the precipitate was carefully collected by filtration. The MSNP templates were removed by extracting the CTAB with HCl containing methanol under nitrogen protection. The resulting MSNP were collected by filtration, washed by methanol, and dried overnight in air.

To visualize the particles under a confocal microscope or perform flow cytometry, fluorescent-labeled MSNP were prepared. In order to determine the uptake mechanism of rod-shaped MSNP, confocal microscope, flow cytometry, transmission electron microscopy, electron tomography, macropinocytosis inhibitor experiments were performed. In order to determine the capability of drug delivery using different particle types, two hydrophobic anticancer drugs, Taxol and camptothecin (CPT), were loaded into different MSNP using 20 mg of each type of particles suspended into a solution containing 0.5 mg of each drug in 1 mL DMSO. After 24 h, the particles were collected by centrifugation, and the trace amounts of DMSO were removed by drying under vacuum. The loading capacity of the particles was measured by microplate reader. MSNP, loaded with CPT or Taxol, were incubated with the cancer cells. The cell killing capability was assessed by an MTS assay.

Some embodiments of the current invention can best be implemented in practice to deliver anticancer drugs in human carcinoma disease that can benefit from a nanotherapeutic MSNP platform. The examples described below demonstrates the improvement of cellular uptake, bio-availability and cell killing capability of drug loaded MSNP in cancer cells. Some practical implementations can include the non-spherical platform used with FDA approved drugs to treat cancers in human subjects. However, the invention is not limited to this example. It is also envisaged that the use of MSNP shape and AR can be useful for other therapeutic areas where drug uptake could be enhanced by AR modification.

Due to the rapid evolution in the techniques that are used to synthesize engineered nanomaterials (ENMs), it is possible to construct different shapes from a single base material, including spheres, rods, disks, ellipsoids and cylinders.[1-5] Besides spherical nanoparticles that have been intensively investigated, non-spherical ENMs with a high aspect ratio (AR) are of great interest since this physicochemical feature has been shown to have a disproportionate impact on biological outcome,[1,3] including determining the rate of cellular uptake,[1] the mechanism of uptake,[1,6] particle transportation,[7,8] biodistribution,[2] and biocompatibility.[9,10] How exactly AR impacts cellular function is unknown but of considerable importance in understanding how to improve nanomaterial safety and delivery through the use of a physical design feature. In order to understand the impact of AR on cellular function, it is necessary to construct a series of ENMs that show AR variation of the same base material. One example has been the synthesis of triacrylate or monomethacrylate nanoparticles through the PRINT fabrication technique, allowing these investigators to look at the uptake of cylindrical particles that exhibit an AR of 1-3 in Hela cells.[1] The authors demonstrated that the particles with an AR of 3 (450 nm>150 nm) were taken up four times more rapidly than the particles with an AR of 1. Another example is the use of a batch of colloidal gold nanoparticles, composed of spheres (14 nm and 74 nm) and rods (14 nm×74 nm) to study cellular uptake in Hela cells.[4] This demonstrated a 2-4 times higher uptake of spherical gold nanoparticles compared to rod-shaped particles with an AR of 5.

A mesoporous silica nanoparticle (MSNP) library was prepared composed of spherical and rod-shaped particles to study the impact of AR variation on cellular uptake in Hela and A549 cancer cells. The advantage of using mesoporous silica is that this material is useful for drug delivery studies as well as safety studies on ENMs.[11-13] AR effects on MSNP cellular uptake would add another design feature that will extend the utility of this multifunctional platform that can be tuned for drug delivery by controlling pore opening with nanovalves, surface ligation, surface charge variation, etc.[12-18] In some examples, described below, data demonstrate that rod-shaped MSNP with an AR of 2.1-2.5 is preferentially endocytosed by an active uptake mechanism that is able of distinguishing these intermediary length from longer and shorter rods, though all non-spherical particles produced exhibited higher active uptake than spherical particles. This implies a cellular mechanism capable of discerning and responding to rod length. Further investigation of the molecular pathway that controls filopodia formation and macropinocytosis demonstrated that intermediary length rods that are capable of stimulating GFP uptake in Rac1, leading to cytoskeletal activation and formation of filopodia. Intermediary length rods may be more effective for the delivery of chemotherapeutic agents to Hela cells.

The examples below demonstrate that Hela and A549 cells endocytose rod-shaped MSNP through a macropinocytosis process that is capable of discerning the AR and adapting the cellular response. In some examples, uptake is maximal for particles with an AR of 2.1-2.5. This differential effect involves filopodia formation that is linked to activation of the actin cytoskeleton by a small GTP-binding protein. Without wishing to be bound by theory, These findings suggest a mechanosensitive mechanism that is capable of translating variations in AR into GTP loading of Rac1. Particles taken up into the pinocytotic vesicles are shuttled into an acidifying lysosomal compartment and can be used to deliver of hydrophobic chemotherapeutic drugs. This utility was demonstrated by the delivery of Taxol and CPT in Hela cells, with maximum cytotoxicity being achieved when the drugs are loaded into rods with an AR of 2.1-2.5.

Current research in the field of biomaterials is witnessing the emergence of a powerful set of new design parameters, including the use of physical shape at micron and nanoscale levels to control biological responses.[3,8,10,39] Shape is an important physical characteristic and has an important role in modeling cellular responsiveness and associated applications in biotechnology.[1] Theoretical models and experimental studies have confirmed the benefits of using non-spherical particles for drug delivery based on their effects on cellular internalization and vascular dynamics.[1,2,7,40] This includes a demonstration that for micron-size particles the local geometry at the point of contact with the cell membrane rather than the overall particle shape dictates whether macrophages initiate internalization.[39] In this regard, it has been demonstrated that when a macrophage encounters an elliptical disc at its pointed edge or side, the particle is rapidly phagocytosed within minutes whereas attachment of the flat side of the disc failed to initiate phagocytosis for an extensive time period.[6,8,39,41] The effect of geometry in phagocytosis could be quantified by measuring the angle between the membrane at the point of initial contact and the line defining the particle curvature at this point. If this angle exceeds a critical value of >45°, the cells lost the ability to entrap the particles.[3,39] The authors proposed that the particle shape at the point of attachment determines the type of actin rearrangements that are required for cellular uptake.[3,39] According to this view, the requisite actin structures can not form if the angle is >45°, leading the macrophages to instead switch to spreading behavior.[39]

At a much smaller length scale, Gratton et al. demonstrated that internalization of cylindrical particles depends on AR.[1] There, the authors evaluated internalization pathways of three different series of micro- and nanoparticles made from the cross-linked PEG-based hydrogels produced by the "particle replication in non-breaking templates" (PRINT) technique.[1] The synthesized materials included cubic microparticles, cylindrical microparticles and cylindrical nanoparticles (200×200 nm; 100×300 nm; 150×450 nm). While all the particles were internalized by Hela cells, the nanoparticles entered more rapidly, with the longer cylinders (150×450 nm) being captured more rapidly than cubic particles of nearly same volume (200×200 nm) or shorter cylinders of lower volume (100×300 nm). Particles with an AR of 3 were internalized about four times more rapidly than spheres of the same volume.[1] In contrast to the results for hydrogel particles, other studies have found that receptor-mediated endocytosis of Au nano-objects was significantly decreased with increased AR.[4,42,43] For instance, Au nanospheres with diameters of 14 nm or 74 nm were taken up three times more readily by Hela cells compared to 74×14 nm rods.[4] Muro et al. compared targeted accumulation of spheres of various diameters (ranging from 100 nm to 10 μm) or elliptical discs of microscale dimensions (1×3 μm) in tissues and found that the targeting efficiency of micron-scale discs is better than spheres, even those with nanoscale dimensions.[44]

The examples below enhance the understanding of the role of AR by demonstrating that for MSNP of the same chemical composition there is differential macropinocytosis of particles with an AR 2.1-2.5. Moreover, this effect is mediated through a pathway that involves Rac1 activation, the actin cytoskeleton and filopodia formation.[45] Not only is the demonstration that rod-shaped MSNP being capable of inducing macropinocytosis through Rac1 activation a novel finding, but also provides a platform for understanding how specific shape variations can be used to modulate cellular function. Macropinocytosis refers to the formation of large endocytic vesicles of irregular shape and size that is generated by actin-driven evaginations of the plasma membrane.[26] Macropinocytosis is an efficient route for the nonselective uptake of soluble macromolecules, and is either constitutive or stimulated by growth factors such as epidermal growth factor, platelet derived growth factor, macrophage colony-stimulating factor, interleukin-4 or phorbol esters.[26,30,46] Interestingly, these agents are all capable of initiating signaling pathways that activate Rae GTPase, which has also been shown to play a role in regulating macropinocytosis.[34] The occurrence of macropinocytosis in a variety of different cell types suggests that it contributes to cellular functions such as nutrient uptake,[47] host-pathogen interactions,[48] antigen processing[49] and directed cell movement.[47] Macropinocytosis differs from other endocytic mechanisms that are involved in the uptake of individual nanoparticles by smaller vesicles.[26] Different from clathrin-dependent, caveolae-mediated or caveolae- and clathrin-independent pathways,[50] macropinocytosis is dependent on signaling to the actin cytoskeleton and actin-driven membrane movement.[26,33] This results in membrane ruffling and the formation of filopodia that are necessary for the closure of the macropinocytotic vesicles.[26] The intracellular fate of macropinosomes varies depending on the cell type but in most cases end up fusing with lysosomes and shrinking.[47]

A key question that remains is how the differences in AR are being discerned and translated into Rac1 activation and actin assembly in Hela and A549 cells? While an exact explanation is unavailable, it is worthwhile considering the role of the integrated-adhesome network that responds to complex chemosensitive and mechanosensitive environmental cues in the extracellular matrix (ECM).[51] Cells demonstrate an extraordinary ability to respond to a wide range of physical signals, either locally or globally and are capable of reacting to ECM topography, including its rigidity,[52] spatial organization and anisotropy.[51,53] The crucial scaffolding interactions involved in the link of the ECM to the actin cytoskeleton involve actin-polymerizing and actin-linking modules associated with the integrin-receptor system.[51] This system as a whole is mechanoresponsive and numerous studies have demonstrated that the biochemical characteristics of the ECM, including its spatial organization, are recognized by cells as a result of differential signaling from integrin-based molecular complexes.[51,54] This molecular machinery can be viewed as a network of tightly interconnected modules that contains ~700 links, most of involve binding interactions with the rest consisting of pathways that modify those interactions.[51] The biological activities of the adhesive components are quite diverse and include several actin regulators that affect the organization of the attached cytoskeleton. These include adapter proteins that link actin to integrins (directly or indirectly) as well as a wide range of signaling molecules, including kinases, phosphatases and G-proteins and their regulators.[51]

How could this model apply to the sensing and response to AR variations of a nanomaterial? While it is unlikely that integrins are directly involved in this process, MSNPs may be decorated with serum proteins that could act as ligands on the particle surface. However, this is an unlikely explanation because macropinocytosis differs from receptor-mediated endocytosis that classically proceed via caveolae or clathrin-mediated uptake. Another possibility is that AR variation could be detected at the contact site of the nanoscale spheres and rods with the cell surface membrane or the interior of the lipid bilayer that enwraps the macropinocytotic vesicles. In this regard, it has been demonstrated that silanol groups on silica nanoparticles are capable of interacting with membrane lipid compounds and possibly also with electrostatically charged membrane proteins.[55,56] It is possible that the number and spatial distribution of these contact sites may be capable of relaying information to Rae 1 by a transduction process that either involves GTP loading via a guanine nucleotide exchange factor or inhibiting the activity of a Rac1 GTPase. The exquisite sensitivity of cells to variations in adhesive patch spacing at the nanoscale level has been demonstrated through the use of nano-lithography approaches, e.g., positioning of nanoscale gold particles (1-15 nm) in spatial arrangements or formation of spacing gradients that can be tuned at 10-200 nm scales.[51,57,58] Examination of cellular spreading on these surfaces have demonstrated that the weakest gradient to which cells can respond corresponds to a strength of ~15 nm per mm, provided that the interparticle spacings remained at 58-73 nm.[51,59,60] Given a typical spreading length of 60 µm, the implication is that cells can respond to 1 nm differences in average ligand patch spacing between the front and rear end of the cell.[51] Thus, the sensitivity to small variations in interparticle spacing is quite remarkable and probably achievable in a time-integrated manner.[51] Interestingly, these variations are much smaller than the typical variations in the inter-ligand spacing that governs integrin interactions with the ECM. Thus, given this exquisite sensitivity at the nanoscale level, a related mechanism may be involved in detecting AR differences in rod-shaped MSNP.

Figure 52B:
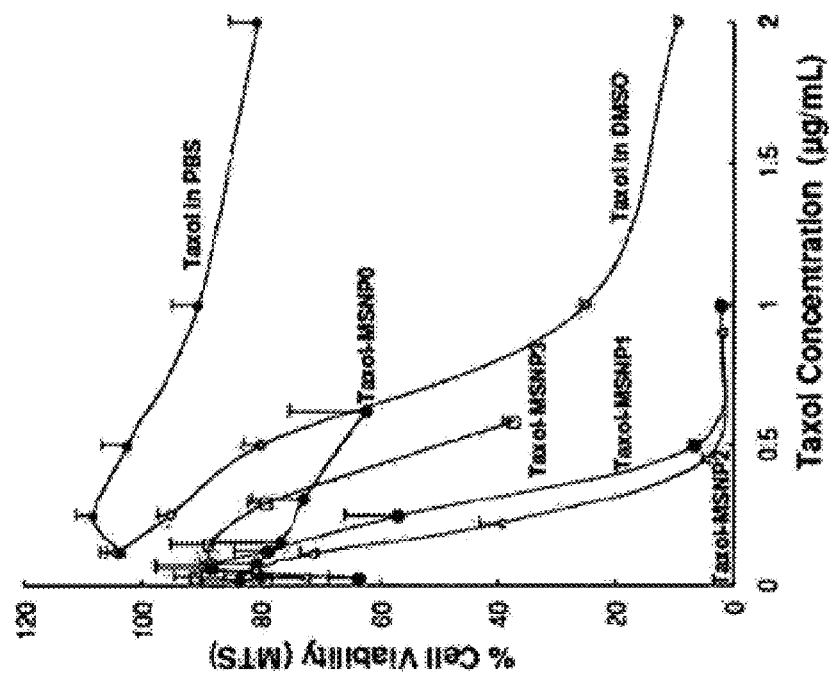
FIGS. 52A and 52B show results of an MTS assay comparing the cytotoxic effects of free CPT and Taxol delivered by the different MSNP types.
Figure 52A:
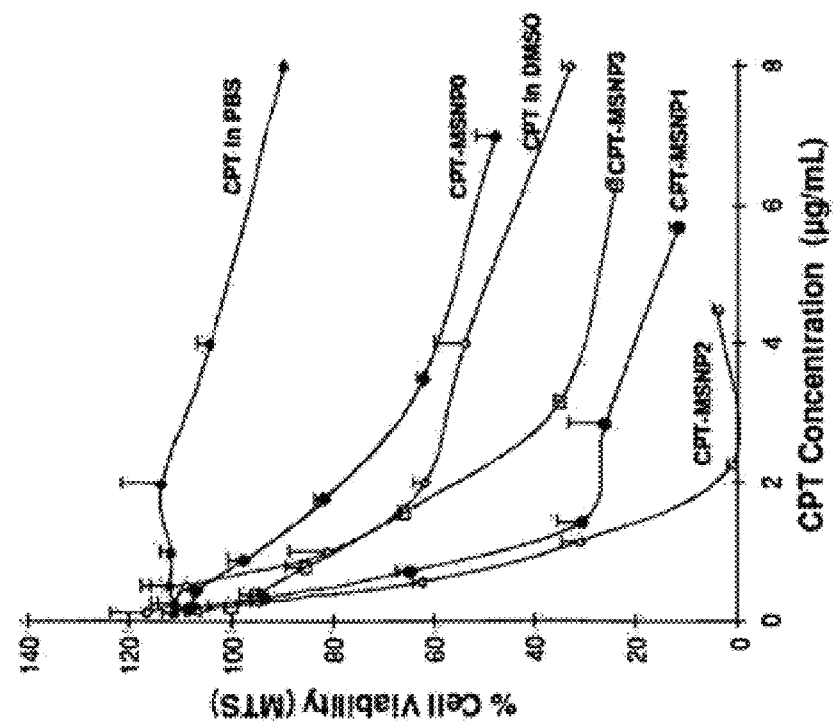
Figure 59:
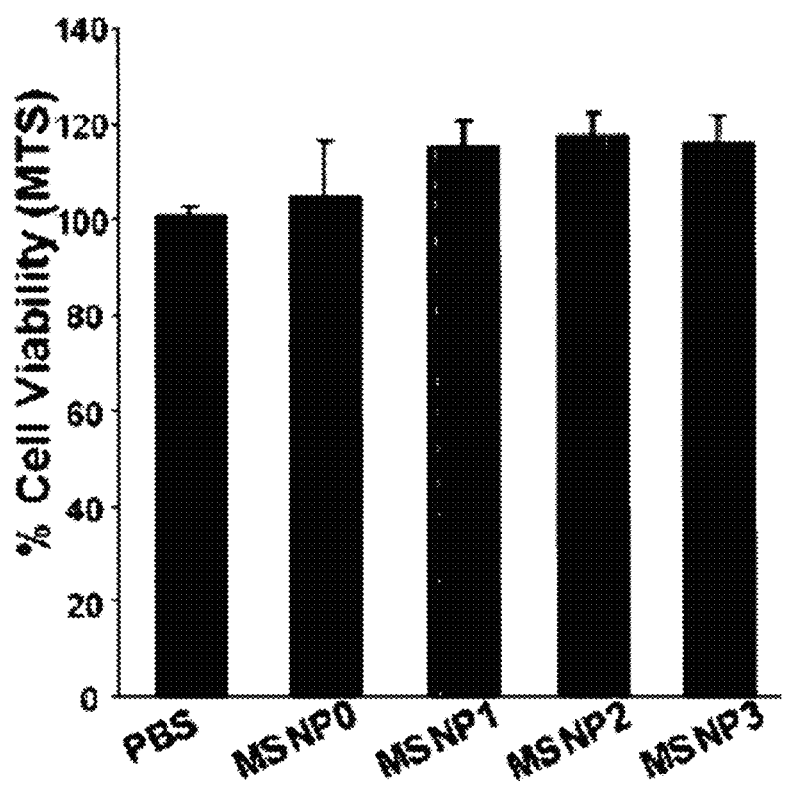
FIG. 59 shows cell viability determination using a MTS assay. $1\times10^4$ Hela cells in 100 μL completed RPMI were plated onto 96-multi-well plates (Costar; Corning, N.Y.). After incubation with various empty particles at doses of 200 μg/mL for 36 h, Hela cells were incubated with the MTS reagent for 2 h and the absorbance measured at 490 nm. The treatment by adding 5 μL PBS into cultured cells serves as control. The MSNP themselves were devoid of toxicity.

Not only do these results advance understanding of the mechanism by which AR differences change cellular uptake, but also adds a shape design feature to the list of tunable MSNP properties that can be exploited to improve drug delivery.[11,15,61,62] Accumulated evidence indicates that spherical nano carriers may not be optimal drug delivery devices due to the poor cellular uptake and unsatisfactory biodistribution compared to disc-shaped objects or particles exhibiting a long AR.[1,2,7] To improve cellular uptake of MSNP, better uptake can be achieved by non-covalent attachment of the cationic polymer, polyethyleneimine, to the particle surface.[12,13] However, cationic functionalization may lead to cytotoxicity.[12,13] Improved delivery and killing in Hela cells may be achieved using particle with higher aspect ratio, for example, an AR of 2.1-2.5 (FIGS. 52 and 59). To further understand the bio-behavior of AR particles in vivo, animal experiments are being performed to test the efficacy of a non-spherical MSNP delivery system.

Through the use of AR variation in a designed batch of MSNPs it can be demonstrated that cells actively respond to the shape change by changing particle uptake through a macropinocytosis process. Not only can Hela and A549 cells distinguish between specific ARs, but also are capable of translating this recognition into activation of Rac1, control actin assembly and optimal filopodia formation that leads to maximal uptake of intermediary length rods. This active uptake process can be inhibited by a list of inhibitors (amiloride, Cyto D and NaN$_3$/2-DG) or dropping the culture temperature to 4° C. In some examples, intermediary length MSNP with an AR of 2.1-2.5 are more efficient at delivery hydrophobic chemotherapeutic agents to Hela cells.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Terms listed in single tense also include multiple unless the context indicates otherwise.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

EXAMPLES

Reagents

Tetraethylorthosilicate (98%), cetyltrimethylammonium bromide (CTAB, 95%), fluorescein isothiocyanate (FITC, 90%), polyethyleneimine (MW 1.2 and 25 KD), poly(ethylene glycol) methyl ether (MW 5 KD), N,N'-disuccinimidyl carbonate (DSC, 95%), 4-(dimethylamino)pyridine (DMAP, 99%), aminopropyltriethoxysilane (APTS, 99%), 3-(trihydroxysilyl)propyl methylphosphonate (42%), succinic anhydride (99%), fluorescamine, paclitaxel, propidium iodide (PI), β-actin antibody, and bovine serum albumin (BSA) were from Sigma (St. Louis, Mo.). Polyethyleneimine (MW 0.6, 1.8, and 10 KD) were from Alfa Aesar (Ward Hill, Mass.). The MTS assay kit was from Promega (Madison, Wis.). Dulbecco's Modified Eagle's medium (DMEM), penicillin/streptomycin, and L-glutamine were purchased from Invitrogen (Carlsbad, Calif.). Fetal calf serum (FCS) was from Atlanta Biologicals, Inc (Lawrenceville, Ga.). siRNA for GFP knock down was purchased from IDT Technologies (Coralville, Iowa). For all experiments and analyses, water was de-ionized and filtered with a 0.45 μm pore size polycarbonate syringe filter (Millipore, Billerica, Mass.). All chemicals were reagent grade and used without further purification or modification.

MSNP Dispersion and Use to Perform Tissue Culture

All cell cultures were maintained in 25 cm² cell culture flasks in which the cells were passaged at 70-80% confluency every 2-4 days. RAW 264.7, BxPC3, PANC-1, and HEPA-I cell lines were cultured in Dulbecco's Modified Eagle Medium (DMEM) (Carlsbad, Calif.) containing 10% fetal calf serum (FCS), 100 U/ml penicillin, 100 μg/ml streptomycin, and 2 mM L-glutamine (complete medium). BEAS-2B cells were cultured in BEGM (Charles City, Iowa) in type I rat tail collagen-coated flasks or plates. Cells were cultured at 37° C. in a humidified 5% $CO_2$ atmosphere. To disperse MSNP, the stock solution (in water) was sonicated (Tekmar Sonic Disruptor probe) for 15 sec prior to aliquoting. In order to coat the surface of MSNP with bovine serum albumin (BSA), the aliquoted NP suspension (~10 μl) was mixed with an equal volume of 4% BSA. Tissue culture media (1 ml) was added to the BSA coated MSNP suspension. Cell culture media deprived of serum (e.g. BEGM) was modified by addition of BSA at a concentration of 2 mg/ml. The cell culture media containing MSNP at the desired concentration was sonicated for 15 sec and characterized as described before.

Assays for Cellular Viability and Mitochondrial Function

Cellular viability was determined by the MTS assay, which looks at the reduction of (3-(4,5-dimethylthiazo 1-2-yl)-5-(3-carboxymethoxyphenyl)-2-(4-sulfophenyl)-2H-tetrazolium (MTS) to formazan in viable cells. Briefly, $2\times10^4$ cells were plated onto 96 multi-well plates (Costar; Corning, N.Y.). After incubation with the indicated dose of MSNP for various lengths of time at 37° C., formazan absorbance was measured at 490 nm. The mean absorbance of non-exposed cells served as the reference for calculating 100% cellular viability.

Cell death and mitochondrial function were detected using propidium iodide (PI) uptake and JC-1 fluorescence. Fluorescent probes were diluted in DMEM before the addition to cells for 30 min at 37° C. in the dark: (i) 5 μg/ml propidium iodide (PI) in 200 μl DMEM (assessment of cell death); (ii) 5 μM JC-1 (assessment of $\Delta\Psi m$). Flow cytometry was performed using a LSR (Becton Dickinson, Mountain View, Calif.). PI was analyzed in FL-2 and JC-1 was analyzed in both FL-1 and FL-2. Forward and side scatter were used to gate out cellular fragments.

Assessment of Cellular MSNP Uptake by Flow Cytometry and Confocal Microscopy

For the performance of flow cytometry, aliquots of $5\times10^4$ cells (RAW 264.7, BEAS-2B, PANC-1, and BxPC3) were cultured in 48-well plates in 0.4 ml medium. RITC-labeled MSNP with a phosphonate surface coating were added to the above cultures at a dose of 25 μg/ml for 30 minutes, followed by incubation with the FITC-labeled MSNP-PEI series at final concentrations of 25 μg/ml for 3 hr. All cell types were trypsinized and washed with trypan blue to quench the fluorescence of cell surface attached MSNP. Cells were analyzed in a LSR flow cytometer using mean FL-2 and FL-1 to assess RITC and FITC fluorescence, respectively. Data are reported as fold increase above control (cells without MSNP).

Cellular uptake of MSNP was performed by adding 25 μg/ml of the various MSNP to 8-well chamber slides (Nunc) in which $5\times10^4$ cells were cultured in each well containing 0.4 ml culture medium. Cell membranes were stained with 5 μg/ml wheat germ agglutinin (WGA) Alexa Fluor® 594 conjugate in PBS for 30 min. Slides were mounted with DAPI (Molecular Probes, Eugene, Oreg.) and visualized under a confocal microscope (Leica Confocal lP/FCS) in the UCLA/CNSI Advanced Light Microscopy/Spectroscopy Shared Facility. High magnification images were obtained with a 63× objective. Optical sections were averaged 2-4 times to reduce noise. Images were processed using Leica Confocal Software.

Example 1—Synthesis and Surface Modification of Mesoporous Silica Nanoparticles MSNP The basic synthesis of MSNP was conducted by mixing the silicate source tetraethylorthosilicate (TEOS) with the templating surfactants cetyltrimethylammonium bromide (CTAB) in basic aqueous solution (pH 11). In a round bottom flask, 100 mg CTAB was dissolved in a round-bottom flask containing solution of 48 ml distilled water and 1.75 ml sodium hydroxide (2 M). The solution was heated to 80° C. and stirred vigorously. After the temperature had stabilized, 0.5 ml TEOS was added slowly into the heated CTAB solution. After 15 min, 0.23 mmol of the organosilane solution was added into the mixture. 3-trihydroxysilylpropyl methylphosphonate was used for phosphonate surface modification, and aminopropyltriethoxy silane (APTS) was used for amine surface modification. After 2 hr, the solution was cooled to room temperature and the materials were washed with methanol using centrifugation. In order to incorporate fluorescent dye molecules in the silicate framework, fluorescein-modified silane was first synthesized and then mixed with TEOS. To synthesize fluorescein-modified silane, 2.4 µL APTS was mixed with 1 mg fluorescein isothiocyanate (FITC) in 0.6 ml absolute ethanol, and stirred for 2 hr under inert atmosphere. In another formulation, rhodamine B isothiocyanate (RITC) was used instead of FITC to synthesize rhodamine B-modified APTS. The dye-modified silane was then mixed with TEOS before adding the mixture into the heated CTAB solution. The surfactants were removed from the pores by refluxing the particles in a mixture of 20 ml methanol and 1 ml hydrochloric acid (12.1 M) for 24 hr. The materials were then centrifuged and washed with methanol.

For the poly(ethylene glycol) modification, 1 g of poly (ethylene glycol) methyl ether (MW 5 KD, mPEG) was dried under vacuum for 30 min and dissolved in 5 ml dioxane (with slight heating). mPEG has only one reactive end that can be attached to the particle surface and limits the coupling process only to that end, whereas normal PEG has two reactive ends and may cause particle cross-linking. 307.4 mg disuccinimidyl carbonate (DSC) was dissolved in 2 ml anhydrous DMF (with slight heating) and mixed with the mPEG solution. 146.6 mg 4-(dimethylamino)pyridine was dissolved in 2 ml acetone and added slowly into the mPEG solution The mixture was stirred for 6 hours under an inert atmosphere. The polymer was precipitated by the addition of 30 ml diethyl ether to the solution and separated by centrifugation. After washing the polymer twice with diethyl ether, the activated mPEG was dried under vacuum. 60 mg of amine-modified MSNP was washed and resuspended in 2 ml anhydrous DMF. 300 mg of the activated mPEG was dissolved in 9 ml DMF and mixed with the particles. The mixture was stirred for 12 hr and washed thoroughly with DMF and PBS.

To perform polyethyleneimine (PEI) modification, 5 mg of phosphonate-modified MSNP were dispersed in a solution of 2.5 mg PEI (MW 25 KD) and 1 ml absolute ethanol. The process to coat the particles with other PEI polymers (MW 0.6, 1.2, 1.8, 10 KD) was carried out similarly. After the mixture was sonicated and stirred for 30 min, the particles coated with PEI were washed with ethanol and PBS. Thermogravimetric analysis showed that the amount of PEI on the particles was approximately 5 weight percent. To succinylate the PEI 25K-coated particles, 1 mg particles were resuspended in 0.25 ml anhydrous DMF and mixed with different amounts of succinic anhydride (0.15 mg, 0.075 mg, and 0.015 mg). The mixture was sonicated and stirred overnight. The succinylated particles were washed with DMF and resuspended in PBS. To fluorescently label PEI (MW 25 KD), 60 mg of PEI 25 KD was dissolved in 10 ml carbonate buffer (pH 9) and mixed with 1 mg rhodamine B isothiocyanate dissolved in 1 ml DMSO. The mixture was stirred for 24 hr at 4° C. and dialyzed against distilled water. The rhodamine B-labeled PEI 25K was attached to the particles by using similar procedure for the unlabeled PEI.

Example 2—Physicochemical Characterization of the NP

MSNP were synthesized according to a modified procedure previously described (Radu et al., J. Am. Chem. Soc., vol. 126, pp. 13216-13217, 2004; Cai et al., Chem. Mater., vol. 13, no. 2, pp. 258-263, 2001). All MSNP were characterized for size, size distribution, shape, and charge (Table 1).

TABLE 1

Size distribution of MSNPs in aqueous solutions.

| | Size (nm) | | | | Zeta Potential (mV) |
| --- | --- | --- | --- | --- | --- |
| | $H_2O$ | DMEM 10% Serum | BEGM | BEGM 2 mg/ml BSA | $H_2O$/DMEM + serum/BEGM + BSA |
| MSNP-OH | 1966 | 408 | 1096 | 416 | −10.5/−6.8/−7.2 |
| MSNP-Phosphate | 1975 | 306 | 867 | 439 | −8.9/−6.5/−5.8 |
| MSNP-PEG | 2675 | 405 | 1215 | 542 | −10.4/−5.9/−4.5 |
| MSNP-PEI 0.6 KD | 1689 | 415 | 1243 | 474 | +29.5/−7.8/−65. |
| MSNP-PEI 1.2 KD | 1684 | 452 | 1298 | 502 | +38.7/−6.5/−7.1 |
| MSNP-PEI 1.8 KD | 1053 | 510 | 1087 | 550 | +36.9/−5.4/−3.2 |
| MSNP-PEI 10 KD | 614 | 702 | 917 | 684 | +34.1/−7.5/−6.9 |
| MSNP-PEI 25 KD | 1473 | 1043 | 1544 | 825 | +30.8/−5.9/−4.0 |

Particle size and zeta potential in solution were measured by a ZetaSizer Nano (Malvern). DMEM = Complete Dulbecco's Modified Eagle Media, which contains 10% fetal calf serum (FCS). BEGM = Bronchial Epithelial Growth Medium, which includes growth factors, cytokines, and supplements (no serum).

The shape and structure were characterized using a transmission electron microscope (JEOL JEM 2010, JEOL USA, Inc., Peabody, Mass.). Microfilms for TEM imaging were made by placing a drop of the respective particle suspension onto a 200-mesh copper TEM grid (Electron Microscopy Sciences, Washington, Pa.) and then drying at room-temperature overnight. A minimum of 5 images of each sample was collected to obtain representative views. Particle size and zeta potential in solution were measured by ZetaSizer Nano (Malvern Instruments Ltd., Worcestershire, UK). This instrument measures the light scattering (DLS) from a suspension at an angle of 173°. Size measurements were performed on dilute suspensions in water or complete cell culture media at pH 7.4. The ZetaSizer Nano was also used to measure the electrophoretic mobility of the MSNP suspended in solution. Electrophoretic mobility is used as an approximation of particle surface charge and can be used to calculate zeta potential. The Helmholtz-Smoluchowski equation was used to recalculate electrophoretic mobility into zeta potential.

Figure 9:
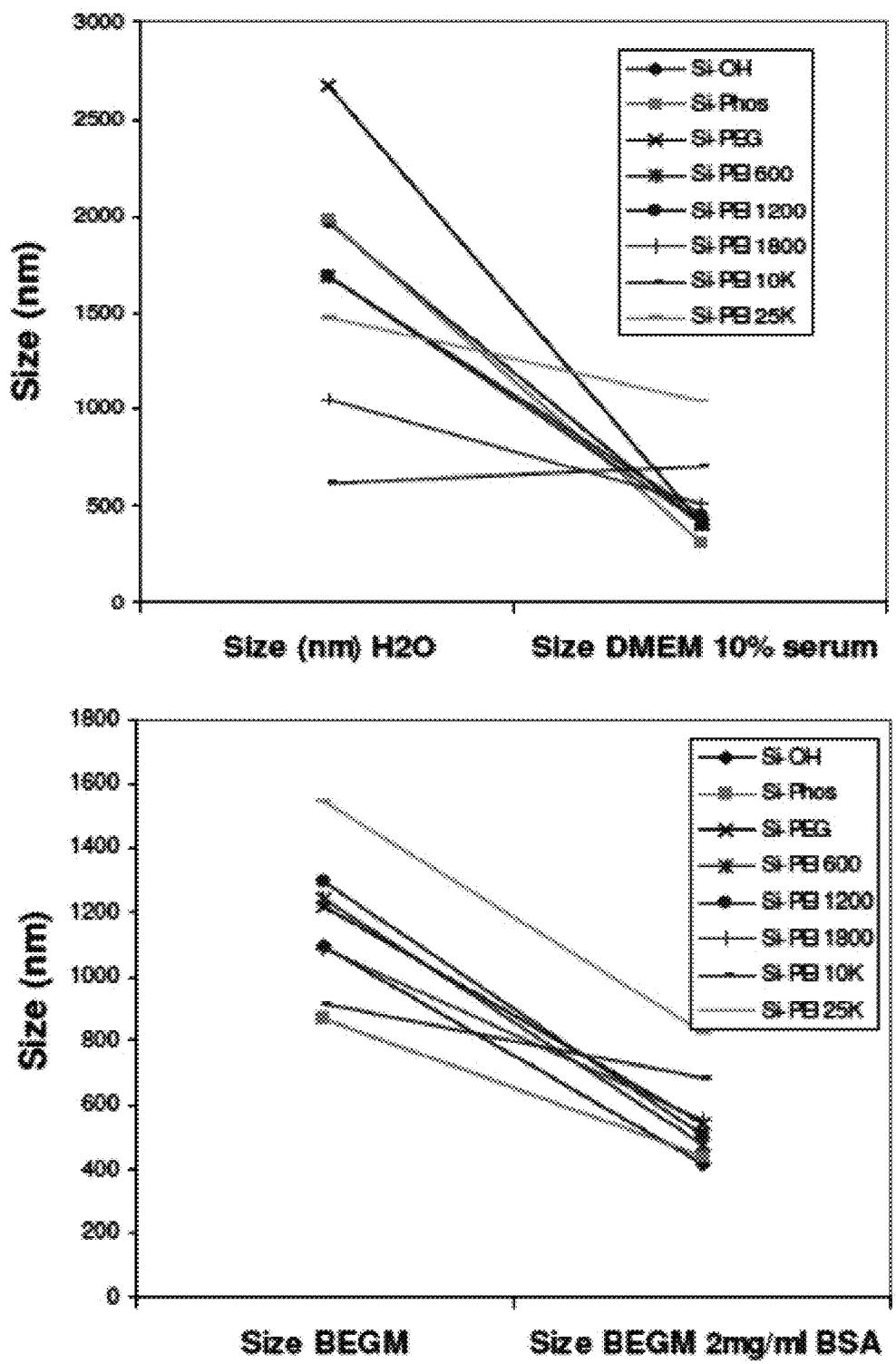
FIG. 9 shows MSNP size distribution in aqueous solutions. Dynamic light scattering (DLS) for MSNP exhibiting different surface modifications was performed in water, DMEM plus 10% FCS, BEGM or BEGM plus 2 mg/ml BSA. The presence of serum and BSA in the cell culture media improves MSNP dispersity.

The primary particle size is in the 100-130 nm range with a uniform pore size ~2.5 nm as shown by TEM (FIG. 1). To conduct biological experimentation, particle size and zeta potential were measured in water as well as tissue culture media (Xia et al., *ACS Nano*, vol. 2, pp. 2121-2134, 2008). For the purposes of this study DMEM supplemented with 10% fetal calf serum (FCS) or BEGM was used as is or supplemented with 2 mg/ml BSA (Table 1). The addition of protein leads to improved particle dispersal by countering the colloidal forces that promote particle aggregation in salt containing media (FIG. 9). While all of the non-PEI coated particles exhibited a negative zeta potential, PEI-coated particles showed a positive charge (Table 1). However, with the addition of FCS or BSA, all PEI-coated particles assumed a negative zeta potential.

Example 3—Differences in the Cytotoxic Potential of Anionic Vs Cationic MSNP

Figure 10A:
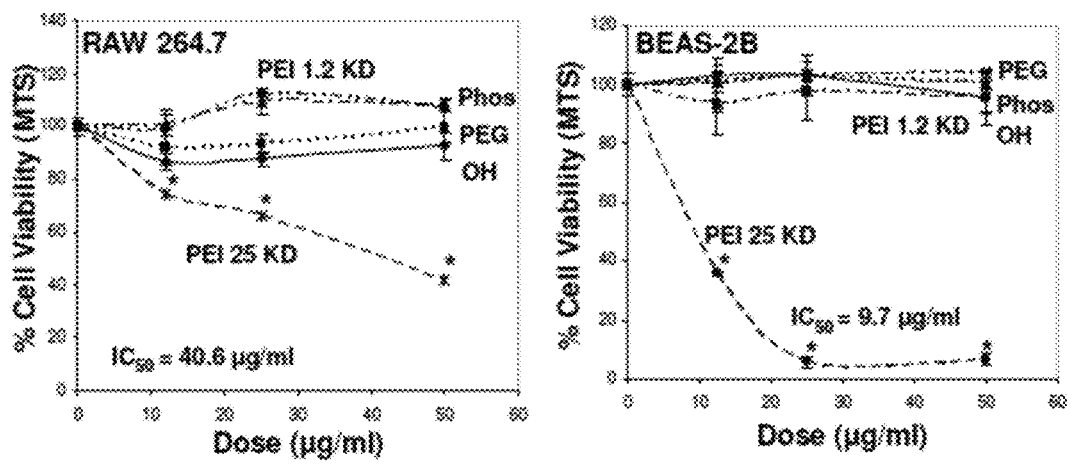
FIGS. 10A and 10B show assessment of cell viability and mitochondrial membrane potential (MMP) in RAW 264.7 and BEAS-2B cells.
Figure 10B:
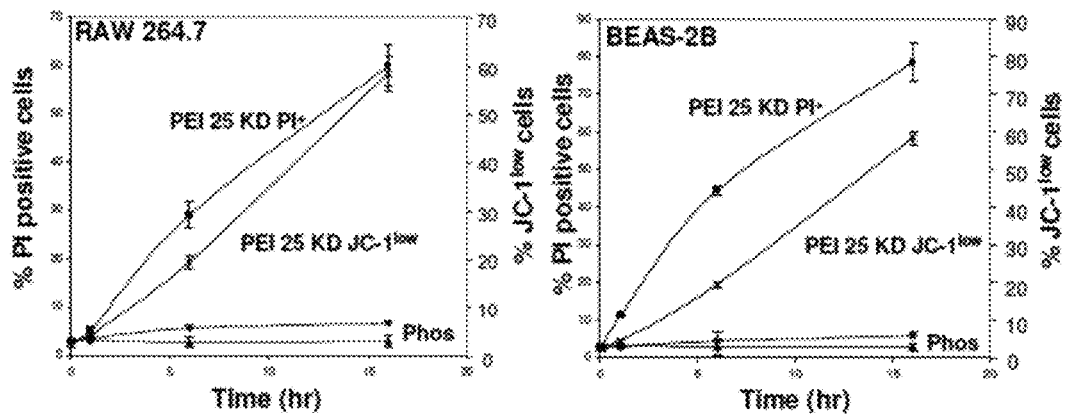

To screen for particle hazard, the MTS assay was used, which reflects dehydrogenase activity in healthy cells (Xia et al., *ACS Nano*, vol. 2, pp. 85-96, 2008). While most of the MSNP did not interfere in MTS activity in the PANC-1 and BxPC3 pancreatic cancer cell lines, particles coated with the 25 KD PEI polymer showed decreased cellular viability (FIG. 1). The particles coated with the 25 KD polymer also induced toxicity in macrophage (RAW 264.7) and bronchial epithelial (BEAS-2B) cell lines staining (FIG. 10). The toxicity was confirmed by propidium iodide (PI) staining, which showed that the rate of cell death was progressive over 15 hour period (FIG. 10). Similar to previous results with cationic polystyrene nanoparticles (Xia et al., *ACS Nano*, vol. 2, pp. 85-96, 2008), the toxicity of cationic MSNP involves an effect on mitochondria as determined by JC-1 fluorescence (FIG. 10). JC-1 measures mitochondrial membrane potential (MMP). In contrast, phosphonate-coated nanoparticles (MSNP-Phos) were non-toxic and did not perturb the mitochondrial function (FIG. 10).

Figure 11A:
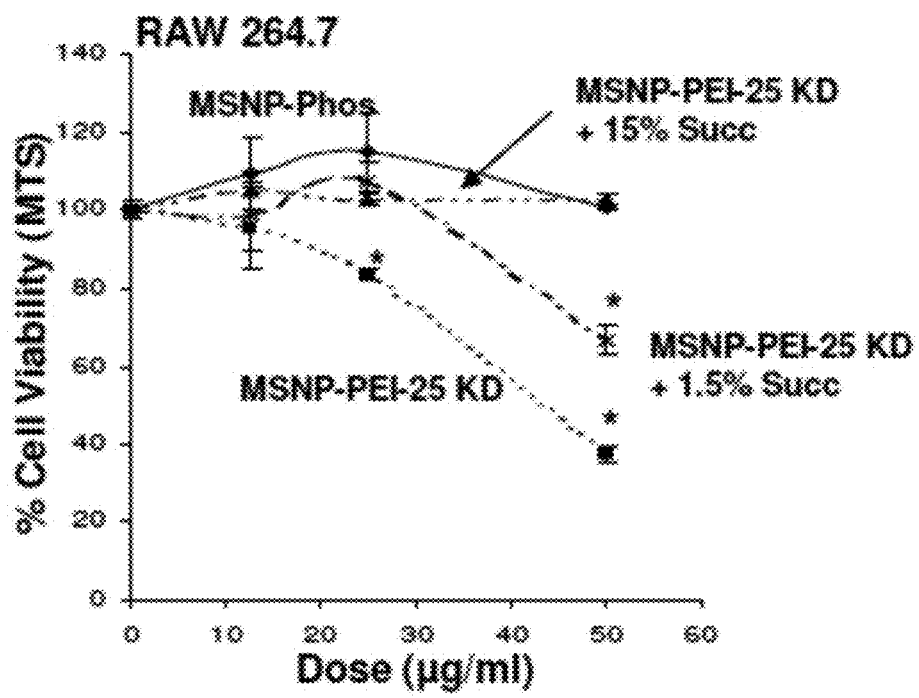
FIGS. 11A and 11B show effect on cell viability after conversion of primary amines to COOH. Succinic anhydride was used to convert the primary $NH_2$— to COOH— groups on MSNP-PEI-25 KD.
Figure 11B:
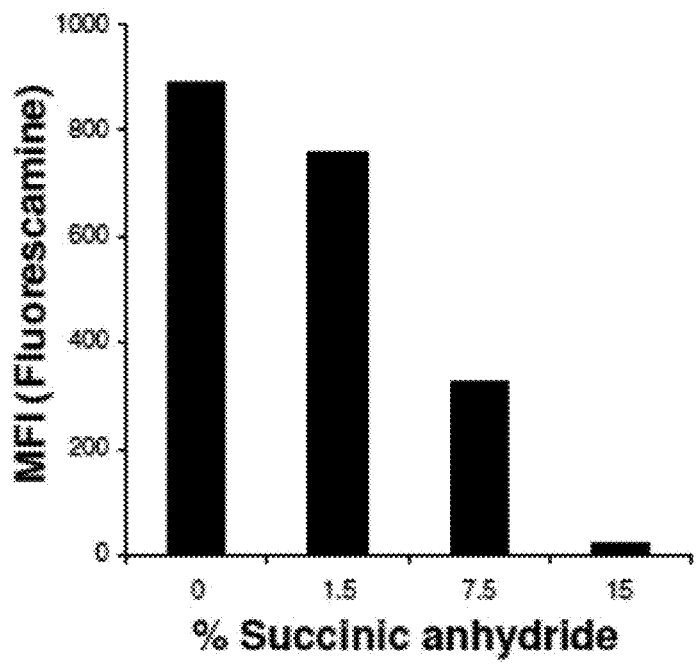
Figure 12:
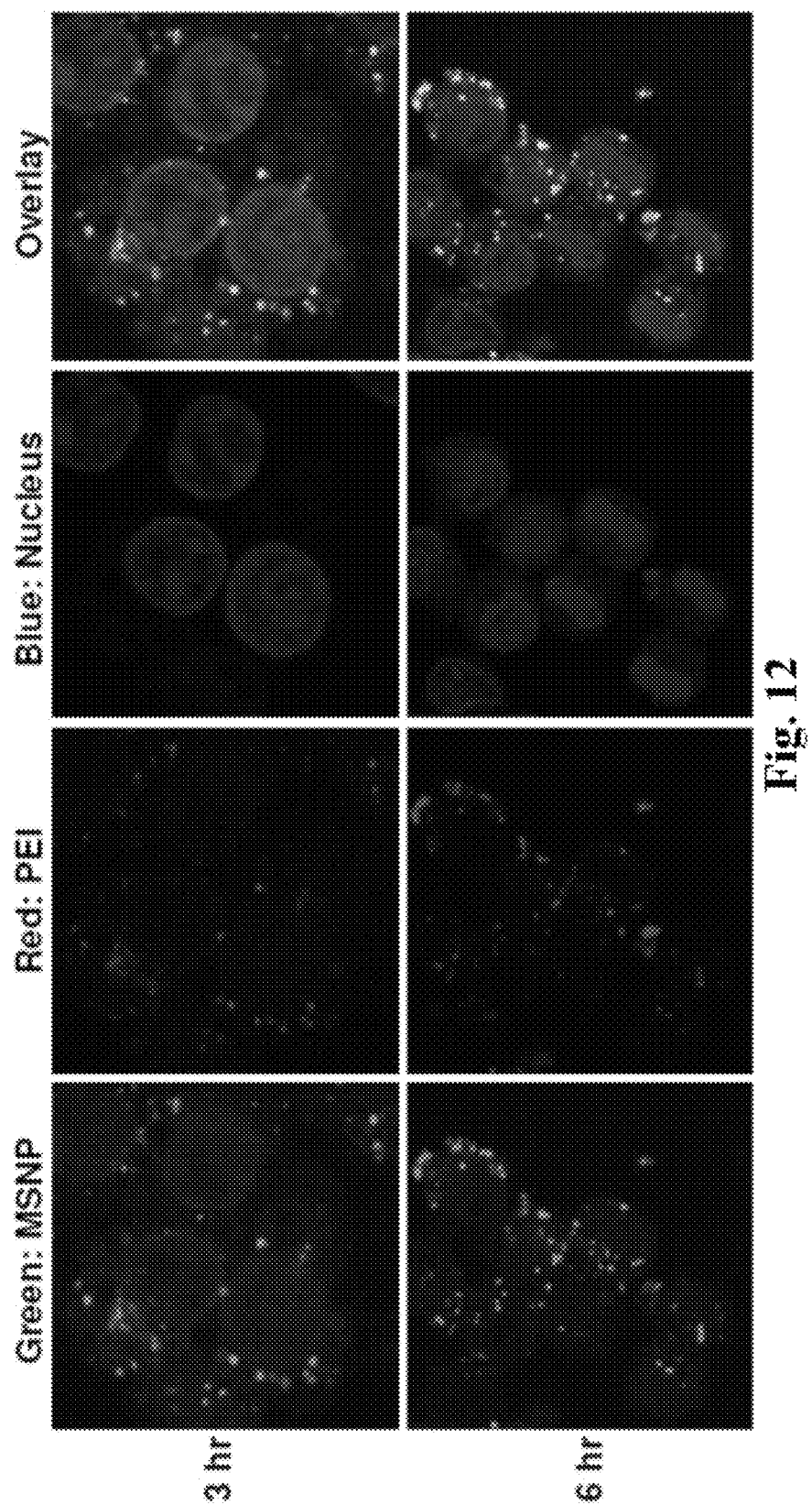
FIG. 12 shows determination of the stability of PEI coating on the MSNP surface. Rhodamine-B labeled PEI was used to coat the surface of FITC-labeled MSNP and the dual-labeled particles were added to RAW 264.7 cells prior to the performance of confocal microscopy. The composite overlay confirms that the polymer and the particle co-localize at the same intracellular site at 3 and 6 hrs.

To confirm that PEI toxicity is due to cationic charge, succinic anhydride was used to convert the primary $NH_2$ to COOH groups (Xia et al., *ACS Nano*, vol. 2, pp. 85-96, 2008). FIG. 11A demonstrates that this conversion reduced the toxicity of MSNP-PEI-25 KD in a dose-dependent fashion. Depletion of the primary $NH_2$ groups was confirmed by fluorescamine, which yields green fluorescence when it reacts with primary amines (FIG. 11B). Thus, succinic anhydride reduced the mean fluorescence intensity (MFI) in a dose-dependent fashion. The stability of PEI attached to the MSNP surface was confirmed by coating FITC-labeled MSNP with rhodamine-B labeled PEI. Confocal microscopy confirmed that both labels co-localize as shown by the composite yellow fluorescent spots in the cell (FIG. 12).

Example 4—Differences in the Cellular Uptake of Anionic Versus Cationic MSNP

Figure 2B:
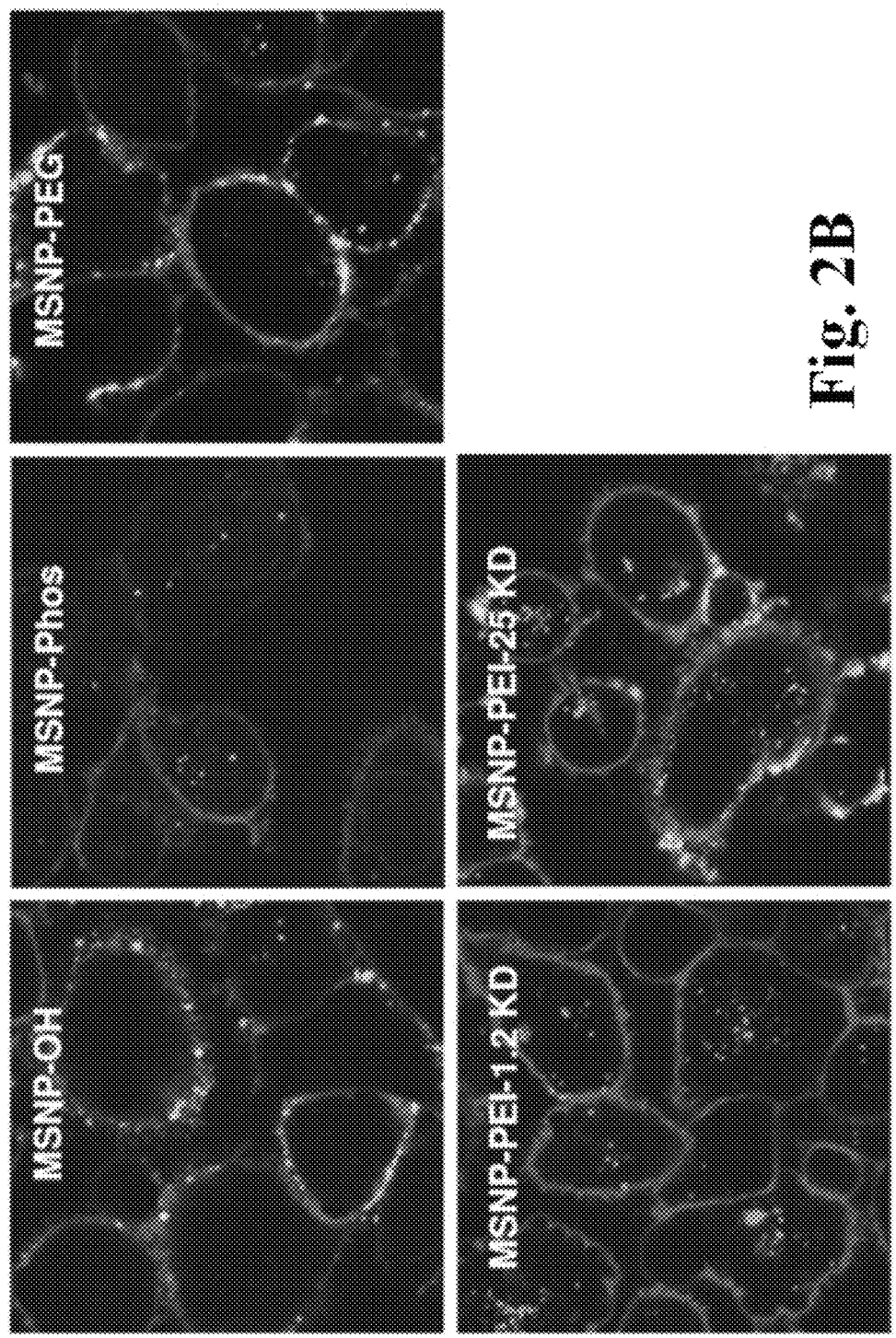
Figure 3A:
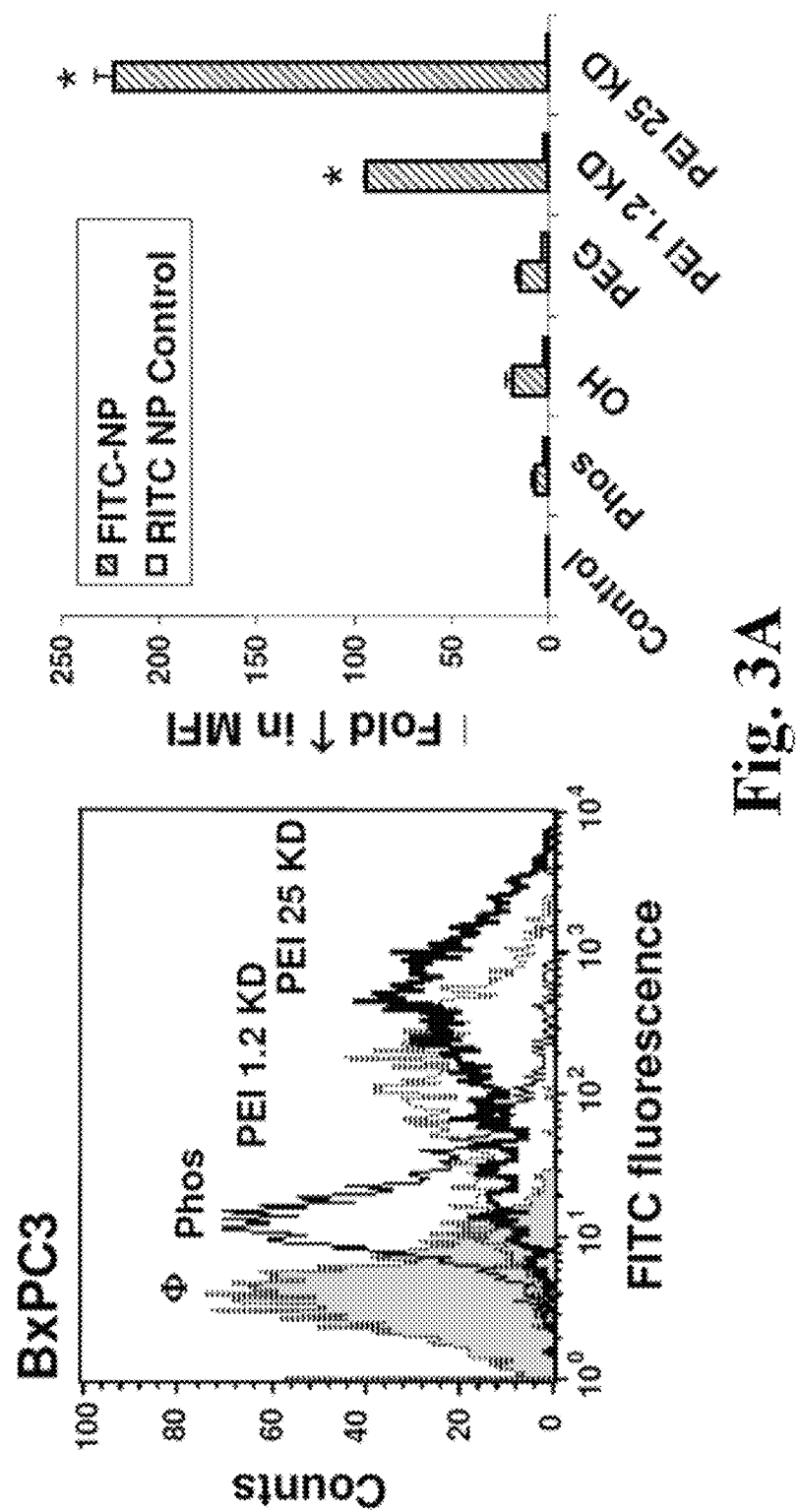
Figure 13A:
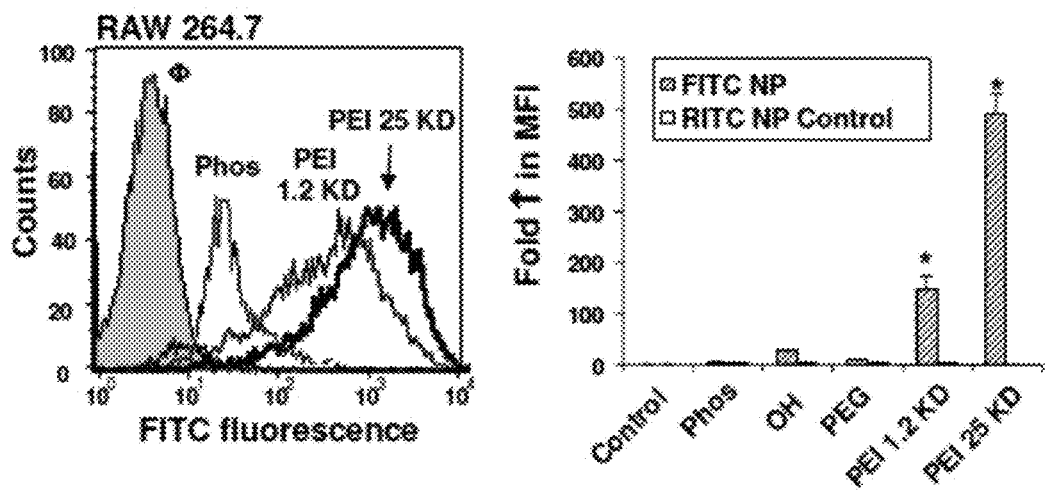
FIGS. 13A and 13B show cellular uptake of FITC-labeled MSNP in RAW 264.7 cells. MSNP were FITC labeled as described in the Examples.
Figure 13B:
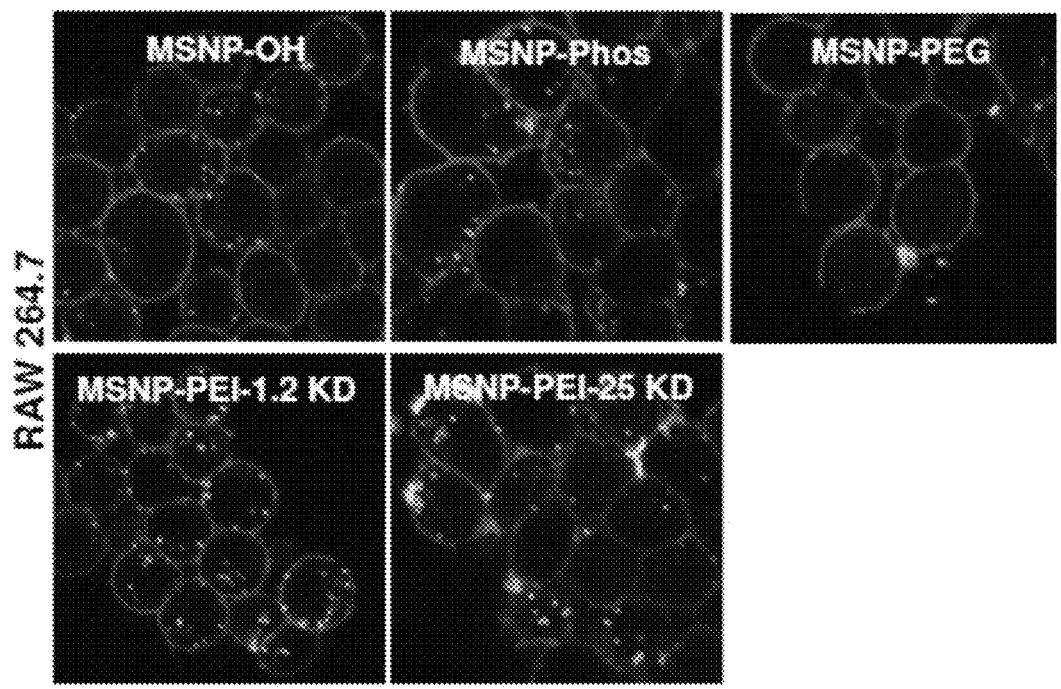

Cellular toxicity of cationic polystyrene nanoparticles involves a high rate of cellular uptake due to tight surface membrane binding, which facilitates particle wrapping and cellular uptake (Xia et al., *Nano Lett*. Vol. 6, pp. 1794-1807, 2006; Xia et al., *ACS Nano*, vol. 2, pp. 85-96, 2008). Cellular uptake of FITC-labeled MSNP was assessed by flow cytometry and confocal microscopy (Xia et al., *ACS Nano*, vol. 2, pp. 85-96, 2008). FITC-labeled MSNP were incubated with PANC-1, BxPC3, RAW 264.7, and BEAS-2B cells. This resulted in a clear shift in the MFI of the different cellular populations following treatment with particles coated with 1.2 and 25 KD PEI polymers as compared to the phosphonate-coated MSNP (FIGS. 2 and 3; FIG. 13). When expressed as fold-increase in the MFI compared to untreated cells, the relative abundance of MSNP-PEI-25 KD and MSNP-PEI-1.2 KD uptake was two orders of magnitude higher than the phosphonate or PEG-coated particles (FIGS. 2 and 3; FIG. 13). In contrast, there was no difference in the uptake of RITC-labeled MSNP in the same cells treated with the FITC-labeled particles. This confirms that the cationic charge is responsible for high cellular uptake. The flow data was corroborated by confocal studies that showed a significant increase in the number of PEI-coated particles in all cell types (FIGS. 2, 3 and 13). Please notice that a large fraction of the MSNP-PEI-25 KD particles localized at the cell membrane as demonstrated by the composite yellow fluorescence in pancreatic cancer cells stained with the red-fluorescent wheat germ agglutinin (FIGS. 2 and 3). It is possible that this membrane binding might contribute to the toxicity of these particles.

Figure 14A:
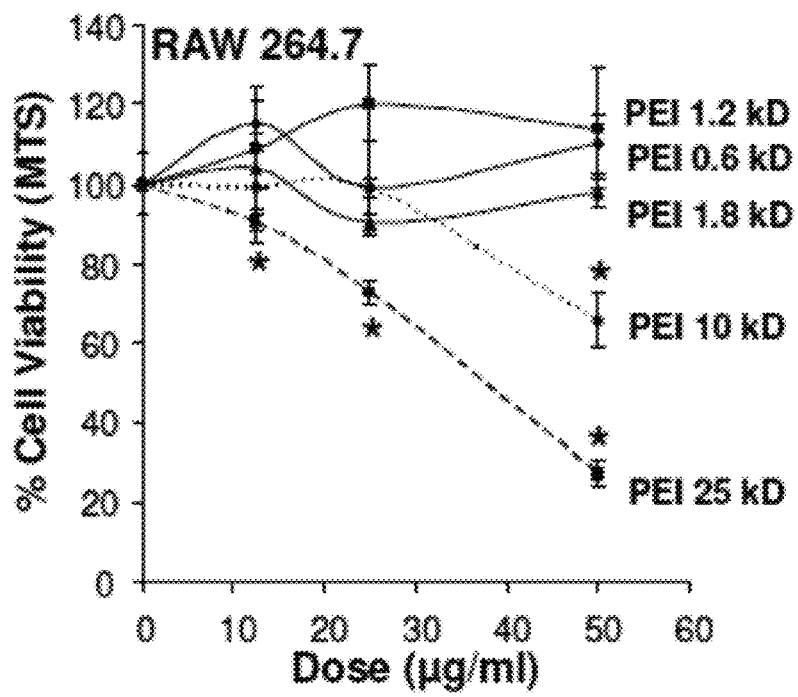
FIGS. 14A and 14B show cell viability detection by the MTS assay in RAW 264.7 (FIG. 14A) and BEAS-2B (FIG. 14B) cells. After incubation with particles coated with different length PEI polymers at doses from 6.25-100 µg/ml for 16 hrs, the MTS assay and data calculation were performed as described in FIG. 1.
Figure 14B:
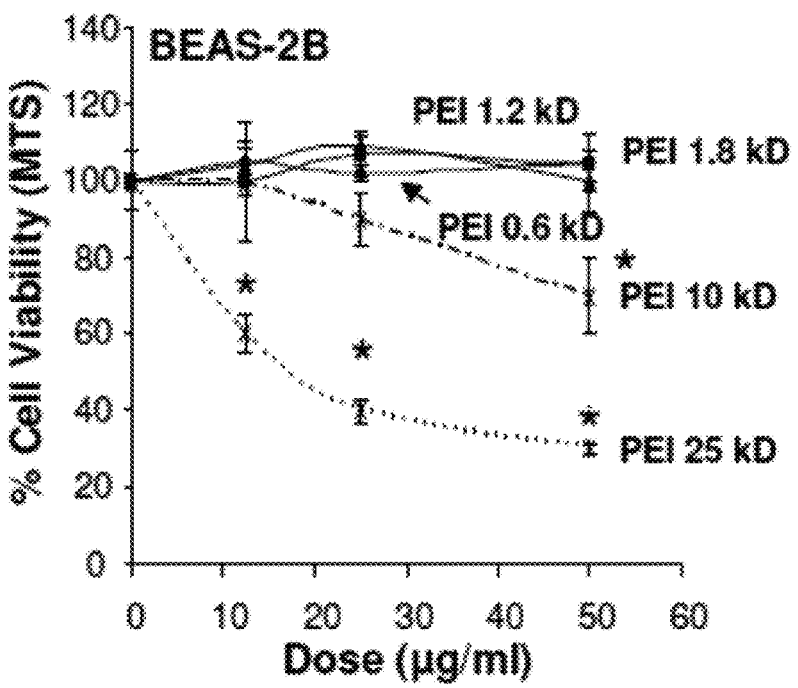

Reducing PEI Polymer Length Maintains Effective Nucleic Acid Delivery but Eliminates Cellular Toxicity While PEI is quite effective for complexing and delivering nucleic acids, polymer-based delivery of DNA and siRNA often leads to cytotoxicity due to damage to the surface membrane, lysosomes and mitochondria (Boussif et al., Proc. Natl. Acad. Sci. U.S.A, vol. 92, pp. 7297-7301, 1995; Florea et al., AAPS PharmSci., vol. 4, p. E12, 2002; Xia et al., *ACS Nano*, vol. 2, pp. 85-96, 2008). However, based on the observation that decoration of MSNP with a 1.2 KD polymer resulted in a non-toxic particle, a range of PEI polymers were explored in terms of achieving cellular delivery versus reduction of toxicity. MSNP were coated with 0.6, 1.2, 1.8, 10 and 25 KD polymers and their cytotoxic potential assessed in various cell types. This included the use of HEPA-1 cells for which there is a commercial variant expressing green fluorescent protein (GFP) for the purposes of assessing siRNA knockdown. No toxicity was seen with particles coated with 0.6, 1.2 and 1.8 KD PEI polymers (FIGS. 4 and 14). While MSNP-PEI-10 KD exerted toxic effects at the highest dose (50 µg/ml) tested, MSNP-PEI-25 KD was responsible for the decline in MTS activity at doses >12.5 µg/ml (FIGS. 4 and 14). This demonstrates that it is possible to adjust MSNP toxicity according to the polymer length used and is the first demonstration that the choice of the PEI polymer length can be used to modify the toxicity of MSNP while still maintaining a useful function.

Preparation of PEI-MSNP-pDNA/siRNA Polyplexes and Agarose Gel Retardation

Agarose gel retardation assay was used to determine the DNA/siRNA binding ability of PEI-coated MSNP. 0.1 µg plasmid DNA (pEGFP) or siRNA in aqueous solution was used to mix with PEI-coated nanoparticles to obtain particle to pDNA ratios (N/P) ratios of 5-600. The mixture was incubated at room temperature for 30 min for complex formation. 10 µL of the polyplex solution mixed with 2 µL of 6× loading buffer was electrophoresed on 1 agarose gel containing 0.5 µg/ml ethidium bromide (EB) with Tris-boric acid (TBE) running buffer (pH 8) at 100 V for 30 min. DNA/RNA bands were visualized by an UV (254 nm) illuminator and photographed with a Bio-Rad imaging system (Hercules, Calif.). The binding capacity was expressed by the N/P ratio that shows total retardation of DNA or siRNA migration (as reflected by the disappearance of DNA/RNA bands on the gel).

DNase I Protection Assay:

Particle/pDNA complexes were prepared at a MSNP/pDNA ratio of 100 with 100 ng pDNA in 10 µl total volume.

The complex solutions were incubated with 1 µl DNase I (2.7 U/µl) in 50 mM Tris-Cl, 10 mM MgCl$_2$, pH 7.4. at 37° C. for 30 min. The DNase I was inactivated by adding 1 µl of 100 mM ethylenediaminetetraacetic acid (EDTA). The pDNA was then released from the complex by adding 1% sodium dodecyl sulfate (SDS), and analyzed by 1% agarose gel electrophoresis.

Figure 5A:
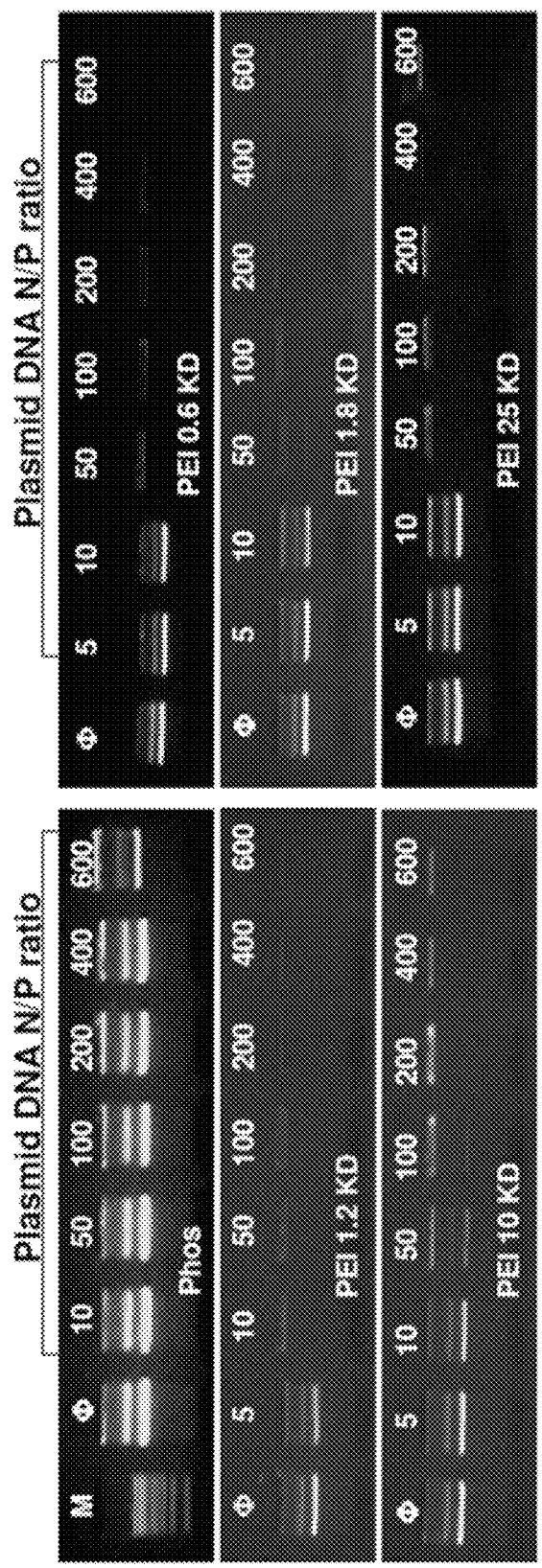

To assess the efficacy of different PEI-coated MSNP in terms of siRNA and plasmid DNA delivery, the nucleic acid binding capacity of the particles was determined using a gel retardation assay. The data show high siRNA and plasmid DNA binding capacity that was mostly independent of the PEI MW (FIG. 5). All available DNA and siRNA molecules were bound to the cationic particle surface at particle-to-nucleic acid ratios of 10-100 (FIG. 5B). Noteworthy, the high binding efficacy of MSNP was accompanied by protection of DNA to DNase I degradation (FIG. 5C). By contrast, phosphonate-coated particles did not show effective DNA binding.

Plasmid DNA and siRNA Transfection with the Use of MSNP-PEI

Plasmid DNA (pDNA) containing a GFP insert was used to transfect HEPA-I cells cultured either in Nunc chamber slides for performance of confocal microscopy or in 48-well plates for assessment by flow cytometry. Cells were plated at a density of 2×10$^4$ cells per well in 0.4 ml medium. pDNA/MSNP complexes were prepared by mixing 100 ng/ml DNA with 25 µg/ml MSNP for 30 min prior to cellular incubation for 24 hr. Cells were fixed for confocal microscopy as described above. Harvested cells were used to conduct flow cytometry on FL-1 channel.

Figure 7A:
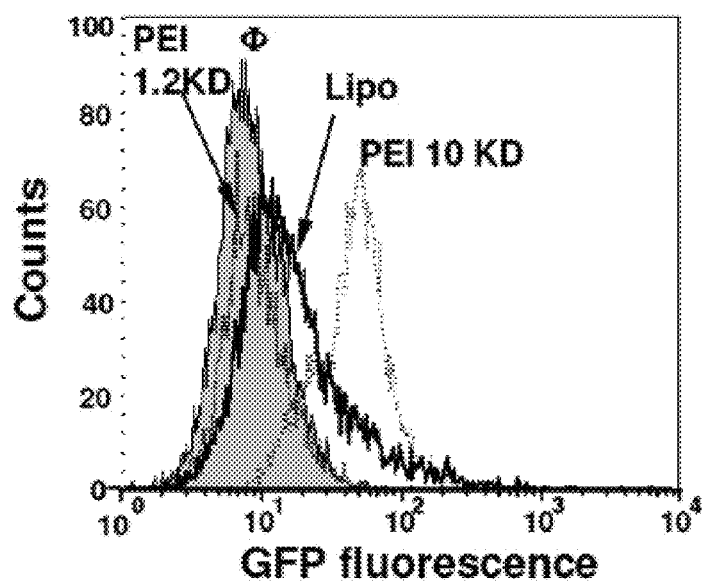
FIGS. 7A and 7B show GFP plasmid DNA transfection into HEPA-I cells. HEPA-I cells were used for GFP plasmid DNA transfection. MSNP coated with different size PEI polymers were used to transfect GFP plasmid DNA and the results were compared with Lipofectamine 2000 as transfection agent.
Figure 7B:
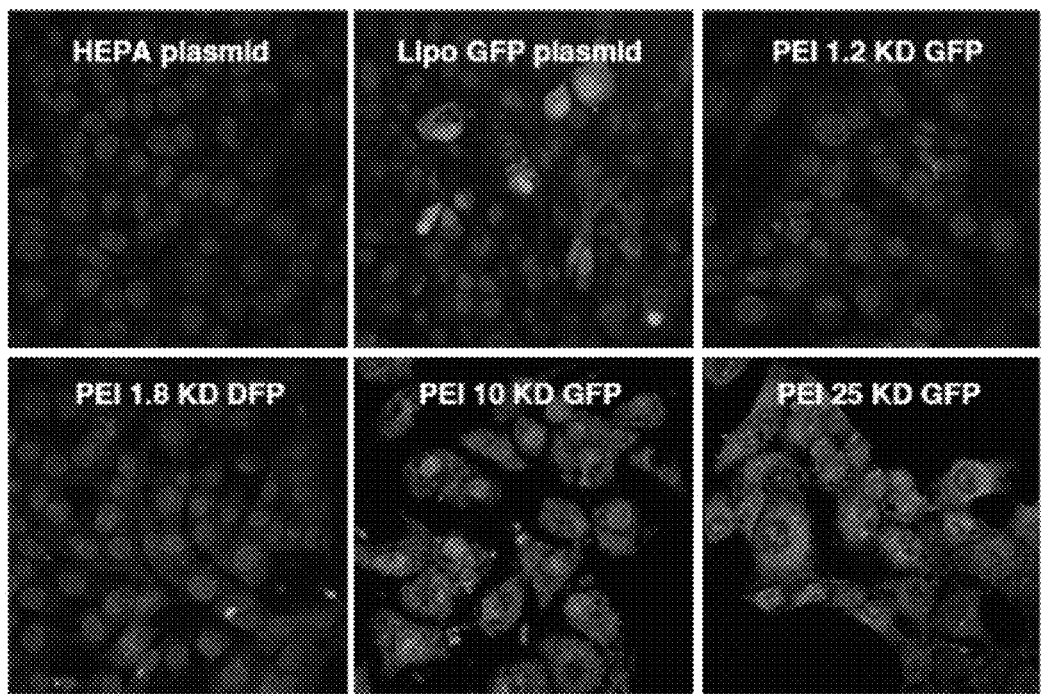

In the next set of experiments the efficacy of DNA delivery was assessed by transfecting a GFP plasmid into HEPA-I cells. While plasmid delivery by the IO and 25 KD PEI-coated particles resulted in abundant cellular fluorescence, only faint fluorescence was observed when the carrier particle was coated with a shorter length polymer (FIG. 7). The transfection efficiency with the longer length polymers compares favorably to the results with Lipofectamine 2000. Moreover, while this commercial agent only transduced a fraction of the cells in the population, MSNP-PEI-10 KD transfected >70% cells in the population (FIG. 7B). This was confirmed by the magnitude of the MFI increase with the particles versus Lipofectamine (FIG. 7A). Although also efficient for DNA delivery, MSNP-PEI-25 KD did result in toxicity as explained previously. This may not constitute a problem when stable transfections are being performed because one selects for viable and proliferating cells containing the expressed gene.

To perform siRNA experiments, HEPA-1 cells were prior transfected with a GFP plasmid and then sorted in the FL-1 channel to select stable GFP expressing cells. The sorted cells were plated at a density of 5×10$^4$ cells per well containing 0.4 ml culture medium in chamber slides for performance of confocal microscopy and in 48-well plates for performance of flow cytometry. MSNP/siRNA complexes were prepared by incubating 500 ng/ml siRNA with 25 µg/ml of MSNP-PEI for 30 min in serum-free DMEM. Cells were then exposed to the complexes for 3 hr. DMEM+ 10% FCS was then added to bring the final volume to 400 µl for 48 hr. Cells were fixed and prepared for confocal microscopy as described above. For flow cytometry cells were harvested and analyzed for fold decrease in GFP expression (FL-1 channel).

Figure 6A:
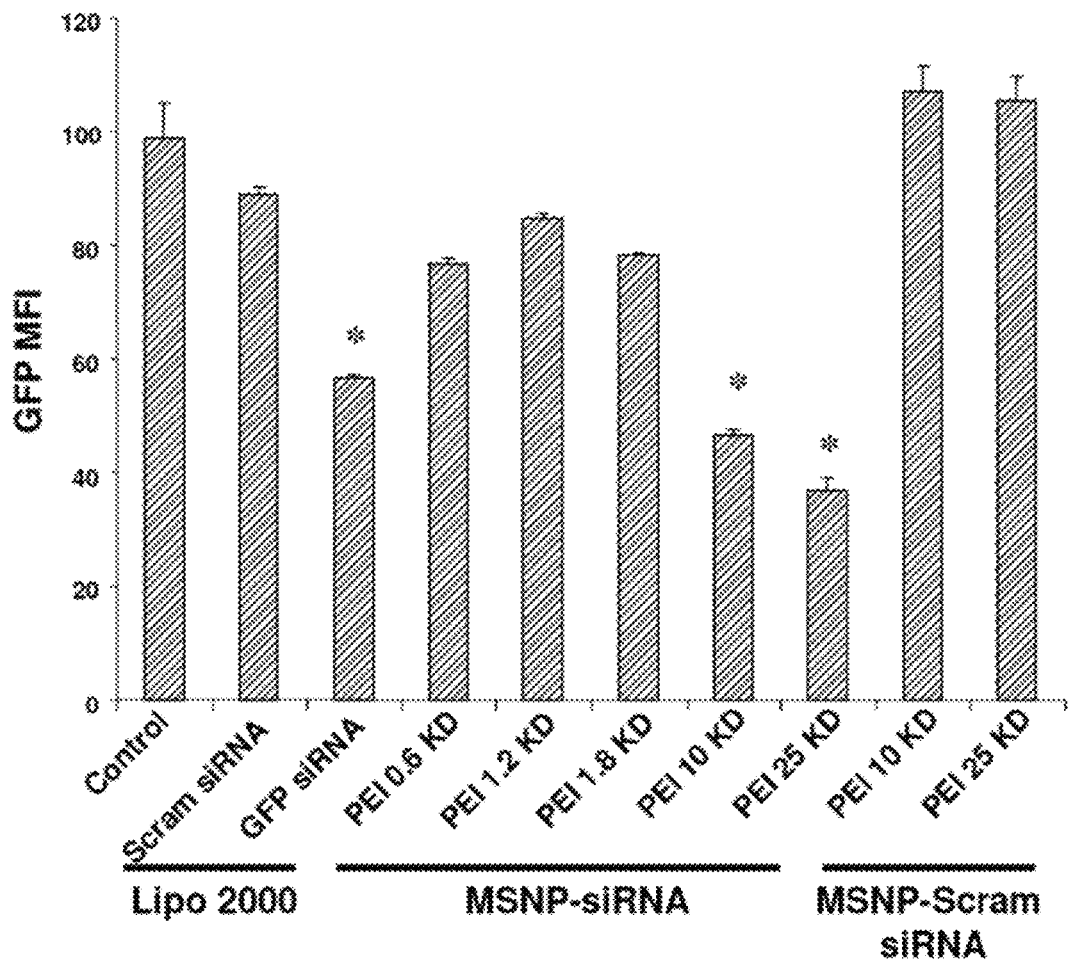
FIGS. 6A and 6B show GFP knockdown by siRNA in stable transfected GFP-HEPA cells. HEPA-I cells with stable GFP expression were used for siRNA knockdown assays. MSNP coated with different size PEI polymers were used to transfect GFP-specific or scrambled siRNA and the results compared with Lipofectamine 2000 as transfection agent.
Figure 6B:
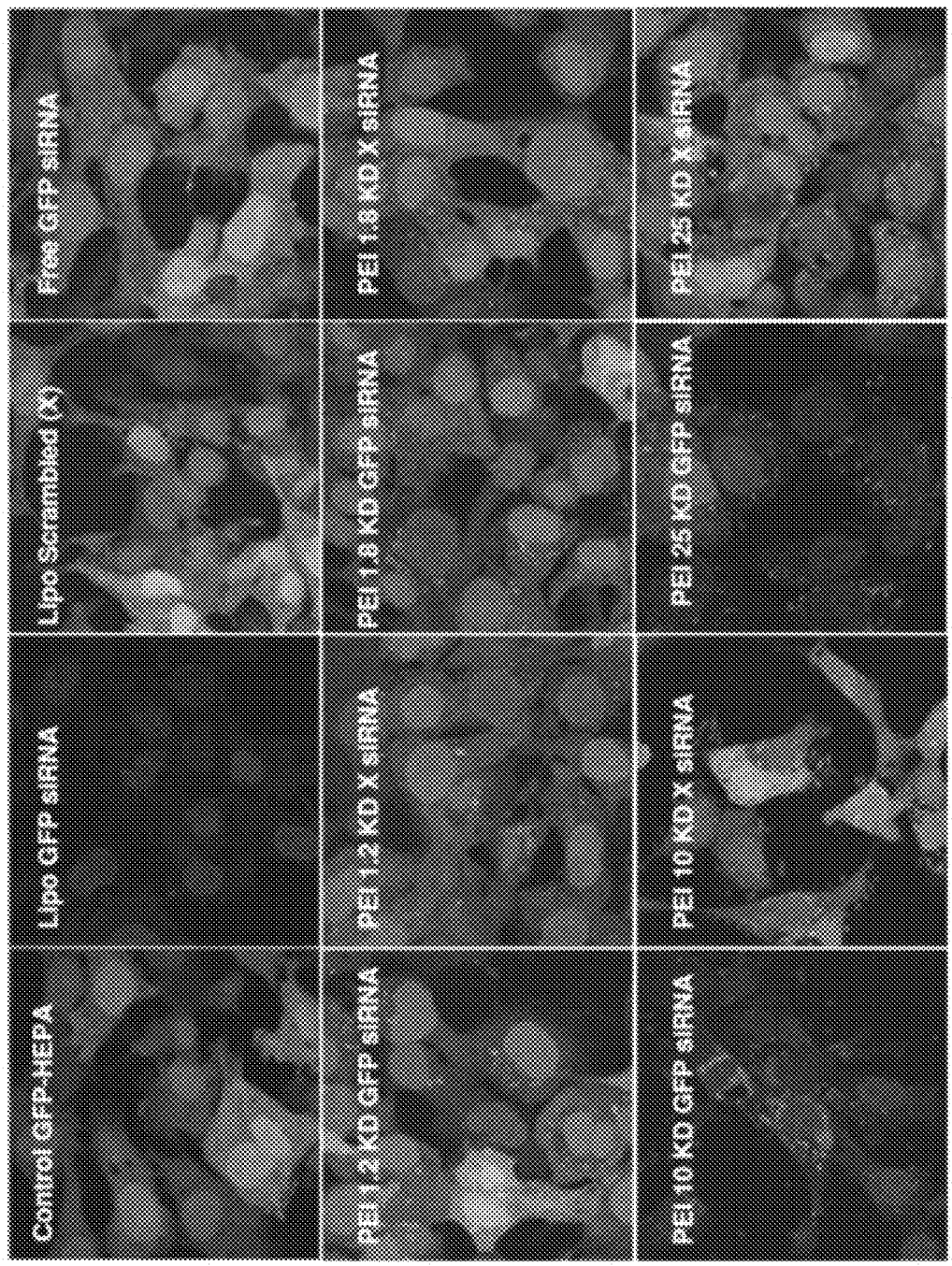
Figure 15A:
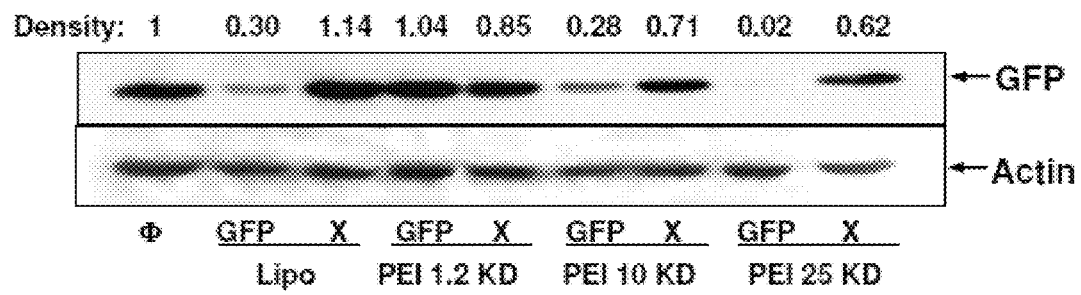
FIGS. 15A and 15B show detection of GFP knockdown by siRNA using western blotting in HEPA-1 cells.
Figure 15B:
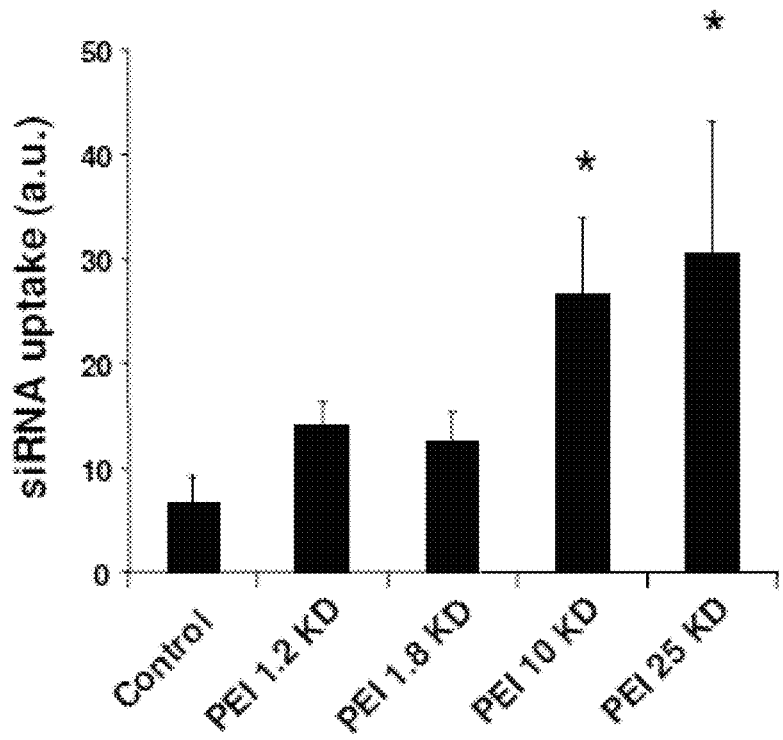

To test whether siRNA delivery to its GFP-expressing HEPA-I cells could provide knockdown of the expression of this fluorescent protein, 100 ng GFP-siRNA was complexed with MSNP-PEI and incubated with the cells for 48 hr. Comparison of the MFI of transfected versus control cells showed that particles coated with 10 and 25 KD polymers were capable of knocking down GFP expression by 55% and 60%, respectively (FIG. 6A). This was comparable to the transfection efficiency of commercially available transfection agent, Lipofectamine 2000. By contrast, scrambled siRNA delivery did not have a GFP knockdown effect (FIG. 6A). Moreover, siRNA delivery by 0.6, 1.2 and 1.8 KD PEI-coated particles did not exert an effect on GFP expression. GFP knockdown was confirmed by confocal microscopy (FIG. 6B) and immunoblotting for GFP protein expression (FIG. 15). Please notice that although the toxicity of the 25 KD polymer may contribute to decreased GFP expression, the 10 KD polymers is not toxic at this dose (FIG. 4). Scrambled siRNA delivery had no effect on GFP expression (FIG. 6B). Confocal studies using Texas Red-labeled siRNA was performed to track the intracellular fate of the particles (FIG. 6B). This confirmed that the particles coated with longer polymers were taken up in larger numbers than the shorter range polymers in HEPA-I cells (FIG. 6B, 15B).

Example 5—Paclitaxel Delivery

Cationic MSNP Efficiency in Delivering Paclitaxel to Pancreatic Cancer Cells

MSNP are capable of delivering water-insoluble drugs to cancer cells (Liong et al., *ACS Nano*, vol. 2, pp. 889-896, 2008). In light of the high cellular uptake of PEI-coated particles, it was logical to ask whether in the traditional use of the MSNP, the polymer attachment still allows effective delivery of the hydrophobic cancer drug, paclitaxel, to PANC-1 and BxPC3 cells.

Drug Loading of Paclitaxel

Paclitaxel was loaded into MSNP-PEI-1.2 KD and -25 KD in DMSO, followed by washing in an aqueous buffer to entrap the hydrophobic drug in the particle pores. Briefly, the modified materials were loaded with paclitaxel by incubating 10 mg of the nanoparticles in a solution of 1 mg of paclitaxel and 0.25 ml of DMSO for 6 hours. After the drug-laden nanoparticles were removed from the suspension by centrifugation and the supernatant removed completely, the materials were dried under vacuum. The drug-laden nanoparticles were washed and sonicated with PBS.

Figure 16:
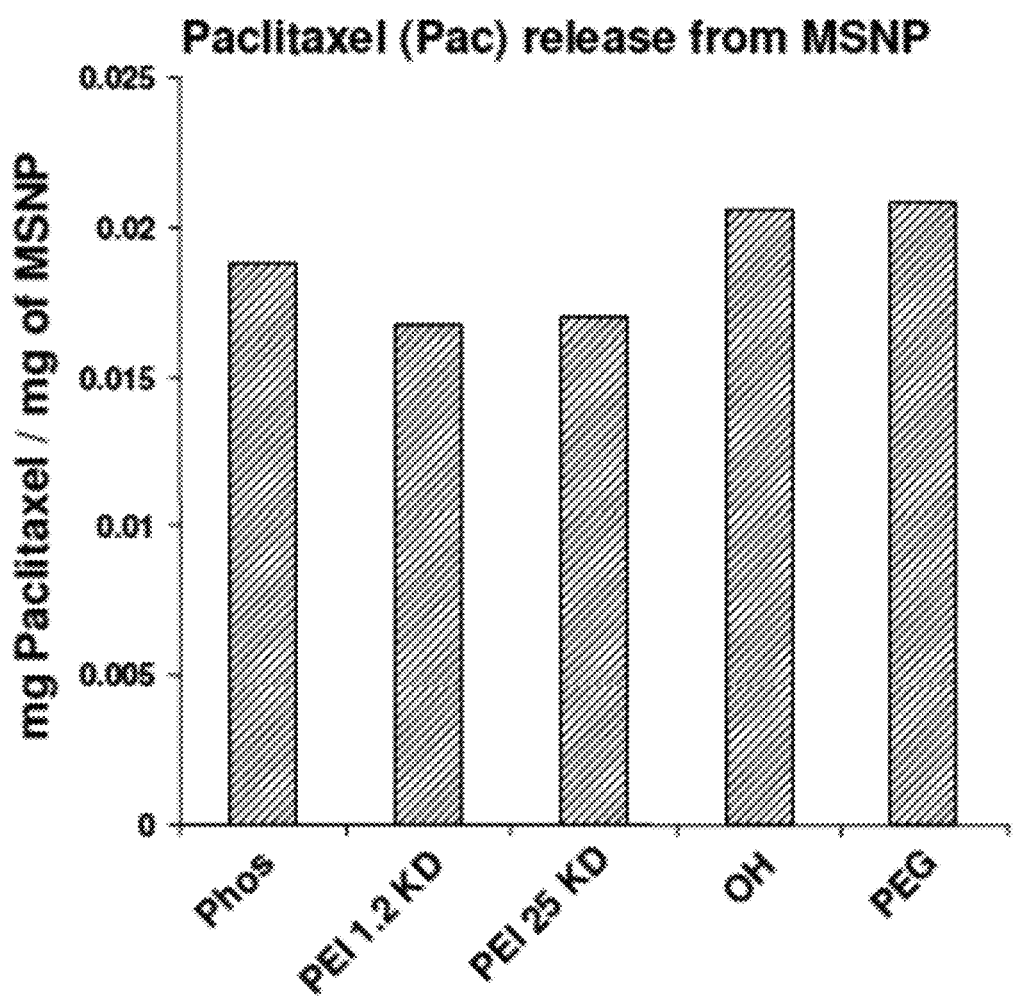
FIG. 16 shows quantification of paclitaxel (Pac) loading capacity in MSNP. MSNP with different surface modifications were loaded with paclitaxel. Methanol was used for complete release of the drug from washed particles and the amount of paclitaxel in the supernatant was determined by UV absorbance at 230 nm.

In order to determine the amount of paclitaxel that partitioned to the MSNP, the aqueous particle suspension were incubated for 6 hours at 4° C. before centrifugation. Methanol was used to release paclitaxel from MSNP to determine the loading capacity. The drug-laden MSNP pellet was resuspended and sonicated in methanol on three occasions and the supernatants were combined to measure the release of the drug by UV absorption at 230 nm. 50 µg/ml particles contained about 1 µM of paclitaxel. Release of the drug from the pores by using methanol confirmed that equal amounts of paclitaxel were loaded into MSNP irrespective of the polymer MW (FIG. 16).

Paclitaxel Delivery by MSNP-PEI

PANC-1 and BxPC3 cells were plated at $2 \times 10^4$ cells per well in a 96 well plate. MSNP particles, loaded with paclitaxel, were incubated with the cells at doses of 10-50 µg/ml for 48-72 hrs. Free paclitaxel corresponding to the amount loaded into MSNP particles was suspended or dissolved in PBS and DMSO to serve as controls. MTS assays were performed after 48 hours to determine the cell viability after treatment.

Subsequent assessment of the impact of paclitaxel on the viability of PANC-1 and BxPC3 cells showed the efficacy of PEI-coated MSNP in drug delivery (FIG. 8). Thus, paclitaxel delivery by MSNP-PEI-1.2 KD induced a rate of cytotoxicity that is superior to the drug delivery by an aqueous suspension of paclitaxel and as efficient as the drug suspended in a DMSO carrier (FIG. 8). While MSNP-PEI-25 KD showed intrinsic particle-related toxicity at doses>25 µg/ml, the effect was comparable to MSNP-PEI-1.2 KD (FIG. 8). These data demonstrate that the enhanced cellular uptake of non-toxic cationic MSNP is capable of enhancing the delivery of hydrophobic cancer drugs. This is also a novel demonstration for the delivery function of MSNP.

Example 6—In Vivo Toxicity Test of MSNP

Animal experiment protocols were reviewed and approved by the The Chancellor's Animal Research Committee (ARC) at UCLA. Animal experiments were performed in accordance with UCLA guidelines for care and treatment of laboratory animals and the NIH Guide for the Care and Use of Laboratory Animals in Research (DHEW78-23). The mice were randomly divided into three groups: MSNP-phosphonate, MSNP-PEI 25 KD and the control group. Six mice were used per group, since this number has enough statistical power to discern differences in the toxic responses. Forty mg/kg particles were used for i.v. injection through tail vein once a week for two weeks. Animal weight was monitored after particle injections. Animals were sacrificed later to obtain blood and organs.

Biochemical Assay of Serum

The serum was obtained by centrifugation of the whole blood at 3000 rpm for 15 min. The biochemical parameters were assayed by UCLA Division of Laboratory Animal Medicine (DLAM) diagnostic laboratory services.

Histology of Major Organs

A small piece of liver, kidney, spleen, lung, heart, and brain was fixed by 10% formalin and then embedded into paraffin, sectioned for 5 µm thick, and mounted on the glass microscope slides by UCLA Division of Laboratory Animal Medicine (DLAM) diagnostic laboratory services. The sections were stained with hematoxylin-eosin and examined by light microscopy.

Results

To use MSNP for nucleic acid and drug delivery, it is necessary to first make sure the particle is safe in animals. And for drug carriers, i.v. injection is the most used route. In vivo toxicity test of MSNP were conducted in mice by i.v. injection of 20 mg/kg nanoparticles once a week for two weeks. Before the injection, the particle size was characterized in saline, which is commonly used in in vivo assays. However, the average size of MSNP-phosphonate and MSNP-PEI 25 KD is 984 and 842 nm in saline, respectively. Recent research showed that protein corona, the protein coating on the particle surface, can stabilize nanoparticle suspension and serum is high in proteins that can be used as a dispersing agent for nanoparticles. 2% mouse serum was added to saline and used to suspend the MSNP. The serum-containing saline substantially decreased the average size of MSNP-phosphonate and MSNP-PEI 25 KD to 249 and 278 nm, respectively.

After two weeks, animals were sacrificed. Blood and major organs such as liver, kidney, spleen, lung, heart, and brain were collected to do serum biochemistry assays and histology, respectively. The serum chemistry tests showed no significant changes in all the tested parameters between MSNP-treated and control mice (Table 2).

TABLE 2

| Serum biochemistry tests (Avg ± SD, n = 6). | | | |
|---|---|---|---|
| | Control (Saline) | MSNP-Phos | MSNP-PEI 25 KD |
| CHOL (mg/dL) | 162.5 ± 8.5 | 153.8 ± 15.4 | 144.4 ± 6.8 |
| CK (U/L) | 3000.3 ± 2285.2 | 2690.5 ± 1129.3 | 3280.9 ± 1512.7 |
| ALT (U/L) | 59.5 ± 6.4 | 55.7 ± 8.4 | 46.1 ± 22.6 |
| AST (U/L) | 184.2 ± 70.2 | 182.2 ± 21.1 | 217.2 ± 65.6 |
| ALP (U/L) | 105.2 ± 8.6 | 102.1 ± 17.5 | 88.6 ± 48.9 |
| TBILI (mg/dL) | 0.7 ± 0.1 | 0.9 ± 0.3 | 0.6 ± 0.1 |
| TPROT (g/dL) | 6.2 ± 0.2 | 6.0 ± 0.4 | 5.9 ± 0.3 |
| GLU (mg/dL) | 140.8 ± 16.5 | 141.2 ± 29.2 | 140.8 ± 34.6 |
| PHOS (mg/dL) | 8.4 ± 0.7 | 7.4 ± 1.0 | 8.3 ± 0.6 |
| CA (mg/dL) | 8.9 ± 1.7 | 9.2 ± 0.4 | 9.4 ± 0.2 |
| CO2_LC (mEq/L) | 10.1 ± 2.2 | 13.3 ± 3.8 | 11.3 ± 1.1 |
| BUN (mg/dL) | 20.8 ± 2.1 | 22.3 ± 9.3 | 22.6 ± 2.6 |
| CREAT (mg/dL) | 0.3 ± 0.0 | 0.3 ± 0.1 | 0.3 ± 0.0 |
| DBILI (mg/dL) | 0.9 ± 0.2 | 1.0 ± 0.5 | 0.7 ± 0.2 |
| ALB (g/dL) | 3.3 ± 0.1 | 3.2 ± 0.2 | 3.2 ± 0.2 |
| AGR (N/A) | 1.2 ± 0.1 | 1.2 ± 0.1 | 1.1 ± 0.1 |
| B_CREA (mg/dL) | 75.3 ± 16.2 | 79.2 ± 30.0 | 82.0 ± 12.4 |
| AMYL (U/L) | 1252.2 ± 215.1 | 1266.0 ± 189.5 | 1139.4 ± 122.0 |
| LDH (U/L) | 681.5 ± 152.8 | 1266.0 ± 189.5 | 1139.4 ± 122.0 |
| MG (mg/dL) | 2.0 ± 0.5 | 2.2 ± 0.2 | 2.3 ± 0.2 |
| TRIG (mg/dL) | 201.2 ± 43.8 | 178.2 ± 65.3 | 156.0 ± 28.5 |

Biochemical parameters includes Cholesterol (CHOL), Creatine Kinase (CK), alanine aminotransferase (ALT), aspartate aminotransferase (AST), Alkaline phosphatase (ALP), total bilirubin (TBILI), total protein (TPROT), Glucose (GLU), Inorganic phosphorus (PROS), Calcium (CA), Carbon Dioxide (CO2_LC), Blood Urea Nitrogen (BUN), Creatinine (CREAT), Direct bilirubin (DBILI), Albumin (ALB), Albumin-globulin ratio (AGR), Blood Creatinine (B_CREA), Amylase (AMYL), Lactate dehydrogenase (LDH), Magnesium (MG), Triglycerides (TRIG).

Figure 17A:
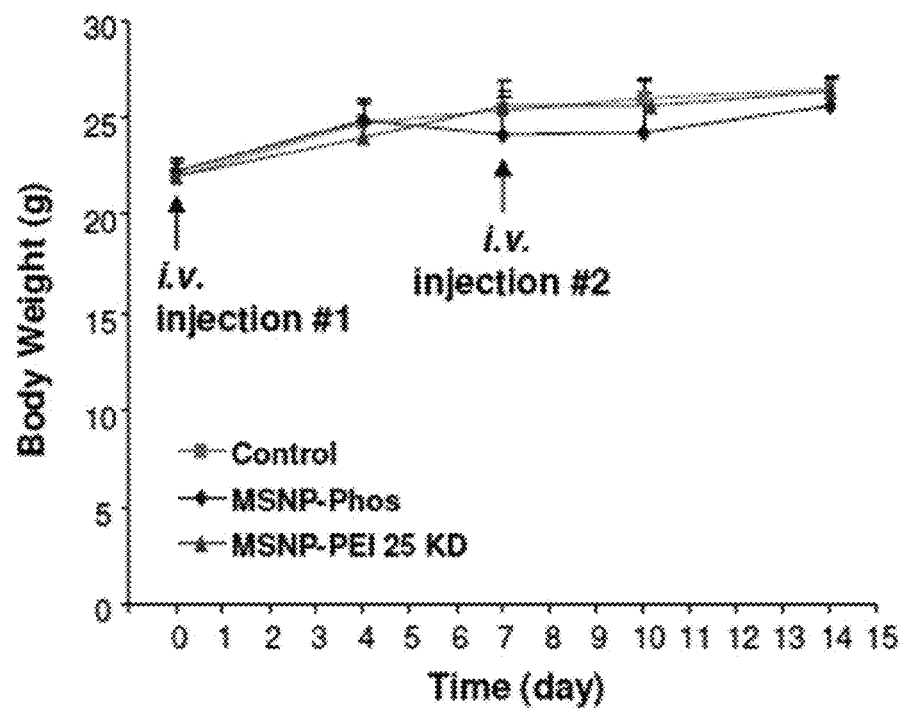
FIGS. 17A and 17B show animal weight and histology of major organs.
Figure 17B:
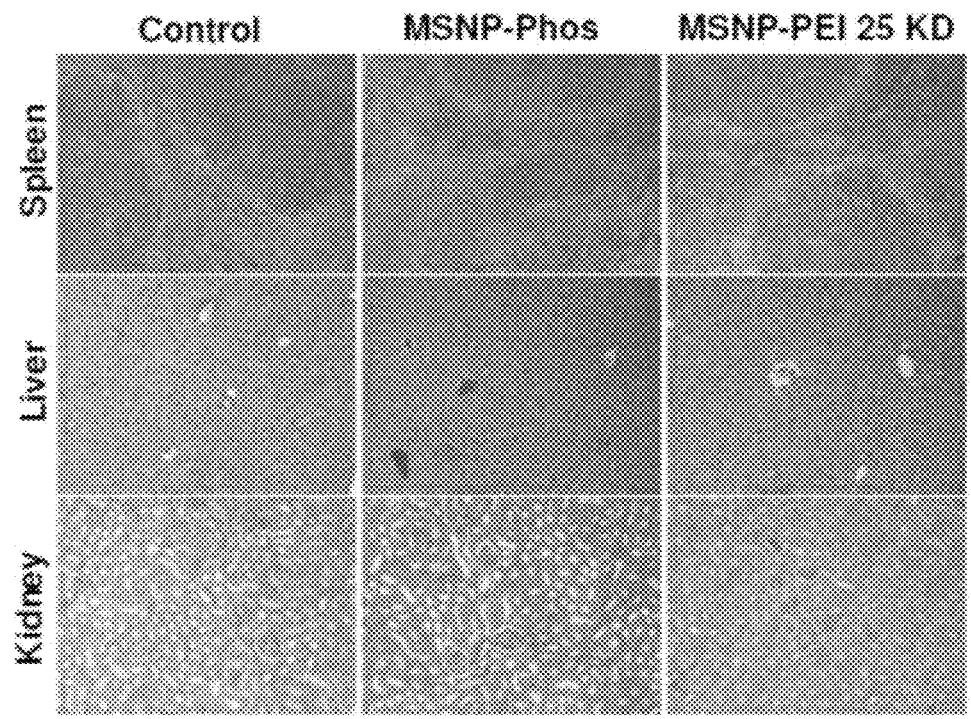

Histology of major organs also showed no major changes among the groups (representative liver, spleen and kidney sections were shown in FIG. 17. These results show MSNP-phosphonate and MSNP-PEI 25 KD do not have acute toxicity to major organs or systems in mice.

Example 7—Dual Deliverity siRNA and Anticancer Compound Materials

Tetraethylorthosilicate (TOES, 98%), cetyltrimethylammonium bromide (CTAB, 95%), fluorescein isothiocyanate (FITC, 90%), doxorubicin hydrochloride (Dox, >98%), camptothecin (CPT, 95%), vinblastine, polyethylenimine (PEI, branched, MW 25 kD), bafilomycin A (≥95%), ammonium chloride, β-actin antibody, and bovine serum albumin (BSA) were from Sigma (St. Louis, Mo.). Polyethylenimine (branched, MW 1.8 and 10 kD) was purchased from Alfa Aesar. 3-trihydroxysilylpropyl methylphosphonate, cyanoethyltriethoxysilane, and aminopropyltriethoxysilane were purchased from Gelest. Dulbecco's Modified Eagle's medium (DMEM), penicillin/streptomycin, and L-glutamine were purchased from Invitrogen (Carlsbad, Calif.). Fetal calf serum (FCS) was from Atlanta Biologicals, Inc (Lawrenceville, Ga.). LAMP-1 antibody was obtained from Abeam (Cambridge, Mass.). siRNA for Pgp knockdown was purchased from IDT Technologies (Coralville, Iowa). Tariquidar (>97%) was purchased from MedKoo Biosciences, Inc. For all experiments and analyses, water was de-ionized and filtered with a 0.45 µm pore size polycarbonate syringe filter (Millipore, Billerica, Mass.). All chemicals were reagent grade and used without further purification or modification.

Cell Lines

Figure 23A:
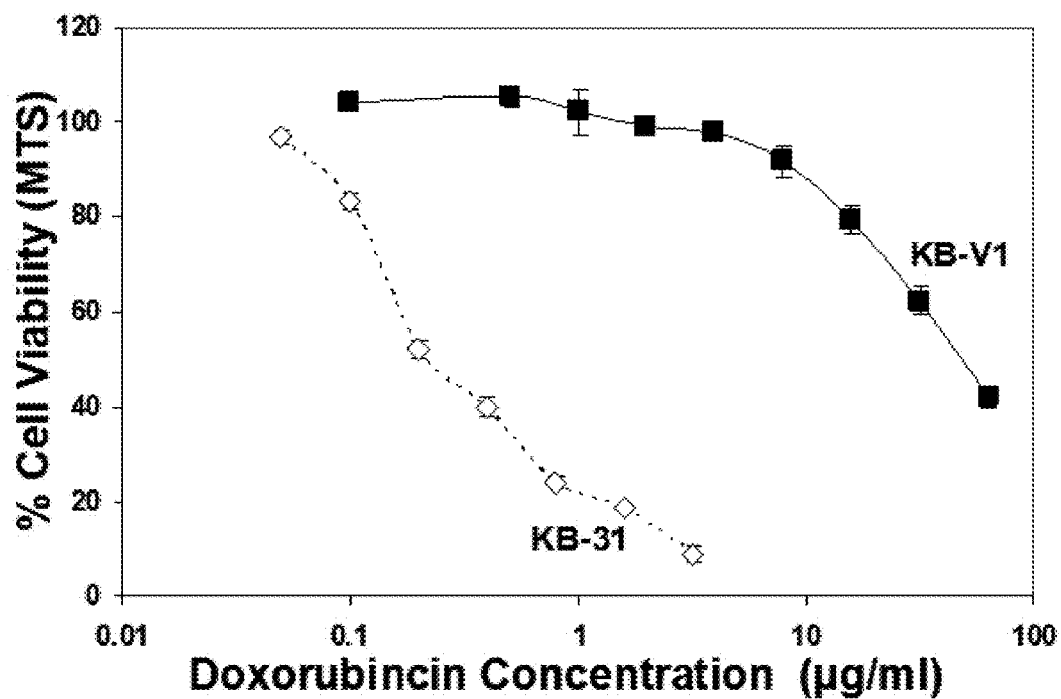
FIGS. 23A and 23B show identification of Dox sensitivity in KB-31 and KB-V1 cells.
Figure 23B:
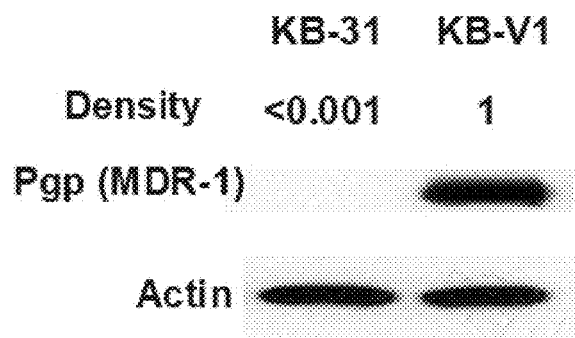

KB-31 and KB-V1 cells lines were confirmed as Dox-sensitive and Dox-resistant cell lines, with $IC_{50}$ values of 0.21 and 53.0 µg/ml, respectively (FIG. 23). Immunoblotting analysis confirmed that the Pgp expression in KB-V1 was >1,000 times that of KB-31 cells (FIG. 23B).

KB-31 and KB-V1 cells were plated at $1 \times 10^4$ cells per well in 96 well plate. The cells were treated with free Dox in solution in doses ranging from 0.05-3.2 µg/ml (KB-31) and 0.1-64 µg/ml (KB-V1) for 72 hrs. The cell viability was determined by the MTS assay. The treated cells were incubated with MTS working solution for 2-3 hrs before measurement. The mean absorbance of non-exposed cells served as the reference value for calculating 100% cellular viability. To view Pgp expression, the cells were washed in PBS and the pellets lysed in a buffer containing Triton X-100 and protease inhibitors after centrifugation. The protein content of the supernatants was determined by the Bradford method. 100 µg total protein was electrophoresed by 10% SOS-PAGE and transferred to a PVDF membrane. After blocking, the membranes were incubated with 1:1000 dilution of primary monoclonal antibody to MDR1 (anti-Pgp C219, Abeam). The membranes were overlayed with goat anti-mouse secondary antibody (1:1000 dilution) before the addition of the HRP-conjugated streptavidin-biotin complex. The proteins were detected using ECL reagent according to the manufacturer's instructions.

Statistical Analysis

Data represent the mean±SD for duplicate or triplicate measurements in each experiment, which was repeated at least 3 times. Differences between the mean values were analyzed by two-sided Student's t test or one way ANVOA and results were considered statistically significant atp <0.05.

PEI Coated MSNP

An important consideration in the use of PEI is its potential cytotoxicity (Xia et al., *ACS Nano*, vol. 3, pp. 3273-3286, 2009). In this regard, the polymer size plays an important role in the cytotoxicity that results from proton sequestration by unsaturated PEI amines in the lysosomal compartment (Xia et al., *ACS Nano*, vol. 3, pp. 3273-3286, 2009). Thus, before the performance of Dox-induced cytotoxicity, it was necessary to compare the cytotoxic potential of MSNP coated with different PEI polymer lengths as shown in the FIG. 26. In brief, the findings were that MSNP coated with the 25 kD polymer showed considerable toxicity in the MTS assay when the particle concentration is >25 µg/ml. By contrast, particles coated with 10 kD PEI have no toxic effects if the concentration is kept <100 µg/ml and the exposure time limited to ≤24 hr (FIG. 26). Consequently, MSNP was used at doses <100 µg/ml and for exposure time periods <24 hrs in the drug delivery studies to avoid effects on cell viability. Although no cytotoxicity was seen with the 1.8 kD PEI polymer (FIG. 26A), this particle is relatively ineffective for siRNA delivery and Pgp knockdown (FIGS. 19B, 19C and 19D).

Because of the potential toxicity of PEI, it was necessary to assess the cell viability of KB-V1 cells incubated with MSNP coated with different PEI polymers. Briefly, $1 \times 10^4$ cells were plated onto 96 multi-well plates (Costar; Corning, N.Y.). After incubation with the indicated amounts of the various PEI coated MSNP for 24 hrs, the MTS assay was performed as described in materials and methods section. MSNP coated with the 10 kD polymer was examined for time periods ranging from 1~48 hrs, aiming to chose an optimized time period for treatment that avoids PEI toxicity. The cells were treated with 100 µg/ml PEI-MSNP for 1, 4, 8, 16, 24, and 48 hrs, and the old medium was replenished by fresh medium for another 71, 68, 56, 48, and 24 hrs culture. The cytotoxicity assay was checked at 72 hrs after particle treatment.

Particle Synthesis, PEI Coating and Interior Surface Functionalization

The MSNPs were synthesized according to previously published sol-gel procedure (Xia et al., *ACS Nano*, vol. 3, pp. 3273-3286, 2009; Jie et al., *Small*, vol. 3, pp. 1341-1346, 2007). Briefly, for the synthesis of unmodified MSNP (OH-MSNP), 100 mg of CTAB was dissolved in a solution of 48 mL water and 0.35 mL sodium hydroxide (2 M) and heated to 80° C. One half mL of TEOS was added into the aqueous solution containing CTAB surfactants. For the phosphonate modification, 3-trihydroxysilylpropyl methylphosphonate was added to the mixture 15 minutes after the addition of TEOS. The CTAB surfactants were then removed from the pores by heating the particles in acidic ethanol. To perform PEI coating, 5 mg of phosphonate-modified MSNP were dispersed in a solution containing 2.5 mg PEI (1.8 kD, 10 kD, 25 kD) in 1 ml absolute ethanol. After sonication and stirring for 30 min the PEI coated particles were washed with PBS. The amount of polymer coated onto the particle surface was approximately 5 weight percentage.

Because Dox is positively charged under physiological pH, it was necessary to demonstrate that phosphonate or other anionic surface groups are effective for drug binding, including in particles that have been coated with PEI. To demonstrate this principle, particle surfaces were decorated with carboxylate (COOH) and amine groups in addition to phosphonate and silanol (OH groups). The surface functionalization was achieved by mixing organoalkoxysilanes (made up in ethanol) with TEOS before adding the mixture into the CTAB solution (Lim et al., J. Am. Chem. Soc., vol. 119, pp. 4090-4091, 1997). For carboxylate modification, 50 µL cyanoethyltriethoxysilane was mixed with 500 µL ethanol and 500 µL TEOS, then added into the surfactant solution. After the surfactant removal process, the particles were further heated in a solution of 50% sulfuric acid to hydrolyze the cyanide groups into carboxylic groups. For amine modification, 50 µL of aminopropyltriethoxysilane was first mixed with 500 µL ethanol and 500 µL TEOS before adding to the surfactant solution. After 2 hrs, the solution was cooled to room temperature and the materials were washed with methanol before the surfactant removal process.

Physicochemical Characterization of MSNP

PEI-coated phosphonate MSNP were characterized for size, zeta potential, and shape, respectively. The shape and porous structure were characterized using transmission electron microscopy (JEOL JEM 2010, JEOL USA, Inc., Peabody, Mass.). Microfilms for TEM imaging were made by placing a drop of the respective MSNP suspensions onto a 200-mesh copper TEM grid (Electron Microscopy Sciences, Washington, Pa.) and then drying at room-temperature overnight. A minimum of 5 images for each sample was captured and representative images included in FIG. 18. Particle size and zeta potential in pure water, after stabilization with 1 mg/mL BSA in water, or in cell culture medium were measured by ZetaSizer Nano (Malvern Instruments Ltd., Worcestershire, UK). All the measurements were performed in 40 µg/ml MSNP suspensions in filtered water or filtered complete cell culture media at pH 7.4. The analysis was also studied on Dox loaded particles. Similar analysis was also performed on cargo (Dox and siRNA) loaded PEI-MSNP samples.

Figures 18A, 18B:
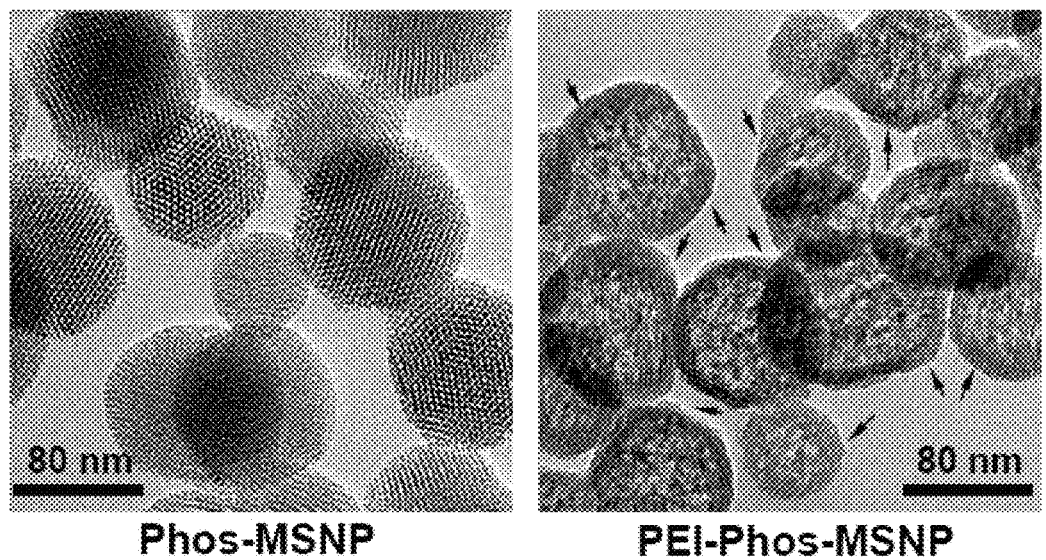
FIGS. 18A and 18B show physicochemical characterization of PEI coated MSNP.

In order to determine if Pgp overexpression in KB-VI cells is impacted by Pgp siRNA delivery, PEI polymers in the size range 1.8-25 kD were electrostatically bound to the phosphonate-MSNP surface. Polymer binding to 100-120 nm size MSNP, exhibiting uniform pore sizes of 2-2.5 nm was confirmed by TEM (FIG. 18A, left). The TEM image of the particles decorated with the 10 kD polymer shows that the surface coating (arrows) did not occupy the porous interior (FIG. 18A, right). To optimize the particle dispersal for biological experimentation, the PEI-coated particles were further treated with 1 mg/ml BSA before transfer to the complete cell culture medium. BSA coating significantly improves particle dispersal in water as well as salt-containing complete DMEM (FIG. 18B). While the PEI-coated particles exhibit a high positive zeta potential value in water, this value changes to slightly negative upon dispersal in complete DMEM containing FCS (FIG. 18B). Note that similar analysis was also performed on the Dox loaded PEI-MSNP samples with or without siRNA binding, and that no significant changes were found with or without cargo loading (Table 3).

TABLE 3

Comparison of particle size and zeta potential of PEI 10 kD MSNP before or after cargo loading. Size and zeta potential remain the same with or without cargo loading.

| Particle | Size in H$_2$O (nm) | Size in BSA (nm) | Size in DMEM (nm) | Zeta Potential in H$_2$O/CDMEM (mV) |
|---|---|---|---|---|
| PEI 10 kD-MSNP | 758 | 241 | 261 | +34.1/−3.8 |
| PEI 10 kD-Dox-MSNP | 711 | 198 | 225 | +28.1/−5.2 |
| siRNA-PEI 10 kD-Dox-MSNP | 832 | 234 | 278 | +25.4/−7.3 |

PEI-MSNP Coating with Pgp siRNA and Use of Agarose Gel Electrophoresis to Determine N/P Ratios An agarose gel retardation assay was used to determine the siRNA binding to PEI-MSNP. 0.1 µg siRNA was mixed with 0.4-6.4 µg amount PEI-MSNP in aqueous solution to obtain particle/nuclei acid (N/P) ratios of 4-64. 10 µL of the polyplex solution was mixed with 2 µL of 6× loading buffer and electrophoresed in a 1.5% agarose gel containing 0.5 µg/ml ethidium bromide (EB) at 100 V for 30 minutes in Tris-boric acid (TBE) running buffer (pH=8). Nucleic acid bands were detected by UV light (254 nm) and the photos were captured in a Bio-Rad imaging system (Hercules, Calif.). The results were used to calculate the threshold N/P ratios for subsequent experiments. The threshold is defined as the lowest N/P ratio value that prevents free siRNA from entering the gel. To determine the influence of Dox loading, the gel electrophoresis assay was also performed.

Figure 19A:
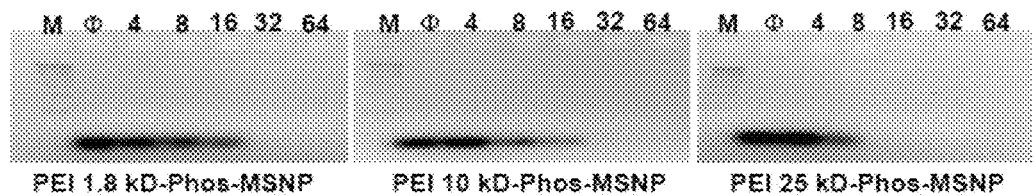
FIGS. 19A-19D show effective Pgp siRNA delivery and gene knockdown in KB-V1 cells.
Figure 19B:
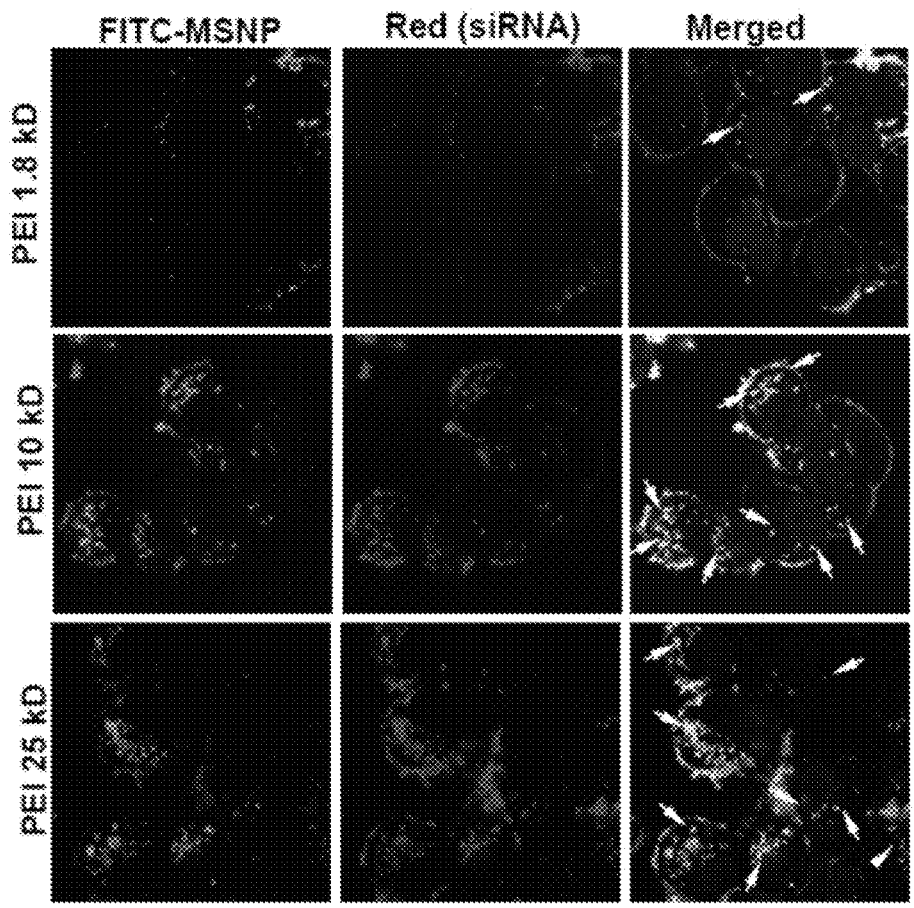
Figure 19C:
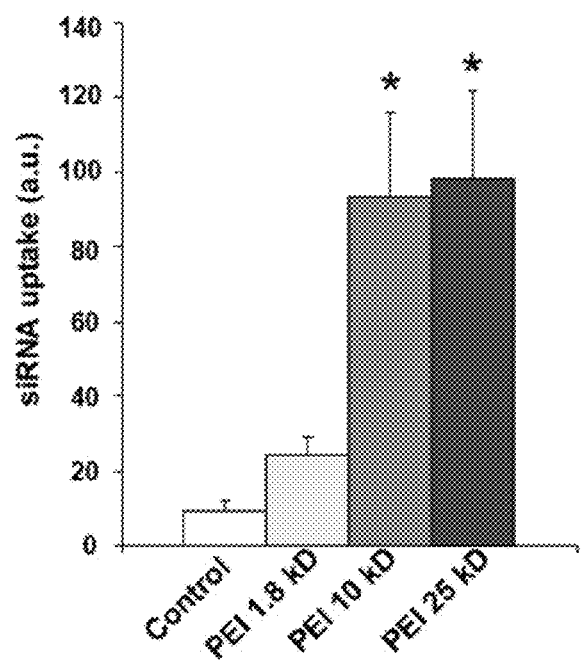
Figure 19D:
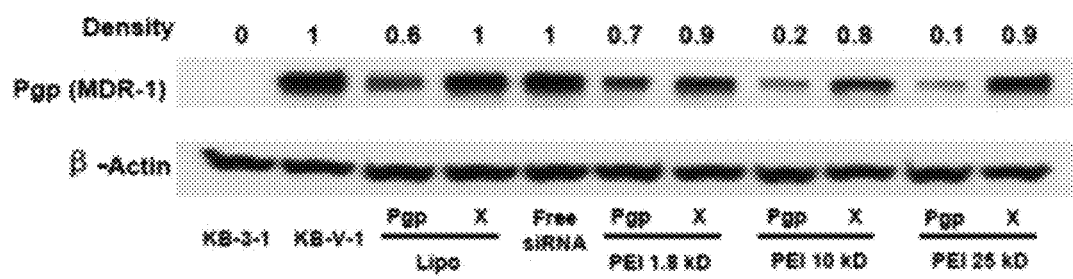
Figure 24:
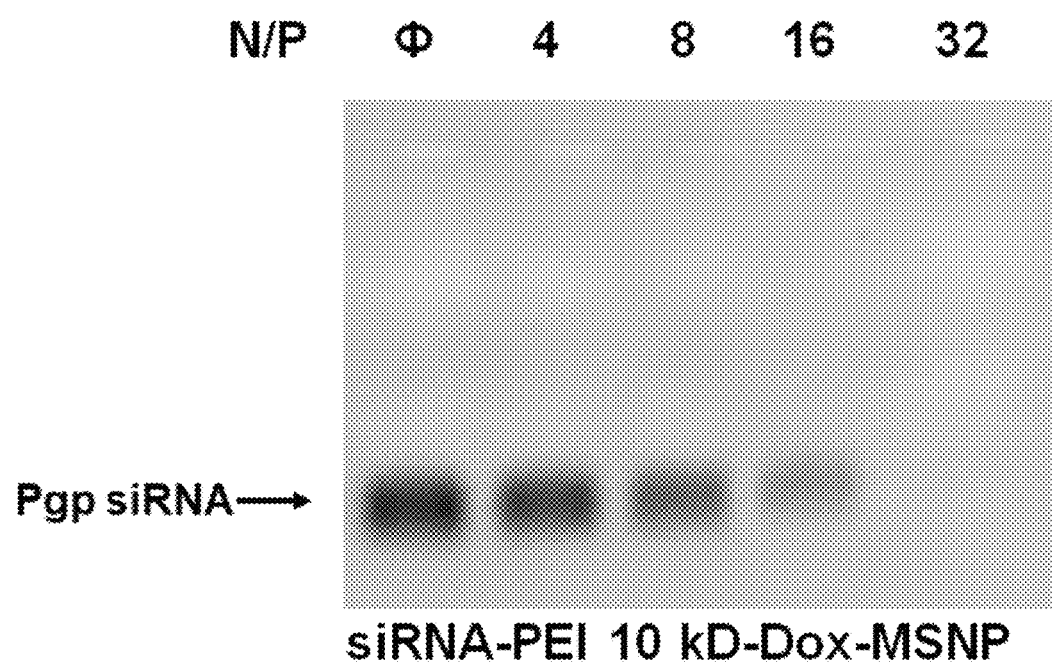
FIG. 24 shows agarose gel electrophoresis of PEI 10 kD-coated MSNP to which Pgp siRNA was complexed at various nanoparticle to nucleic acid (N/P) ratios. The ϕ lane contains Pgp siRNA only. The threshold N/P ratio (N/P=16) remains the same with or without Dox loading (FIG. 19A, middle panel).

In order to determine the optimal N/P ratios for Pgp siRNA delivery, agarose gel electrophoresis was used to evaluate binding of various amounts of siRNA to MSNP coated with the different polymer lengths as shown in FIG. 19A. This demonstrated that binding capacity increases with increasing size of PEI polymers, indicating that all siRNA was bound at a N/P ratio>16 (PEI1.8 kD), >16 (PEI 10 kD) and >8 (PEI 25 kD). Based on this result, N/P ratios of 80, 80 and 10 were used for polymer lengths of 1.8, 10 or 25 kD, respectively for siRNA knockdown experiments. It is worth mentioning that Dox trapped in the pores of MSNP does not influence siRNA binding to the particle surface (FIG. 24) and also that siRNA binding does not significant change the zeta potential of MSNP (Table 3).

Cell Culture

All cell cultures were maintained in 25 cm$^2$ or 75 cm$^2$ cell culture flasks in which the cells were passaged at 70-80% confluency every 2-4 days. The drug-sensitive KB-31 line was cultured in Dulbecco's Modified Eagle Medium (DMEM) (Carlsbad, Calif.) containing 10% fetal calf serum (FCS), 100 U/ml penicillin, 100 µg/ml streptomycin, and 2 mM L-glutamine (complete DMEM medium). The MDR cell line, KB-V1 (kindly provided by Dr. Michael M. Gottesman from National Cancer Institute, NIH, Bethesda, Md.), was maintained in 1 µg/ml of vinblastine (made up from 10 mg/ml stock in DMSO) in complete DMEM (Ludwig et al., Cancer Res., vol. 66, pp. 4808-4815, 2006). While the doubling time of the parental line was approximately 14-18 hrs, the resistant cell line doubled every 25-30 hrs.

Assessment of Cellular Uptake of Dual Fluorescent Labeled siRNA-PEI-MSNP by Confocal Microscopy 200 µg FITC-labeled PEI coated MSNP were incubated with 2.5 µg Texas red-labeled Pgp siRNA for 30 minutes to yield a N/P ratio of 80. Cellular uptake of MSNP was performed by adding 20 µg/ml of the dual-labeled particles to 8-well chamber slides. Each well contained 5×10$^4$ cells in 0.4 ml culture medium. Cell membranes were co-stained with 5 μg/ml Alexa Fluor 633-conjugated wheat germ agglutinin (WGA) in PBS for 30 min. Slides were mounted with Hoechst 33342 and visualized under a confocal microscope (Leica Confocal lP/FCS) in the UCLA/CNSI Advanced Light Microscopy/Spectroscopy Shared Facility. High magnification images were obtained with the 100× objective. The signal intensity of the red channel, reflecting siRNA abundance, was calculated by Image J software (version 1.37c, NIH).

Subsequent performance of confocal microscopy utilizing dual-labeled particles (Texas red-labeled-siRNA adsorbed to FITC-labeled MSNP) demonstrated a high rate of cellular uptake in KB-V1 cells in accordance with polymer length (FIG. 19B). Image J analysis confirmed a significant increase in siRNA uptake for particles coated with the 10 and 25 compared to the 1.8 kD polymer (FIG. 19C). The reason for this high uptake is due to the positively charged amines, which facilitates strong PEI binding to and wrapping by the surface membrane (Xia et al., *ACS Nano*, vol. 3, pp. 3273-3286, 2009). Please notice that the Pgp siRNA (red) and FITC-MSNP (green) co-localize (yellow, merged) in the cell, demonstrating that the nucleic acid is stably attached to the PEI-coated particle surface (FIG. 19B). It has previously been demonstrated that nucleic acids bound to the PEI-MSNP surface are resistant to enzymatic cleavage (Xia et al., *ACS Nano*, vol. 3, pp. 3273-3286, 2009).

siRNA-PEI-MSNP Exposure and Assessment of PGP Expression

PGP siRNA-PEI-MSNP complexes were freshly prepared as described above. The siRNA duplex consists of 5'-r (CGGAAGGCCUAAUGCCGAA) dT (SEQ ID NO: 1) (sense) and 5'-r(UUCGGCAUUAGGCCUUCCG) dG (SEQ ID NO:2) (antisense) strands. First, 5 μl of 250 ng/μl PGP siRNA or scrambled siRNA was added to 100 μg PEI 1.8 kD-MSNP (N/P ratio=80), 100 μg PEI 10 kD-MSNP (N/P ratio=80), or 12.5 ug PEI 25 kD-MSNP (N/P ratio=10), in 5 μl aqueous solution. After incubation at room temperature for 30 min, the complexes were stabilized by 1 mg/mL BSA and then transferred into 1 ml complete DMEM. KB-V1 cells were plated at $2\times10^5$ cells per well, then exposed to the complexes for 16 hrs. Sixteen hours later, the medium was replaced with fresh DMEM containing 10% FCS and cultured for a further 56 hrs. Cells then were harvested for immunoblotting.

Briefly, KB-31 and KB-V1 cells were plated at $1\times10^4$ cells per well in 96 well plate. The cells were treated with free Dox in solution in doses ranging from 0.05-3.2 μg/ml (KB-31) and 0.1-64 μg/ml (KB-V1) for 72 hrs. The cell viability was determined by the MTS assay. The treated cells were incubated with MTS working solution for 2-3 hrs before measurement. The mean absorbance of non-exposed cells served as the reference value for calculating 100% cellular viability. To view Pgp expression, the cells were washed in PBS and the pellets lysed in a buffer containing Triton X-100 and protease inhibitors after centrifugation. The protein content of the supernatants was determined by the Bradford method. 100 μg total protein was electrophoresed by 10% SDS-PAGE and transferred to a PVDF membrane. After blocking, the membranes were incubated with 1:1000 dilution of primary monoclonal antibody to MDR1 (anti-Pgp C219, Abeam). The membranes were overlayed with goat anti-mouse secondary antibody (1:1000 dilution) before the addition of the HRP-conjugated streptavidin-biotin complex. The proteins were detected using ECL reagent according to the manufacturer's instructions.

A commercially available cationic liposomal transfection agent (Lipofectamine 2000) was used as a positive control. Protein abundance was quantified by densitometric scanning using a laser Personal Densitometer SI and Image Quant software (Amersham Biosciences).

Figure 25:
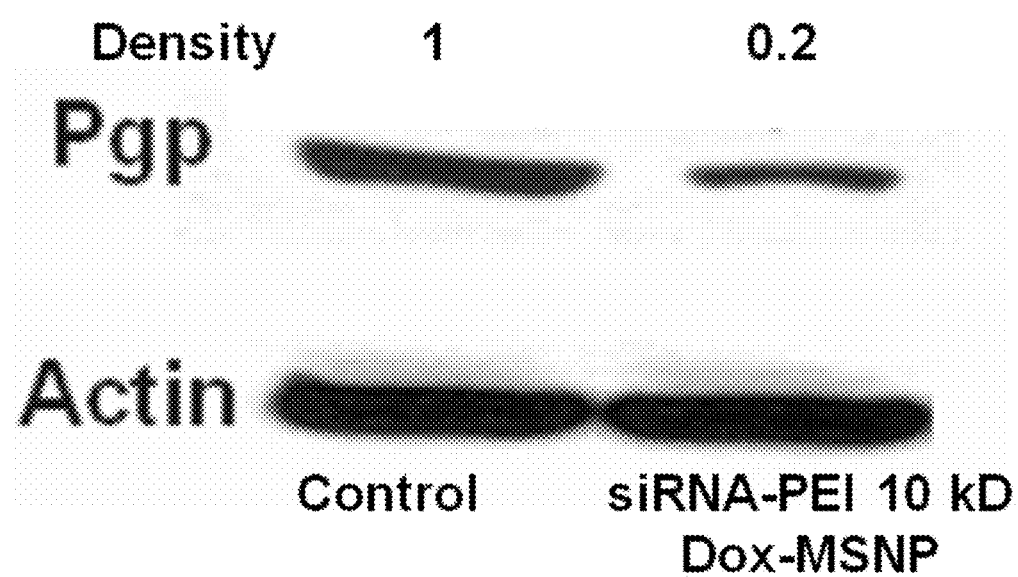
FIG. 25 shows Pgp expression was significantly knocked down (~80%) by siRNA-PEI 10 kD-Dox-MSNP treatment at the dose of 10 µg/ml for 72 hrs. Knockdown of Pgp expression by siRNA is not influenced by Dox loading.

To assess the efficacy of Pgp siRNA delivered by PEI-coated MSNP, Pgp expression was followed by western blotting (FIG. 19D). This demonstrated 80 or 90% reduction, in MDR-1 expression in cells treated with MSNP coated particles that contain the 10 and 25 kD polymers, respectively. This efficacy was maintained in Dox-loaded MSNP (FIG. 25). Scrambled siRNA-PEI-MSNP (marked as "X" in FIG. 19D) was used as a negative control to rule out any impact by the siRNA delivery method. No Pgp knockdown was seen in the scrambled siRNA-MSNP group. The PEI-coated particles were also more effective than the commercially available transfection agent, Lipofectamine 2000, which is widely used in molecular biology.

Optimizing Dox Loading and Release Via a Proton-Sensitive Mechanism In Vitro

Based on its cationic charge at pH 7.4, it was uncertain whether Dox (pKa=8.2) would bind to the negatively charged porous interior, including under circumstances where the exterior surface was occupied by PEI. 10 mg of MSNP functionalized by OH, COOH or phosphonate attachments were mixed with 1 mg of Dox in 0.25 mL water for 12 hrs. As control, positively charged amine-MSNP was used. Subsequently, the particles were collected by centrifugation and washed with water. To corroborate the electrostatic binding hypothesis, the cationic fluorescent dye, Hoechst 33342 (pKa=11.9) was used as model cargo in the same particles. This procedure was repeated in phosphonate MSNP that were coated with 10 and 25 kD PEI polymers. In order to compare the loading yields of above particles, 1 mg Dox-loaded MSNP pellet was resuspended and sonicated in 1 mL of a heated HCl solution (pH=5.0) for 15 minutes. After centrifugation, another 1 mL fresh HCl aqueous solution was added. All the supernatants were combined until the MSNP became colorless. At this point the pH was readjusted to 7.0 by 1 M NaOH and the fluorescence spectrum of Dox measured at excitation and emission wavelength of 485/550 nm in a microplate reader (SpectraMax MS Microplate Reader, Molecular Device, USA). The procedure was also repeated to determine Dox loading in MSNP coated with 10 kD and 25 kD PEI polymers.

The effects of acidification and ethanol extraction of Dox-loaded phosphonate MSNP were assessed. 1 mg Dox-loaded MSNP was suspended into 3 ml phenol red-free DMEM medium acidified to pH 5.0 or replenished with 10% (v/v) ethanol at 37° C. The supernatants were collected at various time points and cleared by centrifugation for measurement of Dox fluorescence. Similar experiments were carried out in siRNA bound phosphonate-MSNP coated with PEI polymers. To see if the release profile will be influenced by siRNA binding, release after 12 hrs was studied using siRNA-PEI-Dox-MSNP.

Figures 27A, 27B:
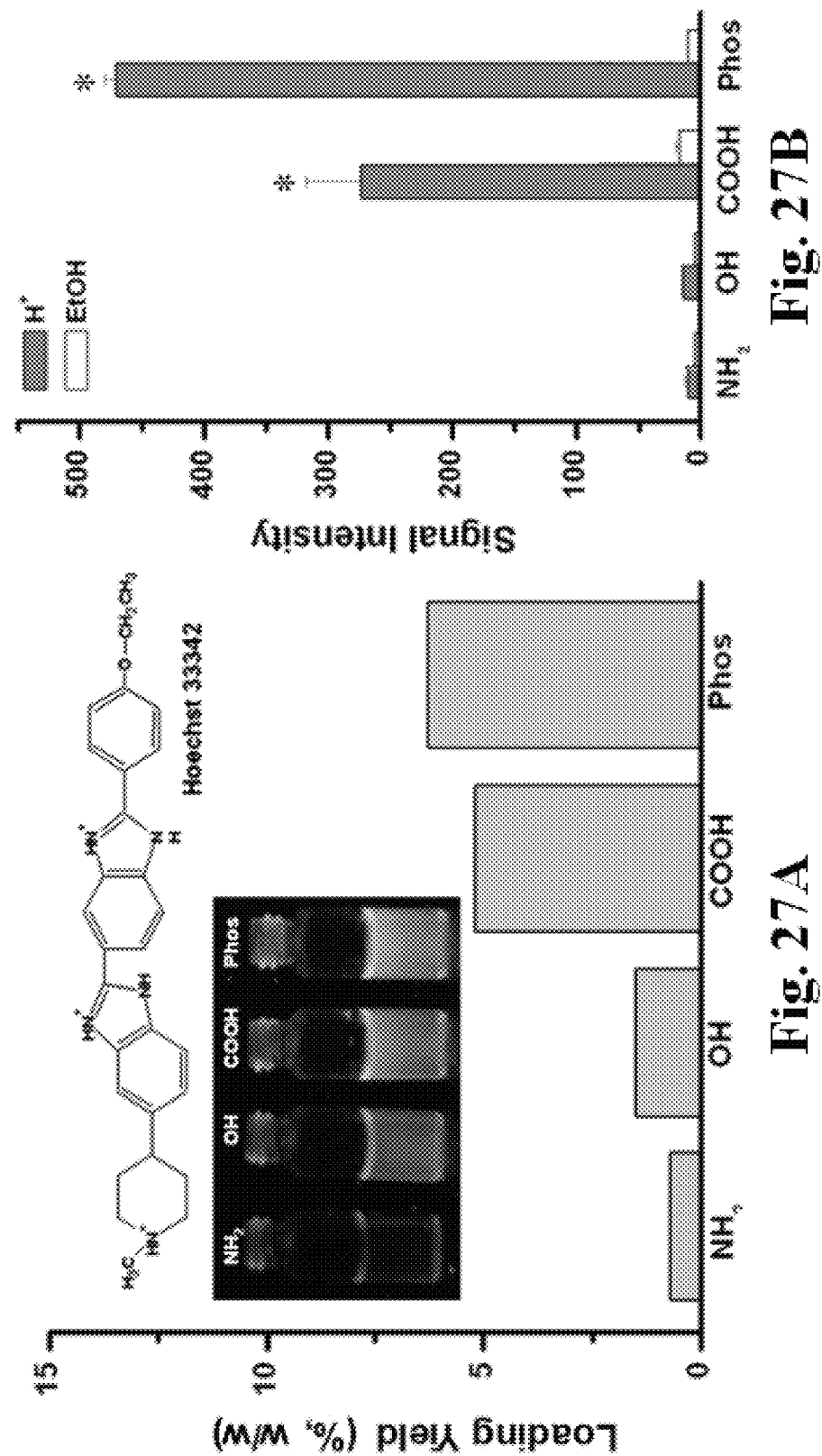
FIGS. 27A and 27B show loading and release profile of Hoechst 33342 loaded MSNP with various surface modifications.

MSNP are capable of loading and releasing water-insoluble drugs (paclitaxel and camptothecin) by a phase transfer mechanism that can be reversed by ethanol washing of the particles to demonstrate the role of hydrophobicity in MSNP drug entrapment (Xia et al., *ACS Nano*, vol. 3, pp. 3273-3286, 2009; Jie et al., *Small*, vol. 3, pp. 1341-1346, 2007). A key question was whether similar effective packaging of water-soluble Dox, is possible at physiological pH, where the drug (pKa=8.2) carries a positive charge. One conceivable approach is electrostatic attachment to the negatively charged MSNP surface. To test this possibility, Dox was loaded in MSNP decorated with OH, COOH or phosphonate groups. These particles were also compared to positively charged particles decorated with amine groups. After washing of the drug-bound particles and quantification of Dox release by HCl, the loading capacities of OH—, COOH— and phosphonate-MSNP were 1.2%, 4.2% and 8.4% (w/w), respectively (FIG. 20A). By contrast, amine-decorated particles showed low (<0.1%, w/w) Dox binding capacity (FIG. 20A). The principle of electrostatic binding to a negatively charged particle surface was also demonstrated through the use of a cationic dye, Hoechst 33342, which bound to negative but not a positive MSNP surface (FIG. 27). Importantly, electrostatic binding of Dox to the phosphonate surface was not negated by when the particles were also coated with 10 or 25 kD PEI polymers; these particles demonstrated equivalent loading capacity to the uncoated phosphonate particles (FIG. 20B).

Figure 20D:
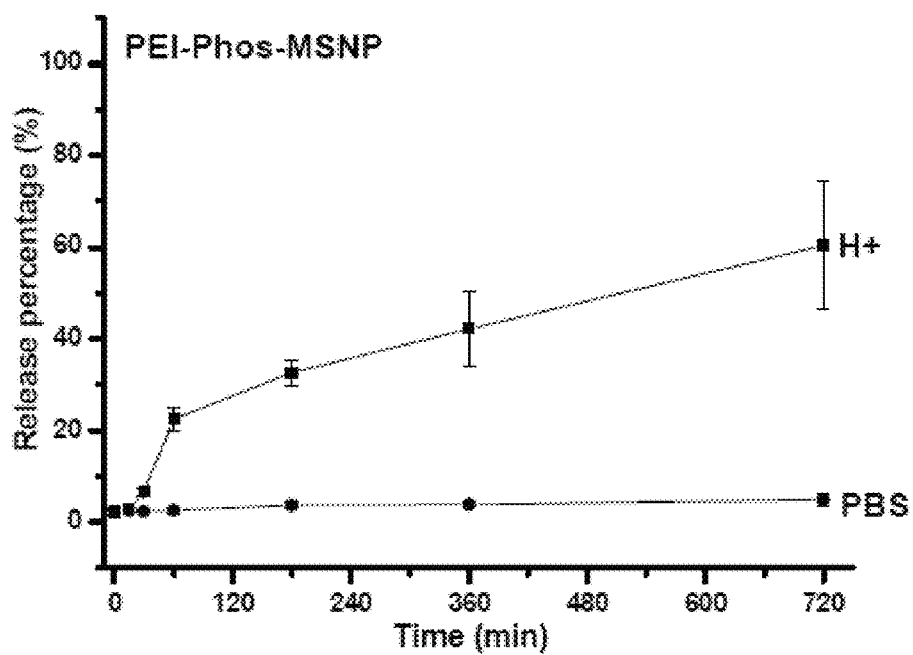
Figure 20F:
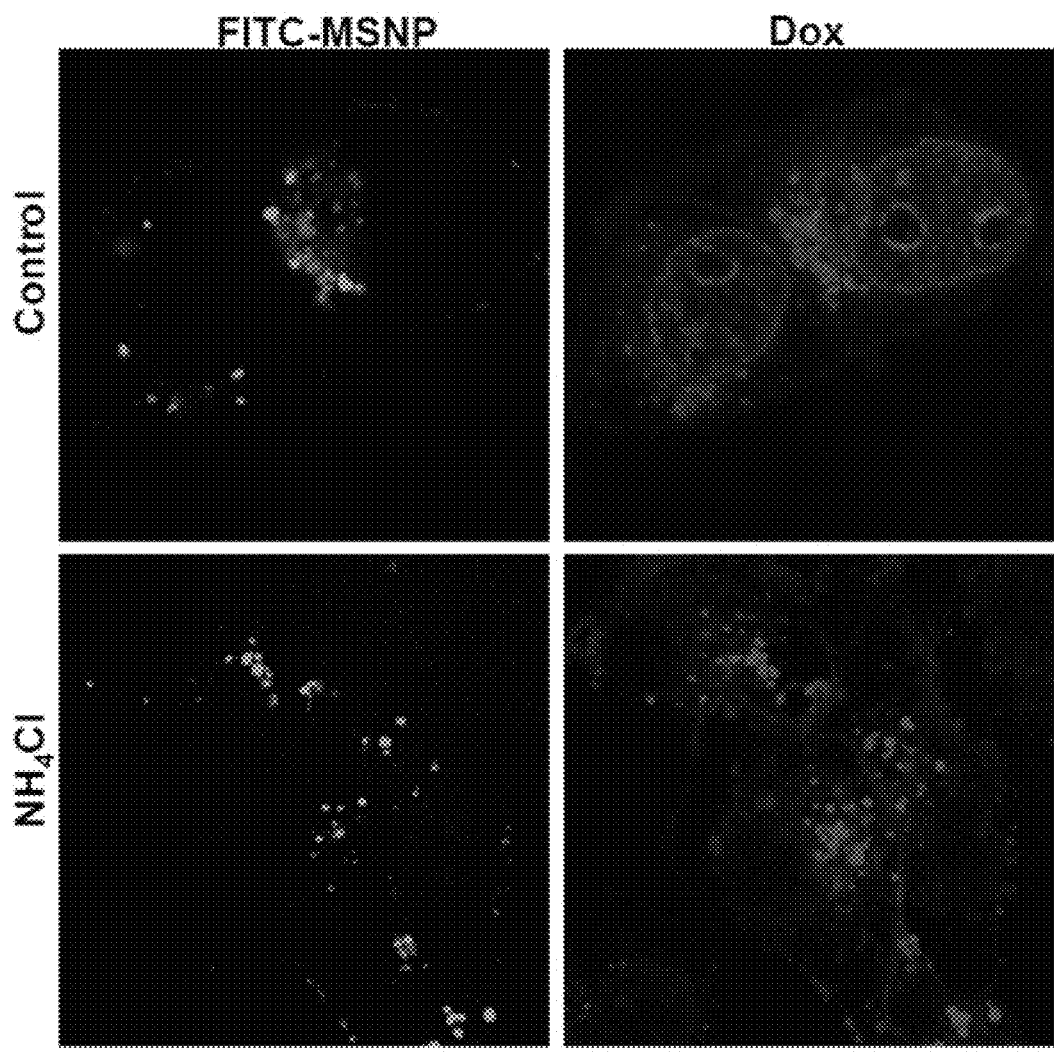
Figure 28:
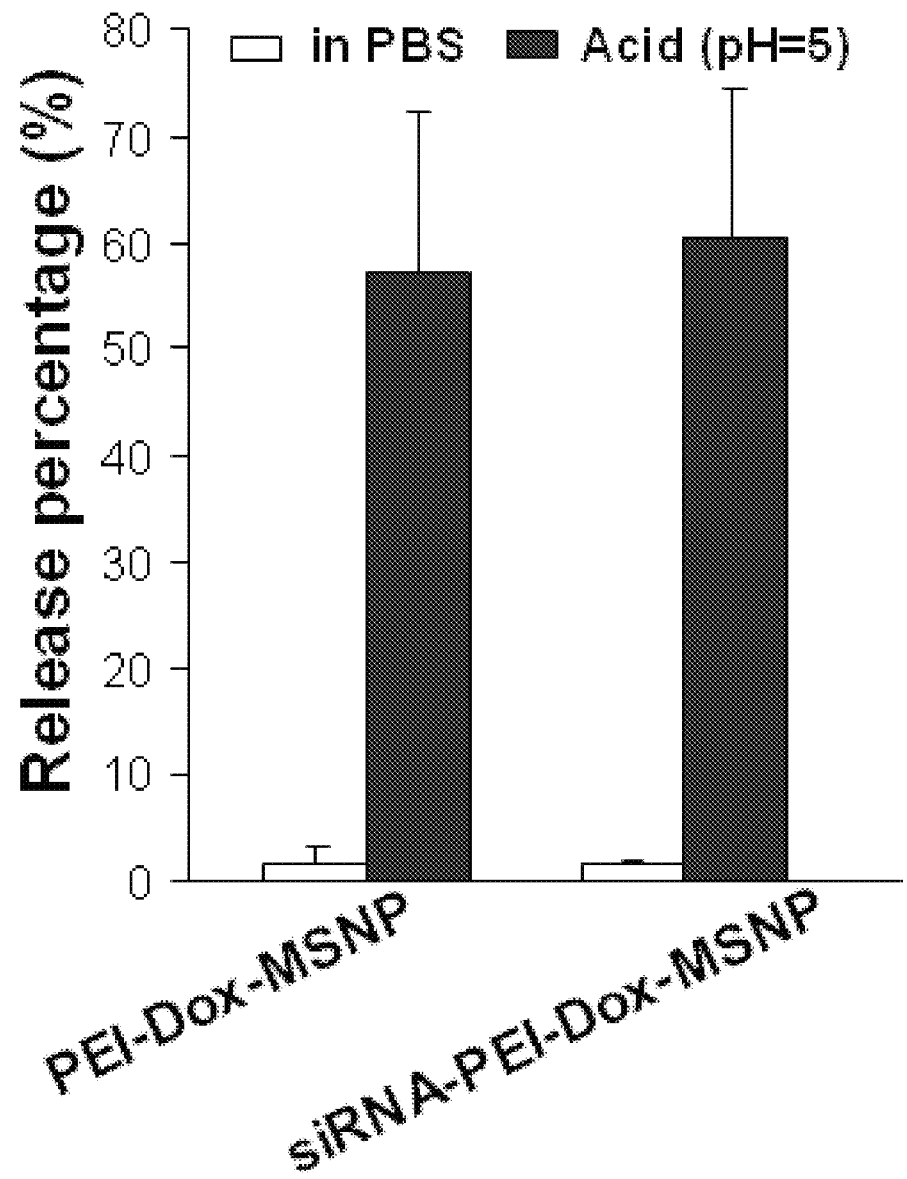
FIG. 28 shows that the Dox release profile remains same with or without siRNA binding on PEI 10 kD-MSNP. The experiment was performed in acidifying phenol red free DMEM medium (pH=5) at the 12 hr time point. PBS was used as control. The date show that Dox release will not be influenced by siRNA that binds to PEI polymer where locates at the exterior of MSNP.

Importantly, Dox could be released in a time-dependent manner from the phosphonate-MSNP or PEI-phosphonate-MSNP surface by lowering of the solution pH (FIGS. 20C and 20D). The Dox release profile was not be affected by siRNA binding to PEI on exterior surface of the particle (FIG. 28). This establishes the possibility that intracellular drug release should be possible if the particles are capable of gaining entrance to acidifying cellular compartments.

To illustrate the drug loading/release mechanism is different between water soluble drug and water insoluble drug, the effect of surface charge on binding and release of the hydrophobic chemotherapeutic agent, CPT was evaluated. 10 mg of surfactant-extracted particles was mixed in a solution of 1 mg of CPT and 0.25 mL DMSO for 12 hrs. The CPT-loaded particles were collected by centrifugation, dried under vacuum, and washed with water. The loading yield, release profile was studied based on the fluorescent readout of CPT ($\lambda_{ex/em}$=370/429 nm) in a microplate reader (FIG. 32).

Confocal Microscopy to Determine MSNP Lodging in an Acidifying Cellular Compartment, Including the Effects of Inhibiting Lysosomal Acidification on Dox Release KB-V1 cells grown on chamber slides were fixed, permeabilized, and labeled with standard immunocytochemistry protocol (Xia et al., ACS Nano, vol. 3, pp. 3273-3286, 2009). LAMP-1 staining was performed by using a 1:500 dilution of mouse-anti-human mAb (H4A3, Abeam, USA) for 16 hrs at 4° C. This was followed by a 1:500 diluted TRITC-conjugated goat-anti-mouse secondary antibody (Santa Cruz, USA) for 1 hr at room temperature. Cell membranes and nuclei were stained with WGA 633 and Hoechst 33342, respectively. Slides were visualized under a confocal microscope (Leica Confocal 1P/FCS). Since the Dox release is a proton-sensitive process, the effect of neutralizing the lysosomal pH with $NH_4Cl$ was also investigated in KB-31 cells. These cells were initially treated with 40 μg/ml FITC-labeled MSNP that were simultaneously coated with the 10 kD PEI polymer with or without the addition of 20 mM $NH_4Cl$. All the images of the particles and fluorescent Dox release were captured by the same confocal microscopy applying same parameter setting over a 72 hour time period.

In order to determine whether this is possible in KB-V1 cells, the intracellular localization of FITC-labeled MSNP was measured in relation to lysosomal co-staining by fluorescent labeled anti-LAMP-1 antibody. Indeed, confocal microscopy confirmed >55% co-localization of the green-labeled particles with the red-labeled lysosomes (FIG. 20E). Moreover, in a subsequent confocal study released Dox from PEI-coated particles after entrance into the lysosome could reach the nucleus, which was brightly stained by the fluorescent drug (FIG. 20F, upper panel). Some of the drug was retained in particles localized in the peri-nuclear region. This visual image changed completely when cells were treated with $NH_4Cl$; most Dox remained confined to the lysosomal compartment with little or no nuclear staining (FIG. 20F, lower panel). This suggests that the interference in lysosomal acidification by $NH_4Cl$ prevents effective Dox release to KB-V1 nuclei.

Determination of Intracellular Dox Concentration

Dox uptake in KB-V1 cells was quantitatively evaluated in a microplate reader at 72 hrs. $5 \times 10^4$ cells were placed into a 96 wells plate and treated with 2 μg/ml free Dox or the equivalent amount of drug loaded into MSNP before or after PEI coating, with or without attachment of Pgp siRNA. Following the washing of the cells in cold PBS, the intracellular Dox fluorescence was detected at excitation and emission wavelength of 485/550 nm in a microplate reader (SpectraMax MS Microplate Reader, Molecular Device, USA). Moreover, confocal images were captured at the end of experiment. Image J software (version 1.37c, NIH) was used to analyze the nuclear fluorescence.

Figure 21A:
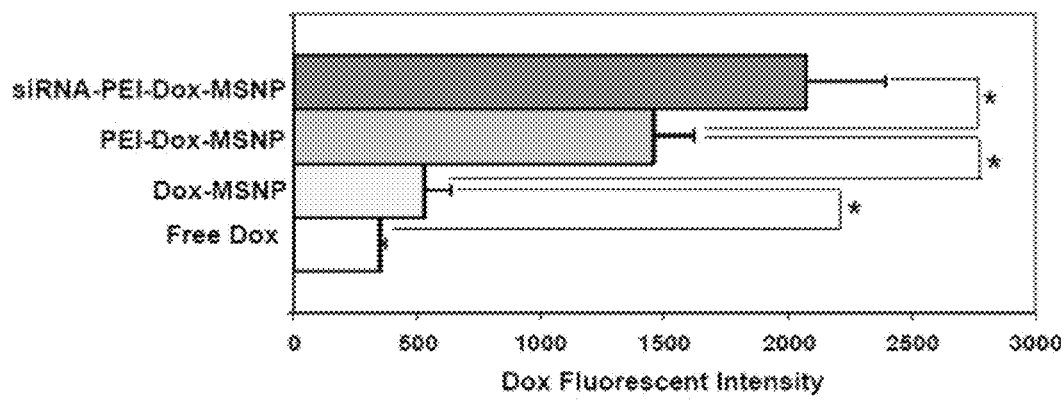
FIGS. 21A-21C show simultaneous delivery of Dox and Pgp siRNA to the nucleus leads to a synergistic increase in cellular and nuclear Dox levels in KB-V1 cells.
Figure 21B:
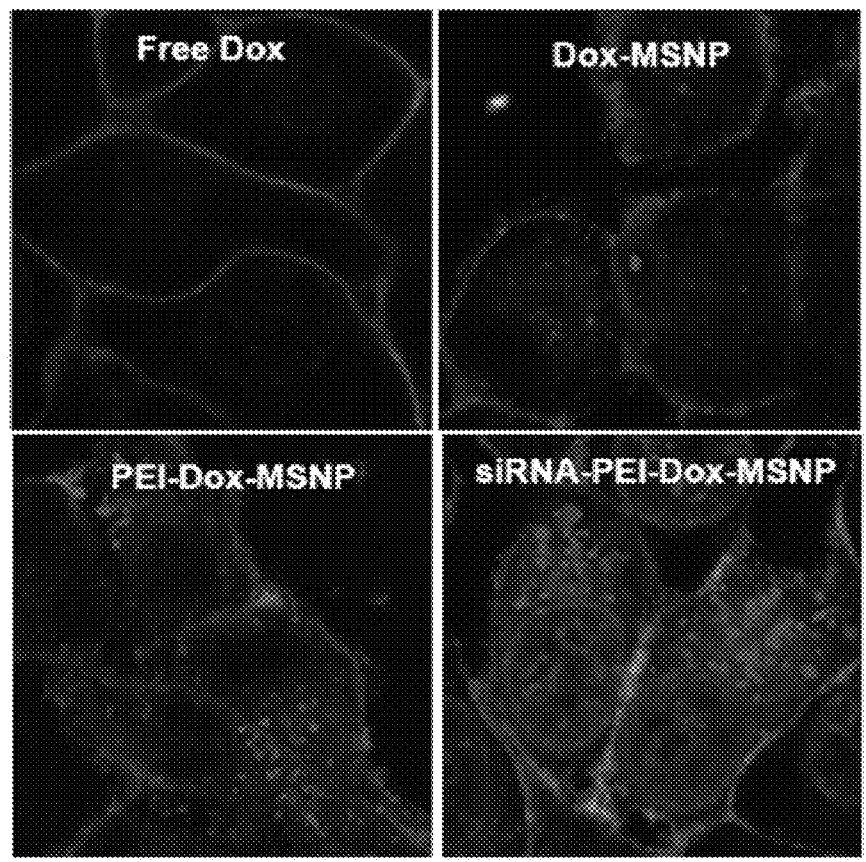
Figure 21C:
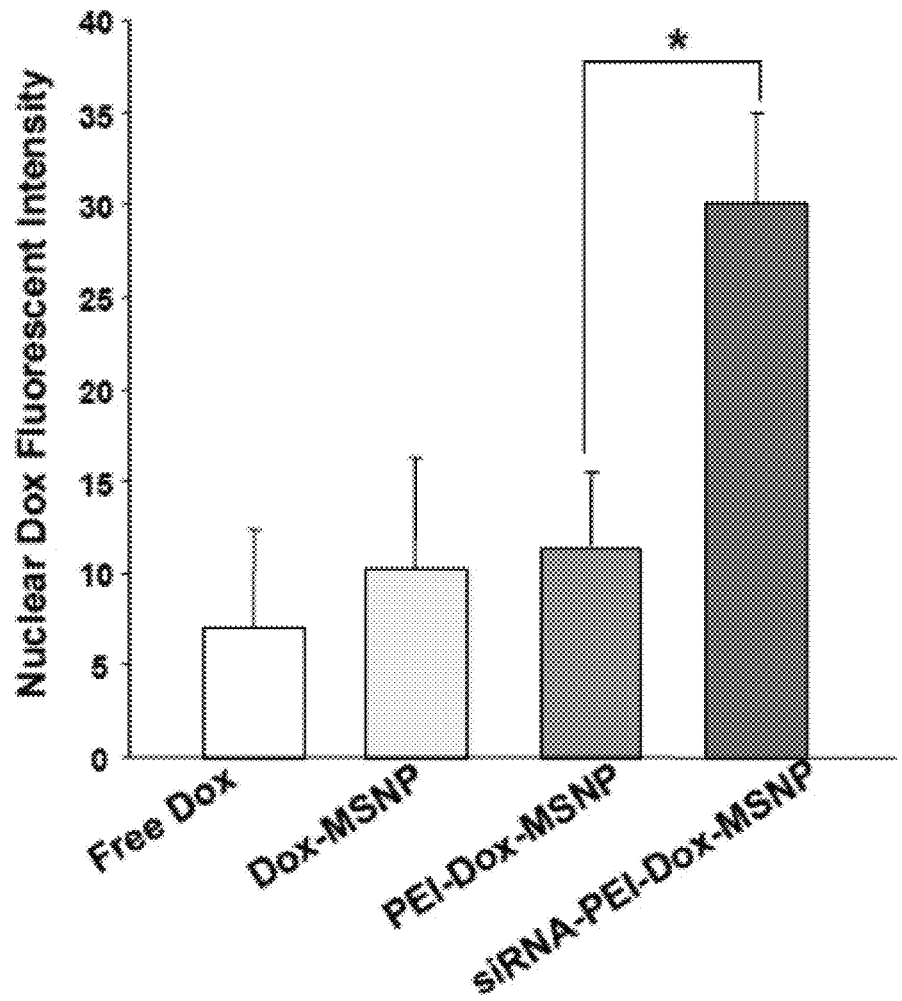

The relative inefficiency of free Dox to induce KB-V1 cytotoxicity may be a result of the rapid rate by which the drug was being exported by the overexpressed Pgp. Intracellular Dox concentration can be determined by measuring cellular Dox fluorescence intensity in a microplate reader (FIG. 21A). The comparatively low drug uptake after treatment with free Dox was slightly improved by delivering the drug via the phosphonate-MSNP. While the total amount of intracellular drug increased when being delivered by particles coated with the 10 kD PEI polymer (FIG. 21A), little of the drug reached the nucleus as determined by confocal imaging (FIG. 21B). Interestingly, the intracellular Dox concentration increased significantly in the presence of siRNA (FIG. 21A) so that there was also a significant increase in nuclear Dox staining by 72 hr (FIG. 21B). This contrasts with most of the Dox being confined to the endosomal compartment in cells not receiving siRNA, suggesting that although PEI-MSNP may take more Dox into to cells, any released drug is rapidly extruded from the cell before reaching the nucleus (FIG. 21B). This suggests that knocking down Pgp expression (FIG. 25) allows a sufficient quantity of the drug being slowly released from the particle to enter the nucleus where it induces cytotoxicity. A quantitative measurement of Dox release to the nucleus through the use of Image J software confirmed a statistically significant increase of the drug in KB-V1 nuclei after delivery by siRNA-PEI-Dox-MSNP as compared to free Dox or Dox loaded into the particles without siRNA (FIG. 21C). Dox delivered by PEI-MSNP in the presence of siRNA significantly enhance intranuclear Dox concentration when compared to free Dox or Dox delivered by MSNP or PEI-MSNP without siRNA.

Assessment of Cytotoxicity and Apoptosis in KB-V1 Cells Treated with Dox-Loaded Particles in the Absence and Presence of Pgp siRNA To measure cytotoxicity of the different Dox formulations, KB-V1 cells were treated with free Dox, Dox-MSNP, PEI-Dox-MSNP and siRNA-PEI-Dox-MSNP, respectively. For the latter two particle types, incubation time was for 16 hrs before replenishment of the old medium with fresh complete DMEM and performance of a MTS assay at 72 hrs. Based on the absorption readout at 490 nm, the $IC_{50}$ of free and Dox-loaded MSNP were calculated. The induction of apoptosis at 72 hours was assessed through the use of Annexin V-SYTOX Blue. Briefly, $5 \times 10^5$ cells were harvested and stained by FITC-Annexin V-SYTOX Blue working solution (Annexin V, Trevigen; SYTOX Blue, Invitrogen) at room temperature for 15 min. The cells were washed in binding buffer before performance of flow cytometry (Becton Dickinson, Mountain View, Calif.). Date analysis was performed by BD CellQuest. To confirm the flow data in which there may be a minor overlap of Dox with FITC-Annexin V, a TUNEL detection kit was used according to the manufacturer's instructions to confirm the induction of apoptosis. Briefly, 72 hrs following treatment with free Dox or Dox loaded particles, cells were washed, fixed, and permeabilized before TUNEL staining. The number of TUNEL-positive cells was assessed under a fluorescent microscope (200×). At least 3 fields were counted by the same investigator to calculate the percentage of TUNEL positive cells.

Figure 22A:
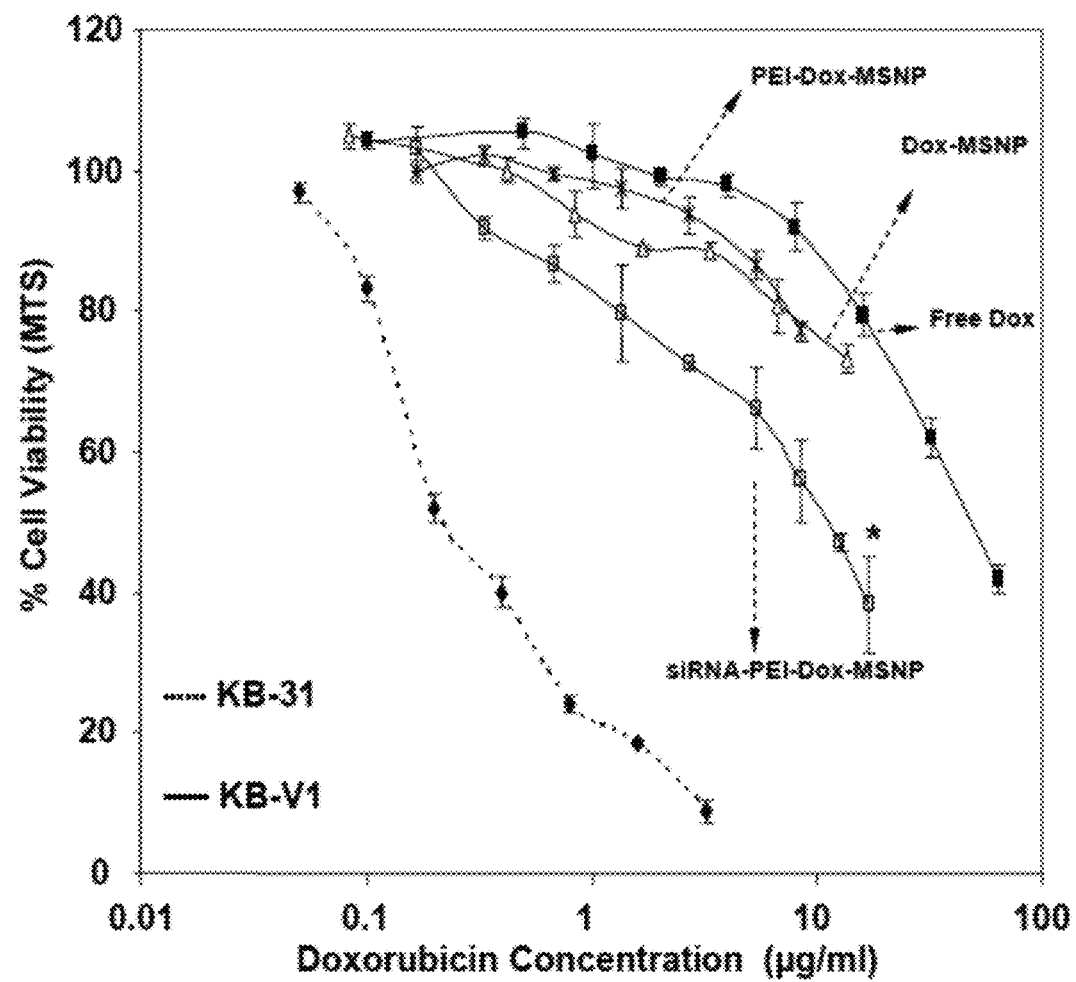
FIGS. 22A and 22B show a comparison of the cytotoxic effects of different delivery modalities of Dox in KB-V1 cells.
Figure 22B:
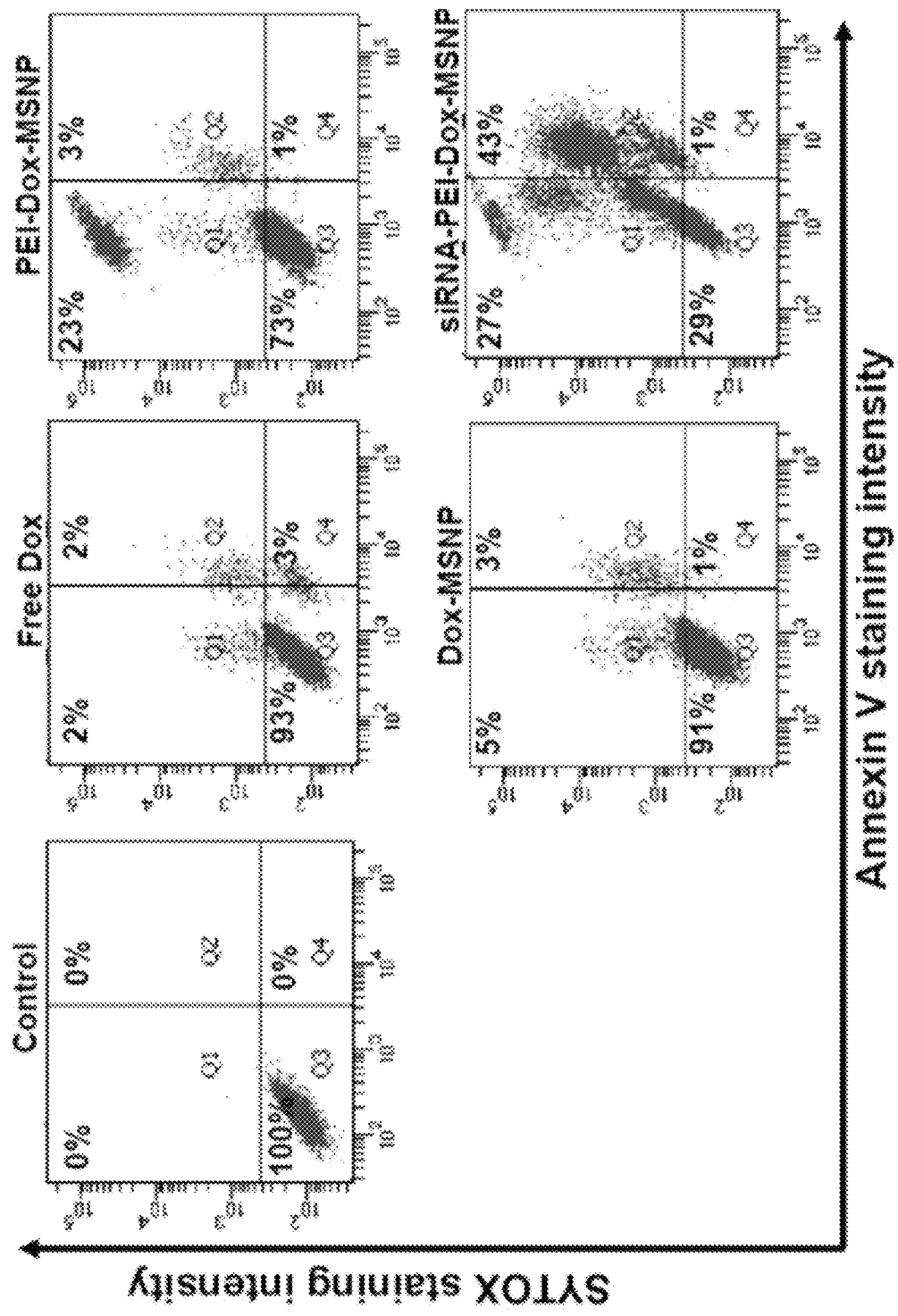
Figure 29:
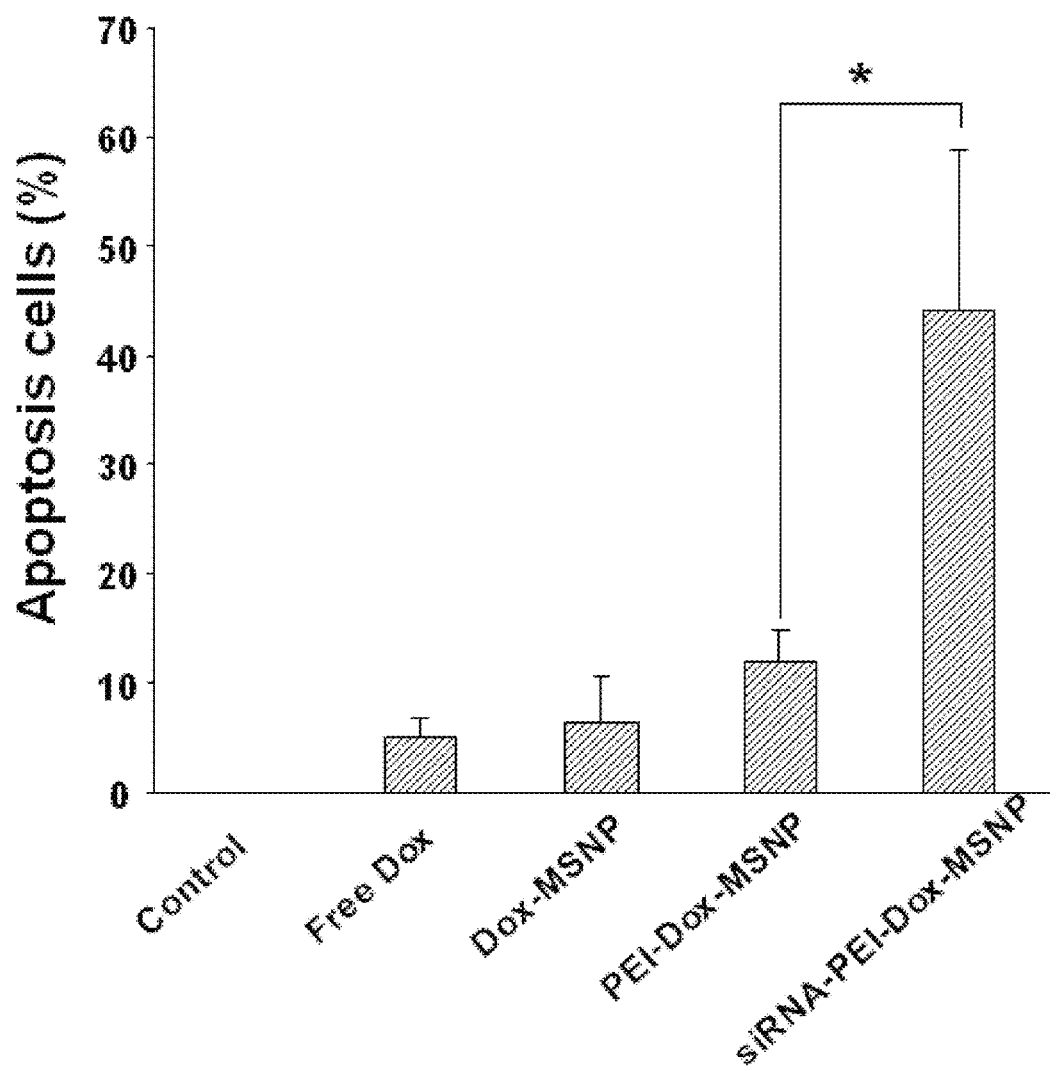
FIG. 29 shows a TUNEL detection kit used according to the manufacturer's instructions to study Dax-induced apoptosis. Percentage of TUNEL positive cell showing enhanced apoptosis by siRNA-PEI-Dox compared to the other Dox modalities. The result shows the same trend of flow cytometry data (FIG. 22B).
Figure 30:
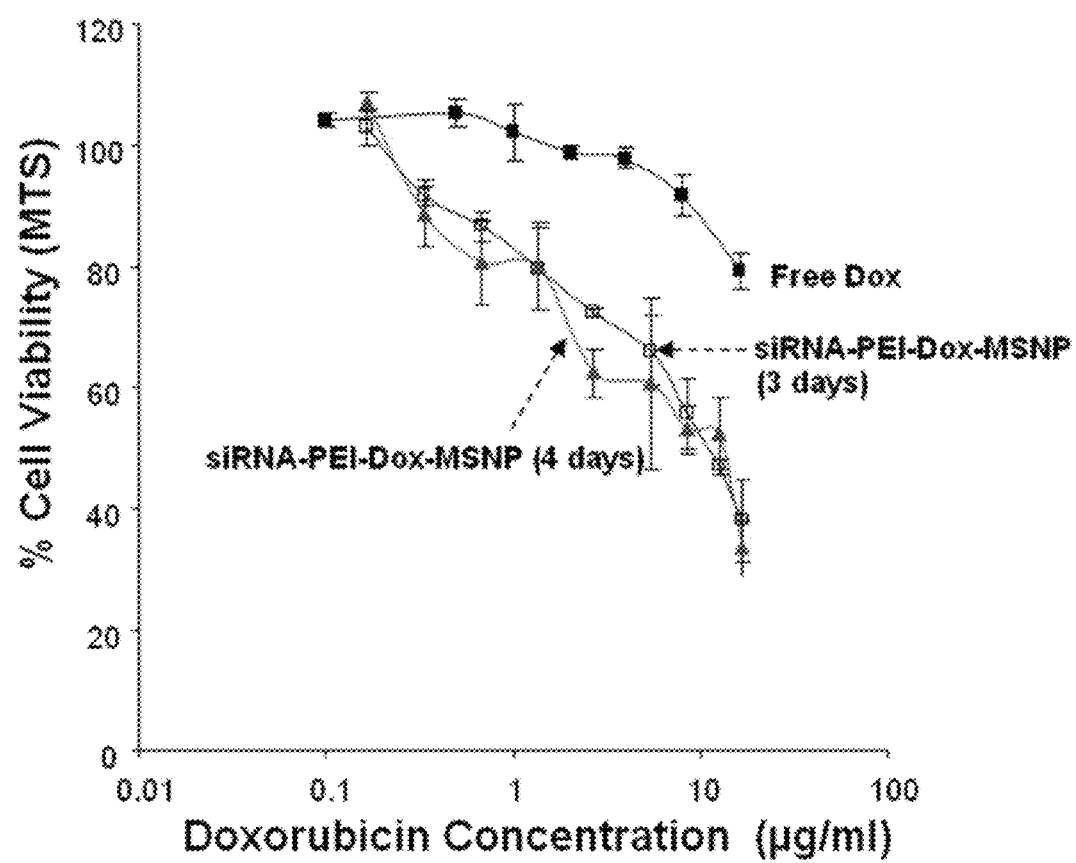
FIG. 30 shows cell viability analyzed after longer exposure periods (4 days) because Pgp knockdown by siRNA may need a certain amount of time, but did not observe a significant improvement in cytotoxicity.
Figure 31:
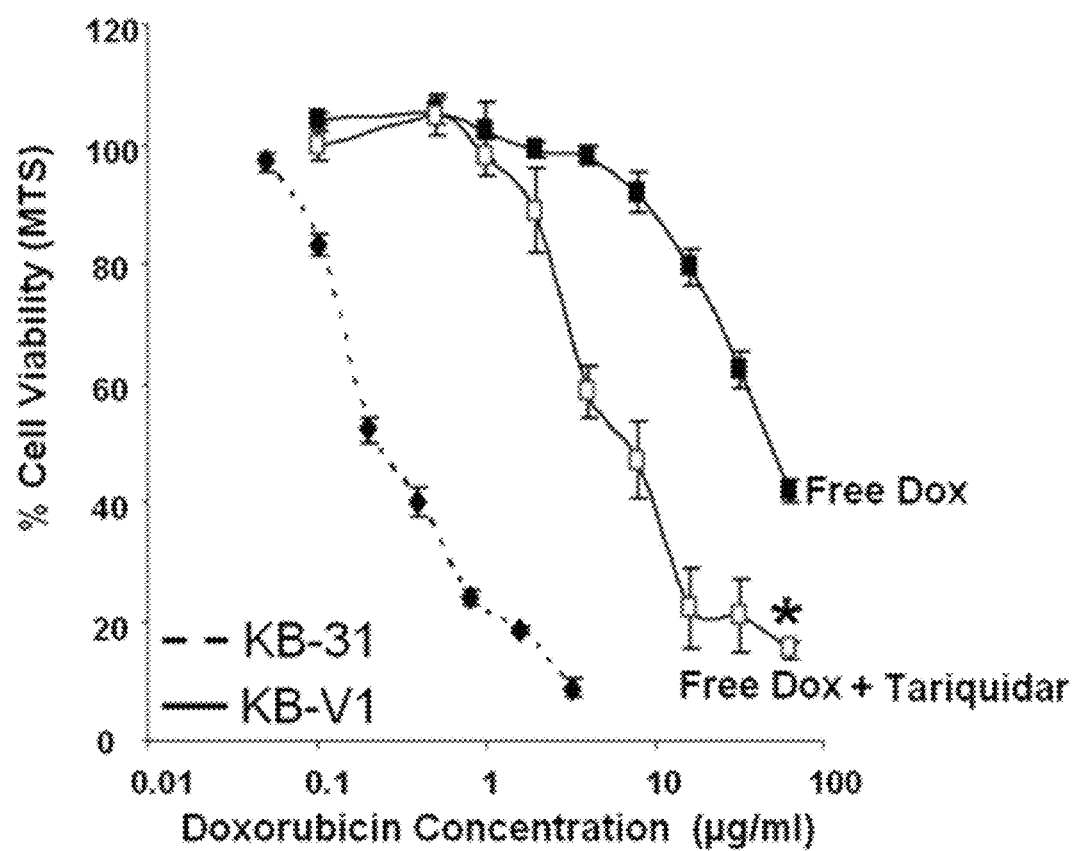
FIG. 31 shows that co-administration of free Dox and Tariquidar (50 nM) partially restores drug sensitivity in KB-V1 cells for 72 hrs. This combination significantly improved cell killing capability in KB-V1 cells, but was not able to completely restore Dox sensitivity to the level seen in KB-31 cells.

In order to reconcile these findings with improved cell killing, the MTS assay was used to compare KB-V1 cytotoxicity under incremental Dox concentrations (FIG. 22A). Based on the calculated $IC_{50}$ values of the various formulations, it was possible to rank the killing efficiency as follows: siRNA-PEI-Dox-MSNP >PEI-Dox-MSNP=Dox-MSNP >free Dox. Moreover, the $IC_{50}$ value of the siRNA-delivering MSNP was approximately 2.5 times lower than the $IC_{50}$ of free Dox or other Dox-loaded particles. This suggests an additive effect between the drug and the siRNA that are being delivered by MSNP. Although it was not possible to restore drug sensitivity to the level seen in KB-31 cells, a much higher percentage of apoptotic KB-V1 cells were observed after treatment with Dox-loaded MSNP that co-delivers siRNA as compared to free Dox or Dox delivered by non-siRNA delivering particles (FIG. 22B). Flow cytometry data was confirmed through the use of another apoptosis assay using TUNEL staining (FIG. 29), which showed an identical trend. Failure to fully restore drug sensitivity could be due to extremely high levels of Pgp expression and/or additional drug resistant pathways in KB-V1 that were not targeted in the current research. Because of the duration of time it takes for the siRNA to exert its effect, cell viability was analyzed after longer treatment periods (e.g. 96 hrs) but did not observe any improvement in cytotoxicity (FIG. 30). In addition, KB-V1 cells were treated by co-administration of Dox and Tariquidar, which is a potent and effective Pgp inhibitor in human clinical trial, to see if KB-V1 sensitivity can be restored to that seen in KB-31 cells. While this combination significantly improves cell killing capability in KB-V1 cells, it is incapable of completely restoring Dox sensitivity to the level seen in KB-31 cells (FIG. 31).

Example 8—Small Particle Size and Surface Modification

A key challenge for improving the efficacy of passive drug delivery to tumor sites by a nanocarrier is to limit reticuloendothelial system (RES) uptake and to maximize the enhanced permeability and retention (EPR) effect. Size reduction and surface functionalization of mesoporous silica nanoparticles (MSNP) reduces particle opsonization while enhancing the passive delivery of monodispersed, 50 nm doxorubicin-laden MSNP to a human squamous carcinoma xenograft in nude mice after intravenous injection. Using near infrared (NIR) fluorescence imaging and elemental Si analysis, passive accumulation of ~12% of the injected particle load was demonstrated at the tumor site, where there is effective cellular uptake and the delivery of doxorubicin to KB-31 cells. This was accompanied by the induction of apoptosis and an enhanced rate of tumor shrinking compared to free doxorubicin. The improved drug delivery was accompanied by a significant reduction in systemic side effects such as animal weight loss as well as reduced liver and renal injury. These results demonstrate that it is possible to achieve effective passive tumor targeting by MSNP size reduction as well as introducing steric hindrance and electrostatic repulsion through coating with a co-polymer. Further endowment of this multifunctional drug delivery platform with targeting ligands and nanovalves may further enhance cell-specific targeting and on-demand release.

A preliminary study using MSNP with a ~100 nm primary particle size has shown that these particles could be taken up and accumulate in a human breast cancer (MCF-7) xenograft in nude mouse (Lu, et al., Small, vol. 6, pp. 1794-1805, 2010). However, the EPR effect was not calculated in this study and it has been realized that the original synthesis method yields particles that agglomerate extensively in biological media. This could make those particles ineffective from an EPR perspective insofar as the preferred particle size is generally considered to be in the 50-100 nm size range (Perrault et al., Nano Lett., vol. 9, pp. 1909-1915, 2009; Lee et al., Mal. Pharm., vol. 7, pp. 1195-1208, 2010; Cho et al., Clin. Cancer Res., vol. 14, pp. 1310-1316, 2008). Thus, size reduction might be helpful to increase the passive targeting effects of MSNP but even if the size was shrunken, the ionic conditions and proteins present in biological fluids could contribute to agglomeration and that may require additional design features (Perrault et al., Nano Lett., vol. 9, pp. 1909-1915, 2009).

In this study a dynamic design strategy was used to improve the biodistribution and the EPR effect of the first generation MSNP to improve doxorubicin delivery to a human squamous carcinoma xenograft in nude mice. A dramatic improvement of the EPR effect was produced by reducing the primary particle size to ~50 nm (Davis et al., Nat. Rev. Drug Discov., vol. 7, pp. 771-782, 2008) as well as by decorating the particle surface with a cationic copolymer. These design features in combination with the electrostatic binding of doxorubicin to phosphonate groups in the particle pore allow efficient doxorubicin delivery, some due to intracellular release, at the cancer site (Meng et al., ACS Nano, vol. 4, pp. 4539-4550, 2010). Not only are these design features superior to induce tumor shrinkage and apoptosis compared to the free drug, but also dramatically improves the safety profile of systemic doxorubicin delivery.

Synthesis and Physicochemical Characterization of MSNP

Materials:

Cetyl trimethylammonium bromide (CTAB, 95%), Pluronic F127, tetraorthoethylsilicate (TEOS, 98%) 3-(trihydroxysilyl)propyl methylphosphonate (42% in H2O), polyethyleneimine (PEI, 1.2 kD), 4-(dimethylamino)pyridine (99%), N,N'-disuccinimidyl carbonate (95%), poly(ethylene glycol) methyl ether (m-PEG, MW 5 kD), phthalic anhydride (99%) and polybrene were purchased from Sigma (St. Louis, Mo.). N-(2-aminoethyl)-3-aminopropyltrimethoxysilane (NAPTS) was purchased from Gelest (Morrisville, Pa.). Amine-reactive near infrared fluor DyLight 680 NHS ester was purchased from Thermo Scientific (Rockford, Ill.). D-Luciferin was purchased from Xenogen (Alameda, Calif.). Apoptosis TUNEL detection kit (Click-iT TUNEL kit), bovine serum albumin (BSA), DPBS solution, L-glutamine, penicillin, streptomycin, and DMEM medium were obtained from Invitrogen. Fetal bovine serum (FBS) was purchased from Atlanta Biologicals. Anti-CD31 antibody was purchased from BD Bioscience. All reagents were used without further purification.

Synthesis of NP1.

Established procedures were followed to synthesize the classically designed or first-generation MSNP (NP-1) (Liong et al., ACS Nano, vol. 2, pp. 889-896, 2008; Meng et al., ACS Nano, vol. 4, pp. 4539-4550, 2010; Meng et al., J Am. Chem. Soc., vol. 132, pp. 12690-12697, 2010; Lu et al., Small, vol. 6, pp. 17949-1805, 2010). Briefly, 250 mg of CTAB was dissolved in 120 mL of water, followed by the addition of 875 µL of 2M NaOH aqueous solution. The solution was heated to and kept at 80° C. for 30 minutes before 1.25 mL of TEOS was added. The solution went from clear to opaque, which is indicative of a hydrolysis process. After 15 minutes, 315 µL of trihydroxysilylpropyl methylphosphonate was added. The reaction was kept at 80° C. for another 2 h. The resulting nanoparticles were centrifuged and washed with methanol. In order to remove the CTAB, the as-synthesized particles were suspended in 60 mL of methanol and 2.3 mL of 12 M hydrochloride acid. The solution was refluxed for 10 h and the MSNP designated NP1 were collected for centrifugation and further washing with methanol.

Synthesis of NP2.

200 mg of PLURONIC® F127 was mixed with 250 mg of CTAB and 120 mL of $H_2O$. The solution was heated to 80° C. and kept for 30 min. 1 mL of TEOS was mixed with 200 µL of NAPTS in 1 mL of ethanol and then added drop-wise into the CT AB solution. 300 µL of trihydroxysilylpropyl methylphosphonate was added 20 min later. The solution was filtered through a 0.22 µm polycarbonate syringe filter (Millipore, Billerica, Mass.) and to remove the CTAB, the filtrate was mixed with 120 mL methanol and 0.8 g of $NH_4NO_3$. The solution was heated to 70° C. for 30 min. The particles were collected by centrifugation and washed with methanol. To conduct PEG coating, m-PEG was used because this polymer contains only a single reactive hydroxyl group that can be used for PEI attachment; regular PEG has two reactive ends that may cause particle cross-linking. For the attachment to PEI, the hydroxyl group on m-PEG was replaced with a NETS-ester (referred as activated m-PEG) that is capable of reacting with the PEI amine residues. 10 mg of the as-synthesized MSNP was suspended in 1.5 mL of DMF and mixed with 50 mg of activated m-PEG (Xia et al., ACS Nano, vol. 3, pp. 3273-3286, 2009). The solution was stirred for a further 24 h and the particles were collected, sequentially washed with DMF and ethanol and eventually re-suspended in water.

Synthesis of NP3.

The reduced size silica core was synthesized as described above. To perform PEI coating, 10 mg of as-synthesized small MSNP was suspended in 1 mL of 2.5 mg/mL PEI ethanolic solution. The solution was sonicated and stirred for 30 min. This process was repeated twice to substitute the F127 coating that was previously achieved by attaching PEI to the NP3 surface. The particles were further washed in ethanol to remove excess PEI and trace amount of F127 residue. The PEI-coated particle was subsequently transferred into 1.5 mL of DMF, mixed with 50 mg of activated m-PEG, and stirred for 24 h. The nanoparticles were washed with DMF, ethanol and re-suspended in water.

Physicochemical Characterization.

All MSNPs were characterized for size distribution, shape, and surface charge. The shape and structure were characterized using a transmission electron microscope (JEOL JEM 2010, JEOL USA, Inc., Peabody, Mass.). TEM samples were prepared by placing a drop of the nanoparticle saline suspension at a concentration of 100 µg/mL onto a 200-mesh copper grid (Electron Microscopy Sciences, Washington, Pa.) and then drying at room temperature overnight. Primary particle size was measured by random sampling of at least 10 particles that were imaged on a TEM grid. Image J software was used to determine the average MSNP diameter. Particle size and zeta potential in solution were measured by ZetaSizer Nano (Malvern Instruments Ltd., Worcestershire, UK). All of the measurements were performed with the nanoparticles suspended in filtered water or saline at 100 µg/mL nanoparticle concentration. Similar analysis was also performed on the doxorubicin-loaded particles.

Figure 33:
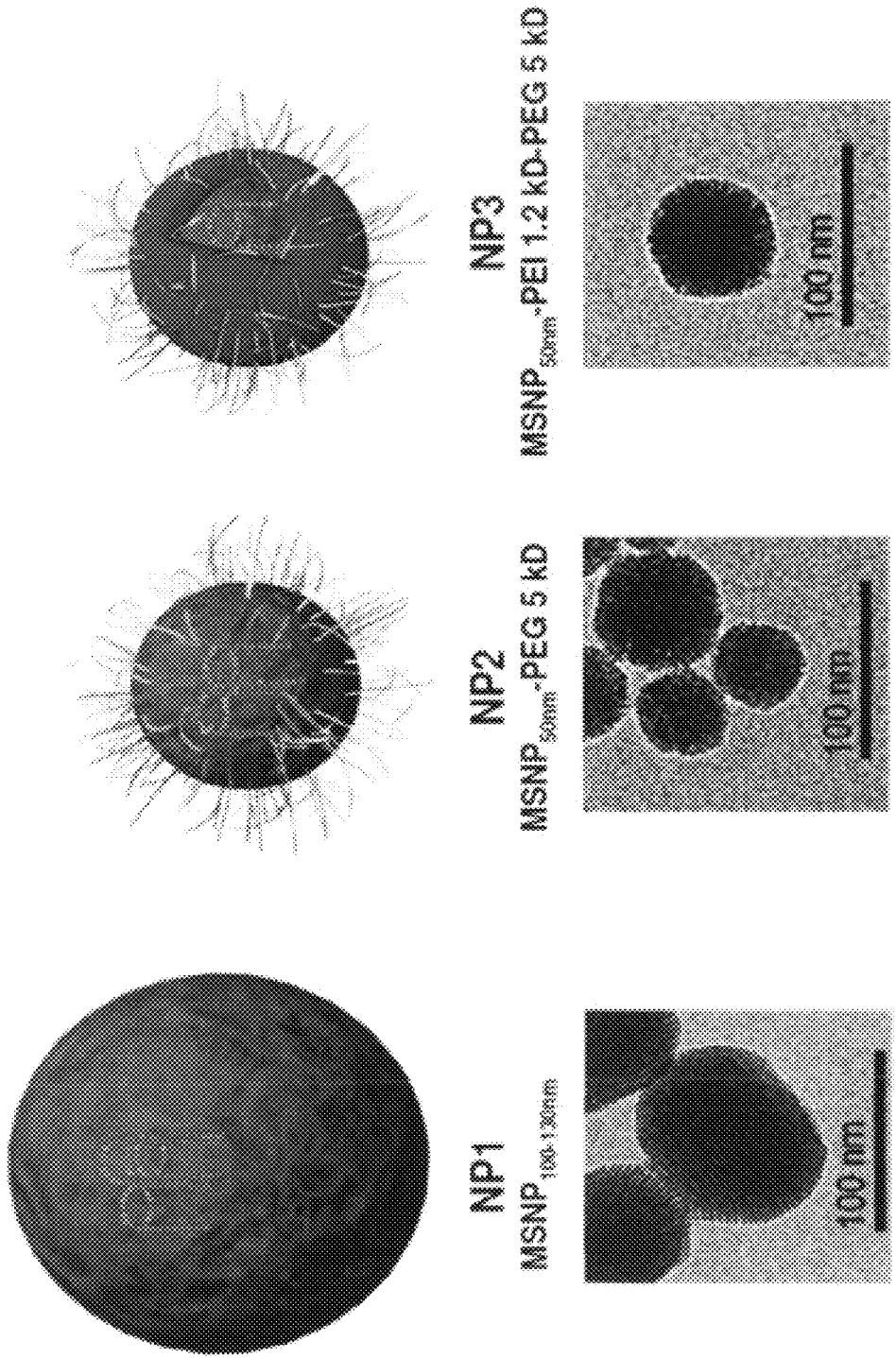
FIG. 33 shows a graphical representation of the MSNP design. NP1 refers to the first generation phosphonate-coated MSNP with a primary particle size of 100 nm. NP2 was PEGylated with a mesoporous silica core size of 50 nm and coated with a 5 kD PEG polymer. NP3 represents the same core size as NP2, but was coated with a 1.2 kD PEI polymer in which some of the amines were reacted with 5 kD PEG. The pore diameter of all three generations of particles was 2.5 nm. The TEM images at the bottom demonstrate the primary particle size and ordered pore structure.
Figure 34A:
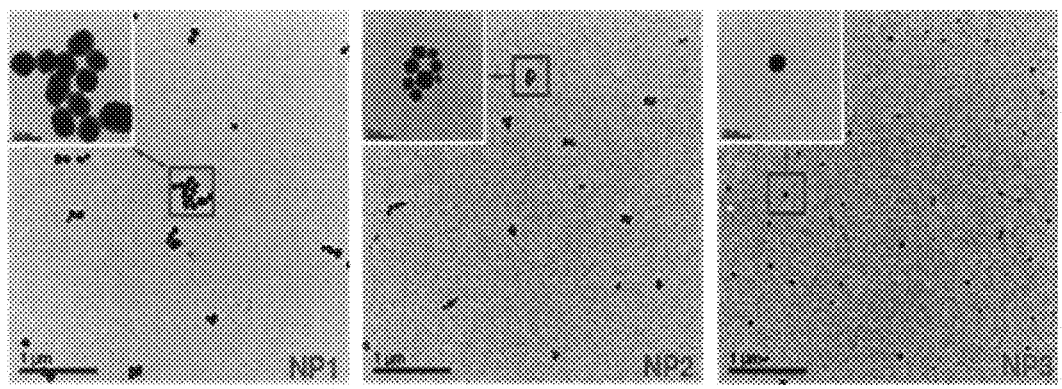
FIGS. 34A-34B show physicochemical characterization of the different MSNPs.
Figure 34B:
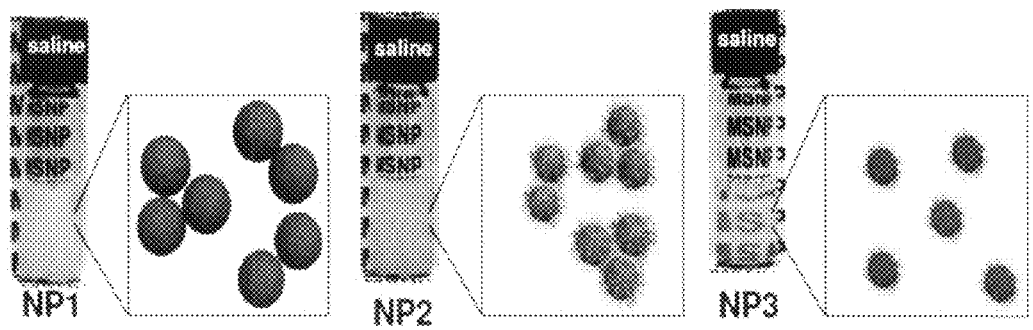

Three generations of particles (designated NP1-NP3) were developed (FIG. 33). NP1 denotes the first generation of a phosphonate-coated MSNP with a primary size of ~100 nm and exhibiting a negative zeta-potential (Table 4). These particles are useful for the electrostatic attachment and proton-dependent doxorubicin release in acidifying endosomal compartments in cancer cells (Liong et al., ACS Nano, vol. 2, pp. 889-896, 2008; Meng et al., ACS Nano, vol. 4, pp. 4539-4550, 2010; Meng et al., J. Am. Chem. Soc., vol. 132, pp. 12690-12697, 2010; Xia et al., ACS Nano, vol. 3, pp. 3273-3286, 2009). NP1 is also capable of delivering camptothecin to a human breast cancer (MCF-7) xenograft (Lu et al., Small, vol. 6, pp. 1794-1805, 2010). However, because of this particle's relatively large primary size and high rate of agglomeration in saline (Table 4 and FIG. 34B) and other biological media (e.g., 306 nm in DMEM medium; 867 nm in BEGM medium) (Xia et al., ACS Nano, vol. 3, pp. 3273-3286, 2009), it was necessary to consider reducing its size as well as changing its surface characteristics to improve the EPR effect. The first approach was synthesis of NP2 (FIG. 33), which exhibits a primary size of 50 nm (as determined by TEM analysis) before undergoing PEGylation. Following its coating with a 5 kD PEG polymer, NP2 exhibits a hydrodynamic diameter of a ~70 nm as determined by DLS (FIGS. 33 and 34). However, while this particle exhibits a negative zeta potential and a hydrodynamic size of 70 nm in water (Table 4), it undergoes considerable agglomeration in saline with potential interference in extravasation at the tumor site. It was therefore necessary to construct a 50 nm primary particle (FIG. 33) coated with a PEI-PEG co-polymer to take advantage of the stronger electrostatic repulsion of a cationic particle surface. This yielded a particle with a positive zeta-potential, hydrodynamic diameter of ~77 nm in water and the size of 110 nm in saline (Table 4). The improved dispersal of NP3 was confirmed by TEM, showing that NP3 is essentially mono dispersed in saline while NP2 and NP1 form incrementally larger agglomerates (FIG. 34B). To further illustrate the dispersal characteristics of the saline-suspended particles, photographic images were obtained and showed optical transparency of the NP3 suspension while the previous particle generations resulted in turbid suspensions (FIG. 34C).

TABLE 4

Comparison of particle sizes.

| Particle type | Primary size (nm) | Size in $H_2O$ (nm) | Size in Saline (nm) | Zeta Potential in $H_2O$/(mV) |
|---|---|---|---|---|
| NP1 | 100 | 260 | 520 | −25.30 |
| NP2 | 50 | 70 | 597 | −20.5 |
| NP3 | 50 | 77 | 110 | +46.7 |

Drug Loading and Loading Yield Measurement.

10 mg of various particles were suspended in 0.5 mL of 5 mg/mL doxorubicin aqueous suspension. The solution was stirred for 24 h and the nanoparticles were collected through centrifugation and carefully washed with $H_2O$. To measure the loading yields of the various particles, 1 mg of doxorubicin-loaded MSNP was resuspended and sonicated in 1 mL heated 0.1 M HCl for 15 min. After centrifugation, another 1 mL of fresh HCl aqueous solution was added. This process was repeated at least for 5 times. The pH of supernatant was readjusted to 7.0 by 1 M NaOH and the fluorescence spectrum of doxorubicin was measured at excitation and emission wavelength of 485/550 nm in a microplate reader (SpectraMax M5Microplate Reader, Molecular Device, USA).

NIR Fluorescent Labeling.

The NIR fluorescent dye, DyLight 680 NHS ester, was used for particle labeling. For NP 1, 10 mg of all the particles was suspended in 1 mL of ethanol and mixed with 0.1 mg of the DyLight 680 and 0.5 µL of NAPTS. The reaction was kept under inert atmosphere and stirred at room temperature for 12 h. The resulting particles were centrifuged and washed with $H_2O$. For NP2 and NP3, 10 mg each were suspended in 1 mL of DMF and mixed with 0.1 mg of DyLight 680. After 12 h, the particles were washed with $H_2O$.

Cell Culture and Luciferase Transfection.

KB-31 cancer cells were maintained in 25 $cm^2$ or 75 $cm^2$ cell culture flasks in which the cells were passaged at 70-80% confluency every 3 days. The cells were cultured in Dulbecco's Modified Eagle Medium (DMEM) (Carlsbad, Calif.) containing 10% FBS, 100 U/mL penicillin, 100 µg/mL streptomycin, and 2 mM L-glutamine (complete medium). To generate a stable cell line constitutively expressing luciferase, $1.5 \times 10^4$ KB-31 cells in 40 µL complete DMEM (supplemented with 10% FBS, 100 U/mL penicillin, 100 µg/mL streptomycin, 2 mM L-glutamine, and 8 µL/mL polybrene) was transduced with 10 µL of a lentivirus (Cignal Finder Lenti Pathway Reporter Qiagen/SA Biosciences; $1.4 \times 10^7$ TU/mL) in 96 well tissue culture plates. Spinoculation (centrifugal inoculation) was performed at 1,200 g for 60 minutes. The viral containing media was removed after 16 h and the cultures replenished with fresh DMEM media. Cells were allowed to proliferate to a population size of $1.2 \times 10^6$ cells. A heterogeneous pool of transduced cells was selected by using 1 µg/mL puromycin for at least 14 days prior to tumor implantation.

Establishment of the KB-31-Luc Tumor Xenograft Model.

Athymic BALB/c nu/nu female mice (6 weeks) were purchased from the Charles River Laboratory, and maintained under pathogen-free conditions. All animal experiments were performed using protocols approved by the UCLA Animal Research Committee. The tumor cell suspension (0.1 ml, $5 \times 10^6$ cells/mL) was injected subcutaneously into the mice. To perform imaging, the tumor-bearing animals were used 2.5 weeks after tumor implantation. In the tumor growth inhibition experiments, the nude mice were randomly divided into 4 groups and received the listed range of treatments, which commenced 1 week after tumor implantation.

Determining MSNP Biodistribution.

The tumor-bearing mice were randomly divided into three groups (n=3). To visualize the tumor, anesthetized mice were i.p. injected with 75 mg/kg D-Luciferin. Eight minutes after injection, bioluminescence images were acquired using an IVIS Imaging System (Xenogen). Acquisition time was 10 s. Subsequently, the mice were intravenously administered with NIR dye-labeled NP1, NP2, or NP3 at doses of 50 mg/kg (~1 mg nanoparticles per mouse), and the fluorescence images were taken at indicated time points. 72 h after injection, the tumor tissue together with major organs (heart, lung, spleen, liver, kidney, brain and cardiac muscle) were collected and used for ex vivo image. Around 100-200 mg tissue for each organ was accurately weighed out, washed, homogenated, and the fluorescence intensities per unitary amount of each organ were measured by a microplate reader (Molecular Device, M5e).

Immunohistochemical Staining to Determine CD31 Expression in the Tumor Tissue.

The tumor-bearing mice were randomly divided into three groups (n=3) and intravenously administered with the doxorubicin loaded NP1, NP2, or NP3 at doses of 50 mg/kg (~1 mg nanoparticles per mouse). The tumor tissues were rapidly collected after 72 h, frozen and OCT embedded before sectioning to provide 4 µm thick slices. The slices were washed three times in PBS, fixed in cold acetone for 15 min and the slide subsequently blocked using 1% normal goat serum at room temperature for 10 min. The sections were overlayed with rat-anti-mouse CD31 monoclonal antibody (1:500) at 4° C. overnight. After removal of the primary antibody and washing in PBS for 3 times, FITC-labeled goat-anti-rat IgG (1:500) was added and incubated for 1 h at room temperature. The slides were visualized under a fluorescence microscope (Zeiss, Germany).

Nude mouse studies to determine the effect of doxorubicin-loaded NP3 on tumor shrinkage. One week after tumor implantation, the KB-31 tumor-bearing mice were randomly divided into four groups of five animals each. These groups were used for comparing the effects of saline, empty nanoparticles, free doxorubicin, and doxorubicin-loaded NP3, respectively. The latter group received intravenous administration of 120 mg/kg (~2.4 mg per animal) NP3, which is equivalent to a doxorubicin dose of 4 mg/kg (~0.08 mg per animal), weekly for 3 weeks. The free doxorubicin group received the same drug dose weekly for 3 weeks, while the group receiving empty NP3 was treated with 120 mg/kg on a weekly basis. The fourth group was treated with saline as control. The body weight and tumor size were accurately recorded twice per week. Tumor weight was calculated according to the formula: Tumor weight (mg)=(length in mm)× (width in mm)$^2$/2 (Meng et al., ACS Nano, vol. 4, pp. 2773-2783, 2010).

TUNEL Staining of the Tumor Tissue.

A section of the tumor from each animal was used for TUNEL staining. The slides containing the tumor section were washed, fixed, and permeabilized before performance of TUNEL staining according to the manufacturer's instructions (Invitrogen, Carlsbad, Calif.). Nuclei were stained by Hoechst 33342 dye. The number of TUNEL positive cells (green staining) was assessed under a fluorescent microscope (200×). The same sections were also used for recording of the red fluorescent images of the doxorubicin that was present in the particles or the tissues. At least three fields were counted by the same investigator to calculate the percentage of TUNEL positive cells.

Blood Biochemistry to Assess Possible Toxicity.

Following the animal experiments described above, the mice were sacrificed on 21$^{st}$ day and serum collected by centrifuging the whole blood at 5,000 rpm for 15 min. The biochemical parameters, including cholesterol (CHOL), triglycerides (TRG), alanine aminotransferase (ALT), aspartate aminotransferase (AST), total bilirubin (TBILI), glucose (GLU), inorganic phosphorus (PHOS), total protein (TPR), calcium (CAL), blood urea nitrogen (BUN), creatinine (CRE), and albumin (ALB) were assayed by UCLA Division of Laboratory Animal Medicine (DLAM) diagnostic laboratory services.

Tumor and Major Organ Histology.

Appropriate size sections of the tumor, liver, kidney, spleen, lung, heart, and brain were fixed in 10% formalin and then embedded into paraffin. Tissue sections of 4 µm thickness were mounted on glass slides by the UCLA Division of Laboratory Animal Medicine (DLAM) diagnostic laboratory services. The sections were stained with hematoxylin-eosin (H&E) and examined by light microscopy. The slides were read by an experienced veterinary pathologist.

Drug Loading and Loading Yield Measurement.

10 mg of various particles were suspended in 0.5 mL of 5 mg/mL doxorubicin aqueous suspension. The solution was stirred for 24 h and the nanoparticles were collected through centrifugation and carefully washed with $H_2O$. To measure the loading yields of the various particles, 1 mg of doxorubicin-loaded MSNP was resuspended and sonicated in 1 mL heated 0.1 M HCl for 15 min. After centrifugation, another 1 mL of fresh HCl aqueous solution was added. This process was repeated at least for 5 times. The pH of supernatant was readjusted to 7.0 by 1 M NaOH and the fluorescence spectrum of doxorubicin was measured at excitation and emission wavelength of 485/550 nm in a microplate reader (SpectraMax M5Microplate Reader, Molecular Device, USA).

Comparison of the Biodistribution of Labeled and Drug Laden NP1-NP3 In Vivo

Figure 35A:
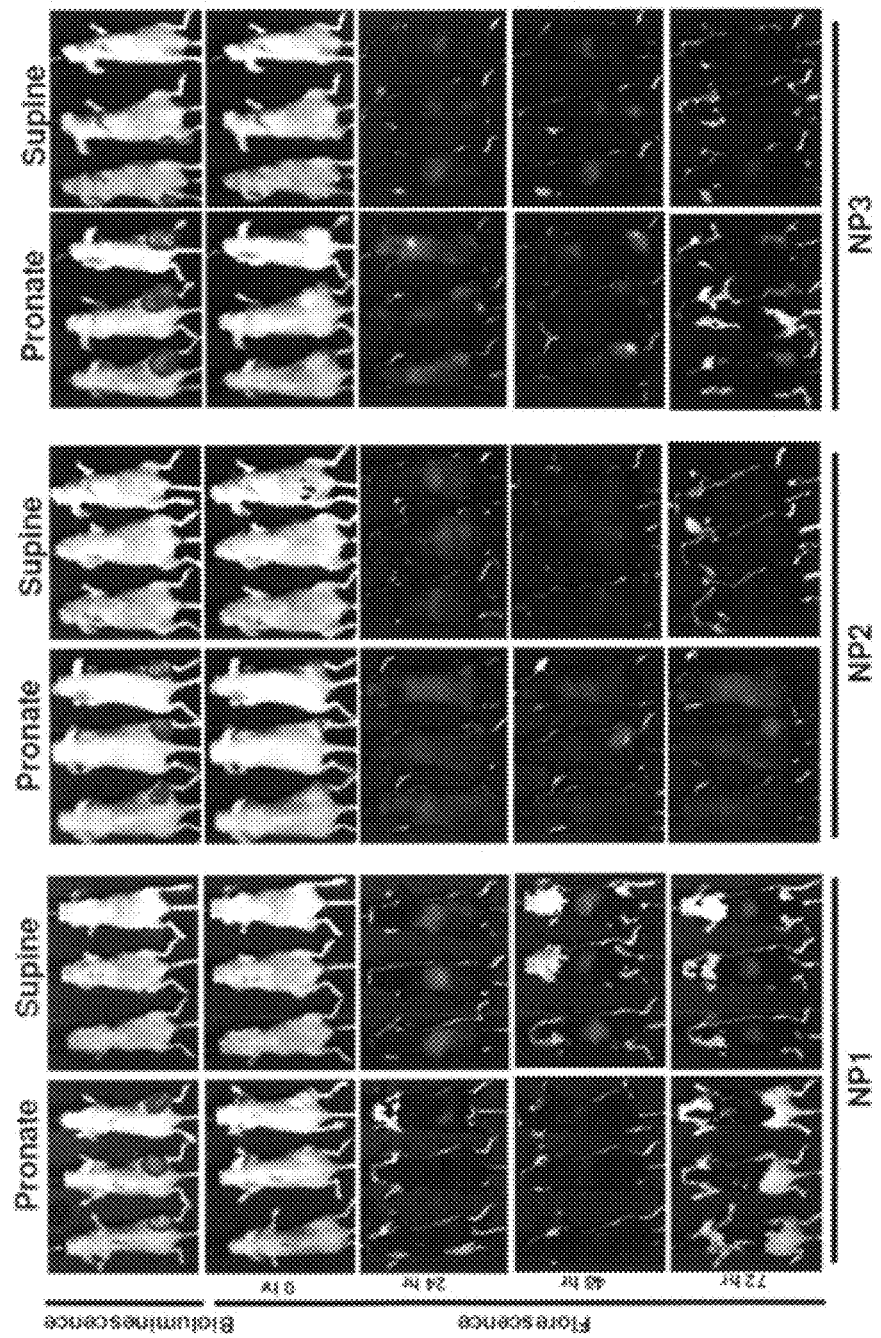
Figure 40:
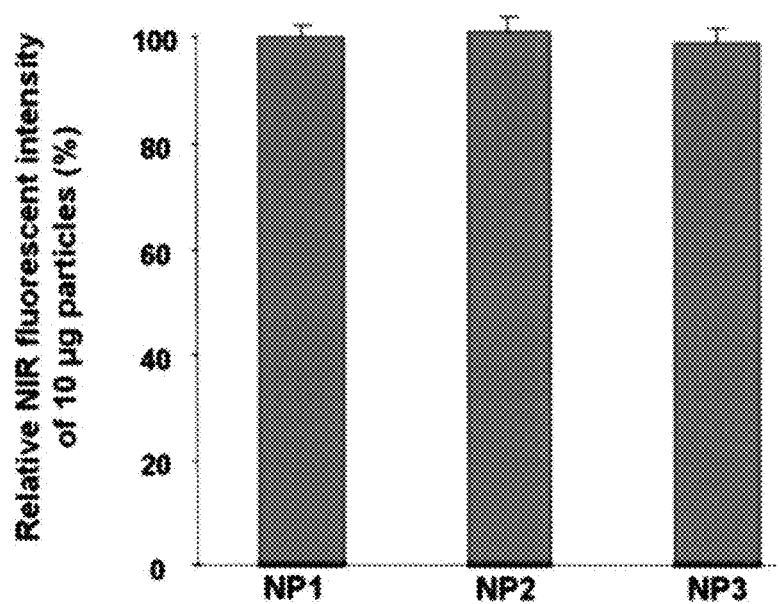
FIG. 40 shows fluorescent labeling efficiencies of NP1-NP3 were determined in a microplate reader. The Dylight 680-labeled different particles were washed and suspended in water at 100 µg/mL. 100 µL of each particle suspension was loaded into a 96-well plate and the fluorescent intensity was detected at excitation and emission wavelength of 680/715 nm with a microplate reader (M5e, Molecular Device). The fluorescent intensities of NP2 and NP3 were expressed as a unit of the fluorescence intensity of NP1, which was considered as 100%. The results indicate that there is no significant difference (p<0.05) in the fluorescent labeling efficiency among different particle types.

In order to determine whether the redesign of particle size and surface coating improve the biodistribution of the various MSNP types, imaging studies were performed in a nude mouse model used for subcutaneous growth of a human tumor xenograft. To visualize the tumor growth in a doxorubicin-sensitive HeLa squamous carcinoma cell line, KB-31 cells were used for stable transfection with a luciferase vector and then used that for obtaining bioluminescence images in the mice following intraperitoneal (i.p.) injection of D-Luciferin (FIG. 35A, $1^{st}$ row). To also visualize the particles in vivo, the MSNP were designed to incorporate a near-infrared (NIR) dye that exhibits high photon penetration in the animal tissue (Frangioni et al., Curr. Opin. Chem, vol. 7, pp. 626-634, 2003; Farist et al., Clin. Phys. Phgsiol. Meas., vol. 12, pp. 353-358, 1991). In order to quantitatively compare the biodistribution of NP1-NP3, the data show that the particles had similar labeling efficiency per unit mass (FIG. 40). Initial reference images were obtained prior to particle injection to show a very low NIR background in the tumor-bearing animals (FIG. 35A, 2rd row). These animals were then injected with 50 mg/kg of each NIR dye-labeled particle types via the tail vein and fluorescence images captured at the indicated time points (FIG. 35A, 3rd-5th row). The supine images indicate that the majority of NP1 were captured by the liver and spleen within 24 h and this profiling was maintained for at least 72 h. By contrast, NP2 showed less prominent liver uptake with a sustained systemic distribution (longer circulation time), indicating the ability of PEG coating to decrease particle opsonization and removal by the RES. Interestingly, a barely visible tumor signal could only be obtained in one of three animals (FIG. 35A, middle panel). A similar reduction in RES uptake and increased circulation time were obtained for NP3, which showed prominent particle uptake in the tumor tissue at 24 h, suggestive of a strong EPR effect (FIG. 35A, right panel). Moreover, the fluorescence intensity at the tumor site increased gradually, peaking at 48 h and was then sustained for at least 72 h.

Figure 41:
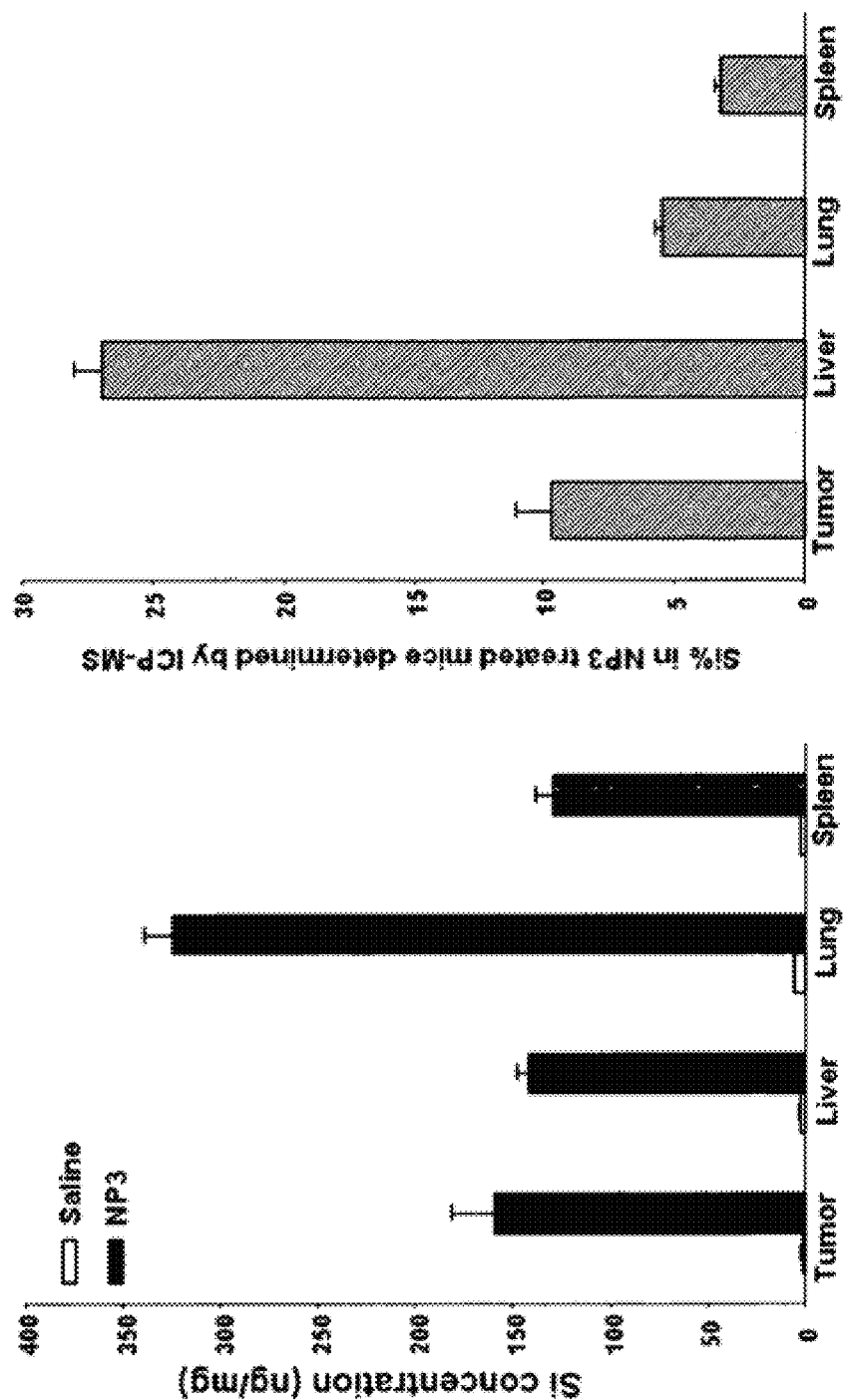
FIGS. 41A and 41B show the biodistribution data determined by fluorescence intensity measurement, where the Si content of tumor, liver, lung and spleen tissue was detected by ICP-MS in animals intravenously injected one with saline or empty NP3 at 50 mg/kg. The animals were sacrificed 3 days after injection. Briefly, each tissue was accurately weighed and soaked in ultrahigh purity $HNO_3$ and $H_2O_2$ overnight. This solution was heated at 80° C. for 1 h the next day. At the same time, $H_2O_2$ solution was added to drive off nitrogen oxide vapor until the solution became colorless and clear. The aqueous solutions were analyzed by a Perkin-Elmer SCIEX Elan DRCII to determine the Si concentration. Elemental indium at 20 ng/mL, was used as an internal standard.

In order to obtain more quantitative data that can be used for calculating the EPR effect, the same animals were sacrificed at 72 h post-injection and ex vivo fluorescence intensity images were obtained for the tumor tissue as well as major organs such as liver, spleen, lung, kidney, brain, muscle and heart (FIG. 35B). Consistent with the in vivo images, NP3 showed the highest fluorescence intensity in the tumor tissue compared to other particle types (FIG. 35B). However, NP3 showed abundant distribution to the liver and spleen as well as relatively high fluorescence intensity in the lung compared to the other particle types. The collected organs were accurately weighed and used for the quantitative analysis of particle distribution by expressing the fluorescence intensity per unit mass of tissue (FIG. 35C). This readout demonstrated the highest particle concentration at the tumor site in animals treated with NP3 (FIG. 35C). When expressed as a percentage of the total mass of the particles administered, ~1%, ~3% and ~12% of NP1, NP2 and NP3 load, respectively could be seen to biodistribute to the tumor tissue at 72 h (FIG. 35D). To further confirm the EPR calculation based on fluorescence intensity, inductively coupled plasma mass spectrometry (ICP-MS) was used to quantify the Si abundance in the major target organs (tumor, liver, kidney and spleen) of saline- and NP3-treated animals (FIG. 41). Consistent with the fluorescence data, ~10% of the total administered elemental Si dose could be demonstrated in the NP3 treated tumor tissue (FIG. 41). While slightly lower than the estimation of the EPR effect by using fluorescence intensity, it has to be considered that some degree of heterogeneity in tumor vascularity can influence fluorescent imaging intensity to explain this small difference (Bettio et al., J. Nucl. Med., vol. 2006, pp. 1153-1160, 2006). All considered, the estimated EPR of ~12% in the KB-31 model is exceptionally good compared to other polymer/co-polymer based drug and siRNA nanocarrier delivery platforms, where a passive targeting rate of 3.5-10% has been reported for different particle types (de Wolf et al., Int. J. Pharm., vol. 331, pp. 167-175, 2007; Kaul et al., J. Drug Target., vol. 12, pp. 585-591, 2004; Verbaan et al., J. Gene Med., vol. 6, pp. 64-75, 2004; Fenske et al., Curr. Opin. Mal. Ther., vol. 3, pp. 153-158, 2001).

Figure 36:
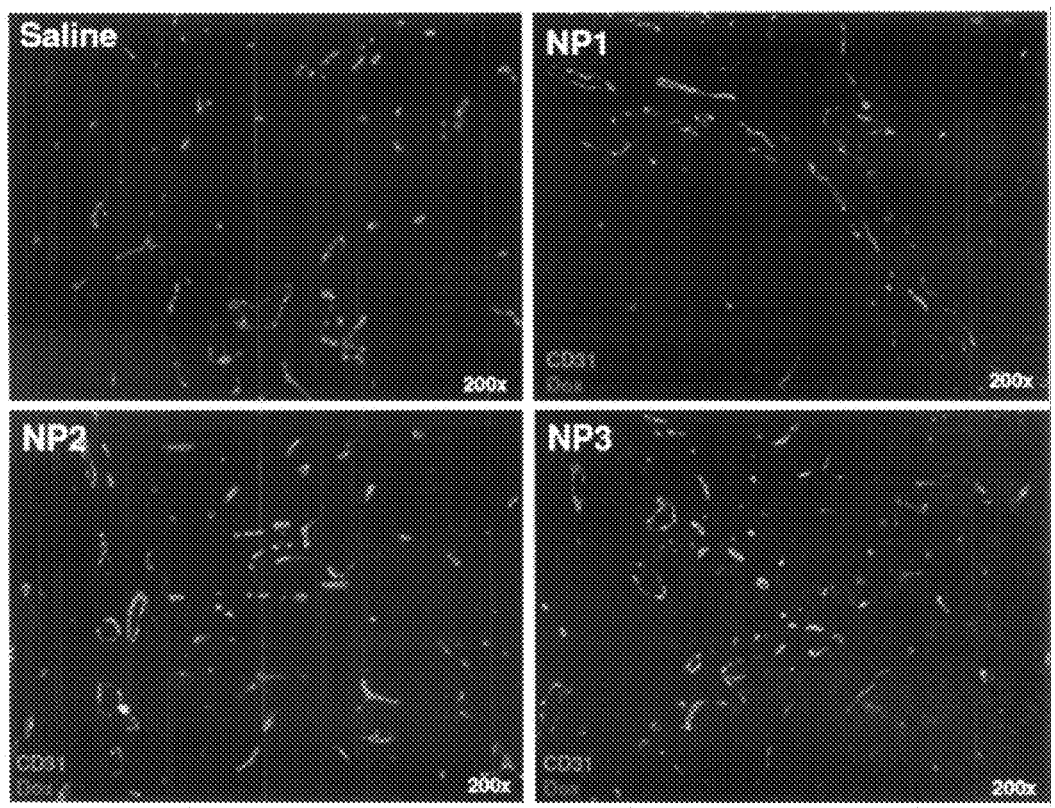
FIG. 36 shows dual color fluorescence to show the tumor localization of the doxorubicin in relation to the tumor blood vessels detected by a CD31 biomarker. Tumor-bearing mice received intravenous administration of doxorubicin-loaded particles, each at a dose of 50 mg/kg for 72 h. Tumor tissues were collected immediately following animal sacrifice. Histological staining of the OCT embedded frozen tumor tissues in each group was performed by the UCLA Division of Laboratory Animal Medicine (DLAM) diagnostic laboratory services. The sections were incubated with a CD31 primary antibody and visualized by FITC-conjugated secondary antibody. The red fluorescence of doxorubicin was also captured for the same slide view and merged images were prepared to show intratumoral distribution of the drug in relation to the blood vessels. Slides were visualized under a fluorescence microscope (Zeiss, Germany). It is possible to discern some speckled fluorescence in the lower panels, suggesting that some of the drug is still encapsulated in the particles.

In order to determine whether drug loading exerts an effect on particle biodistribution, doxorubicin was loaded into NP1, NP2 and NP3 at w/w ratios of 3.3%, 2.5% and 3%, respectively. The red fluorescence properties of doxorubicin allowed us to make semi-quantitative visual comparisons of the amount of drug in the tumor tissue. In order to facilitate this interpretation the tumor blood vessels were visualized by CD31 immunohistochemistry (FIG. 36). This allowed us to visually compare the relative abundance of the drug fluorescence signal in relation to its intratumoral distribution. This analysis showed that doxorubicin delivery by NP3 was the most effective for this type of tumor and this particle generation was chosen for subsequent studies to perform intravenous drug delivery in the xenograft model as well as for safety assessment compared to treatment with free doxorubicin.

Figure 37A:
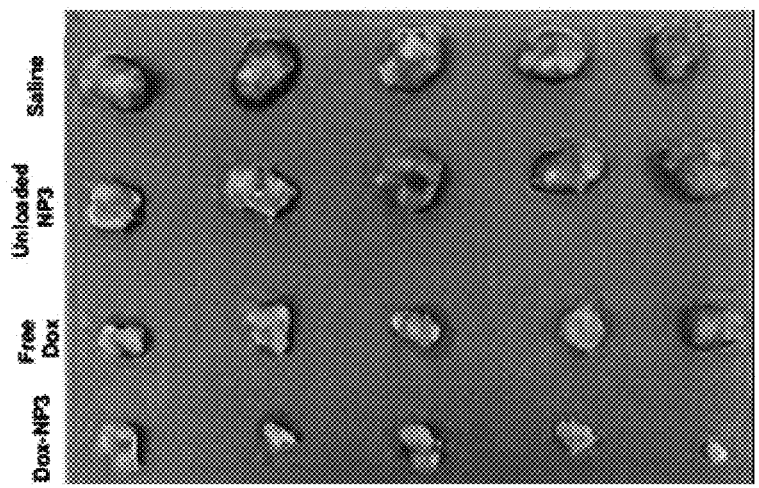
FIGS. 37A and 37B show tumor growth inhibition of doxorubicin loaded NP3 in tumor-bearing nude mice.
Figure 37B:
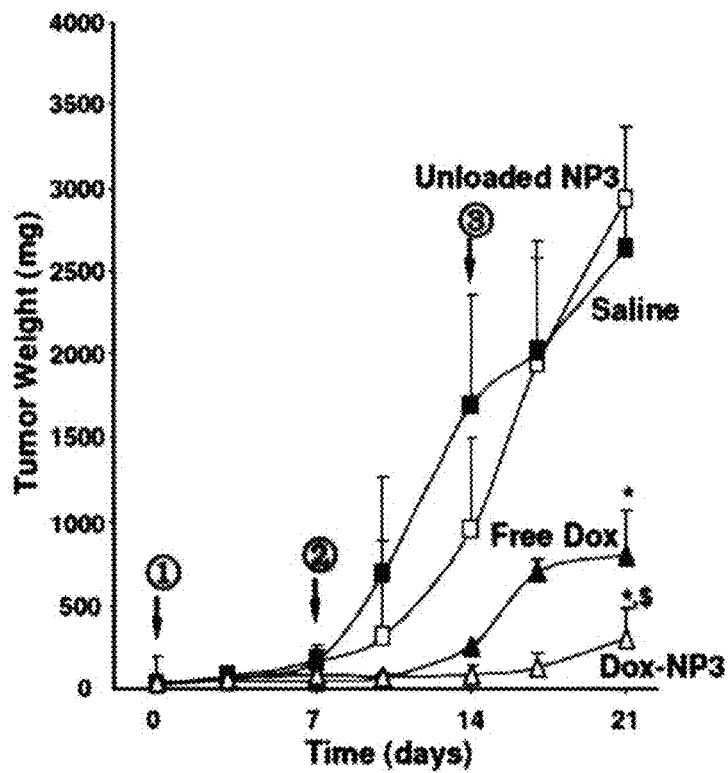
Figure 42:
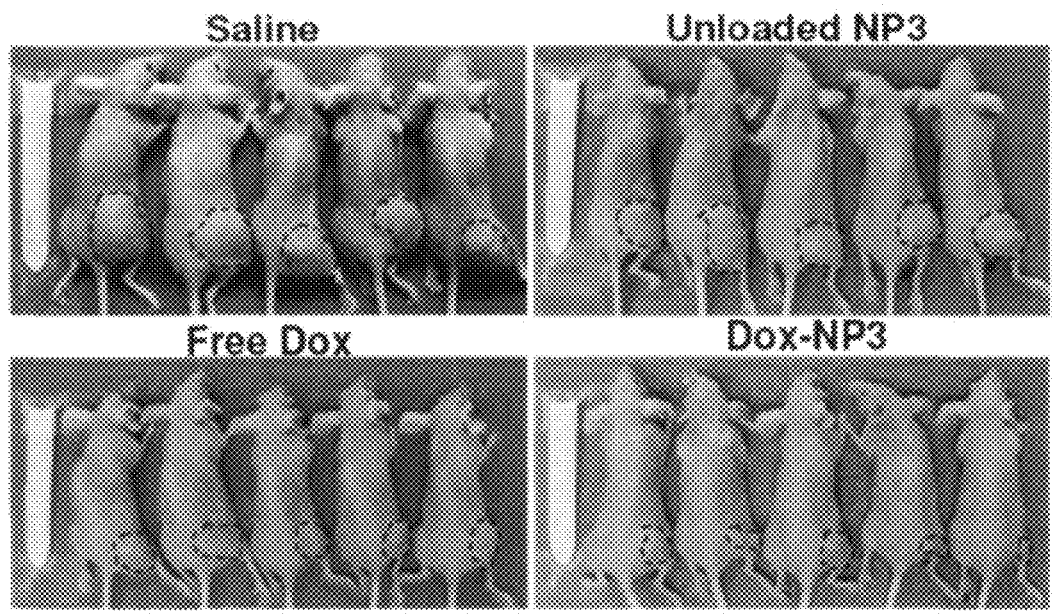
FIG. 42 shows morphological observation of tumor xenografts at the end of the tumor treatment experiment in intact mice. Tumor-bearing animals were treated with saline, free doxorubicin (free Dox), unloaded NP3 and doxorubicin loaded NP3 (Dox-NP3) as described in FIG. 39. The localization of the tumor is outlined by a broken line. Compared with free doxorubicin that is dissolved in saline, the drug delivery by NP3 exhibited a significantly improvement in tumor shrinkage. No cancer growth inhibition was found using unloaded NP3 or saline only.

Doxorubicin Delivery and Release by NP3 at the Tumor Site Leads to Efficient Apoptosis and Tumor Shrinkage Since NP3 exhibits the best EPR effect and is responsible for the highest doxorubicin accumulation in the tumor site, it was asked how drug-laden particles compared to free doxorubicin or empty particles in terms of their ability to induce apoptosis and inhibit tumor growth in the KB-31 tumor model. Tumor-bearing animals were injected intravenously on a weekly basis for 3 weeks with a NP3 dose of 120 mg/kg. This is equivalent to the administration of 4 mg/kg doxorubicin per injection and was compared to delivering the same dose of free doxorubicin, injected weekly for 3 weeks. A saline-treated control was included as well as a group of animals treated with empty particles. When comparing the effect on tumor size, doxorubicin loaded NP3 showed a significantly higher rate of tumor shrinkage than the free drug (FIGS. 37A and 42). No tumor inhibition was found with saline treatment or the use of empty particles (FIGS. 37A and 42). Following sacrifice of the animals, the tumor tissues were collected for accurate weighing (FIGS. 37B and 42). This demonstrated 85% tumor inhibition by doxorubicin-loaded NP3 compared to 70% inhibition by the free drug (FIG. 37B). This difference is statistically significant (p<0.05).

Figure 38C:
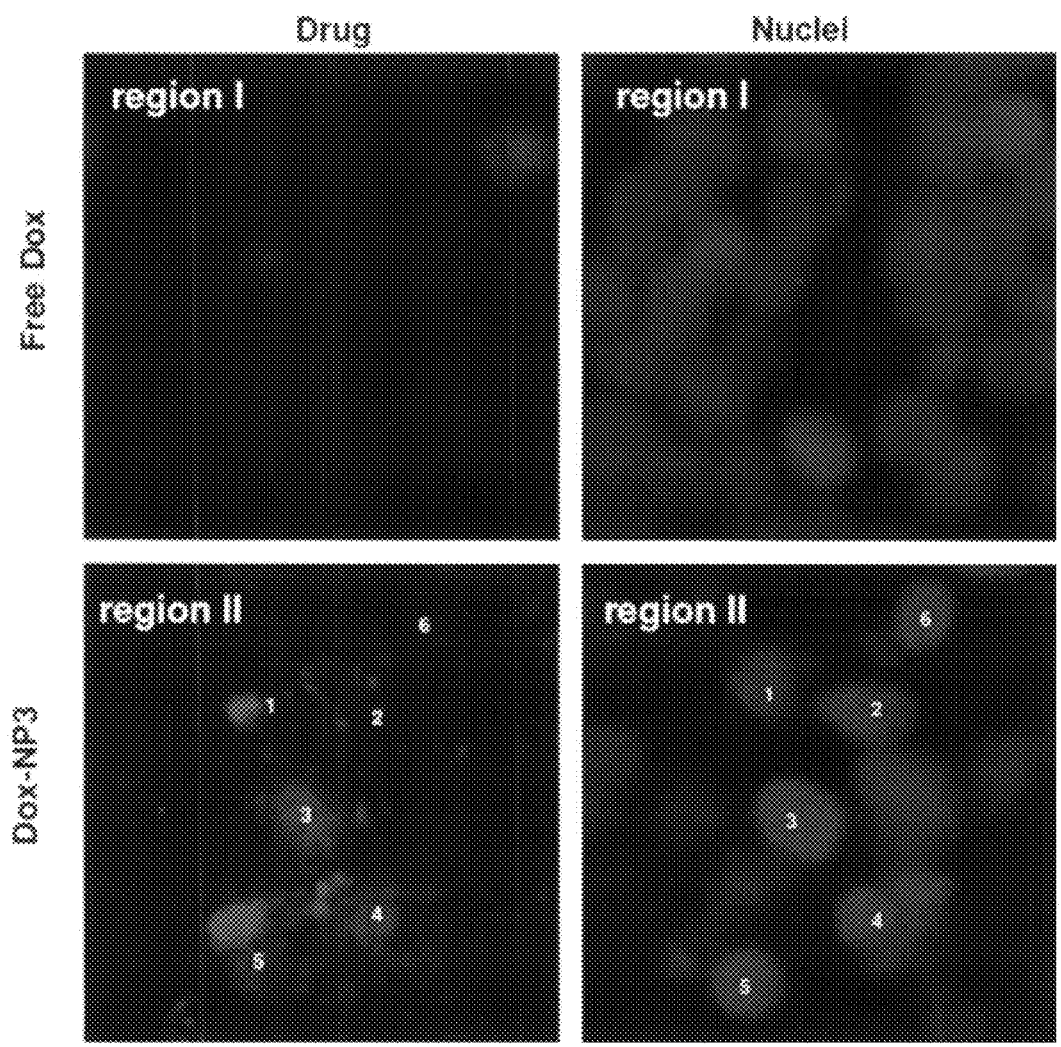

Since doxorubicin inhibits cancer cell growth through induction of apoptosis (Gamen et al., Exp. Cell Res., vol. 258, pp. 223-235, 2000), TUNEL staining was used to compare the abundance and localization of TUNEL-positive cells (green fluorescence) in relation to the doxorubicin fluorescence (FIG. 38A). This analysis also allowed us to detect the drug-laden particles in relation to the cells undergoing apoptosis. By merging the red and green fluorescent images, the yellow composites show that there is indeed an overlap between the drug and apoptotic cells (FIG. 38A, bottom panel). By contrast, the tissues from animals treated with free doxorubicin showed significantly less drug signal, fewer apoptotic cells and lesser fluorescence overlap (FIG. 38A, left panel). Quantification of the number of TUNEL-positive cells was significantly higher during NP3 delivery of doxorubicin (~38%) compared to mice treated with free drug alone (~13%) (FIG. 38B). Additional nuclear staining with Hoechst dye as well as image enlargement of regions "I" and "II" in FIG. 38A further demonstrated that the doxorubicin-laden particles could be visualized as red fluorescent specks or dots, frequently appearing in a perinuclear arrangement (FIG. 38C, lower panel). This is in favor of cellular entrance of the particles, with presumably some of the drug release taking place in the acidifying endosomal compartment as previously demonstrated by us in KB-31 cells (Meng et al., J Am. Chem. Soc., vol. 132, pp. 12690-12697, 2010). This stands in contrast to the dull homogeneous background in cancer cells of the mice treated with the free drug (FIG. 38C, upper panel).

Figure 39A:
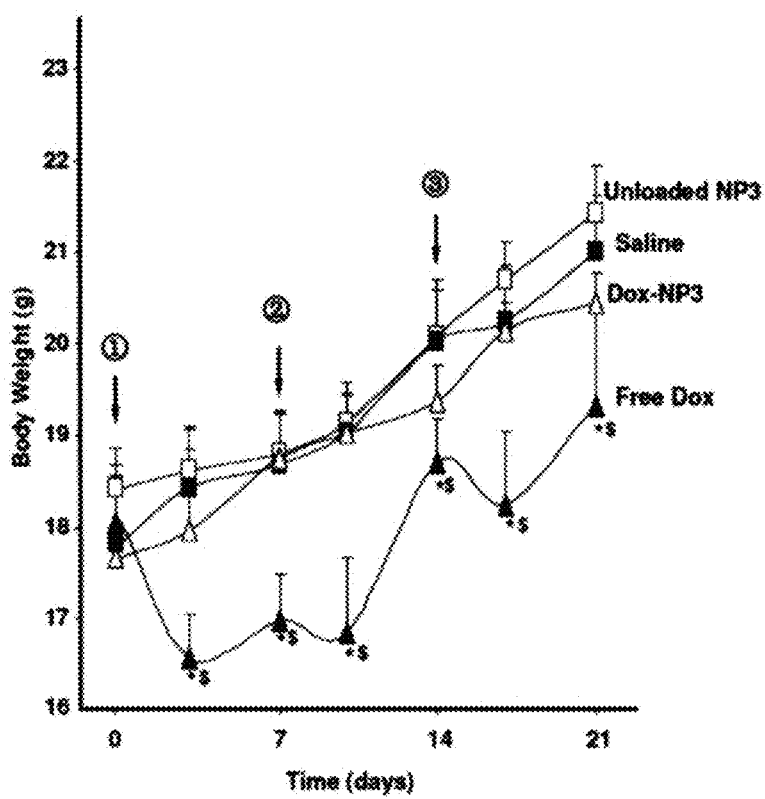
FIGS. 39A and 39B show assessment of treatment on animal weight as well as liver and kidney histology.

Doxorubicin Delivery by NP3 Reduces Systemic, Hepatic and Renal Toxicity Compared to Free Drug The safety of MSNP drug delivery is of key importance in the assessment of this delivery platform. This includes the inherent safety of the delivery vehicle as well as any potential benefits that may accrue from encapsulated drug delivery. Accordingly, safety profiling was performed by comparing the effects of saline, free doxorubicin, empty NP3 and doxorubicin-laden NP3. The safety profiling included assessment of total body weight, blood chemistry, histological examination of major organs as well as performance of a red blood cell lysis assay. Compared to saline treated tumor-bearing mice, no significant body weight changes were observed during the administration of either empty NP3 or nanoparticles loaded with doxorubicin (FIG. 39A). In contrast, animals receiving free doxorubicin administration showed a cyclical decrease in body weight following each of the weekly drug administrations (FIG. 39A). Moreover, these animals also showed significant elevations of the liver function enzymes, alanine aminotransferase (ALT) and aspartate aminotransferase (AST), as well as an increased total bilirubin (TBIL) value compared to the saline control (Table 5). In addition, the doxorubicin treated animals showed a mild increase in inorganic phosphate (PHOS) levels (Table 5). In contrast, when doxorubicin was delivered by NP3, the ALT, PHOS and TBIL levels stayed normal with only a smaller but significant increase in the AST level (Table 5). In mice treated with the empty NP3 carrier, biochemical analysis did not show any significant changes in liver function, kidney function (blood urea nitrogen, BUN; creatinine, CRE), cholesterol (CHOL), triglycerides (TRG), glucose (GLU), PHOS, total protein (TPR), calcium (CAL) and albumin (ALB) (Table 5).

TABLE 5

Serum biochemistry profiles.

| Biochemical parameters[a] | Saline | Unloaded NP3 | Free Dox | Dox-NP3 |
|---|---|---|---|---|
| CHOL (mg/dL) | 110.0 ± 18.2 | 118.0 ± 18.4 | 97.8 ± 12.8 | 122.3 ± 8.5 |
| TRG (mg/dL) | 79.0 ± 36.5 | 110.3 ± 22.5 | 91.5 ± 21.2 | 96.0 ± 24.9 |
| ALT (u/L) | 23.3 ± 6.8 | 26.7 ± 4.0 | 36.8 ± 8.0* | 27.3 ± 2.1[#] |
| AST (U/L) | 132.0 ± 23.4 | 183.3 ± 23.2 | 347.8 ± 73.9* | 174.0 ± 38.2[#] |
| TBIL (mg/dL) | 0.2 ± 0.0 | 0.3 ± 0.0 | 0.4 ± 0.0* | 0.2 ± 0.0[#] |
| GLU (mg/dL) | 111.3 ± 18.6 | 106.0 ± 20.4 | 102.5 ± 29.2 | 108.0 ± 9.4 |
| PHOS (mg/dL) | 8.6 ± 0.7 | 8.5 ± 0.2 | 9.5 ± 0.8* | 7.5 ± 0.7[#] |
| TPR (g/dL) | 4.8 ± 0.3 | 5.7 ± 0.2 | 5.0 ± 0.4 | 5.4 ± 0.2 |
| CAL (mg/dL) | 9.4 ± 0.2 | 9.7 ± 0.2 | 9.0 ± 0.5 | 9.8 ± 0.1 |
| BUN (mg/dL) | 16.0 ± 2.6 | 20.0 ± 4.4 | 17.3 ± 2.6 | 19.0 ± 4.1 |
| CRE (mg/dL) | 0.3 ± 0.0 | 0.3 ± 0.0 | 0.3 ± 0.1 | 0.3 ± 0.0 |
| ALB (g/dL) | 2.3 ± 0.2 | 2.8 ± 0.1 | 2.4 ± 0.2 | 2.6 ± 0.1 |

[a]Blood was collected from the sacrificed animals and the serum obtained by centrifuging the whole blood at 5,000 rpm for 15 min. The biochemical parameters were assayed by UCLA Division of Laboratory Animal Medicine (DLAM) diagnostic laboratory services. These parameters include cholesterol (CHOL), triglycerides (TRG), alanine aminotransferase (ALT), aspartate aminotransferase (AST), total bilirubin (TBILI), glucose (GLU), inorganic phosphorus (PHOS), total protein (TPR), calcium (CAL), blood urea nitrogen (BUN), creatinine (CRE), and albumin (ALB).
*p < 0.05, compared to saline;
[#]p < 0.05, compared to free doxorubicin.

Figure 39B:
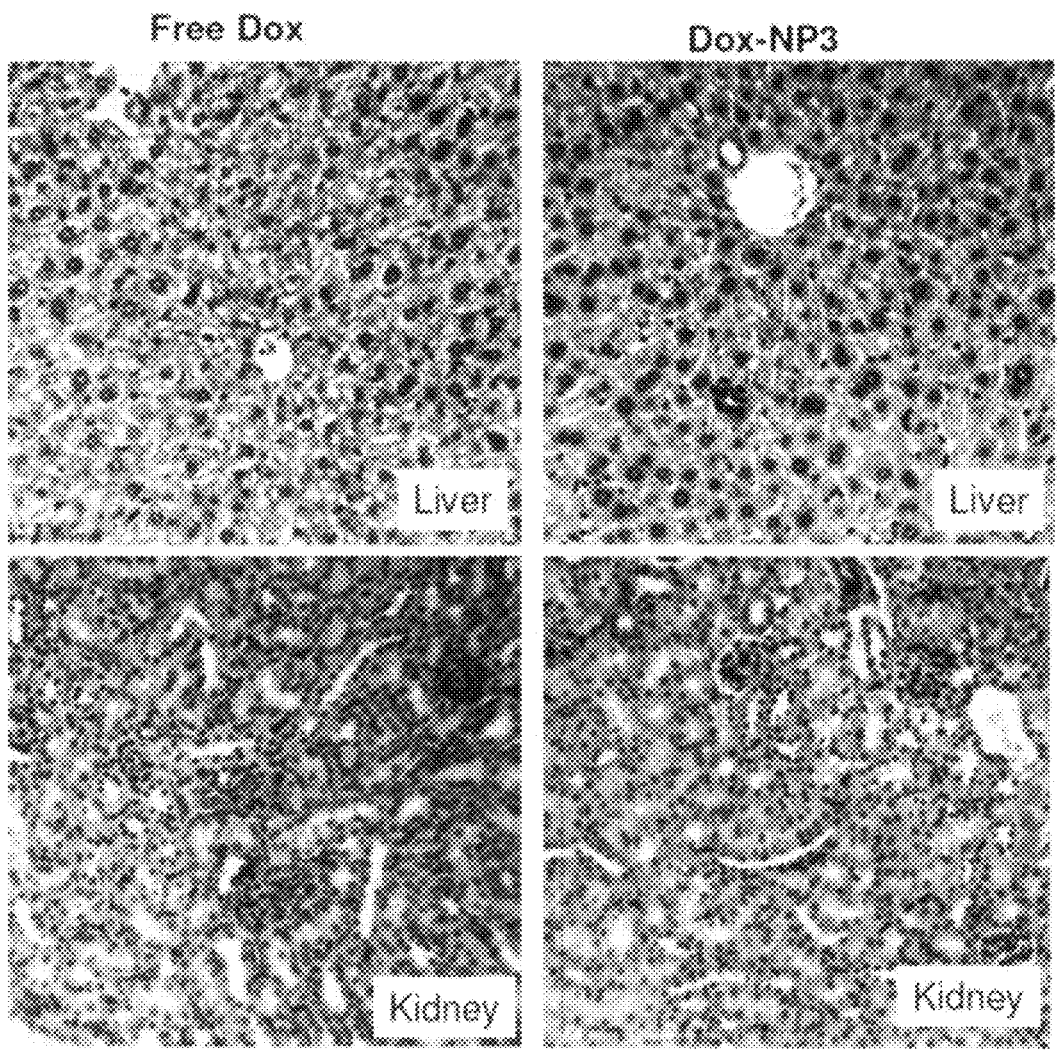
Figure 43:
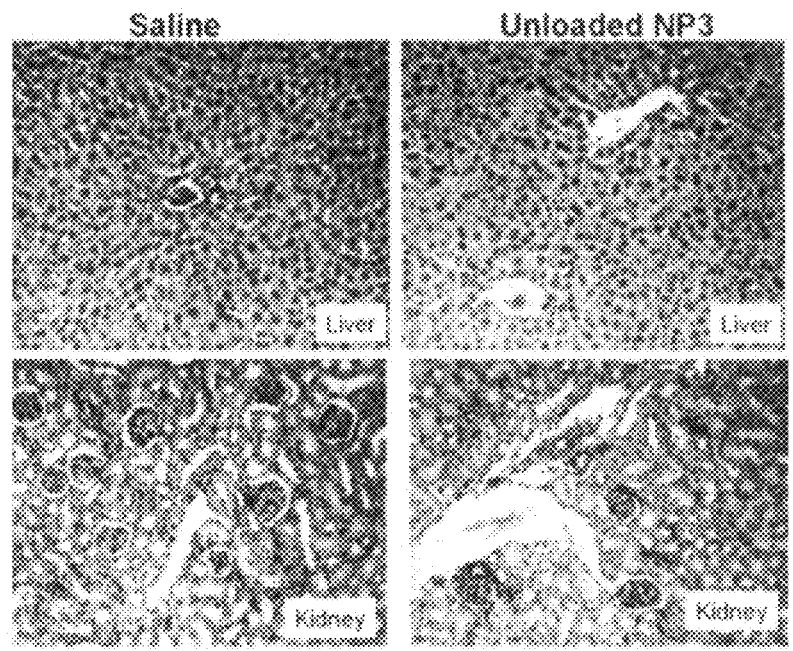
FIG. 43 shows a comparison of liver and kidney histology in animals receiving saline only or empty particles. The animals received weekly intravenous administration of saline or empty NP3 at 50 mg/kg for 3 weeks. The animals were sacrificed 3 weeks after the first treatment. Histological analysis of liver and kidney sections were performed by the UCLA DLAM diagnostic laboratory services. The sections were stained with hematoxylin/eosin (H&E) and examined by light microscopy. Representative images are shown. Both the liver and kidney histology of animals receiving empty NP3 or saline was interpreted as normal.
Figure 44:
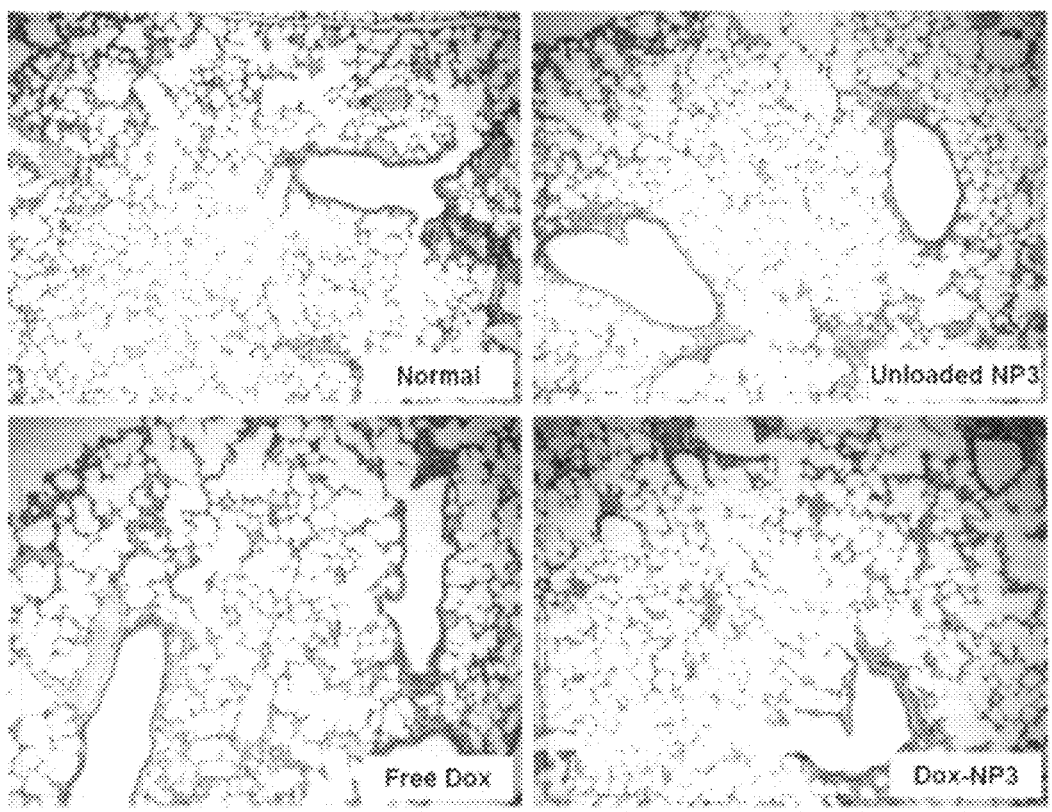
FIG. 44 shows histological examination of the lung tissue of tumor-bearing animals after the various treatments. These animals the same animal groups as in FIG. 7B and S4. The results did not show any gross changes in lung pathology among different groups.
Figure 45:
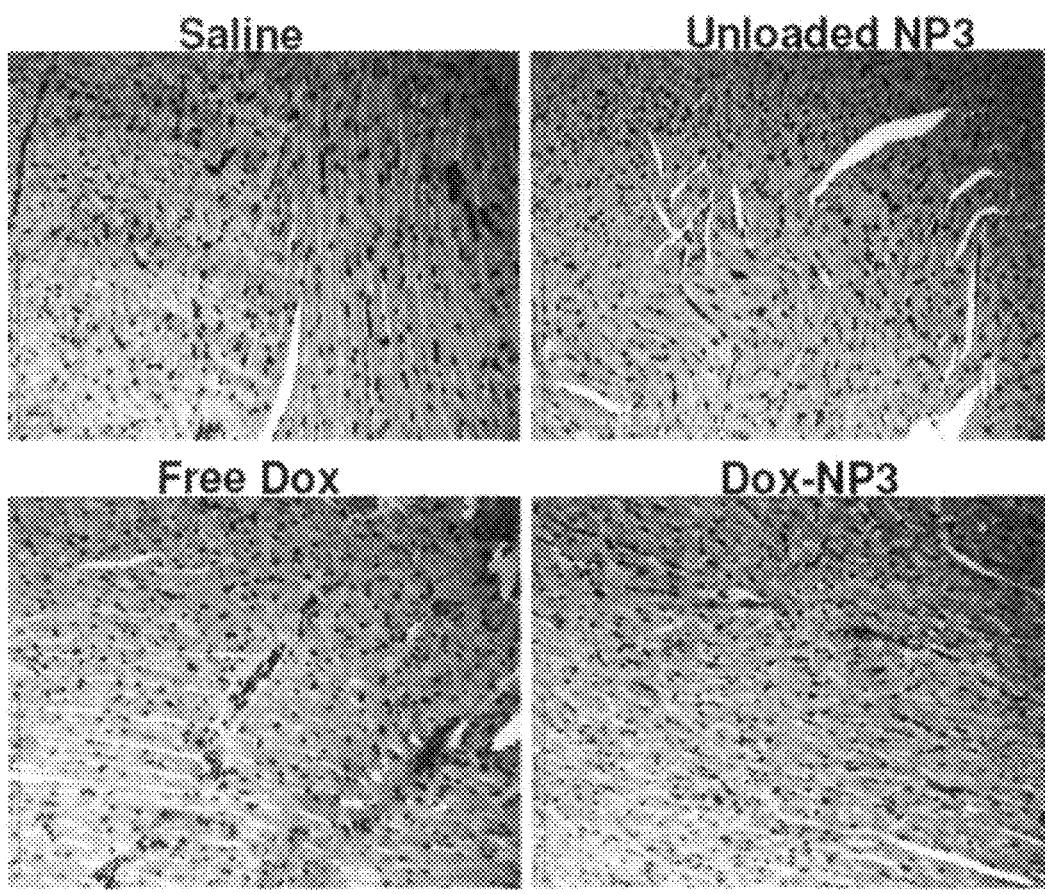
FIG. 45 shows histological examination of the heart tissue of tumor-bearing animal after its various treatments. These animals are from the same experiment shown in FIGS. 39 and 43. The results did not show any gross histological differences among the different groups.

Histological examination of the liver showed prominent hepatic steatosis in the animals treated with free doxorubicin (FIG. 39B, upper panel) (Garg et al., J. Clin. Endocrinol. Metab., vol. 2002, pp. 87-3019-3022). Steatosis represents fatty degeneration as a result of metabolic impairment of triglyceride synthesis and elimination and is a frequent feature of toxic liver injury, including during chemotherapy (Nomura et al., Am. J. Roentgenol., vol. 189, pp. 1484-1488, 2007; Kandutsch et al., Eur. J. Surg. Oneal., vol. 34, pp. 1231-1236, 2008). No steatosis was observed in any of the other treatment groups (FIG. 43, upper panel). Free doxorubicin delivery also resulted in nephrotoxicity, which manifested as glomerular swelling (FIG. 39B, lower panel) (Yagmurca et al., Clinica. Chimica. Acta., vol. 348, pp. 27-34, 2004). No significant abnormalities were found in the mice treated by saline or empty particle (FIG. 43, lower panel). Since the NP3 also abundantly biodistributed in lung, histological examination of the lung tissue was performed but did not show any gross pathology resulting from empty or drug-loaded NP3 (FIG. 44). Interestingly, histological examination of myocardial tissue did not show any gross pathology in any of the experimental groups (FIG. 45). This is probably due to the relatively low doxorubicin dose and short treatment period (Aro la et al., Cancer Res., vol. 60, pp. 1789-1792, 2000).

Figure 46:
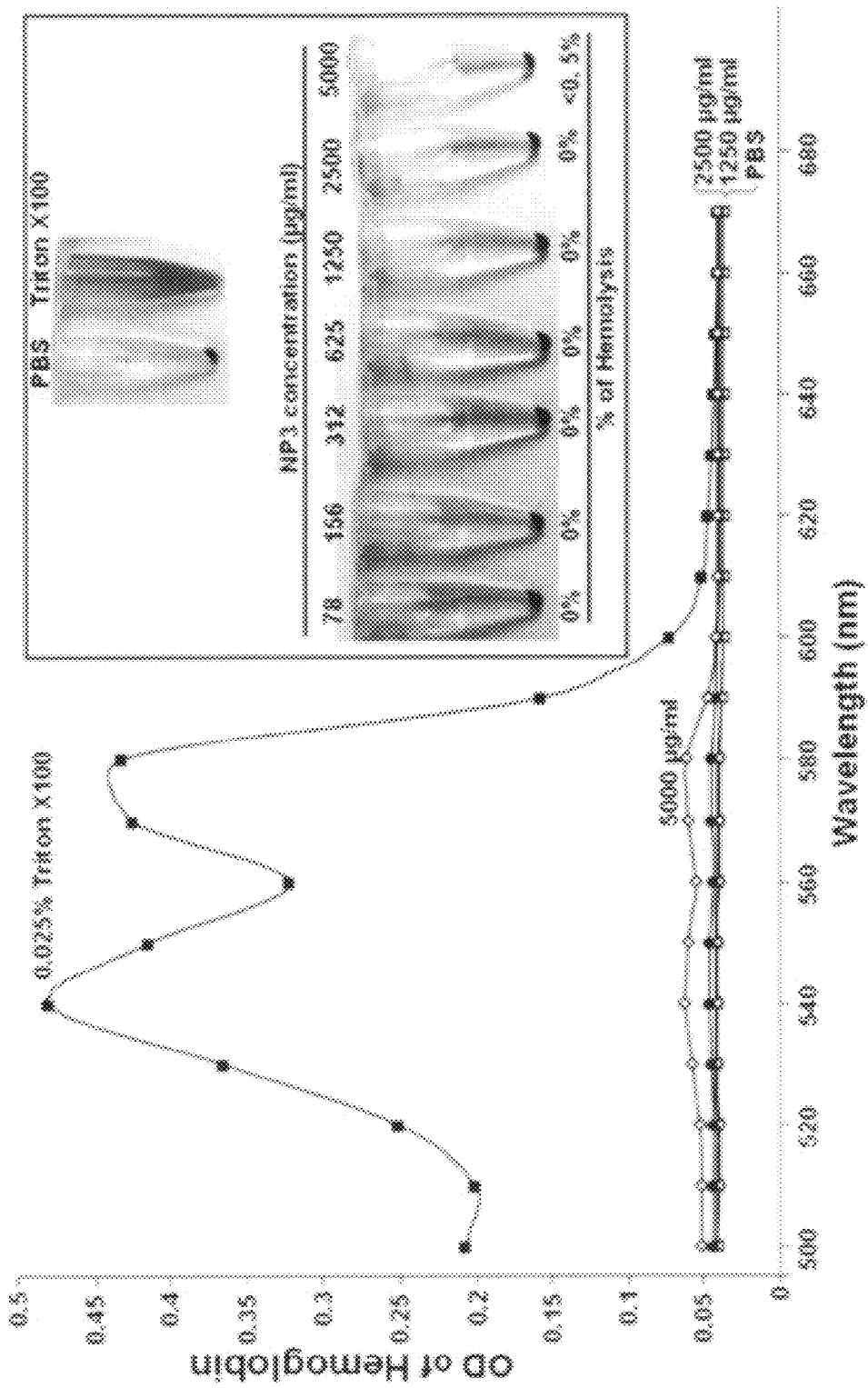
FIG. 46 shows a hemolysis assay to determine membrane lysis of heparinized mouse red blood cells (RBC). Briefly, heparinized mouse blood was collected and washed by PBS. The RBC were suspended at $1\times10^9$ cells per mL and exposed to the indicated concentrations of empty NP3 for 4 h at 37° C. PBS and 0.025% Triton X-100 served as negative and positive controls, respectively. The samples were centrifuged and the absorbance of hemoglobin in the supernatants at 500-650 nm was measured by a microplate reader (M5e, Molecular Device). There was no hemoglobin release in response to particle concentration of up to 2500 µg/mL.

Because of the cationic (PEI) component the co-polymer coating is potentially toxic to cell membranes, including the ability to lyse red blood cells (RBC), a hemolysis assay was performed using heparinized mouse RBC (Slowing et al., Small, vol. 5, pp. 57-62, 2009). The results did not show any hemoglobin release in response to empty NP3 at concentrations as high as 2500 µg/mL (FIG. 46). This is at least 10 times higher than the therapeutic dose requirements. These results are in agreement previous studies showing that coating of the MSNP surface with shorter length (<10 KD) PEI polymers do not lead to significant toxicity in a range of normal and tumor cells (Xia et al., ACS Nano, vol. 3, pp. 3273-3286, 2009).

Attachment of polyethyleneimine-Polyethylene glycol (PEI-PEG) copolymer on a 50 nm MSNP core has been shown to lead to an increase in circulatory half-life as well as exceptionally good EPR effects compared to other polymer/co-polymer based drug and siRNA nanocarrier delivery platforms, where a passive targeting rate of 3.5-10% has been reported for different particle types. Not only are these design features superior for the induction of apoptosis and tumor shrinkage compared to the free drug but also improved the safety of doxorubicin delivery.

By using size tuning and decoration of the MSNP surface with a PEI-PEG co-polymer, particle dispersal and biodistribution were improved to achieve therapeutically useful doxorubicin delivery to a tumor xenograft site in nude mice. Through the use of NIR fluorescence imaging and elemental Si analysis, a 50 nm particle, consisting of mesoporous silica core coated with the PEI-PEG co-polymer was capable of achieving an excellent EPR effect compared to non-coated larger particles (NP 1) or a 50 nm particle decorated with PEG only (NP2). In addition to passive particle accumulation at the tumor site, NP3 was also capable of entering KB-31 tumor cells to deliver a toxic dose of doxorubicin and ability to induce a higher rate of apoptosis compared to the free drug. The encapsulated drug was also associated with less systemic, hepatic and renal toxicity compared to free doxorubicin. This is the first demonstration of how the optimal design of the MSNP platform can achieve passive drug delivery, which in combination with intracellular uptake resulted in an efficacious antitumor effect.

The integrated use of a series of design improvements to achieve in vivo tumor shrinkage and EPR >10% has not been described previously for MSNPs. The best recorded EPR effects with a polymer or co-polymer based nanocarrier system with therapeutic efficacy was in the range of 3.5 to 10% (de Wolf et al., Int. J. Pharm., vol. 331, pp. 167-175, 2007); Kursa et al., Bioconjugate Chem., vol. 14, pp. 222-231, 2002; Kircheis et al., Cancer Gene. Ther., vol. 9, pp. 673-680, 2002). The ability to exceed this delivery with this MSNP platform is highly significant since this has been achieved without targeting ligands or the use of sophisticated design features such as the attachment of nanovalves (Lu et al., Small, vol. 3, pp. 1341-1346, 2007; Liong et al., ACS Nano, vol. 2, pp. 889-896, 2008; Meng et al., J. Am. Chem. Soc., vol. 132, pp. 12690-12697, 2010). The first step was to construct a 50 nm mesoporous silica core to approach a carrier size more conducive for slipping past the malformed blood vessel fenestrations in the tumor. This feature was achieved by using a co-templating agent method for particle synthesis. This involves addition of an optimal amount of Pluronic Fl 27 to cetyl trimethylammonium bromide (CTAB), which is the standard surfactant used for synthesis of the first-generation MSNP (Liong et al., ACS Nano, vol. 2, pp. 889-896, 2008; Meng et al., ACS Nano, vol. 4, pp. 4539-4550, 2010; Meng et al., J. Am. Chem. Soc., vol. 132, pp. 12690-12697, 2010; Xia et al., ACS Nano, vol. 3, pp. 3273-3286, 2009). The Pluronic F127 changes the structure of the CTAB micelles, which affects their micelle packing behavior and therefore leading to a smaller particle size (Febvay et al., Nano Lett., vol. 10, pp. 2211-2219, 2010). Pluronic F127 also improves the dispersion of the hydrophobic silica precursor, tetraorthoethylsilicate (TEOS), and also coats newly formed MSNPs, helping to protect them from agglomeration and oligomerization.

The second key design feature is PEGylation of the MSNP surface which results in reduced RES uptake, as demonstrated for NP2 and NP3. This prolongs the particles' circulation time, which has a direct bearing on the EPR effect. Similar to previous findings, He et al. previously demonstrated that PEGylation of an 80 nm MSNP results in a longer blood-circulation lifetime compared to naked particles in healthy ICR mice (He et al., Small, vol. 7, pp. 271-280, 2011). However, PEGylation alone only achieved an EPR effect of ~3% for NP2, because the particles agglomerated to ~600 nm size, thereby preventing extravasation the tumor site. Although PEG provides steric hindrance that could theoretically interfere in nanoparticle aggregation in water, the increased ionic strength of biological media compresses the electric double layer on the particle surface (Petersen et al., Bioconjugate Chem., vol. 13, pp. 845-854, 2002; Tang et al., Biomaterials, vol. 24, pp. 2351-2362, 2003; Kunath et al., Pharm. Res., vol. 19, pp. 810-817, 2002). This significantly weakens the repulsion between particles. The introduction of cationic charge by using a PEI co-polymer overcame this problem. It is also important to mention that reduced particle opsonization after PEGylation may also reduce immunogenic potential, thereby adding an additional safe design feature (Xia et al., ACS Nano, vol. 3, pp. 3273-3286, 2009).

Figure 47:
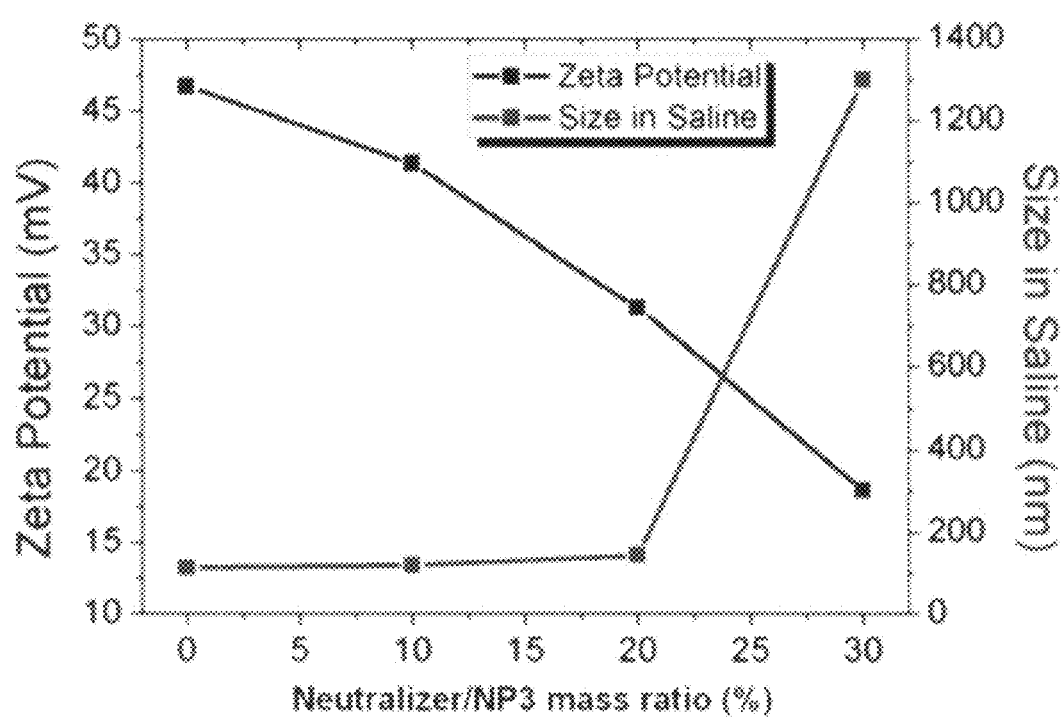
FIG. 47 shows neutralization of amine groups in NP3 to show the effects of particle size. Free amine groups in PEI were neutralized with phthalic anhydride. 10 mg of NP3 was suspended in 1 mL of N, N-Dimethylformamide (DMF) and mixed with 1.0-3.0 mg of phthalic anhydride to obtain an increasing mass ratio (w/w) of the neutralizer with respect to the NP3 weight. Each mixed solution was stirred for 24 h and the neutralized NP3 was washed with DMF and $H_2O$ before use. Size and zeta potential were determined by ZetaSizer Nano (Malvern Instruments Ltd., Worcestershire, UK). The data demonstrate the importance of the addition of cationic charge in controlling the particle size after coating with a PEI-PEG co-polymer.

The attachment of the PEI-PEG co-polymer was undertaken with a view of improving the MSNP dispersal and thereby reducing the particle's hydrodynamic size to be as close as possible to the primary particle size. The effectiveness of the strategy was demonstrated by the acquisition of a positive zeta-potential on NP3 as well as achieving a monodisperse suspension with an average hydrodynamic size ~100 nm in saline. Similar use of a co-polymer strategy to shrink particle size to improve dispersal was previously demonstrated in the preparation of albumin nanoparticles (Zhang et al., Biomaterials, vol. 31, pp. 952-963, 2010), PEI-PEG block co-polymer (Petersen et al., Bioconjugate Chem., vol. 13, pp. 845-854, 2002; Tang et al., Biomaterials, vol. 24, pp. 2351-2362, 2003; Kunath et al., Pharm. Res., vol. 19, pp. 810-817, 2002), gold nanoparticles (Kawano et al., J. Controlled Release, vol. 111, pp. 382-389, 2006), and silica particles (Thierry et al., Langmuir, vol. 24, pp. 8143-8150, 2008). In particular, the use of a PEI-PEG co-polymer resulted in the smallest possible hydrodynamic size and the best state of dispersal of these materials compared to coating with PEG only. To illustrate the importance of the cationic charge in achieving these design features, amine groups on the PEI in the co-polymer were neutralized with phthalic anhydride and could demonstrate that the less cationic NP3 underwent a dramatic size increase in saline (FIG. 47). Consistent with research using trimethylammonium modified MSNP with a primary size 50-100 nm capable of liver accumulation (Lee et al., Adv. Funct. Mater., vol. 19, pp. 215-222, 2009), it would appear that the size reduction effect of the PEI-PEG coating is the major reason for improving biodistribution and therapeutic outcome. The placement of a positive charge on the MSNP surface endows these particles with the ability to bind, protect and deliver nucleic acids as described in Examples 1-7 above. PEI coating is useful for the delivery of a P-glycoprotein (Pgp) siRNA that restores doxorubicin sensitivity in a doxorubicin-resistant HeLa cell line (Meng et al., ACS Nano, vol. 4, pp. 4539-4550, 2010).

The EPR effect of therapeutic nanoparticles plays a key role in their accumulation at the tumor site. Compared to nanoparticles containing surface ligands that promote active targeting of tumor cells or tumor tissue, the use of the EPR effect is considered to be a passive targeting strategy (Maeda et al., H.; Kabanov, A.; Kataoka, K.; Okano, T.; Fang, J.; Sawa, T.; Maeda, H., Factors and Mechanism of "EPR" Effect and the Enhanced Antitumor Effects of Macromolecular Drugs Including SMANCS. In Polymer Drugs in the Clinical Stage, Springer US: 2004, 519, 29-49; Fang et al., Adv. Drug Delivery Rev., vol. 63, pp. 136-151, 2011). Nonetheless, the EPR effect is tunable and can be accomplished through redesign of the nanocarrier or manipulating the tumor microenvironment. Examples of the latter strategy include elevation of systemic blood pressure by angiotensis II (Suzuki et al., J. Natl. Cancer Inst., vol. 67, pp. 663-669, 1981), using a vasodilator such as NO releasing agents (Seki et al., Cancer Sci., vol. 100, pp. 2426-2430, 2009) or increasing vascular permeability with biomolecules such as VEGF and iRGD peptide (Minko et al., Pharm. Res., vol. 17, pp. 505-517, 2000; Sugahara et al., Science, vol. 328, pp. 1031-1035, 2010). However, all of these adjuvant treatments pose some hazard and may not be useful for every treatment consideration. Redesign of the nano material could also impact the EPR effect as reviewed above. It is important to mention here that after their extravasation, the cellular attachment and uptake of the nanoparticles are dependent on their diffusion and that the diffusion constant is inversely correlated to nanoparticle size (Lee et a., Mal. Pharm., vol. 7, pp. 1195-1208, 2010). In this regard it has previously been shown that the size reduction of block co-polymer micelles through a correct combination of polymers could enhance this nanocarrier's uptake in a human breast cancer xenograft (Lee et al., Mal. Pharm., vol. 7, pp. 1195-1208, 2010). It is further worth noting that the EPR effect is highly dependent on the cancer type, including the extent of neo-angiogenesis and the vascularity of the tumor (Maeda et al., Bioconjugate Chem., vol. 21, pp. 797-802, 2010; Mao et al., Pharm. Res., vol. 22, pp, 2058-2068, 2005). While in a previous study MSNP was capable of accumulating in a human breast carcinoma (MCF-7) xenograft (Lu et al., Small, vol. 6, pp. 1794-1805, 2010), a satisfactory EPR effect was not achieved with this material in the KB-31 model. However, size reduction and coating the 50 nm particles with a PEI-PEG co-polymer could increase particle uptake by an order of magnitude in KB-31 tumor sites. Moreover, the passive enhancement of NP3 accumulation at these tumor sites is accompanied by intracellular uptake without requiring the attachment of a ligand. The cationic particle surface could play an active role in promoting this uptake as previously demonstrated in a variety of cancer cell types in vitro (Xia et al., ACS Nano, vol. 3, pp. 3273-3286, 2009).

Key to any therapeutic intervention is the inherent safety of the delivery system. The empty NP3 failed to elicit any adverse effects after intravenous injection as determined by animal body weight, blood biochemistry, and histological analysis of major organs and tissues. Moreover, these particles did not damage red cell membranes when using a hemolysis assay (FIG. 46). Another design feature to consider from a safety perspective is particle coating with a PEI polymer. While it is well known that PEI by itself or coated onto particle surfaces could lead to toxicity, demonstrated to be dependent on the polymer length and cationic charge density (Xia et al., ACS Nano, vol. 3, pp. 3273-3286, 2009). Thus, while high molecular weight (≥10 kD) PEI polymers can induce considerable cellular toxicity in a variety of normal and transformed cell types, there is no generation of cellular toxicity by the 1.2 kD polymer (Xia et al., ACS Nano, vol. 3, pp. 3273-3286, 2009). This was confirmed by conducting cytotoxicity studies with NP3 in cancer cell lines (not shown). The apparent reason is the distribution and density of cationic charge on the longer length versus the shorter length PEI polymers, allowing the longer length polymers to induce membrane damage as well as the possibility of inducing a so-called "proton sponge effect" that is associated with lysosomal damage density (Xia et al., ACS Nano, vol. 3, pp. 3273-3286, 2009; Zhang et al., ACS Nano 2011, 10.1021/nn200328m). It is also worth mentioning that intravenous injection of the equivalent of NP1 coated with a 25 kD PEI polymer in mice did not elicit any significant toxicity in a previous study in mice (Xia et al., ACS Nano, vol. 3, pp. 3273-3286, 2009).

Equally important is the demonstration of the improvement of the high level of doxorubicin toxicity by encapsulating the drug in NP3 (Portney et al., Anal. Bioanal. Chem., vol. 386, pp. 620-630, 2006; Vallet-Regi et al., Chem. Mater., vol. 13, pp. 308-311, 2000). Thus, compared to the free drug, doxorubicin encapsulation did not exert an effect on total body weight or impacting liver and kidney function (FIGS. 39C and 43). Interestingly, evidence of histological damage to the myocardium was not observed in this study, even with free doxorubicin (Hayek et al., N Engl. J Med., vol. 352, pp. 2456-2457, 2005). This may be due to the comparative high sensitivity of KB-31 cancer cells to the effects of doxorubicin (Meng et al., ACS Nano, vol. 4, pp. 4539-4550, 2010). This reduction of systemic toxicity is likely due to the drug being bound to the negatively charged phosphonate groups in the particle pores, therefore not being released in the bloodstream. Doxorubicin release from phosphonate-coated MSNP pores take place in acidifying endosomal compartment in KB-31 cells (Meng et al., ACS Nano, vol. 4, pp. 4539-4550, 2010). While it is difficult to study endosomal release at the intact animal level, fluorescence visualization data demonstrate the presence of doxorubicin containing NP3 in a perinuclear distribution in KB-31 cells undergoing apoptosis in vivo (FIG. 38C). Thus, intracellular drug release may contribute to the higher rate of KB-31 cell apoptosis in this study. This feature may be enhanced by using a pH-dependent nanovalve that is capable of opening intracellularly in KB-31 cells with the capability of doxorubicin release to the nucleus (Meng et al., J Am. Chem. Soc., vol. 132, pp. 12690-12697, 2010).

It is important to mention that similar to other nanocarriers (Li et al., Mal. Pharm., vol. 5, pp. 496-504, 2008) that the vast majority of systemically administered MSNPs are sequestered by the RES irrespective of the design feature. The lack of observable toxicity of the doxorubicin-laden particles in the liver and spleen is an interesting finding that has not been resolved as yet. Without wishing to be bound by theory, one possibility is that the traditional biomarkers used for following liver injury are ineffective in reflecting RES damage, but another explanation is that the RES and organs like the liver are quite resilient in dealing with doxorubicin toxicity when the drug is encapsulated. This could involve protective features such as hepatobiliary transfer, which has been shown to be quite prominent in another MSNP study (Souris et al., Biomaterials, vol. 31, pp. 5564-5574, 2010). It is also possible that the relatively slow rate of drug release from the particle pores could prevent acute toxicity due to drug conjugation, inactivation or excretion (Maeda et al., Eur. J Pharm. Biopharm., vol. 71, pp. 409-419, 2009; Torchilin et al., Adv. Drug Deliver. Rev., vol. 63, pp. 131-135, 2011). There is also a considerable capacity of mononuclear macrophages to destroy or sequester particulate matter (Noguchi et al., Cancer Sci., vol. 89, pp. 307-314, 1998). It is important to mention that in a previous study tracking of elemental Si following systemic MSNP administration could lead to the recovery of ~94% of the injected MSNP bolus in the urine and feces within 4 days (Lee et al., Angew. Chem. Int. Ed., vol. 49, pp. 8214-8219, 2010). This is in agreement with the demonstration by Souris et al. of the rapid bioelimination of MSNP through hepatobiliary excretion in murine experiments (Souris et al., Biomaterials, vol. 31, pp. 5564-5574, 2010). This constitutes another important safety feature of a nanocarrier that could either be degraded in situ into cellular subcomponents or could be excreted from the body once the carrier has served its therapeutic purpose. The in vivo biodegradability and bioelimination of MSNP is comparable to abiotic studies, showing the gradual decomposition of MSNP in simulated body fluids at 37° C., including demonstrating a breakdown of the MSNP architecture with a decrease in their BET surface area (Cauda et al., Micropor. Mesopor. Mat., vol. 132, pp. 60-71, 2010).

Size tuning and decoration of the MSNP surface with a PEI-PEG co-polymer constitutes an efficient doxorubicin delivery strategy for a human squamous carcinoma xenograft in nude mice. In vivo imaging and elemental analysis demonstrate that these design modifications lead to an excellent EPR effect and sufficient nanocarrier accumulation to achieve tumor cell killing that is more effective than the free drug. This delivery may minimize the chemotherapeutic side effects at the intact animal level as well as susceptible organs. These results are encouraging from the perspective of moving the MSNP platform into clinical trials as well as introducing additional design features that will make it possible to perform theranostics as well to obtain on-demand drug release at the tumor site by a series of nanovalves that can be controlled through pH, temperature, photon wavelength or a magnetic field.

Example 9—MSNP with Increased Aspect Ratio

Experiment Reagents.

Commercial reagents and analytical materials used in this study include: tetraethoxysilane (TEOS, 98%, Aldrich), cetyltrimethylammonium bromide (CTAB, 98%, Aldrich), perfluorooctanoic acid (PFOA, 96%, Aldrich), methanol (99.9%, Fisher), triethylamine (99.5%, Aldrich), ethanol (200 proof, Pharmaco-AAPER), 3-aminopropyltriethoxysilane (APTES, 99%, Gelest), rhodamine-B-isothiocyanate (RITC, Aldrich), fluorescein isothiocyanate (FITC, >90%, Aldrich), amiloride (Aldrich), cytochalasin D (Aldrich), sodium azide ($NaN_3$, Aldrich), and 2-deoxyglucose (2-DG, Aldrich), camptothecin (CPT, 99%, Aldrich), Taxol (99%, Aldrich). RPMI 1640 cell culture medium, penicillin/streptomycin, L-glutamine, Alexa 594-phalloidin, and Hoechst 33342 were purchased from Invitrogen (Carlsbad, Calif.). Fetal bovine serum (FBS) was from Atlanta Biologicals, Inc (Lawrenceville, Ga.). Anti-LAMP-1 and anti-GTP-Rac1 antibody were obtained from Abcam (Cambridge, Mass.) and Cell signaling (Danvers, Mass.). Anti-total-Rac1, anti-clathrin and anti-caveolin antibodies were purchased from Santa Cruz Biotechnology (Santa Cruz, Calif.). Deionized $H_2O$ was obtained from a Millipore water purification system. Toluene (99.5%) refluxed before use.

MSNP Synthesis.

MSNPs were synthesized via a modified procedure to yield rod-shaped structures.[19] MSNP with different AR were chemically synthesized by a sol-gel approach using a surfactant/co-structure direct agent (CSDA) mixture as template. Different shaped MSNP and AR were synthesized by varying the PFO/CTAB molar ratio as follows: MSNP0=0; MSNP1=0.015; MSNP2=0.03; MSNP3=0.06. The PFO/CTAB mixture was stirred at 600 rpm for 1 h at room temperature before the addition of 2.1 mL 2 M NaOH. Subsequently, the solution temperature was raised to 80° C. before the addition of 4.1 mL of TEOS. This mixture was stirred for an additional 2 h and the precipitate was carefully collected by filtration. After washing 3 times with methanol and deionized water, the solids were air dried overnight at room temperature. The MSNP templates were removed by extracting the CTAB with HCl containing methanol under nitrogen protection. The resulting MSNP were collected by filtration, washed by methanol, and dried overnight in air. Depending on the shape and AR, the particles were designated MSNP0, MSNP1, MSNP2 and MSNP3 as explained in Table 6. To visualize the particles under a confocal microscope or perform flow cytometry, FITC- or RITC-labeled MSNP were prepared by suspending 200 mg of MSNP in 10 mL of dry toluene with 3 µL of APTES, followed by the attachment of FITC or RITC in ethanol. The labeled MSNP were collected by centrifugation and washed by methanol and water before use.

Physicochemical Characterization of MSNP.

MSNP were characterized for shape (aspect ratio), surface area, hydrodynamic size, and zeta potential. The shape and morphology of the MSNP were characterized by scanning electron microscopy (SEM, JSM-6700F) at 15 kV. The pore structure and aspect ratio were studied by using a transmission electron microscope, JEM 1200-EX operated at 80 kV. Microfilms for TEM imaging were obtained by placing a drop of the respective MSNP suspensions onto a 200-mesh copper TEM grid and drying at room-temperature overnight. The AR values were determined by measuring the length and diameter of at least 30 randomly selected particles. X-ray diffraction (XRD) patterns were recorded on a Panalytical X'Pert Pro Powder Diffractometer with Ni-filtered Cu Kα radiation. UV-vis spectra were collected using a Cary 5000 UV-vis-NIR spectrophotometer. For surface area measurement, $N_2$ adsorption-desorption isotherms were obtained on a Quadrasorb SI surface area analyzer and pore size analyzer (Quantachrome instruments, Florida, USA). The BET model was applied to evaluate the specific surface areas and the Barret-Joyner-Halenda (BJH) method was used to calculate the pore size. Particle hydrodynamic size and zeta potential were measured in pure water or cell culture medium using a ZetaSizer Nano (Malvern Instruments Ltd., Worcestershire, UK).

Figure 48A:
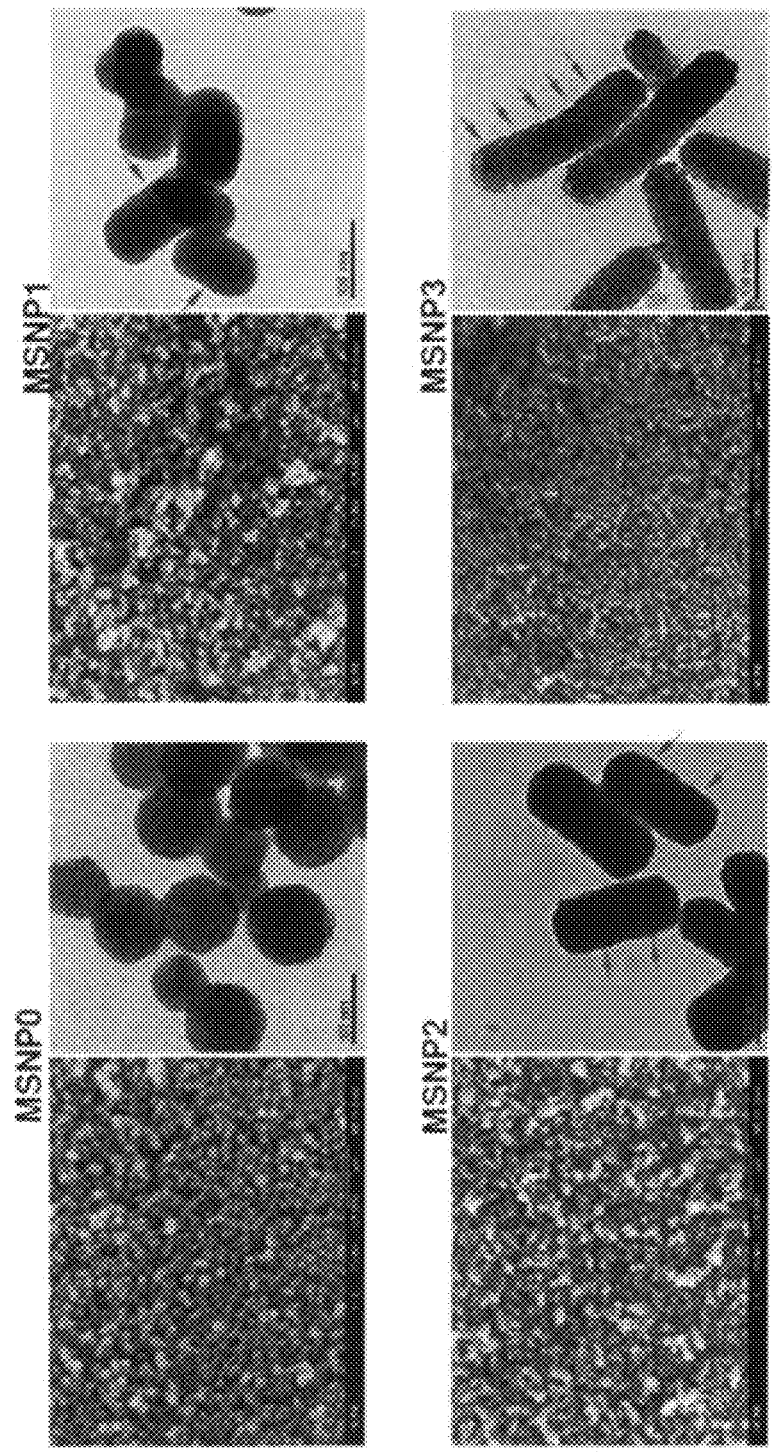
FIGS. 48A and 48B show physicochemical characterization of MSNP.
Figure 48B:
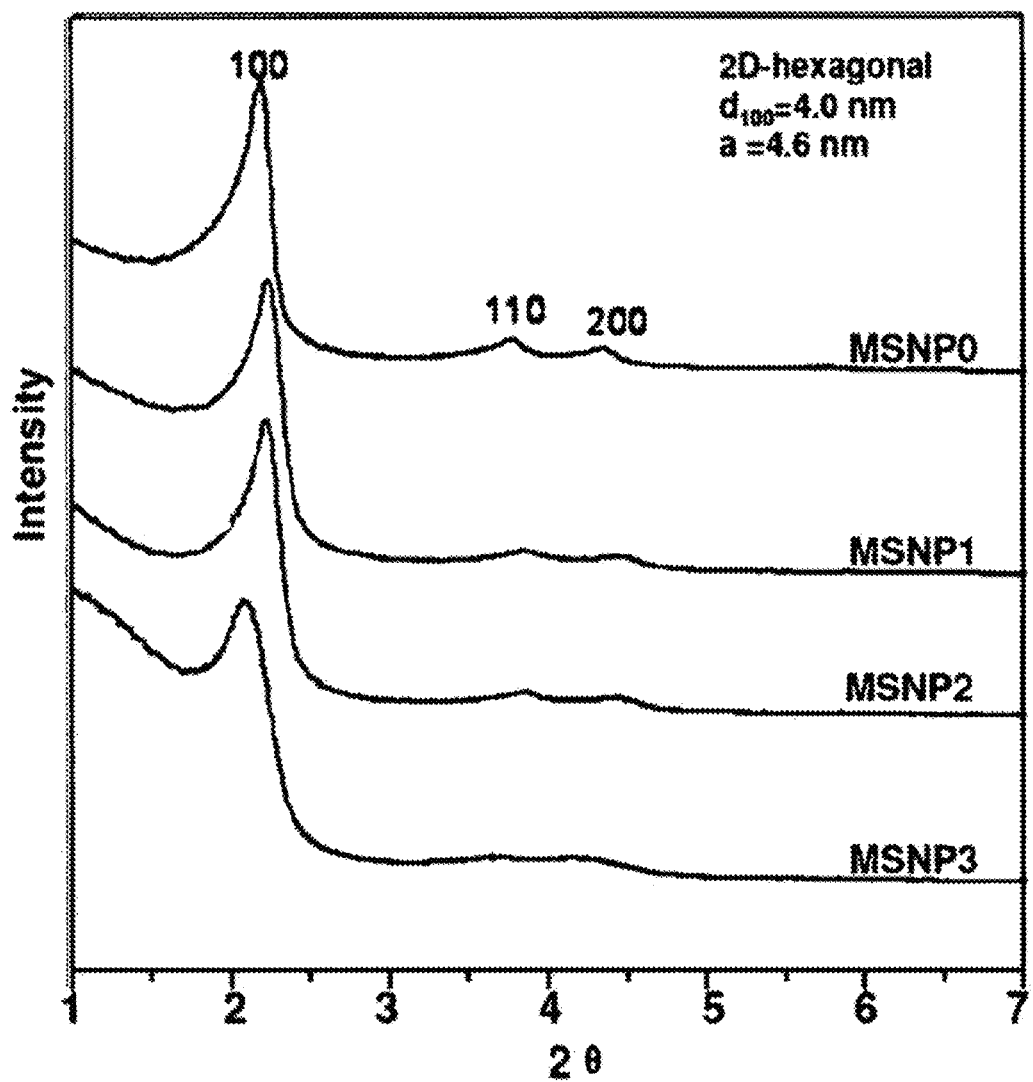

The morphology of the rods, in comparison to the spherical particles, is shown in the SEM and TEM images in FIG. 48A. MSNP0 are spheres of ~110 nm diameter, exhibiting uniform pore sizes of 2.5 nm and an AR=1 (FIG. 1A). By increasing the perfluorooctanoic acid (PFOA)/cetyltrimethylammonium bromide (CTAB) doping ratio during the synthesis, it was possible to obtain rod-shaped cylinders with dimensions of 110-130/60-80 nm (MSNP1), 160-190/60-90 nm (MSNP2), and 260-300/50-70 nm (MSNP3), respectively (Table 6). These values were used to calculate the AR, which varied from 1.5-1.7 (MSNP1), 2.1-2.5 (MSNP2) and 4-4.5 (MSNP3). In spite of differences in the AR, the pore structure and pore sizes of the rods are similar (FIG. 48 and Table 6). However, with an increase in the AR of the MSNP from 1 to 4.5, the surface area of these particles decreased from 1077.9 $m^2/g$ to 760.2 $m^2/g$ (Table 6). Small angle powder XRD (FIG. 48B) analysis showed 3 well-resolved peaks that can be indexed as the 100, 110 and 200 reflections and confirms the hexagonal symmetry (p6m) of the pore structure.[2] The rod-shaped particles showed periodical "fringes" along their length (indicated by arrows in FIG. 48A), which represent the ordered helical hexagonal pore arrangements as reported in the literature.[19,21,22]

to demonstrate that cells can distinguish between a spherical shape and a rod-shaped particle. All cell types were trypsinized and washed in PBS for 3 times. Cells were analyzed in a SCAN flow cytometer using mean FL-2 and FL-1 to assess RITC and FITC fluorescence, respectively. Data are reported as fold increase in mean fluorescence intensity (MFI), using MSNP0 uptake as reference.

For the confocal studies, cellular uptake of the spheres and different AR particles was performed by adding 20 µg/mL FITC-labeled particles to 8-well chamber slides. Each well contained $5 \times 10^4$ cells in 0.5 mL culture medium. Cell membranes were co-stained with 5 µg/mL Alexa Fluor 633-conjugated wheat germ agglutinin (WGA) in PBS for 30 min. Slides were mounted with Hoechst 33342 and visualized under a confocal microscope (Leica Confocal lP/FCS) in the UCLNCNSI Advanced Light Microscopy/Spectroscopy Shared Facility. High magnification images were obtained with the 100× objective.

TABLE 6

Physicochemical characterization of MSNP.

| Samples | MSNP0 | MSNP2 | MSNP2 | MSNP3 |
|---|---|---|---|---|
| Aspect ratio | 1~1.2 | 1.5~1.7 | 2.1~2.5 | 4.0~4.5 |
| $D_{100}$ (nm) | 4 | 4 | 4 | 4 |
| Pore diameter (nm) | 2.5 | 2.5 | 2.5 | 2.5 |
| Surface area ($m^2/g$) | 1077.9 | 926.1 | 896.9 | 760.2 |
| Size in $H_2O$/RPMI/CRPMI (nm)[a] | 219/1036/239 | 207/723/229 | 198/902/337 | 185/1023/249 |
| Zeta potential in $H_2O$/CRPMI (Mv) | 15.7/−5.7 | 17.1/−6.9 | 13.0/−5.7 | 13.5/−6.2 |

[a]Particle size measurements were performed using dilute suspensions (100 µg/mL) in water or RPMI at pH 7.4 in a ZetaSizer Nano (Malvern Instruments Ltd., Worcestershire, UK). To disperse the particles, the stock solutions in water (20 mg/mL) were sonicated (Tekmar Sonic Disrupter probe) for 15 s before use. In order to coat the surface of MSNP with FBS, 19 µL of particle suspension was mixed with 1 µL FBS before addition to complete medium and sonication for 15 s. RPMI denotes the particle size in RPMI cell culture medium without serum; CRPMI reflects the size of MSNP that pre-coated using FBS in complete RPMI containing 10% FBS.

To optimize the particle dispersal for purposes of biological experimentation, the MSNP were suspended in distilled water containing 5% fetal bovine serum (FBS) and ultimately transferred into complete RPMI containing 10% FBS.[13] Not only does this sequence of particle suspension prevent agglomeration due to culture medium ionic effects but also adjusts the particles' zeta potentials from positive to negative as a result of protein adsorption (Table 6).

MSNP Dispersion and Use to Perform Tissue Culture.

All cell cultures were maintained in 75 $cm^2$ cell culture flasks in which the cells were passaged at 70-80% confluency every 2-3 days. The human cervical (Hela) and lung cancer (A549) cells were cultured in RPMI 1640 containing 10% FBS, 100 U/mL penicillin, 100 µg/mL streptomycin, and 2 mM L-glutamine (complete RPMI medium). To disperse MSNP in cell culture medium, the water stock solution was sonicated (Tekmar Sonic Disruptor probe) for 10 s before use. In order to coat the surface of MSNP with FBS, 19 µL MSNP suspension was mixed with 1 µL FBS. Complete cell culture media was then added to the serum-coated MSNP suspension.

Assessment of cellular MSNP uptake by flow cytometry and confocal microscopy. For the performance of flow cytometry, aliquots of $1 \times 10^5$ cells (Hela & A549 cells) were cultured in 12-well plates in 1 mL medium. RITC-labeled spherical MSNP were added to the above cultures at 20 µg/mL for 1 h, washed carefully in PBS and then incubated with different FITC-labeled MSNP at 20 µg/mL for 6 h. The purpose of prior incubation with the RITC-labeled spheres is AR Influences Cellular Uptake of MSNPs in Hela Cells and A549 Cells.

Figure 53:
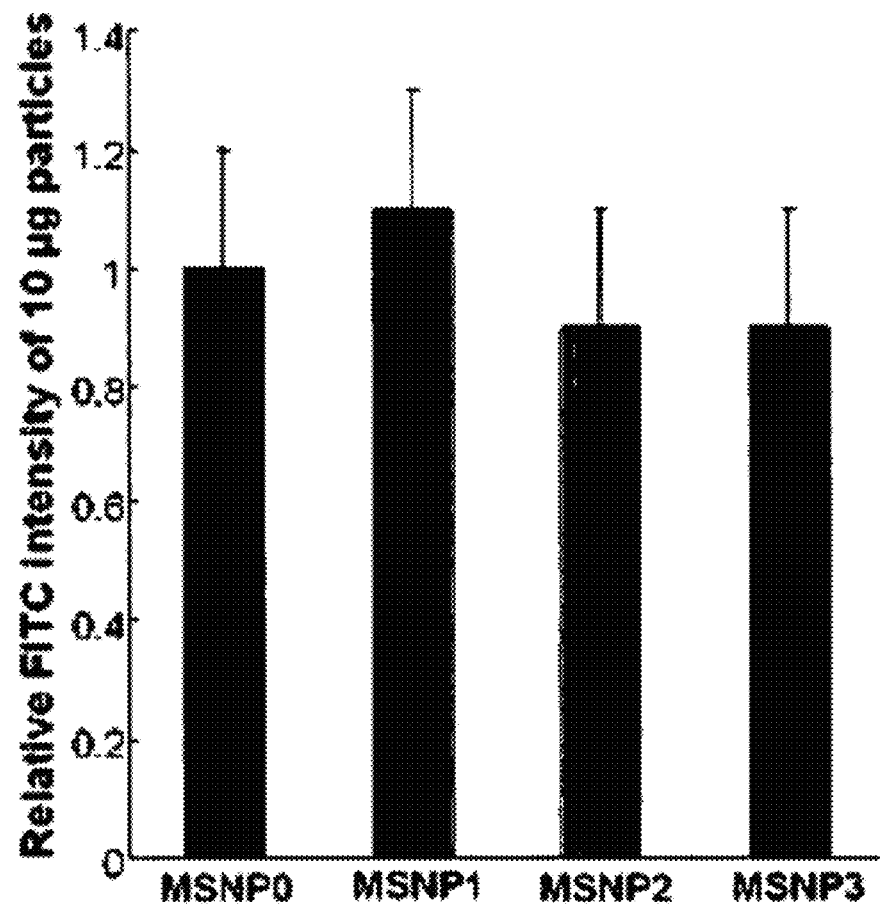
FIG. 53 shows fluorescent labeling efficiency of the different particle types determined in a microplate reader. The FITC-labeled MSNPs were washed and suspended in water at 100 µg/mL. 100 µLeach particle suspensions were loaded into a 96-well plate and the fluorescent intensity was detected at excitation and emission wavelength of 488/525 nm with a microplate reader (M5e, Molecular Device). The fluorescent intensities of MSNP1-MSNP3 were expressed as a unit of the fluorescence intensity of MSNP0, which was regarded as 1.0. The result indicated that there was no significant difference (p>0.05) in the fluorescent labeling efficiency among different MSNPs.

Previous publications have shown that a non-spherical shape enhances the abundance and rate of cellular uptake of nanoparticles.[1,3,6,23] In order to assess cellular uptake of FITC-labeled MSNP in Hela cells and A549 cell line, a combination of flow cytometry and confocal microscopy was used. The fluorescence labeling efficiency is similar for all particle surfaces, allowing us to compare the uptake abundance directly (FIG. 53). Compared to spherical particles (MSNP0), there was a significant increase in the mean fluorescence intensity (MFI) of cells exposed to rod-shaped particles (FIG. 49A). This amounted to an 18-, 40- and 8-fold increase of the MFI for MSNP1, MSNP2 and MSNP3, respectively. Interestingly, the cellular association of MSNP2 was consistently increased compared to MSNP1 or MSNP3, suggesting that the intermediary AR is preferred for cellular uptake. The preference for a rod vs. a spherical shape was further confirmed by comparing FITC-labeled materials with RITC-labeled spheres (FIG. 49A). While all the cell populations internalized the RITC-labeled spheres to the same degree, there was a definitive increase in the uptake of the FITC-labeled rods in proportion to the ratios cited above.

Figure 49B:
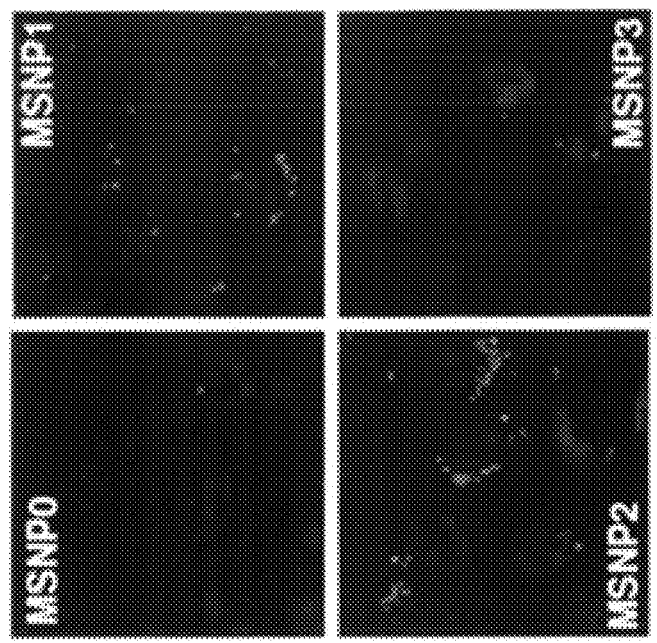
FIGS. 49A-49C show the abundance and rate of cellular uptake of FITC-labeled MSNP in Hela cells.
Figure 49A:
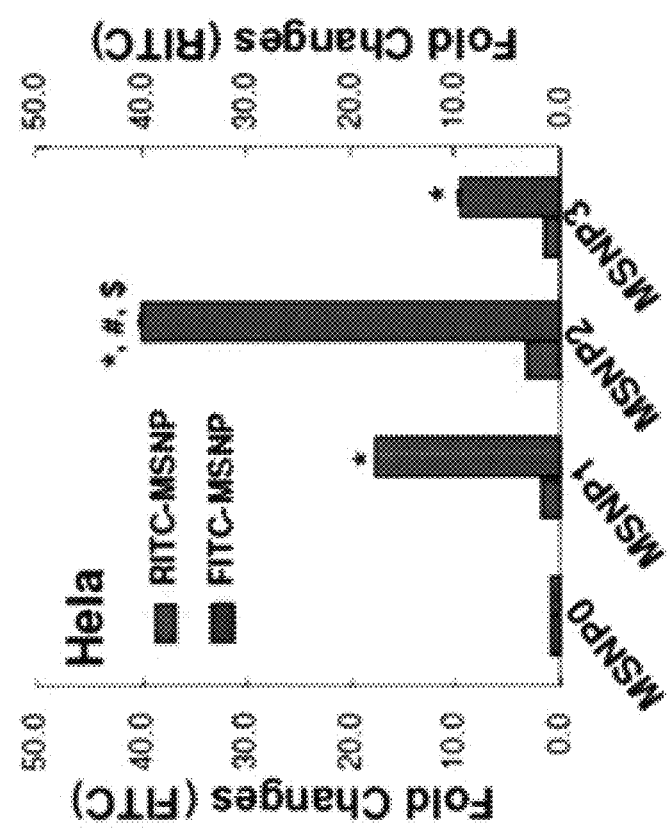
Figure 49C:
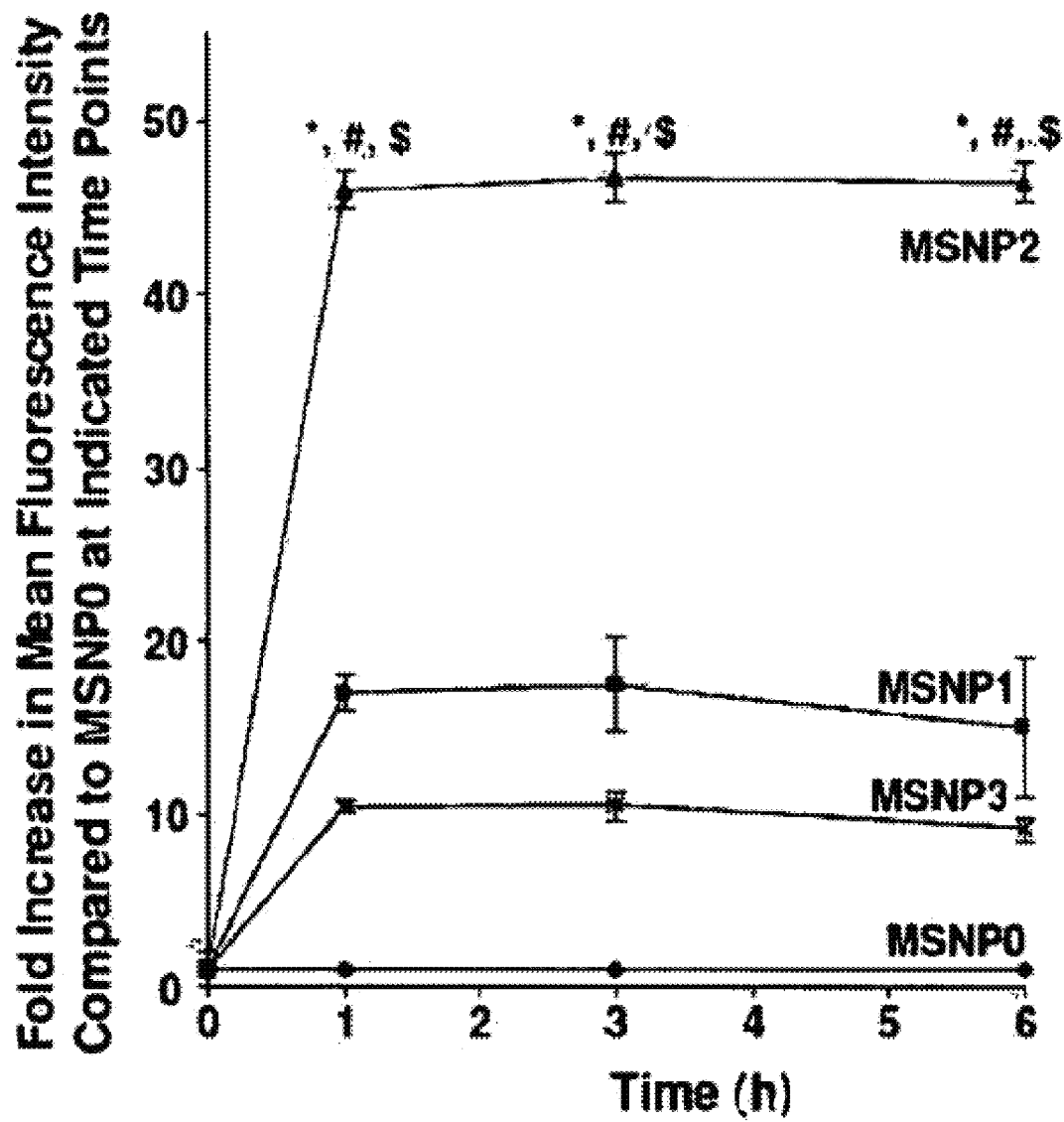

The flow data was confirmed by confocal images showing higher uptake of FITC-labeled rods compared to the FITC-labeled spheres (FIG. 49B). Moreover, among the rods, the particles with an AR of 2.1-2.5 were endocytosed to greater abundance (FIG. 49B) and at more rapid rate compared to MSNP1 and MSNP3 (FIG. 49C). Moreover, MSNP2 appeared to localize predominantly in the perinuclear region of Hela cells whereas MSNP1 and MSNP3 were more randomly distributed (FIG. 49B).

Figure 54A:
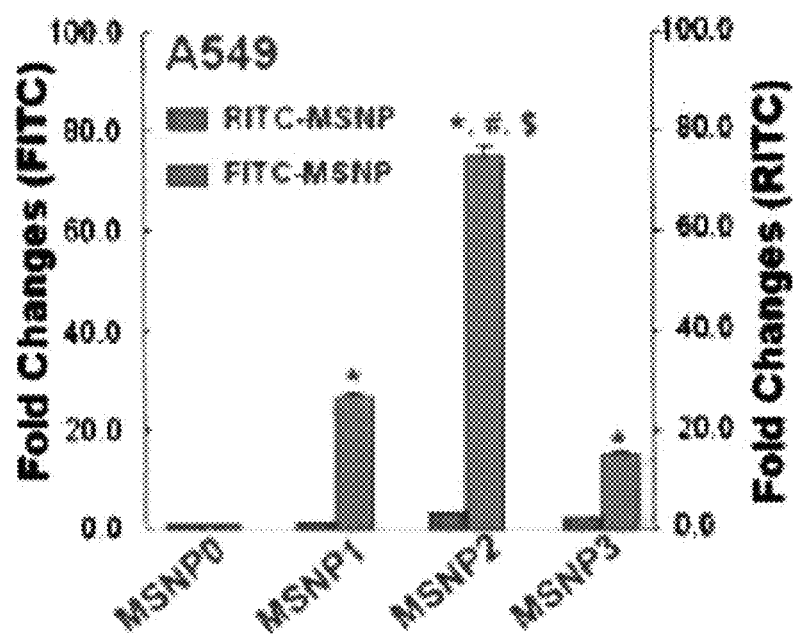
FIGS. 54A and 54B show cellular uptake of FITC-labeled MSNP in A549 lung cancer cells.
Figure 54B:
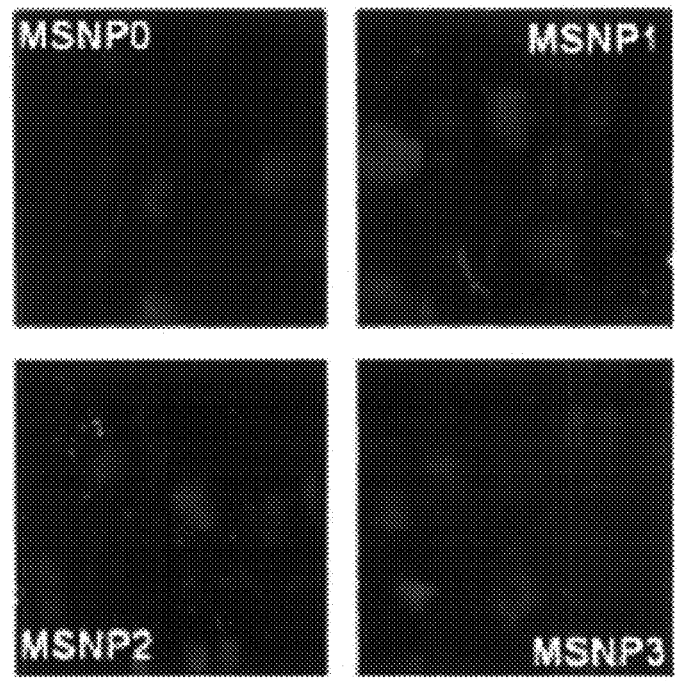

To further confirm that the impact of AR is not unique to Hela cells, the experiments were repeated in the A549 lung cancer cell line (FIG. 54). Consistent with the Hela data, MSNP2 yielded the highest cellular uptake compared to spheres or longer/shorter rods (FIG. 54).

Transmission Electron Microscopy of MSNP Treated Cells.

Hela cells were treated with each of the MSNP variants at 20 µg/mL for 3 h. The cells were washed in PBS and immediately fixed with 2.5% glutaraldehyde in PBS. After secondary fixation in 1% $OsO_4$ in PBS, the cells were dehydrated in a graded ethanol series, treated with propylene oxide, and embedded in resin. Approximately 60-70 nm thick sections were cut on a Lei ca ultramicrotome and picked up on formvar-coated copper grids. The sections were examined in a CM120 electron microscope (Philips).

Electron Tomography.

TEM grids were used for the tomography imaging on an FEI Tecnai F20 microscope operated at 200 kV. Tilt series were acquired by tilting the specimen from −70° to 70° at 1° increments and with a TIETZ F415MP 16 megapixel CCD camera at a magnification of 26,600× and then aligned using the ETOMO program in the IMOD package.[63] The aligned tilt series were then further processed using the reconstruction Inspect3D program from FEI, with the SIRT option, to improve reconstruction accuracy and contrast. 3D movies of the aligned tilt series were generated using both Inspect3d and Windows movie maker. Visualization of 3D tomographic reconstructions were performed using 3DMOD of IMOD[63] and Amira (http://www.amira.com/).

F-Actin Staining and Filopodia Counting.

Hela cells were seeded into 8-well chamber slides and incubated with or without MSNP at a concentration of 20 µg/mL for 6 h. Cells were washed 3 times in PBS, fixed with 3.7% formaldehyde for 30 min, and permeabilized with 0.25% Triton X-100 for 10 min. For F-actin staining, cells were incubated with Alex 594 phalloidin in the dark for 30 min at room temperature. The slides were viewed using a confocal microscope equipped with a 100× oil-immersion objective. The average number of filopodia per cell as determined by actin fiber staining was calculated by counting at least 20 randomly selected cells in each exposure category.[29] After filopodia counting, two-sided Student's t test was performed to determine whether there was a statistically significant difference.[29]

Drug and Temperature Inhibition Studies.

Hela cells were seeded in a 12-wells plate at the density of 1×10[5] per well. The cells were pre-cultured in serum free RPMI 1640 medium containing amiloride (75 Cyto D (2.5 µg/mL), or 0.1% $NaN_3$/50 mM 2-DG for 3 h. Alternatively, cells were placed at 4° C. After 3 h pretreatment, the media was exchanged into fresh complete RPMI 1640 that contained 20 µg/mL FITC-labeled MSNP2, one of the chemical inhibitors (amiloride, Cyto D or $NaN_3$/2-DG), and 10% FBS. To observe a temperature effect, the cellular incubation with particles was carried out at 4° C. for 6 h. Following a 6 h incubation period, the cells were washed with PBS and then processed for flow cytometry as described above. The filopodia counting was performed by confocal microscopy as described above.

MSNP2 Uptake Requires Cytoskeleton Activation and Filopodia Formation.

Figure 50A:
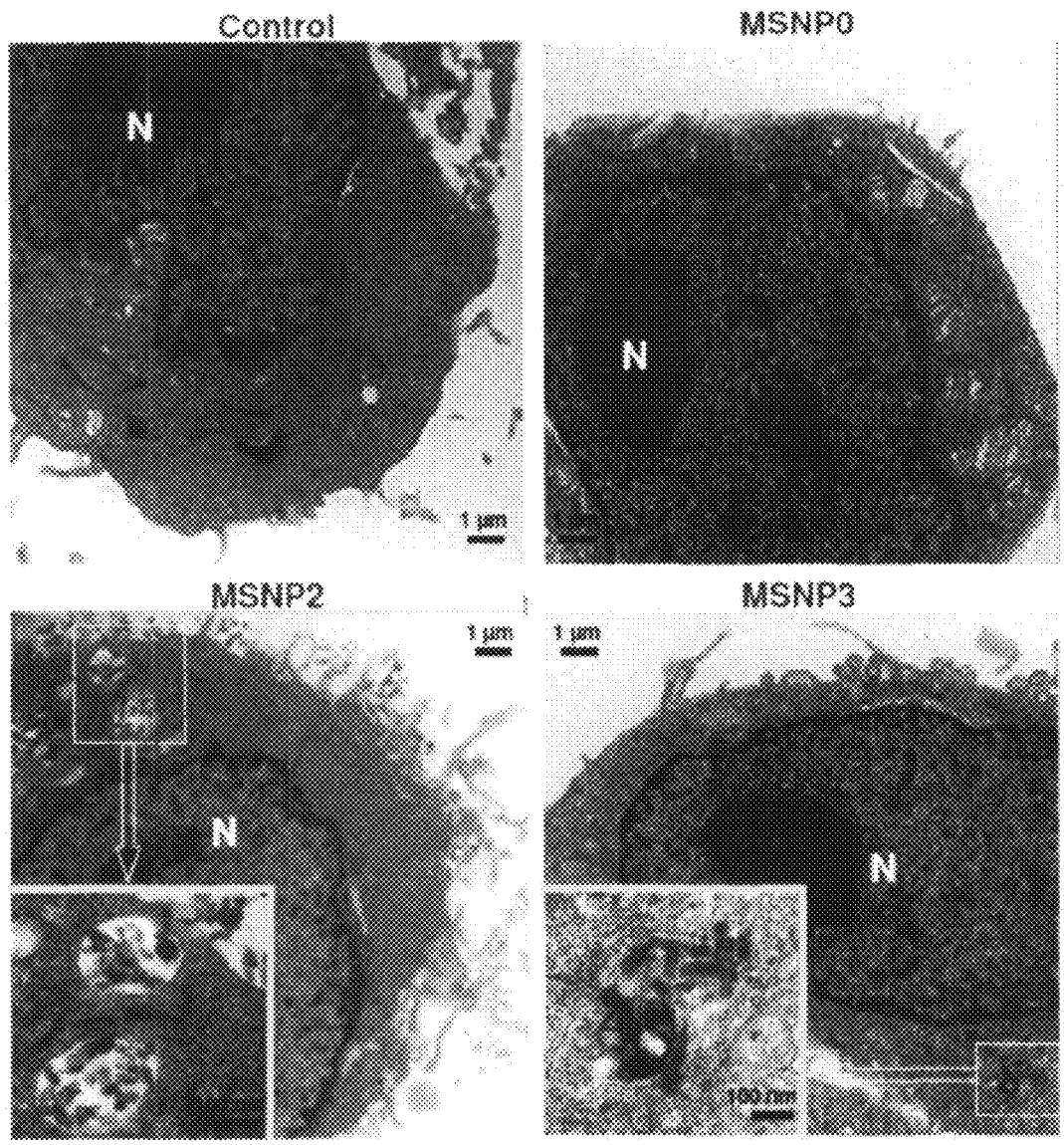
Figure 55:
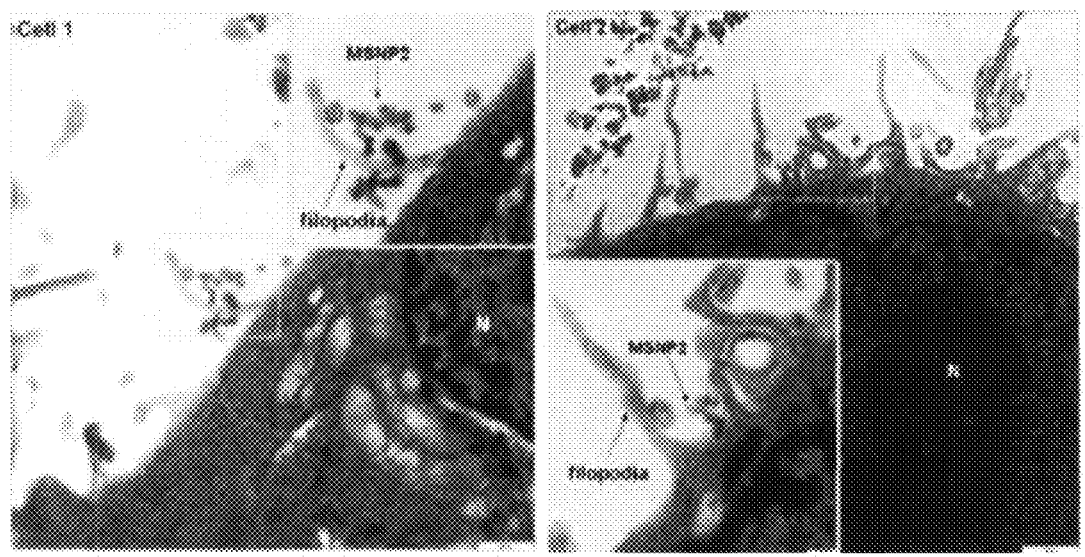
FIG. 55 shows additional ultrastructure analysis using TEM to elucidate MSNP uptake by macropinocytosis in Hela cells. Hela cells were exposed to 20 µg/mL MSNP2 for 3 h. The arrows in the figures point out filopodia and MSNP2 nanoparticles, respectively. "N" denotes nuclear.
Figure 56:
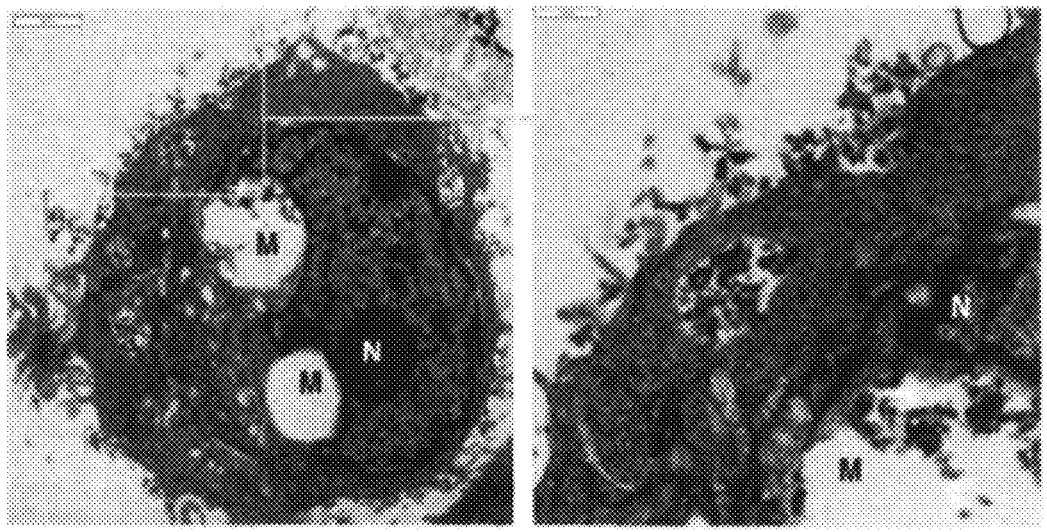
FIG. 56 shows electron tomography analysis and 3D image reconstruction of the TEM images generated during Hela cell incubation with 20 µg/mL MSNP2. TEM grids were used for the tomography analysis on an FEI Tecnai F20 microscope operated at 200 kV. Images were captured by tilting the specimen from −70° to 70° with 1° steps. Tilt series images were captured with a TIETZ F415MP 16 megapixel CCD camera at a magnification of 26,600× and then aligned using the Etomo program in the IMOD package. The aligned tilt series were further processed using the reconstruction features of the FEI software, Inspect3d's SIRT, to improve the contrast. Videos of the aligned tilt series were generated using both Inspect3d and Windows movie maker (still images shown in FIG. 60). These data confirm MSNP2 uptake by macropinocytosis and actually yield resolution of the particles pores inside the cell. M: macropinosome. N: nuclear.
Figure 60A:
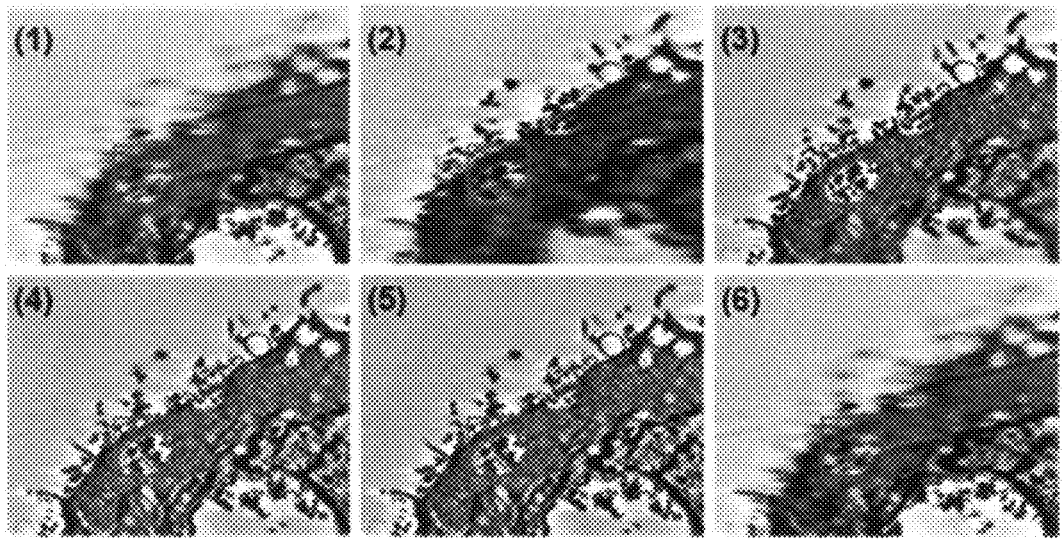
FIGS. 60A and 60B show electron tomography analysis and 3D image reconstruction of the TEM images generated during HeLa cell incubation with 20 μg/mL MSNP rod with an aspect ratio of 2.1-2.5 for 3 h. TEM grids were used for the tomography analysis on an FEI Tecnai F20 microscope operated at 200 kV. Images were captured by tilting the specimen from −70° to 70° with 1° steps. Tilt series images were captured with a TIETZ F415MP 16 megapixel CCD camera at a magnification of 26,600× and then aligned using the Etomo program in the IMOD package. The aligned tilt series were further processed using the reconstruction features of the FEI software, Inspect3d's SIRT, to improve the contrast. Videos of the aligned tilt series were generated using both Inspect3d and Windows movie maker. Still shots from the video were shown in FIG. 60A (Image 1 to Image 6). Similarly, a higher magnification of the region of interest (box) in FIG. 60A was imaged (FIG. 60B). MSNP rod with an aspect ratio of 2.1-2.5 were taken up by a process of macropinocytosis as evidenced by the presence of filopodia and formation of macropinocytotic vesicles. Noteworthy, the number of filopodia and extent of membrane ruffling were dramatically enhanced in cells exposed to MSNP rods with an aspect ratio of 2.1-2.5. Electron tomography and 3D image reconstruction was powerful enough to capture the porous structure of the particles inside the cells, an ultrastructural feature that has not previously been accomplished.
Figure 60B:
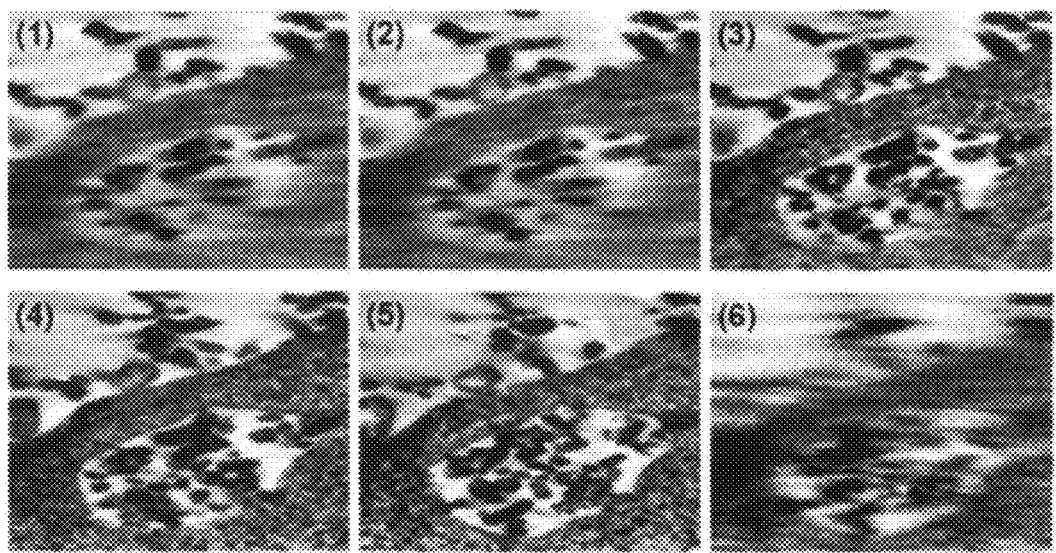

Electron microscopy (EM) was used for ultrastructural resolution of the route of MSNP uptake in Hela cells (FIG. 50). Although Hela cells are capable of endocytosing nanoparticles by various routes,[1,24] MSNPs were taken up by a process of macropinocytosis as evidenced by the presence of filopodia and formation of macropinocytotic vesicles (FIG. 50A).[25] Noteworthy, the number of filopodia and extent of membrane ruffling were dramatically enhanced in cells exposed to MSNP2 compared to cells exposed to MSNP3 (FIG. 50A) or MSNP1 (not shown). More detailed TEM images of MSNP2 macropinocytosis are shown in FIG. 55 together with electron tomography and 3D image reconstruction (FIGS. 56 and 60). Electron tomography was powerful enough to capture the porous structure of the particles inside the cells, an ultrastructural feature that has not previously been accomplished previously.

Since macropinocytosis and filopodia formation is dependent on actin assembly at the surface membrane,[26-28] Alexa 594-phalloidin staining was performed to visualize these cytoskeletal changes. The confocal images demonstrate that compared to spheres or shorter and longer rods, MSNP2 induced the most prominent changes in actin polymerization in Hela cells (FIG. 50B). Scoring of the number of filopodia by a technique previously published in the literature[29] (and explained in the legend of FIG. 50C), demonstrated a 7-fold increase in filopodia number in cells treated with MSNP2 compared to MSNP0, MSNP1 and MSNP3 (FIG. 50C). In addition, the actin assembly in response to MSNP2 was sustained for at least 6 h compared to the transient effects seen with stimuli such as epidermal growth factor.[26]

Figure 50E:
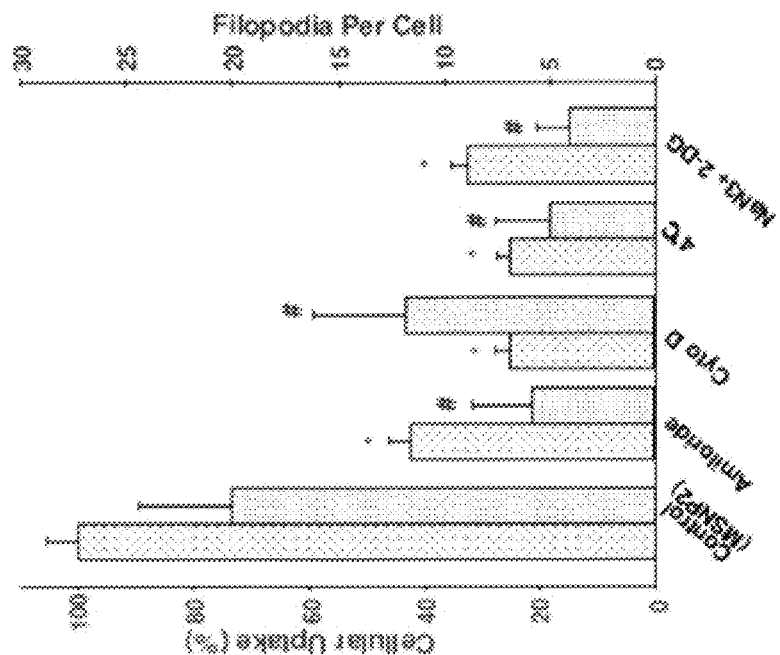
Figure 50D:
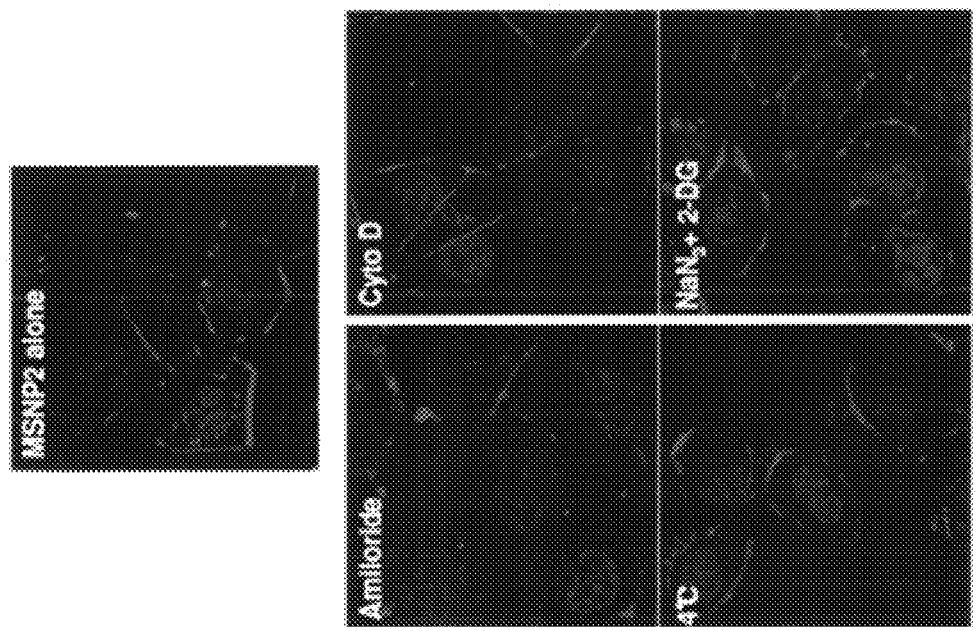

Chemical inhibitors are widely used to confirm the occurrence of macropinocytosis and as a means of distinguishing this uptake mechanism from clathrin- and caveolae-mediated uptake.[26,30] Prior cellular treatment with amiloride26 as well as the cytoskeletal inhibitor cytochalasin D (Cyto D)[1,31] decreased MSNP2 uptake by >50% (FIG. 50D). These agents also interfered in MSNP-induced filopodia formation (Figure SOE). The energy dependence of the macropinocytosis pathway was confirmed by culturing the cells at 4° C.[32] or pretreating them with sodium azide (NaN3)/2-deoxyglucose (2-DG) for 3 h before the addition of the particles (FIG. 50D).[1] All of the above inhibitors also decreased filopodia formation and MSNP uptake by >60% (FIG. 50E).

Figure 57:
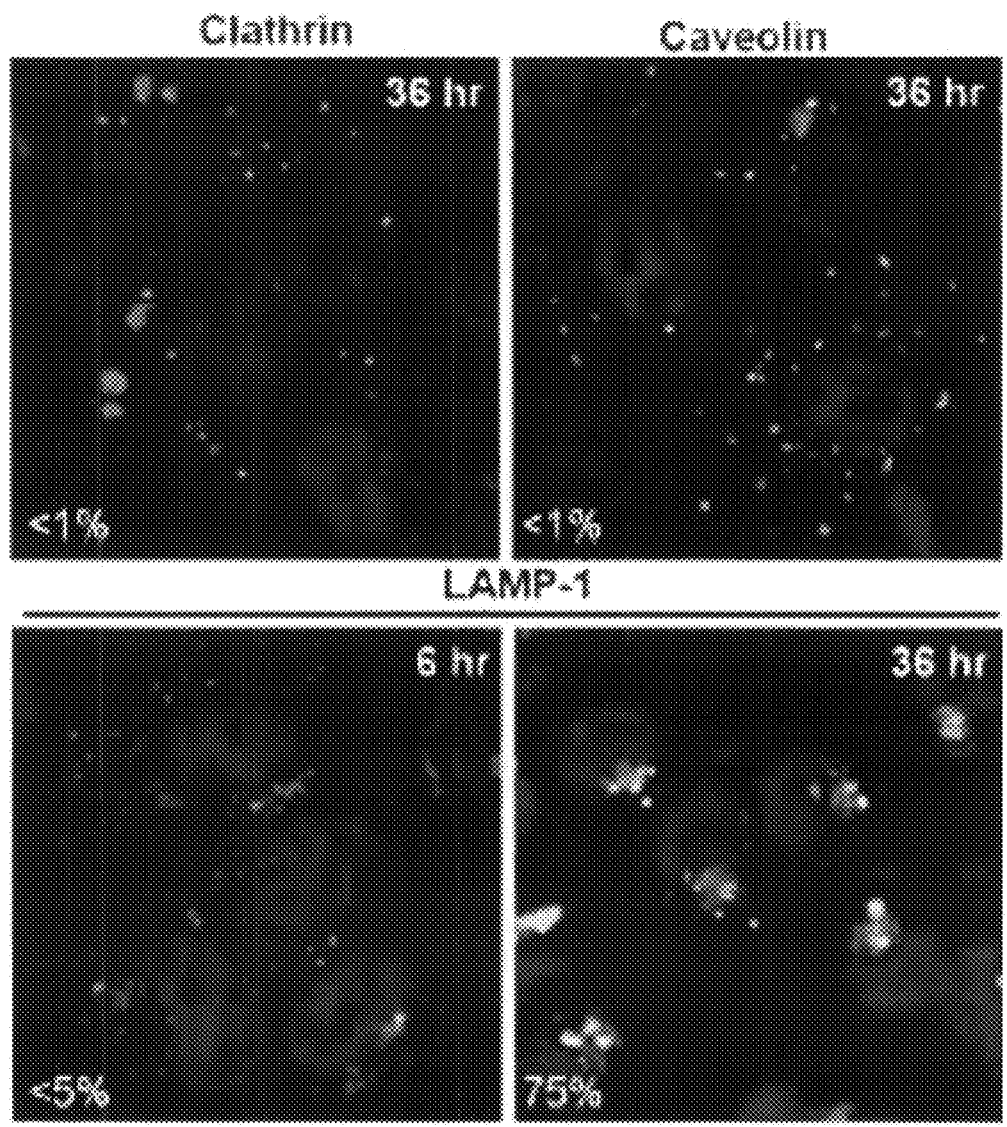
FIG. 57 shows confocal microscopy to study the subcellular localization of FITC-labeled MSNP2 in Hela cells. Hela cells were treated with 20 μg/mL FITC-labeled MSNP for the indicated time periods. After fixation and permeabilization, cells were stained with anti-clathrin (Santa Cruz, Biotechnology), anti-caveolin-1 (BD BioSciences), and anti-LAMP-1 (Abeam) antibodies, and visualized with Alexa 594-conjugated secondary antibody. The colocalization ratio, as determined by Imaging J software, indicates <1% colocalization of the green-labeled nanoparticles with the red-labeled clathrin and caveolae at 36 h. The colocalization ratios with the LAMP-1 positive compartment were estimated to be <5% and 75%, respectively, at the 6 h and 36 h time points.

To study the subcellular fate of endocytosed MSNP2, confocal microscopy was used to localize FITC-labeled MSNP2 in relation to clathrin-coated vesicles, caveolae and lysosomes in Hela cells (FIG. 57).[33] These endocytotic compartments were localized by RITC-labeled secondary antibodies capable of binding to primary antibodies recognizing clathrin, caveolin-1 and LAMP-1, respectively. Image J software analysis to quantify FITC-labeled MSNP2 co localization with labeled compartments showed that while <1% of these rods were localized in clathrin or caveolin-1 stained compartments (FIG. 57, upper panel), more MSNP2 entered a LAMP-1 positive compartment (FIG. 57, lower panel). Thus, while <5% of the particles entered the LAMP-1 positive compartment by 6 h, this fraction increased to 75% by 36 h. All considered, these data indicate that MSNP2 are primarily taken up by macropinocytosis and ultimately shuttled into an acidifying endosomes that specialize in particle degradation. Interestingly, the MSNP-laden lysosomes could be seen to change their localization from a random to a clustered arrangement in the cell (FIG. 57, bottom right panel). The significance of this redistribution is uncertain.

Assessment of Cellular Rac1 Activation.

To study Rac1 activation, Hela cells were serum-starved for 4 h before introduction of the particles that were dispersed in RPMI containing 10% FBS. Cells were incubated with the particles for 30 min at a concentration of 20 µg/mL. Because FBS may also contribute to Rac1 activation due to the presence of growth factors, it was necessary to include a control where serum starved cells were exposed to complete RPMI for 30 min to allow adjustment for any possible Rac1 activation due to the complete medium. After fixation and permeabilization, cells were stained with antibodies recognizing the activated, OTP-bound form of Rac1 or total Rac1 protein.[35-37] The primary antibodies were detected by secondary antibodies conjugated to Alexa 594 or FITC, respectively. Nuclei were stained by Hoechst 33342. The Alexa 594 fluorescence intensity as a measure of Rac1 activation was determined by Image J software. The fluorescence intensity of control cells incubated in serum-containing medium for 30 min was chosen as reference with fluorescent intensity=1. The fluorescence intensity of cells treated with the various MSNPs was then expressed as the fold-increase compared to this control value. The experiment was repeated in presence of amiloride, Cyto D, $NaN_3$/2-DG as well as 4° C. as described above.

MSNP2 Promotes Active Macropinocytosis Through Rac1 Activation.

Figure 51B:
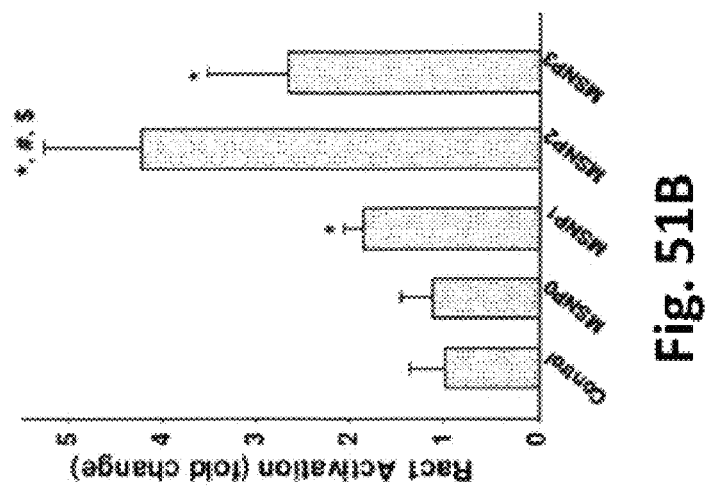
FIGS. 51A and 51B show confocal microscopy showing the effect of the different particle types on Rac1 activation in Hela cells.
Figure 51A:
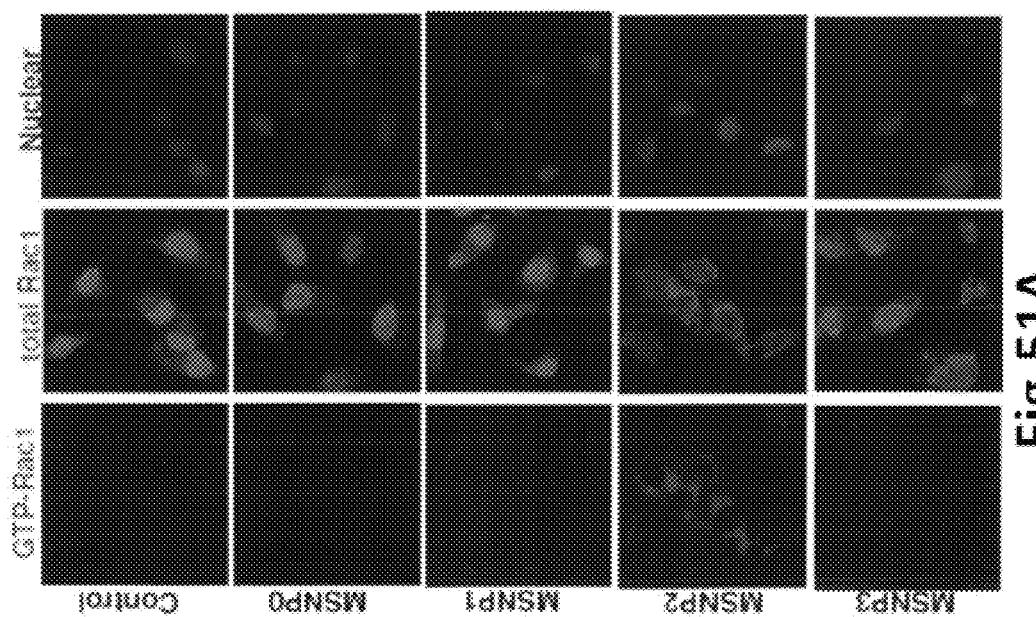

Macropinocytosis is frequently initiated by external stimuli, such as viruses[25] or growth factors[34] capable of activating membrane-associated signaling cascades that play a role in actin polymerization and plasma membrane ruffling.[26,30] One of the signaling mechanisms involves the activation of the OTP-binding protein, Rac1, which plays a role in membrane ruffling, cytoskeletal changes and closure of macropinosome.[26,30] In order to see if Rae 1 is activated during MSNP macropinocytosis, an immunochemical technique was used that distinguishes activated, OTP-bound Rac1 from total cellular Rac1 protein.[35-37] This was accomplished by using a secondary Alexa 594-conjugated antibody that recognizes anti-OTP-Rac1 as well as a FITC-labeled secondary antibody that binds to a framework site in Rac1.[35-37] Use of these antibody pairs for confocal studies in Hela cells showed more intense Rac1 activation (red fluorescence) in cells treated with MSNP2 compared to cells exposed to MSNP0, MSNPI or MSNP3 (FIG. 51). In contrast, the total Rac1 abundance (green fluorescence) remained the same across the cell populations. Use of Image J software to calculate the increase in Alexa 594 fluorescence demonstrated an approximately 4-fold increase in abundance of activated Rac1 following MSNP2 treatment (FIG. 51B). Longer and shorter rods induced less prominent Rac1 activation (FIG. 51B). These response differences were sustained for at least 30 minutes. Noteworthy, Rac1 activation was suppressed in MSNP2-exposed cells treated with amiloride, $NaN_3$/2-DG, or cultured at 4° C. (FIG. 58). In contrast, Cyto D, which functions downstream of Rac1, had no significant effect (FIG. 58).

Drug Loading and Loading Capacity Measurement.

Two hydrophobic anticancer drugs, Taxol and camptothecin (CPT), were loaded into different MSNP using 20 mg of each type of particles suspended into a solution containing 0.5 mg of each drug in 1 mL DMSO. After 24 h, the particles were collected by centrifugation, and the trace amounts of DMSO were removed by drying under vacuum. The drug-laden particles were washed and stored as an aqueous stock solution at 20 mg/mL. To measure the loading capacity of the particles, they were resuspended in methanol and thoroughly sonicated to remove the drug from the pores. After centrifugation and removal of the supernatant, the process was repeated 3 times to elute all drug. The supernatants were combined and the amount of free drug calculated using Taxol absorbance at 229 nm and the CPT fluorescence at excitation and emission wavelengths of 370 and 448 nm, respectively, in a microplate reader (SpectraMax MS Microplate Reader, Molecular Device, USA).

Assessment of Hela cytotoxicity in response to treatment with drug loaded particles. Hela cells were plated at 1×10⁴ cells per well in 96 well plates. MSNP, loaded with CPT or Taxol, were incubated with the cells to deliver CPT concentrations of 0.1-8.0 μg/mL and Taxol concentrations of 0.1-2.0 μg/mL for 36 h. The effect of the MSNP-bound drug was compared to similar amounts of free drug delivered in PBS or DMSO/PBS. A MTS assay was performed 36 h after drug and particle exposure to assess cellular viability as previous described by us.[13]

Statistical Analysis.

Data represent the mean±SD for duplicate or triplicate measurements in each experiment. Differences between the mean values were analyzed by two-sided Student's t test or one way ANVOA. All experiments were repeated at least twice.

Delivery of hydrophobic chemotherapeutic agents by long AR particles. Due to the ordered porous structure and large surface area capable of cargo loading, MSNPs have emerged as a multifunctional drug delivery platform.[11-15, 38] In light of the facilitated cellular uptake of MSNP2, the cytotoxic effects of two hydrophobic chemotherapeutic agents, camptothecin (CPT) and paclitaxel (Taxol) were compared, delivered by spherical and long AR particles. The drugs were loaded into the particles by a phase transition approach that was previously developed.[11-13] Particle-mediated drug delivery was compared against the free drugs (dissolved in PBS alone or PBS supplemented with 0.1% DMSO), using a MTS assay. Use of this assay to compare equivalent amounts of drugs being delivered over a 36 h time period demonstrated that the cytotoxic potential of drug-laden MSNP2>MSNP1>MSNP3>MSNP0≈drugs delivered by PBS/DMSO >>drugs delivered by PBS (FIG. 52). Notice that the particle themselves were devoid of toxicity as shown in FIG. 59.

REFERENCES

1. Gratton, S. E. A.; Ropp, P. A.; Pohlhaus, P. D.; Luft, J. C.; Madden, V. J.; Napier, M. E.; DeSimone, J. M. The Effect of Particle Design on Cellular Internalization Pathways. Proc. Natl. Acad. Sci. U.S.A. 2008, 105, 11613-11618.
2. Decuzzi, P.; Godin, B.; Tanaka, T.; Lee, S. Y.; Chiappini, C.; Liu, X.; Ferrari, M. Size and Shape Effects in the Biodistribution of Intravascularly Injected Particles. J. Control. Release 2010, 141, 320-327.
3. Mitragotri, S.; Lahann, J. Physical Approaches to Biomaterial Design. Nat. Mater. 2009, 8, 15-23.
4. Chithrani, B. D.; Ghazani, A. A.; Chan, W. C. W. Determining the Size and Shape Dependence of Gold Nanoparticle Uptake into Mammalian Cells. Nano Lett. 2006, 6, 662-668.
5. Yang, S.; Zhou, X.; Yuan, P.; Yu, M.; Xie, S.; Zou, J.; Lu, G.; Yu, C. Siliceous Nanopods from a Compromised Dual-Templating Approach. Angew. Chem. Int. Ed. Engl. 2007, 46, 8579-8582.
6. Doshi, N.; Mitragotri, S. Macrophages Recognize Size and Shape of Their Targets. PLoS ONE 2010, 5, e10051.
7. Lee, S.-Y.; Ferrari, M.; Decuzzi, P. Shaping Nano-/Microparticles for Enhanced Vascular Interaction in Laminar Flows. Nanotechnology 2009, 20, 495101.
8. Champion, J. A.; Katare, Y. K.; Mitragotri, S. Particle shape: A New Design Parameter for Micro- and Nanoscale Drug Delivery Carriers. J Control. Release 2007, 121, 3-9.

9. Meng, H.; Xia, T.; George, S.; Nel, A. E. A Predictive Toxicological Paradigm for the Safety Assessment of Nanomaterials. *ACS Nano* 2009, 3, 1620-1627.
10. Nel, A. E.; Madler, L.; Velegol, D.; Xia, T.; Hoek, E. M. V.; Somasundaran, P.; Klaessig, F.; Castranova, V.; Thompson, M. Understanding Biophysicochemical Interactions at the Nano-Bio Interface. *Nat. Mater.* 2009, 8, 543-557.
11. Lu, J.; Liong, M.; Zink, J. I.; Tamanoi, F., Mesoporous Silica Nanoparticles as a Delivery System for Hydrophobic Anticancer Drugs. *Small* 2007, 3, 1341-1346.
12. Meng, H.; Liong, M.; Xia, T.; Li, Z.; Ji, Z.; Zink, J. I.; Nel, A. E. Engineered Design of Mesoporous Silica Nanoparticles to Deliver Doxorubicin and P-Glycoprotein siRNA to Overcome Drug Resistance in a Cancer Cell Line. *ACS Nano* 2010, 4, 4539-4550.
13. Xia, T.; Kovochich, M.; Liong, M.; Meng, H.; Kabehie, S.; George, S.; Zink, J. I.; Nel, A. E. Polyethyleneimine Coating Enhances the Cellular Uptake of Mesoporous Silica Nanoparticles and Allows Safe Delivery of siRNA and DNA Constructs. *ACS Nano* 2009, 3, 3273-3286.
14. Liong, M.; Lu, J.; Kovochich, M.; Xia, T.; Ruehm, S. G.; Nel, A. E.; Tamanoi, F.; Zink, J. I. Multifunctional Inorganic Nanoparticles for Imaging, Targeting, and Drug Delivery. *ACS Nano* 2008, 2, 889-896.
15. Meng, H.; Xue, M.; Xia, T.; Zhao, Y.-L.; Tamanoi, F.; Stoddart, J. F.; Zink, J. I.; Nel, A. E. Autonomous in vitro Anticancer Drug Release from Mesoporous Silica Nanoparticles by pH-Sensitive Nanovalves. *J Am. Chem. Soc.* 2010, 132, 12690-12697.
16. Liong, M.; Angelos, S.; Choi, E.; Patel, K.; Stoddart, J. F.; Zink, J. I., Mesostructured Multifunctional Nanoparticles for Imaging and Drug Delivery. *J Mater. Chem.* 2009, 19, 6251-6257.
17. Ferris, D. P.; Zhao, Y.-L.; Khashab, N. M.; Khatib, H. A.; Stoddart, J. F.; Zink, J. I., Light-Operated Mechanized Nanoparticles. *J. Am. Chem. Soc.* 2009, 131, 1686-1688.
18. Coti, K. K.; Belowich, M. E.; Liong, M.; Ambrogio, M. W.; Lau, Y. A.; Khatib, H. A.; Zink, J. I.; Khashab, N. M.; Stoddart, J. F., Mechanised Nanoparticles for Drug Delivery. *Nanoscale* 2009, 1, 16-39.
19. Yang, S.; Zhao, L.; Yu, C.; Zhou, X.; Tang, J.; Yuan, P.; Chen, D.; Zhao, D. On the Origin of Helical Mesostructures. *J Am. Chem. Soc.* 2006, 128, 10460-10466.
20. Kresge, C. T.; Leonowicz, M. E.; Roth, W. J.; Vartuli, J. C.; Beck, J. S. Ordered Mesoporous Molecular Sieves Synthesized by a Liquid-Crystal Template Mechanism. *Nature* 1992, 359, 710-712.
21. Zhang, L.; Qiao, S. Z.; Cheng, L.; Yan, Z.; Lu, G. Q. M. Fabrication of a Magnetic Helical Mesostructured Silica Rod. *Nanotechnology* 2008, 19, 435608.
22. Ohsuna, T.; Liu, Z.; Che, S.; Terasaki, O. Characterization of Chiral Mesoporous Materials by Transmission Electron Microscopy. *Small* 2005, 1, 233-237.
23. Huang, X.; Teng, X.; Chen, D.; Tang, F.; He, J. The Effect of the Shape of Mesoporous Silica Nanoparticles on Cellular Uptake and Cell Function. *Biomaterials* 2010, 31, 438-448.
24. Dausend, J.; Musyanovych, A.; Dass, M.; Walther, P.; Schrezenmeier, H.; Landfester, K.; Mailander, V. Uptake Mechanism of Oppositely Charged Fluorescent Nanoparticles in HeLa Cells. *Macromol. Biosci.* 2008, 8, 1135-1143.
25. Kalin, S.; Amstutz, B.; Gastaldelli, M.; Wolfrum, N.; Boucke, K.; Havenga, M.; DiGennaro, F.; Liska, N.; Hemmi, S.; Greber, U. F. Macropinocytotic Uptake and Infection of Human Epithelial Cells with Species B2 Adenovirus Type 35. *J Viral.* 2010, 84, 5336-5350.
26. Mercer, J.; Helenius, A. Virus Entry by Macropinocytosis. *Nat. Cell Biol.* 2009, 11, 510-520.
27. Nakase, I.; Niwa, M.; Takeuchi, T.; Sonomura, K.; Kawabata, N.; Koike, Y.; Takehashi, M.; Tanaka, S.; Ueda, K.; Simpson, J. C.; Jones, A. T.; Sugiura, Y.; Futaki, S. Cellular Uptake of Arginine-Rich Peptides: Roles for Macropinocytosis and Actin Rearrangement. *Mal. Ther.* 2004, 10, 1011-1022.
28. Hillaireau, H.; Couvreur, P. Nanocarriers' Entry into the Cell: Relevance to Drug Delivery. *Cell. Mal. Life Sci.* 2009, 66, 2873-2896.
29. Sheldon, H.; Andre, M.; Legg, J. A.; Heal, P.; Herbert, J. M.; Sainson, R.; Sharma, A. S.; Kitajewski, J. K.; Heath, V. L.; Bicknell, R. Active Involvement of Robo1 and Robo4 in Filopodia Formation and Endothelial Cell Motility Mediated via WASP and Other Actin Nucleation-Promoting Factors. *FASEB J* 2009, 23, 513-522.
30. West, M. A.; Bretscher, M. S.; C, W. Distinct Endocytotic Pathways in Epidermal Growth Factor-Stimulated Human Carcinoma A431 Cells. *J Cell Biol.* 1989, 109, 2731-2739
31. Schrijvers, D. M.; Martinet, W.; De Meyer, G. R. Y.; Andries, L.; Herman, A. G.; Kockx, M. M. Flow Cytometric Evaluation of a Model for Phagocytosis of Cells Undergoing Apoptosis. *J Immunol. Methods* 2004, 287, 101-108.
32. Li, W.; Chen, C.; Ye, C.; Wei, T.; Zhao, Y. Z.; Lao, F. L.; Chen, Z.; Meng, H.; Gao, Y.; Yuan, H.; Xing, G.; Zhao, F.; Chai, Z.; Zhang, X.; Yang, F.; Han, D.; Tang, X.; Zhang, Y. The Translocation of Fullerenic Nanoparticles into Lysosome via the Pathway of Clathrin-Mediated Endocytosis. *Nanotechnology* 2008, 19, 145102.
33. Conner, S. D.; Schmid, S. L. Regulated Portals of Entry into the Cell. *Nature* 2003, 422, 37-44.
34. Ridley, A. J.; Paterson, H. F.; Johnston, C. L.; Diekmann, D.; Hall, A. The Small GTP-binding Protein Rae Regulates Growth Factor-Induced Membrane Ruffling. *Cell* 1992, 70, 401-410.
35. Li, Q.; Ho, C. S.; Marinescu, V.; Bhatti, H.; Bokoch, G. M.; Ernst, S. A.; Holz, R. W.; Stuenkel, E. L. Facilitation of Ca2+-Dependent Exocytosis by Rac1-GTPase in Bovine Chromaffin Cells. *J. Physiol.* 2003, 550, 431-445.
36. Osada, T.; Watanabe, S.; Tanaka, H.; Hirose, M.; Miyazaki, A.; Sato, N. Effect of Mechanical Strain on Gastric Cellular Migration and Proliferation During Mucosal Healing: Role of Rho Dependent and Rae Dependent Cytoskeletal Reorganisation. *Gut* 1999, 45, 508-515.
37. Ueda, S.; Kataoka, T.; Satoh, T. Activation of the Small GTPase Rac1 by a Specific Guanine-Nucleotide-Exchange Factor Suffices to Induce Glucose Uptake into Skeletal-Muscle Cells. *Biol. Cell.* 2008, 100, 645-657.
38. Slowing, I. I.; Trewyn, B. G.; Lin, V. S. Y. Mesoporous Silica Nanoparticles for Intracellular Delivery of Membrane-Impermeable Proteins. *J Am. Chem. Soc.* 2007, 129, 8845-8849.
39. Champion, J. A.; Mitragotri, S. Role of Target Geometry in Phagocytosis. *Proc. Natl. Acad. Sci. U.S.A.* 2006, 103, 4930-4934.
40. Decuzzi, P.; Ferrari, M. The Receptor-Mediated Endocytosis of Nonspherical Particles. *Biophys. J* 2008, 94, 3790-3797.
41. Champion, J. A.; Katare, Y. K.; Mitragotri, S. Making Polymeric Micro- and Nanoparticles of Complex Shapes. *Proc. Natl. Acad. Sci. U.S.A.* 2007, 104, 11901-11904.

42. Arnida; Malugin, A.; Ghandehari, H. Cellular Uptake and Toxicity of Gold Nanoparticles in Prostate Cancer Cells: A Comparative Study of Rods and Spheres. J Appl. Toxicol. 2010, 30, 212-217.
43. Chithrani, B. D.; Chan, W. C. W. Elucidating the Mechanism of Cellular Uptake and Removal of Protein-Coated Gold Nanoparticles of Different Sizes and Shapes. Nano Lett. 2007, 7, 1542-1550.
44. Muro, S.; Garnacho, C.; Champion, J. A.; Leferovich, J.; Gajewski, C.; Schuchman, E. H.; Mitragotri, S.; Muzykantov, V. R. Control of Endothelial Targeting and Intracellular Delivery of Therapeutic Enzymes by Modulating the Size and Shape of ICAM-1-targeted Carriers. Mal. Ther. 2008, 16, 1450-1458.
45. Hayakawa, K.; Tatsumi, H.; Sokabe, M. Actin Stress Fibers Transmit and Focus Force to Activate Mechanosensitive Channels. J. Cell Sci. 2008, 121, 496-503.
46. Fiorentini, C.; Falzano, L.; Fabbri, A.; Stringaro, A.; Logozzi, M.; Travaglione, S.; Contamin, S.; Arancia, G.; Malorni, W.; Fais, S. Activation of Rho GTPases by Cytotoxic Necrotizing Factor 1 Induces Macropinocytosis and Scavenging Activity in Epithelial Cells. Mal. Biol. Cell 2001, 12, 2061-2073.
47. Dharmawardhane, S.; Schurmann, A.; Sells, M. A.; Chernoff, J.; Schmid, S. L.; Bokoch, G. M. Regulation of Macropinocytosis by p21-activated Kinase-I. Mal. Biol. Cell 2000, 11, 3341-3352.
48. Chen, L.-M.; Hobbie, S.; Galan, J. E. Requirement of CDC42 for Salmonella-Induced Cytoskeletal and Nuclear Responses. Science 1996, 274, 2115-2118.
49. Sandgren, K. J.; Wilkinson, J.; Miranda-Saksena, M.; McInerney, G. M.; Byth-Wilson, K.; Robinson, P. J.; Cunningham, A. L. A Differential Role for Macropinocytosis in Mediating Entry of the Two Forms of Vaccinia Virus into Dendritic Cells. PLoS Pathog. 6, el 000866.
50. Sahay, G.; Alakhova, D. Y.; Kabanov, A. V. Endocytosis of Nanomedicines. J. Control. Release 2010, 145, 182-195.
51. Geiger, B.; Spatz, J. P.; Bershadsky, A. D. Environmental Sensing Through Focal Adhesions. Nat. Rev. Mal. Cell Biol. 2009, 10, 21-33.
52. Discher, D. E.; Janmey, P.; Wang, Y. Tissue Cells Feel and Respond to the Stiffness of Their Substrate. Science 2005, 310, 1139-1143.
53. Thery, M.; Racine, V.; Piel, M.; Pepin, A.; Dimitrov, A.; Chen, Y.; Sibarita, J.-B.; Bornens, M. Anisotropy of Cell Adhesive Microenvironment Governs Cell Internal Organization and Orientation of Polarity. Proc. Natl. Acad. Sci. U.S.A. 2006, 103, 19771-19776.
54. Butler, B.; Gao, C.; Mersich, A. T.; Blystone, S. D. Purified Integrin Adhesion Complexes Exhibit Actin-Polymerization Activity. Curr. Biol. 2006, 16, 242-251.
55. Roiter, Y.; Ornatska, M.; Rammohan, A. R.; Balakrishnan, J.; Heine, D. R.; Minko, S. Interaction of Nanoparticles with Lipid Membrane. Nano Lett. 2008, 8, 941-944.
56. Slowing, I. I.; Wu, C. W.; Vivero-Escoto, J. L.; Lin, V. S. Y. Mesoporous Silica Nanoparticles for Reducing Hemolytic Activity Towards Mammalian Red Blood Cells. Small 2009, 5, 57-62.
57. Glass, R.; Arnold, M.; Bliimmel, J.; Kiiller, A.; Moller, M.; Spatz, J. P. Micro-Nanostructured Interfaces Fabricated by the Use of Inorganic Block Copolymer Micellar Monolayers as Negative Resist for Electron-Beam Lithography. Adv. Funct. Mater. 2003, 13, 569-575.
58. Glass, R.; Arnold, M.; Cavalcanti-Adam E. A.; Bliimmel, J.; Haferkemper, C.; Dodd C.; Spatz, J. P. Block Copolymer Micelle Nanolithography on Non-Conductive Substrates. New J. of Phys. 2004, 6, 101.
59. Arnold, M.; Cavalcanti-Adam, E. A.; Glass, R.; Bliimmel, J.; Eck, W.; Kantlehner, M.; Kessler, H.; Spatz, J. P., Activation of Integrin Function by Nanopatterned Adhesive Interfaces. ChemPhysChem 2004, 5, 383-388.
60. Cavalcanti-Adam, E. A.; Volberg, T.; Micoulet, A.; Kessler, H.; Geiger, B.; Spatz, J. P. Cell Spreading and Focal Adhesion Dynamics Are Regulated by Spacing of Integrin Ligands. Biophys. J. 2007, 92, 2964-2974.
61. Karmali, P. P.; Kotamraju, V. R.; Kastantin, M.; Black, M.; Missirlis, D.; Tirrell, M.; Ruoslahti, E. Targeting of albumin-embedded paclitaxel nanoparticles to tumors. Nanomedicine 2009, 5, 73-82.
62. Lobo, C.; Lopes, G.; Silva, O.; Gluck, S. Paclitaxel Albumin-Bound Particles (Abraxane™) in Combination with Bevacizumab with or without Gemcitabine: Early Experience at the University of Miami/Braman Family Breast Cancer Institute. Biomed. Pharmacother. 2007, 61, 531-533.
63. Kremer, J. R.; Mastronarde, D. N.; McIntosh, J. R., Computer Visualization of Three-dimensional Image Data Using IMOD. J Struct. Biol. 1996, 116, 71-76.

The embodiments illustrated and discussed in this specification are intended only to teach those skilled in the art the best way known to the inventors to make and use the invention. Figures are not drawn to scale. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A dual delivery nanocarrier, comprising:
   a silica body defining a plurality of pores and an outer surface between pore openings of said plurality of pores, where said silica body is functionalized with anionic surface groups;
   a cationic polymer electrostatically bound to the surface of said silica body, wherein said cationic polymer does not occupy the interior of said pores;
   an oligonucleotide bound to the cationic polymer wherein the oligonucleotide comprises an siRNA that reduces translation of protein causing drug resistance in a cell; and
   an anti-cancer compound disposed within said plurality of pores, where said anti-cancer compound is cationic at physiological pH;
   wherein said nanocarrier is effective to transfect a mammalian cancer cell and to increase drug sensitivity of said cancer cell, is non-toxic when administered in vivo in a mammal; and
   said nanocarrier provides intracellular release of said anti-cancer compound in vivo.

2. The nanocarrier of claim 1, wherein the siRNA reduces translation of p-glycoprotein.

3. The nanocarrier of claim 1, wherein the anti-cancer compound comprises doxirubicin.

4. The nanocarrier of claim 1, wherein the cationic polymer comprises a polymer selected from the group consisting of polyethyleneimine, polyamidoamine, polylysine, poly(allylamine), and poly(diallyldimethylammonium chloride).

5. The nanocarrier of claim 1, wherein the cationic polymer comprises polyethyleneimine.

6. The nanocarrier of claim 1, wherein the cationic polymer is a cationic co-polymer.

7. The nanocarrier of claim 1, wherein the cationic co-polymer is a co-polymer of poly(ethyleneimine) and poly(ethylene glycol).

8. The nanocarrier of claim 1, wherein said oligonucleotide is electrostatically bound to said cationic polymer.

9. The nanocarrier of claim 1, wherein said siRNA comprises a duplex, where said duplex comprises the sense nucleotide sequence 5'-r(CGGAAGGCCUAAUGCCGAA) dTdT (SEQ ID NO: 1) and the antisense nucleotide sequence 5'-r(UUCGGCAUUAGGCCUUCCG)dG (SEQ ID NO:2).

10. The nanocarrier of claim 1, wherein the silica body is mesoporous.

11. The nanocarrier of claim 1, wherein the pores have an ensemble average diameter between about 1 nm and about 50 nm.

12. The nanocarrier of claim 1, wherein said anionic surface groups comprise phosphonate moieties.

13. The nanocarrier of claim 1, wherein said anionic surface groups comprise trihydroxysilylpropyl methylphosphonate.

14. The nanocarrier of claim 1, further comprising a light-emitting compound, peptide, protein, oligonucleotide, sugar, oligosaccharide, or polysaccharide covalently bonded to the surface of the silica body.

15. The nanocarrier of claim 1 further comprising a core structure within said silica body.

16. The nanocarrier of claim 15, wherein said core structure is a superparamagnetic nanocrystal, silver nanocrystal, or gold nanocrystal.

17. A method of treating a cancer, said method comprising administering to a subject in need thereof an effective amount of a nanocarrier of claim 1.

18. The method of claim 17, wherein said anti-cancer compound comprises doxirubicin.

19. The nanocarrier of claim 1, wherein the pores are substantially cylindrical pores having an ensemble average diameter less than about 100 nm.

20. The nanocarrier of claim 2, wherein the anti-cancer compound comprises doxirubicin.

21. The nanocarrier of claim 20, wherein:
   said anionic surface groups comprise a phosphonate; and
   said cationic polymer comprises polyethylenimine (PEI).

22. The nanocarrier of claim 21, wherein said siRNA comprises a duplex, where said duplex comprises the sense nucleotide sequence 5'-r(CGGAAGGCCUAAUGCCGAA) dTdT (SEQ ID NO: 1) and the antisense nucleotide sequence 5'-r(UUCGGCAUUAGGCCUUCCG)dG (SEQ ID NO:2).

23. The nanocarrier of claim 22, wherein the pores are substantially cylindrical pores having an ensemble average diameter between about 1 nm and about 10 nm.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial
<220> FEATURE:
<223> OTHER INFORMATION: siRNA sense strand
<220> FEATURE:
<221> NAME/KEY: misc_feature
<222> LOCATION: (20)..(21)
<223> OTHER INFORMATION: n is deoxythymidine
```

```
<400> SEQUENCE: 1
cggaaggccu aaugccgaan n                                          21

<210> SEQ ID NO 2
<211> LENGTH: 20
<212> TYPE: RNA
<213> ORGANISM: Artificial
<220> FEATURE:
<223> OTHER INFORMATION: siRNA antisense strand
<220> FEATURE:
<221> NAME/KEY: misc_feature
<222> LOCATION: (20)..(20)
<223> OTHER INFORMATION: n is deoxyguanosine

<400> SEQUENCE: 2
uucggcauua ggccuuccgn                                            20
```